(12) United States Patent
Zhou et al.

(10) Patent No.: US 8,791,137 B2
(45) Date of Patent: *Jul. 29, 2014

(54) THERAPEUTIC COMPOUNDS

(75) Inventors: Xianbo Zhou, Ridgefield, CT (US); Roderick E. M. Scott, New York, NY (US); Rusiko Bourtchouladze, New York, NY (US); Alan P Kaplan, Kings Park, CA (US); Terence P Keenan, Bay Shore, NY (US); Andrew McRiner, Centerport, NY (US)

(73) Assignee: Dart Neuroscience (Cayman) Ltd., Camana Bay, Grand Cayman (KY)

( * ) Notice: Subject to any disclaimer, the term of this patent is extended or adjusted under 35 U.S.C. 154(b) by 581 days.

This patent is subject to a terminal disclaimer.

(21) Appl. No.: 12/849,418

(22) Filed: Aug. 3, 2010

(65) Prior Publication Data

US 2010/0317648 A1 Dec. 16, 2010

Related U.S. Application Data

(63) Continuation of application No. 11/679,775, filed on Feb. 27, 2007, now Pat. No. 7,919,626.

(60) Provisional application No. 60/777,332, filed on Feb. 28, 2006, provisional application No. 60/890,455, filed on Feb. 16, 2007.

(51) Int. Cl.
*A61K 31/445* (2006.01)
*C07D 409/14* (2006.01)

(52) U.S. Cl.
USPC .......................................... 514/326; 546/211

(58) Field of Classification Search
None
See application file for complete search history.

(56) References Cited

U.S. PATENT DOCUMENTS

| 5,204,482 | A | 4/1993 | Gassner et al. | |
|---|---|---|---|---|
| 6,727,264 | B1 * | 4/2004 | Marzabadi et al. | 514/323 |
| 6,897,232 | B2 | 5/2005 | Schindler et al. | |
| 7,919,626 | B2 * | 4/2011 | Zhou et al. | 546/184 |
| 2003/0105336 | A1 | 6/2003 | Schindler et al. | |
| 2005/0176799 | A1 | 8/2005 | Schindler et al. | |
| 2006/0041006 | A1 | 2/2006 | Ibrahim et al. | |
| 2011/0160248 | A1 * | 6/2011 | Zhou et al. | 514/326 |

FOREIGN PATENT DOCUMENTS

| CA | 2521199 A1 | 10/2004 |
|---|---|---|
| EP | 1024138 A1 | 8/2000 |
| JP | 11-240832 | 9/1999 |
| WO | 0125200 A1 | 4/2001 |
| WO | 2004013130 | 2/2004 |
| WO | 2004060882 | 7/2004 |
| WO | 2004076418 A1 | 9/2004 |
| WO | 2004103278 A2 | 12/2004 |
| WO | 2006046916 | 5/2006 |
| WO | 2007002559 | 1/2007 |
| WO | 2007030574 | 3/2007 |

OTHER PUBLICATIONS

Thomas et al., Expert Opinion on Drug Discovery 4(2):195-205 (2009).
Patent Abstracts of Japan for JP 11-240832 Yamanouchi Pharmaceutical Co. Ltd. pp. 1-2 (Sep. 7, 1999).
Australian Office Action for Patent Appl. No. 2007221020 "Patent Examination Report No. 2" pp. 1-3, Nov. 16, 2012.

* cited by examiner

*Primary Examiner* — Noble Jarrell
(74) *Attorney, Agent, or Firm* — Don J. Pelto, Esquire; Sheppard, Mullin, Richter & Hampton LLP

(57) ABSTRACT

The invention provides a compound of formula I:

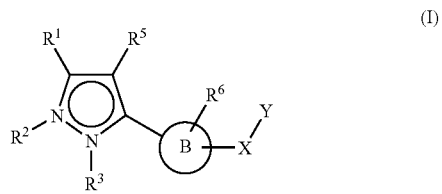

(I)

wherein $R^1$-$R^6$, X, Y, and B have any of the values described herein, as well as salts of such compounds, compositions comprising such compounds, and therapeutic methods that comprise the administration of such compounds. The compounds are inhibitors of MAO-B enzyme function and are useful for improving cognitive function and for treating psychiatric disorders in animals.

4 Claims, 1 Drawing Sheet

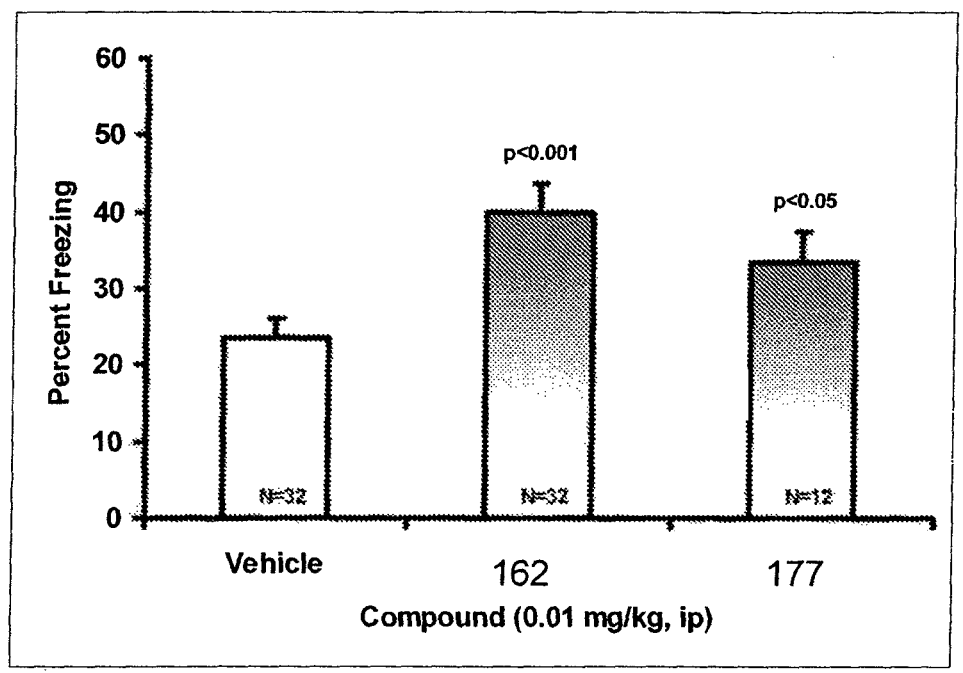

THERAPEUTIC COMPOUNDS

CROSS-REFERENCE TO RELATED APPLICATIONS

This is a continuation application under 37 C.F.R. §1.53(b) of U.S. patent application Ser. No. 11/679,775, filed on Feb. 27, 2007, now U.S. Pat. No. 7,919,626, which claims priority under 35 U.S.C. §119(e) to U.S. Provisional Patent Application Nos. 60/777,332 and 60/890,455, filed on Feb. 28, 2006 and Feb. 16, 2007 respectively, each of which are hereby expressly incorporated by reference in their entireties.

BACKGROUND OF THE INVENTION

Monoamine oxidase (MAO, EC 1.4.3.4) is a flavin dependent metabolic enzyme responsible for the oxidative deamination of both endogenous, aminergic neurotransmitters and xenobiotic amines. There are two reported isoforms of MAO, MAO-A and MAO-B, which arise from two independent genes (Bach, et. al., *Proc. Natl. Acad. Sci.,* 1988, 85, 4934-4938). Both forms of MAO are distributed in a variety of tissues in varying amounts throughout the body; in the human brain, MAO-B is present to a greater extent then MAO-A (Saura, et. al., *Neuroscience,* 1996, 70, 755-774).

MAO-A has greater selectivity for serotonin and adrenalin while MAO-B is selective for tyramine and phenethyl amine while both isoforms will metabolize dopamine. Studies have shown that the level of MAO-B activity in the brain increases with age (Fowler, et. al., *J. Neural Transm.,* 1980, 49, 1-20). The process of oxidative deamination, which produces both peroxide and aldehydes as byproducts, has also been associated with an increase in oxidative damage in the brain, especially to dopaminergic neurons, potentially exacerbating the neuronal degeneration associated with diseases such as Alzheimer's Disease and Parkinson's Disease. There are also reports that the level of MAO-B activity present is greater in patients with Alzheimer's disease which may be linked to the increased cognitive impairment of Alzheimer patients (Dostert, et. al, *Biochem. Pharmacol.,* 1989, 38, 555-561; and Emilsson, et al., *Neuroscience Letters,* 2002, 326, 56-60). This link between oxidative stress and progression of neuronal damage suggests that inhibition of MAO-B will minimize the degenerative effects of both of these diseases, presumably by preventing the metabolism of monoamines in the brain. Furthermore, the relative increase in dopamine levels, due to inhibition of its metabolism, may have effects on downstream regulation of plasticity-associated cognitive function, which may help repair, not just impede the progression of these diseases.

The use of selective MAO-B inhibitors for neurological diseases has been known for some time (Bentue-Ferrer, *CNS Drugs,* 1996, 6, 217-236). Most early MAO inhibitors for the treatment of depression were irreversible inhibitors with minimal selectivity for MAO-B versus MAO-A. This can be problematic due to potential side effects associated with both the subsequent inability of the irreversibly inhibited enzyme to effectively metabolize dietary amines associated with cardiovascular events (the "cheese effect") and the potential for drug-drug interactions with other drugs that are metabolized by MAO-B. More recent drugs, including selegiline and rasagiline, while still irreversible inhibitors, have greater selectivity for MAO-B, and have better side-effect profiles (Chen & Swope, *J Clin Pharmacol.* 2005 45, 878-94). There is currently a need for compounds that are useful for enhancing cognitive function and for treating cognitive deterioration in Parkinson's Disease and Alzheimer's Disease, as well as compounds that can generally improve cognition in normal, diseased, and aging subjects. Preferably, such agents will have higher potency and/or fewer side-effects than current therapies.

SUMMARY OF THE INVENTION

The invention provides MAO-B inhibiting compounds that are useful, for example, for enhancing cognitive function in animals (e.g. humans). Accordingly, the invention provides a method for inhibiting one or more MAO enzymes in an animal comprising administering to the animal an effective MAO inhibiting amount of a compound of formula I.

Enumerated Embodiments

The invention provides the following enumerated embodiments:

1. A method for inhibiting one or more MAO enzymes in an animal comprising administering to the animal an effective MAO inhibiting amount of a compound, or a pharmaceutically acceptable salt thereof, of formula I:

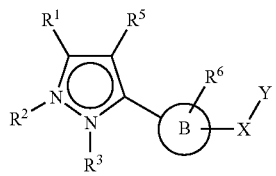

(I)

wherein:

$R^1$ is $(C_1-C_6)$alkyl, $(C_1-C_6)$haloalkyl, or aryl, unsubstituted or substituted with one or more $R_e$;

one of $R^2$ and $R^3$ is absent and the other is hydrogen, $(C_1-C_6)$alkyl, halo$(C_1-C_6)$alkyl, hydroxy$(C_1-C_6)$alkyl, $(C_3-C_8)$cycloalkyl, amino$(C_2-C_6)$alkyl, or aryl, each unsubstituted or substituted with one or more groups selected from alkyl, halo, haloalkyl or nitro, Het, $(C_3-C_8)$cycloalkyl$(C_1-C_6)$alkyl, aryl$(C_1-C_6)$alkyl, $(C_1-C_6)$ or Het$(C_1-C_6)$alkyl;

B is aryl or heteroaryl;

X is —C(=O), —C(=S), —C($R^4$)$_2$, —C(OH)—, or —S(O)$_z$;

each z is independently 0, 1, or 2;

Y is $R^4$, —N($R^4$)$_2$, —S$R^4$, or —C($R^4$)$_3$;

each $R^4$ is independently selected from the group consisting of hydrogen, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkoxycarbonyl, $(C_3-C_8)$cycloalkyl, $(C_3-C_8)$cycloalkyl$(C_1-C_6)$alkyl, $(C_1-C_6)$alkoxy$(C_2-C_6)$alkyl, hydroxy$(C_2-C_6)$alkyl, cyano$(C_1-C_6)$alkyl, $(C_1-C_6)$alkthio$(C_2-C_6)$alkyl, aryl, aryl$(C_1-C_6)$alkyl, aryloxy$(C_2-C_6)$alkyl, halo$(C_2-C_6)$alkyl, $(C_1-C_6)$alkoxycarbonyl$(C_1-C_6)$alkyl, $NR_aR_b$, Het, or Het$(C_1-C_6)$alkyl, unsubstituted or substituted with one or more $R_d$; or two $R^4$ groups are taken together with the atom to which they are attached to form aryl, Het, or a saturated or unsaturated 3-8 membered monocyclic or 8-12 membered bicyclic ring system comprising carbon atoms and optionally comprising one or more additional heteroatoms selected from O, S(O)$_z$, and $NR_c$, wherein each ring system is optionally substituted with one or more $R_d$;

each $R_a$ and $R_b$ is independently hydrogen or $(C_1-C_6)$alkyl;

each $R_c$ is independently hydrogen, aryl, S(O)$_2$, $(C_1-C_6)$alkanoyl, hydroxy$(C_1-C_6)$alkyl, alkoxy$(C_1-C_6)$alkyl, Het, ($C_1$-$C_6$)alkoxycabonyl or ($C_1$-$C_6$)alkyl, unsubstituted or substituted with one or more substituents $R_e$;

each $R_d$ is independently halo, hydroxy, cyano, nitro, azido, amino, ($C_1$-$C_6$)alkylamino, amino($C_1$-$C_6$)alkyl, amido, ($C_1$-$C_6$)alkyamido, aryl amido, carboxylic acid, ($C_1$-$C_6$)alkyl, hydroxy($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkanoyl, ($C_1$-$C_6$)alkoxycarbonyl, carboxy, ($C_1$-$C_6$)alkanoyloxy, Het, aryl, Het($C_1$-$C_6$)alkyl, or aryl($C_1$-$C_6$)alkyl, ($C_1$-$C_6$)alkylaryl, sulfonyl, sulfonamido, urea, carbamate, unsubstituted or substituted with one or more substituents $R_e$, or two $R_d$ come together with the atom to which they are attached to form a ketone or spirocyclic carbocyclic or heterocyclic ring, or two $R_d$ come together with the atoms to which they are attached to form a bicyclic carbocyclic or heterocyclic ring, wherein each spirocyclic or bicyclic ring is unsubstituted or substituted with one or more halo, hydroxy, cyano, nitro, azido, ($C_1$-$C_6$)alkyl, hydroxy($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkanoyl, ($C_1$-$C_6$)alkoxycarbonyl, carboxy, ($C_1$-$C_6$)alkanoyloxy, $NR_fR_g$, $R_fR_gNC(=O)$—, phenyl, or phenyl($C_1$-$C_6$)alkyl, sulfonyl, sulfonamido, urea, carbamate, wherein $R_f$ and $R_g$ together with the nitrogen to which they are attached form a piperidino, pyrrolidino, morpholino, or thiomorpholino ring, unsubstituted or substituted with one or more substituents $R_e$;

each $R_e$ is independently selected from halo, hydroxy, cyano, nitro, azido, ($C_1$-$C_6$)alkyl, Het, aryl, ($C_1$-$C_6$)alkylHet, ($C_1$-$C_6$)alkylaryl, ($C_1$-$C_6$)alkylHet($C_1$-$C_6$)alkyl, ($C_1$-$C_6$)alkyl aryl($C_1$-$C_6$)alkyl, ($C_1$-$C_6$)haloalkyl, ($C_1$-$C_6$)alkoxy, ($C_1$-$C_6$)haloalkoxy, ($C_1$-$C_6$)alkanoyl, ($C_1$-$C_6$)alkoxycarbonyl, carboxy, and ($C_1$-$C_6$)alkanoyloxy;

$R^5$ is H, ($C_1$-$C_6$)alkyl, ($C_1$-$C_6$)alkenyl, ($C_1$-$C_6$)alkynyl, aryl($C_1$-$C_6$)alkyl; and each $R^6$ is H, ($C_1$-$C_6$)alkyl, amino, amido, keto, or aryl($C_1$-$C_6$)alkyl; with the proviso that when X is —C(=O), Y is not H.

2. The method of embodiment 1 wherein B is 6-12 membered monocyclic or bicyclic heteroaryl.

3. The method of either of the previous embodiments wherein B is heteroaryl with more than one heteroatom.

4. The method of any of the previous embodiments wherein B is aryl.

5. A method for improving cognitive function in an animal in need of such treatment comprising administering to the animal an effective amount of the compound of formula I, or a pharmaceutically acceptable salt thereof, of any of the previous embodiments.

6. The method of any of the previous embodiments wherein the animal is a healthy animal.

7. The method of any of the previous embodiments wherein the animal is an aged animal.

8. A method for activating the CREB pathway in an animal in need of such treatment comprising administering to the animal an effective CREB pathway activating amount of the compound of formula I, or a pharmaceutically acceptable salt thereof, of any of the previous embodiments.

9. A method for treating age-associated memory impairment, cognitive impairment, Alzheimer's disease or Parkinson's disease in an animal in need of such treatment comprising administering to the animal an effective amount of the compound of formula I, or a pharmaceutically acceptable salt thereof, of any of the previous embodiments.

10. The method of any of the previous embodiments, wherein the animal has a psychiatric disorder.

11. The method of any of the previous embodiments, wherein the animal has a psychotic disorder, a neurological disorder, or a neurotic disorder.

12. The method of any of the previous embodiments, wherein the animal has a disorder of the central nervous system.

13. The method of any of the previous embodiments, wherein the animal has head trauma, brain trauma or cerebrovascular disease.

14. The method of any of the previous embodiments, wherein the animal has attention deficit disorder.

15. The method of any of the previous embodiments, wherein the psychotic disorder is schizophrenia.

16. The method of any of the previous embodiments, wherein the animal has an affective disorder.

17. The method of any of the previous embodiments, wherein the cerebrovascular disease is vascular dementia.

18. The method of any of the previous embodiments, wherein the cognitive impairment is associated with depression.

19. A method for treating a psychiatric disorder in an animal comprising administering to an animal in need thereof an effective amount of the compound of formula I, or a pharmaceutically acceptable salt thereof, of any of the previous embodiments.

20. The method of any of the previous embodiments, wherein the psychiatric disorder is a psychotic disorder, a neurological disorder, or a neurotic disorder.

21. The method of any of the previous embodiments, wherein the psychiatric disorder is a disorder of the central nervous system.

22. The method of any of the previous embodiments, wherein the disorder of the central nervous system is age-associated memory impairment, mild cognitive impairment, Alzheimer's disease or Parkinson's disease.

23. The method of any of the previous embodiments, wherein the psychiatric disorder is associated with head trauma, brain trauma or cerebrovascular disease.

24. The method of any of the previous embodiments, wherein the psychiatric disorder is attention deficit disorder.

25. The method of any of the previous embodiments, wherein the psychotic disorder is schizophrenia.

26. The method of any of the previous embodiments, wherein the psychiatric disorder is an affective disorder.

27. The method of any of the previous embodiments, wherein the cerebrovascular disease is vascular dementia.

28. The method of any of the previous embodiments, wherein the psychiatric disorder is depression.

29. The method of any of the previous embodiments wherein the animal is a healthy animal.

30. The method of any of the previous embodiments wherein the animal is an aged animal.

31. The method of any one of any of the previous embodiments wherein $R^1$ is ($C_1$-$C_6$)alkyl ($C_1$-$C_6$)haloalkyl, or phenyl that is optionally substituted with one or more substituents independently selected from halo, cyano, nitro, azido, ($C_1$-$C_6$)alkyl, ($C_1$-$C_6$)haloalkyl, ($C_1$-$C_6$)alkoxy, ($C_1$-$C_6$)haloalkoxy, ($C_1$-$C_6$)alkanoyl, ($C_1$-$C_6$)alkoxycarbonyl, carboxy, and ($C_1$-$C_6$)alkanoyloxy.

32. The method of any one of any of the previous embodiments wherein $R^1$ is trifluoromethyl, phenyl, methyl, or isopropyl.

33. The method of any one of any of the previous embodiments wherein $R^2$ is absent.

34. The method of any one of any of the previous embodiments wherein $R^3$ is absent.

35. The method of any one of any of the previous embodiments wherein $R^2$ is ($C_1$-$C_6$)alkyl, ($C_3$-$C_8$)cycloalkyl, aryl, Het, or Het($C_1$-$C_6$)alkyl.

36. The method of any one of any of the previous embodiments wherein $R^2$ is hydrogen, methyl, ethyl, propyl, isopropyl, phenyl, cyclopentyl, 2-pyridyl, 2-morpholinoethyl, 2,2,2-trifluoroethyl, or 2-hydroxyethyl.

37. The method of any one of any of the previous embodiments wherein $R^3$ is hydrogen, $(C_1-C_6)$alkyl, halo$(C_1-C_6)$alkyl, hydroxy$(C_1-C_6)$alkyl, $(C_3-C_8)$cycloalkyl, aryl, Het, aryl$(C_1-C_6)$alkyl, or Het$(C_1-C_6)$alkyl.

38. The method of any one of any of the previous embodiments wherein $R^3$ is hydrogen, methyl, ethyl, propyl, isopropyl, 2-pyridyl, cyclopentyl, phenyl, 4-trifluoromethylphenyl, 3-trifluoromethylphenyl, 2-trifluoromethylphenyl, 2,2,2-trifluoroethyl, 2-hydroxyethyl, 4-chlorophenyl, benzyl, 4-nitrophenyl, 2-morpholinoethyl, or cyclohexyl.

39. The method of any one of any of the previous embodiments wherein B is a benzene, thiophene, or pyridine ring.

40. The method of any one of any of the previous embodiments wherein B is a thiophene ring.

41. The method of any one of any of the previous embodiments wherein X is —C(=O).

42. The method of any one of any of the previous embodiments wherein each $R^4$ is independently H, $(C_1-C_6)$alkyl, $(C_2-C_6)$alkenyl, $(C_2-C_6)$alkynyl $(C_1-C_6)$alkoxy, $(C_1-C_6)$alkanoyl, $(C_1-C_6)$alkoxycarbonyl, $(C_3-C_8)$cycloalkyl, $(C_3-C_8)$cycloalkyl$(C_1-C_6)$alkyl, $(C_1-C_6)$alkoxy$(C_2-C_6)$alkyl, hydroxy$(C_2-C_6)$alkyl, cyano$(C_1-C_6)$alkyl, $(C_1-C_6)$alkthio$(C_2-C_6)$alkyl, aryl, aryl$(C_1-C_6)$alkyl, aryloxy$(C_2-C_6)$alkyl, halo$(C_2-C_6)$alkyl, $(C_1-C_6)$alkoxycarbonyl$(C_1-C_6)$alkyl, $NR_bR_c$, Het, or Het$(C_1-C_6)$alkyl.

43. The method of any one of any of the previous embodiments wherein each $R^4$ is independently hydrogen, methyl, ethyl, butyl, propyl, isopropyl, 2-fluorophenethyl, 2-pyrrolidinoethyl, 2-furylmethyl, 4-methylbenzyl, cyclopropylmethyl, cyclohexylmethyl, 4-methoxybenzyl, 4-fluorobenzyl, 4-pyridylmethyl, 4-chlorobenzyl, cyclohexyl, benzyl, 4-methylphenyl, 3-pyrrolidin-1-ylpropyl, 3-chlorobenzyl, 3,5-dimethylbenzyl, 2-(ethylthio)ethyl, isobutyl, allyl, 2-hydroxyethyl, phenyl, 3-fluoro-6-methylbenzyl, 3-pyridylmethyl, 4-fluorophenethyl, 2-phenoxyethyl, 5-methyl-fur-2-ylmethyl, 2,2,2-trifluoroethyl, 2-methoxyethyl, 2-methylbutyl, 2-imidazol-4-ylethyl, phenethyl, 2-morpholinoethyl, 3-methylbutyl, 2-piperidinoethyl, 3-methoxypropyl, 3-chlorobenzyl, 2-furylmethyl, 3,5-difluorobenzyl, 2-(2-furyl)ethyl, 3-imidazol-1-ylpropyl, 2-cyanoethyl, 2-ethylbutyl, 2-pyrid-3-ylethyl, S-α-hydroxy-β-methylphenethyl, S-α-methylphenethyl, 4,4-dimethoxybutyl, 3-(2-oxopyrrolidin-1-yl)propyl, 2,2-dimethoxyethyl, 4-methylphenethyl, cyanomethyl, 3-ethoxypropyl, 3-(N,N-dimethylamino)propyl, 3-morpholinopropyl, 2-hydroxypropyl, 2-methylpropyl, ethoxycarbonylmethyl, 2-methylphenyl, 2-hydroxyphenyl, tetrahydrofuran-2-ylmethyl, R-tetrahydrofuran-2-ylmethyl, S-tetrahydrofuran-2-ylmethyl, 2-aminoethyl, 5-aminopentyl, 4-(4-chlorophenyl)piperazine, or N-piperidinyl.

44. The method of any one of any of the previous embodiments wherein each $R^4$ is independently hydrogen or $(C_1-C_6)$alkyl.

45. The method of any one of any of the previous embodiments wherein both $R^4$ are taken together with the atom to which they are attached to form a saturated or partially unsaturated 3-8 membered monocyclic or 8-12 membered bicyclic or spirocyclic ring system comprising carbon atoms and optionally comprising one or more additional heteroatoms selected from O, $S(O)_z$, and $NR_c$, which ring system is optionally substituted with one or more $R_d$;

Z is 0, 1, or 2;

each $R_e$ is independently hydrogen, aryl, amide, $S(O)_2$, $(C_1-C_6)$alkanoyl, hydroxy$(C_1-C_6)$alkyl, alkoxy$(C_1-C_6)$alkyl, Het, $(C_1-C_6)$alkoxycabonyl or $(C_1-C_6)$alkyl, unsubstituted or substituted with one or more subtituents $R_e$;

each $R_d$ is independently selected from halo, hydroxy, cyano, nitro, azido, $(C_1-C_6)$alkyl, $(C_1-C_6)$haloalkyl, $(C_1-C_6)$alkoxy, $(C_1-C_6)$haloalkoxy, $(C_1-C_6)$alkanoyl, $(C_1-C_6)$alkoxycarbonyl, carboxy, $NR_fR_g$, and $(C_1-C_6)$alkanoyloxy; and each $R_f$ and $R_g$ is independently hydrogen or $(C_1-C_6)$alkyl; or $R_f$ and $R_g$ together with the nitrogen to which they are attached form a piperidino, pyrrolidino, morpholino, or thiomorpholino ring.

46. The method of any one of any of the previous embodiments wherein both $R^4$ are taken together with the atom to which they are attached to form aziridine, morpholine, piperidine, 4-methylpiperidine, 2-hydroxymethylpyrrolidine, pyrrolidine, azetidine, 3-pyrroline, 4-(4-fluorophenyl)piperazine, 3,5-dimethylmorpholine, 4-(2-hydroxyethyl)piperazine, 3,5-dimethylpiperidine, indoline, R-3-hydroxypyrrolidine, 1,4-dioxa-8-aza-spiro[4.5]decane, 1,2,3,4-tetrahydroisoquinoline, 2,3,4,5,6,7-hexahydroazepine, 4-hydroxymethylpiperidine, 4-(N,N-dimethylamino)piperidine, 4-(1-pyrrolidinyl)piperidine, 4-phenylpiperidine, 4-hydroxy-4-phenylpiperidine, 4-(carboxamide)piperidine, 4-hydroxypiperidine, 4-phenylpiperazine, 4-acetylpiperazine, 3-carboxamidepiperidine, 2-carboxypiperidine, 4-trifluoromethylpiperidine, 3-trifluoromethylpiperidine, perhydroazocine, 3,6-dimethylpiperazine, 4-aminopiperidine, 4-hydroxy-4-trifluoromethylpiperidine, 4-methylhomopiperizine, thiomorpholine 1,1 dioxide, 4-(2'-pyridyl)piperazine, 4-(2'-methoxy)ethylpiperazine, 4-t-butoxycarbonylaminopiperidine, Perhydro-1,2-thiazine 1,1-dioxide, 3-aminopiperidine, Hexahydro-pyridazine, 4-Difluoromethylene-piperidine, 3-hydroxypiperidine, 4-ethylpiperazine, 4-fluoropiperidine, 4,4-difluoropiperidine, 3-fluoropiperidine, 3,3-difluoropiperidine, 4-isopropylpiperazine, 4-t-butoxycarbonylpiperazine, or 4-benzylpiperidine.

47. The method of any one of any of the previous embodiments wherein both $R^4$ are taken together with the atom to which they are attached to form a piperidine ring, which is optionally substituted with one or more halo, hydroxy, cyano, nitro, azido, $(C_1-C_6)$alkyl, hydroxy$(C_1-C_6)$alkyl, halo$(C_1-C_6)$alkyl, $(C_1-C_6)$alkoxy, halo$(C_1-C_6)$alkoxy, $(C_1-C_6)$alkanoyl, $(C_1-C_6)$alkoxycarbonyl, carboxy, $(C_1-C_6)$alkanoyloxy, $NR_fR_g$, $R_fR_gNC(=O)$—, phenyl, or phenyl$(C_1-C_6)$alkyl, wherein any phenyl is optionally substituted with one or more $R_d$; each $R_d$ is independently selected from halo, hydroxy, cyano, nitro, azido, $(C_1-C_6)$alkyl, $(C_1-C_6)$haloalkyl, $(C_1-C_6)$alkoxy, $(C_1-C_6)$haloalkoxy, $(C_1-C_6)$alkanoyl, $(C_1-C_6)$alkoxycarbonyl, carboxy, and $(C_1-C_6)$alkanoyloxy; and each $R_f$ and $R_g$ is independently hydrogen or $(C_1-C_6)$alkyl; or $R_f$ and $R_g$ together with the nitrogen to which they are attached form a piperidino, pyrrolidino, morpholino, or thiomorpholino ring.

48. The method of any one of any of the previous embodiments wherein both $R^4$ are taken together with the atom to which they are attached to form a piperidine ring.

49. The method of any one of any of the previous embodiments wherein the compound of formula I is a compound of formula II:

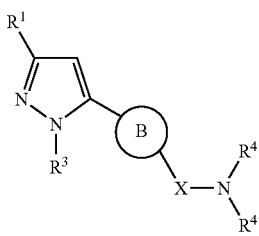

(II)

50. The method of any one of any of the previous embodiments wherein the compound of formula I is a compound of formula III:

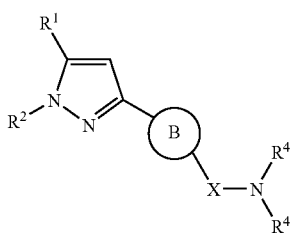

(III)

51. The method of any one of any of the previous embodiments wherein the compound of formula I is a compound of formula IIIa:

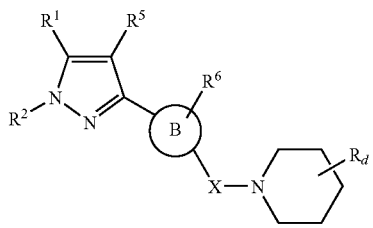

(IIIa)

52. The method of any one of any of the previous embodiments wherein the compound of formula I is a compound of formula IV:

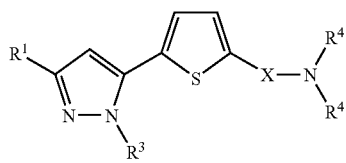

(IV)

53. The method of any one of any of the previous embodiments wherein the compound of formula I is a compound of formula IVa:

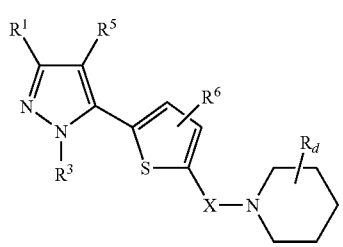

(IVa)

54. The method of any one of any of the previous embodiments wherein the compound of formula I is a compound of formula V:

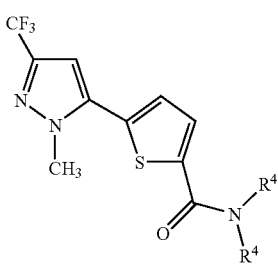

(V)

55. The method of any one of any of the previous embodiments wherein the compound of formula I is a compound of formula Va:

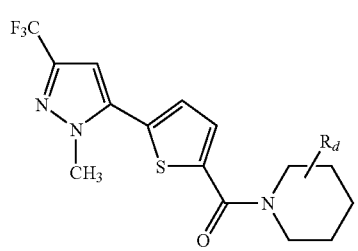

(Va)

56. The method of any one of any of the previous embodiments wherein the compound of formula I is a compound of formula Vb:

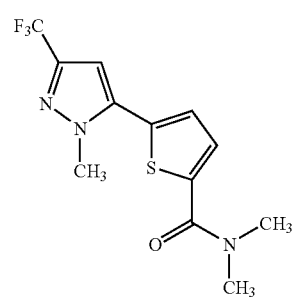

(Vb)

57. The method of any one of any of the previous embodiments wherein the compound of formula I is a compound of formula VI:

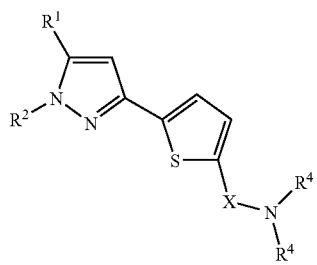

(VI)

58. The method of any one of any of the previous embodiments wherein the compound of formula I is a compound of formula VIa:

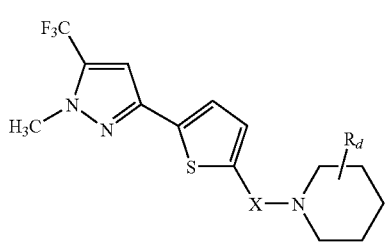

(VIa)

59. The method of any one of any of the previous embodiments wherein the compound of formula I is a compound of formula VIb:

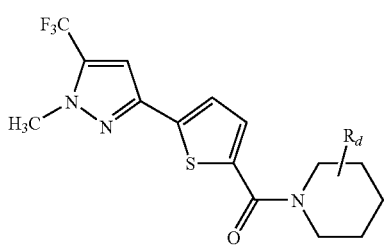

(VIb)

60. The method of any one of any of the previous embodiments wherein the compound of formula I is a compound of formula VII:

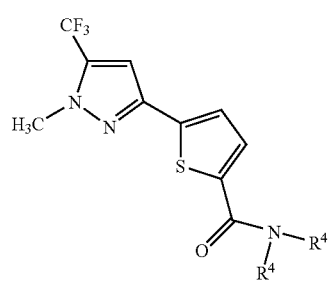

(VII)

61. The method of any one of any of the previous embodiments, wherein the compound of formula I is a compound of formula VIIa:

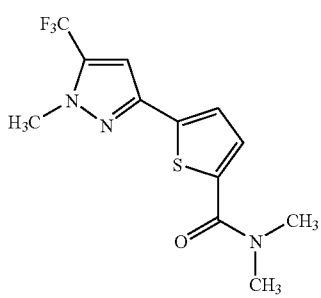

(VIIa)

62. The method of any one of any of the previous embodiments wherein the compound of formula I is a compound of formula VIIIa:

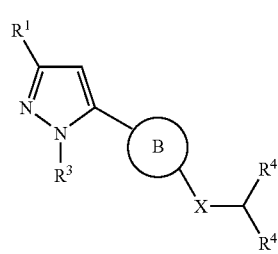

(VIIIa)

63. The method of any one of any of the previous embodiments wherein the compound of formula I is a compound of formula VIIIb:

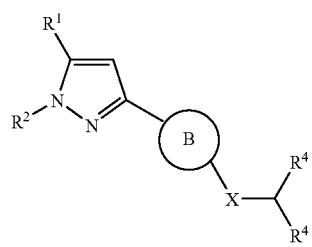

(VIIIb)

64. A compound of formula I:

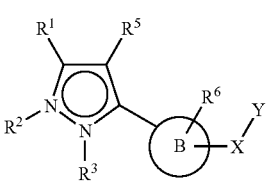

(I)

wherein:
$R^1$ is $(C_1-C_6)$alkyl, $(C_1-C_6)$haloalkyl, or aryl, unsubstituted or substituted with one or more $R_e$;
one of $R^2$ and $R^3$ is absent and the other is hydrogen, $(C_1-C_6)$alkyl, halo$(C_1-C_6)$alkyl, hydroxy$(C_1-C_6)$alkyl, $(C_3-C_8)$cycloalkyl, amino$(C_2-C_6)$alkyl, or aryl, each unsubstituted or substituted with one or more groups selected from alkyl, halo, haloalkyl or nitro, Het, $(C_3-C_8)$cycloalkyl$(C_1-C_6)$alkyl, aryl$(C_1-C_6)$alkyl, $(C_1-C_6)$ or Het$(C_1-C_6)$alkyl;

B is aryl or heteroaryl;

X is —C(=O), —C(=S), —C($R^4$)$_2$, or —S(O)$_z$;

each z is independently 0, 1, or 2;

Y is $R^4$, —N($R^4$)$_2$, —S$R^4$, or —C($R^4$)$_3$;

each $R^4$ is independently selected from the group consisting of hydrogen, ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkoxycarbonyl, ($C_3$-$C_8$)cycloalkyl, ($C_3$-$C_8$)cycloalkyl($C_1$-$C_6$)alkyl, ($C_1$-$C_6$)alkoxy($C_2$-$C_6$)alkyl, hydroxy($C_2$-$C_6$)alkyl, cyano($C_1$-$C_6$)alkyl, ($C_1$-$C_6$)alkthio($C_2$-$C_6$)alkyl, aryl, aryl($C_1$-$C_6$)alkyl, aryloxy($C_2$-$C_6$)alkyl, halo($C_2$-$C_6$)alkyl, ($C_1$-$C_6$)alkoxycarbonyl($C_1$-$C_6$)alkyl, $NR_aR_b$, Het, or Het($C_1$-$C_6$)alkyl, wherein each alkyl, aryl, or Het is unsubstituted or substituted with one or more $R_d$; or two $R^4$ groups are taken together with the atom to which they are attached to form aryl, Het, or a saturated or unsaturated 3-8 membered monocyclic or 8-12 membered bicyclic ring system comprising carbon atoms and optionally comprising one or more additional heteroatoms selected from O, S(O)$_z$, and $NR_C$, wherein each ring system is optionally substituted with one or more $R_d$;

each $R_a$ and $R_b$, is independently hydrogen or ($C_1$-$C_6$) alkyl;

each $R_c$ is independently hydrogen, aryl, S(O)$_2$, ($C_1$-$C_6$) alkanoyl, hydroxy($C_1$-$C_6$)alkyl, alkoxy($C_1$-$C_6$)alkyl, Het, ($C_1$-$C_6$)alkoxycabonyl or ($C_1$-$C_6$)alkyl, unsubstituted or substituted with one or more subtituents $R_e$;

each $R_d$ is independently halo, hydroxy, cyano, nitro, azido, amino, ($C_1$-$C_6$)alkylamino, amino($C_1$-$C_6$)alkyl, amido, ($C_1$-$C_6$)alkyamido, aryl amido, carboxylic acid, ($C_1$-$C_6$)alkyl, hydroxy($C_1$-$C_6$)alkyl, halo($C_1$-$C_6$)alkyl, ($C_1$-$C_6$) alkoxy, halo($C_1$-$C_6$)alkoxy, ($C_1$-$C_6$)alkanoyl, ($C_1$-$C_6$) alkoxycarbonyl, carboxy, ($C_1$-$C_6$)alkanoyloxy, Het, aryl, Het ($C_1$-$C_6$)alkyl, or aryl($C_1$-$C_6$)alkyl, ($C_1$-$C_6$)alkylaryl, sulfonyl, sulfonamido, urea, carbamate, unsubstituted or substituted with one or more substituents $R_e$, or two $R_d$ come together with the atom to which they are attached to form a ketone or spirocyclic carbocyclic or heterocyclic ring, or two $R_d$ come together with the atoms to which they are attached to form a bicyclic carbocyclic or heterocyclic ring, wherein each spirocyclic or bicyclic ring is unsubstituted or substituted with one or more halo, hydroxy, cyano, nitro, azido, ($C_1$-$C_6$) alkyl, hydroxy($C_1$-$C_6$)alkyl, halo($C_1$-$C_6$)alkyl, ($C_1$-$C_6$) alkoxy, halo($C_1$-$C_6$)alkoxy, ($C_1$-$C_6$)alkanoyl, ($C_1$-$C_6$) alkoxycarbonyl, carboxy, ($C_1$-$C_6$)alkanoyloxy, $NR_fR_g$, $R_fR_gNC(=O)$—, phenyl, or phenyl($C_1$-$C_6$)alkyl, sulfonyl, sulfonamido, urea, carbamate, wherein $R_f$ and $R_g$ together with the nitrogen to which they are attached form a piperidino, pyrrolidino, morpholino, or thiomorpholino ring, unsubstituted or substituted with one or more substituents $R_e$;

each $R_e$ is independently selected from halo, hydroxy, cyano, nitro, azido, ($C_1$-$C_6$)alkyl, Het, aryl, ($C_1$-$C_6$)alkylHet, ($C_1$-$C_6$)alkylaryl, ($C_1$-$C_6$)alkylHet($C_1$-$C_6$)alkyl, ($C_1$-$C_6$) alkylaryl($C_1$-$C_6$)alkyl, ($C_1$-$C_6$)haloalkyl, ($C_1$-$C_6$)alkoxy, ($C_1$-$C_6$)haloalkoxy, ($C_1$-$C_6$)alkanoyl, ($C_1$-$C_6$)alkoxycarbonyl, carboxy, and ($C_1$-$C_6$)alkanoyloxy;

$R^5$ is H, ($C_1$-$C_6$)alkyl, ($C_1$-$C_6$)alkenyl, ($C_1$-$C_6$)alkynyl, aryl($C_1$-$C_6$)alkyl; and each $R^6$ is H, ($C_1$-$C_6$)alkyl, amino, amido, keto, or aryl($C_1$-$C_6$)alkyl; with the proviso that when B is thiophene, $R^1$ is trifluoromethyl, $R^2$ is methyl, $R^3$ and $R^6$ are absent, $R^5$ is H, X is C(=O) and Y is N($R^4$)$_2$, both $R^4$ are not methyl.

65. The compound of any of the previous embodiments that is selected from the group consisting of

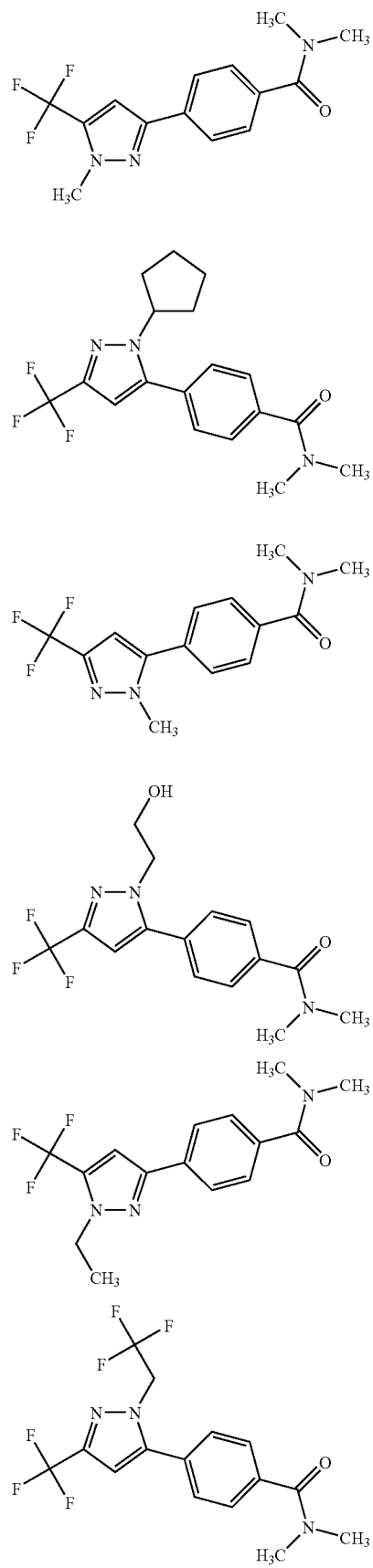

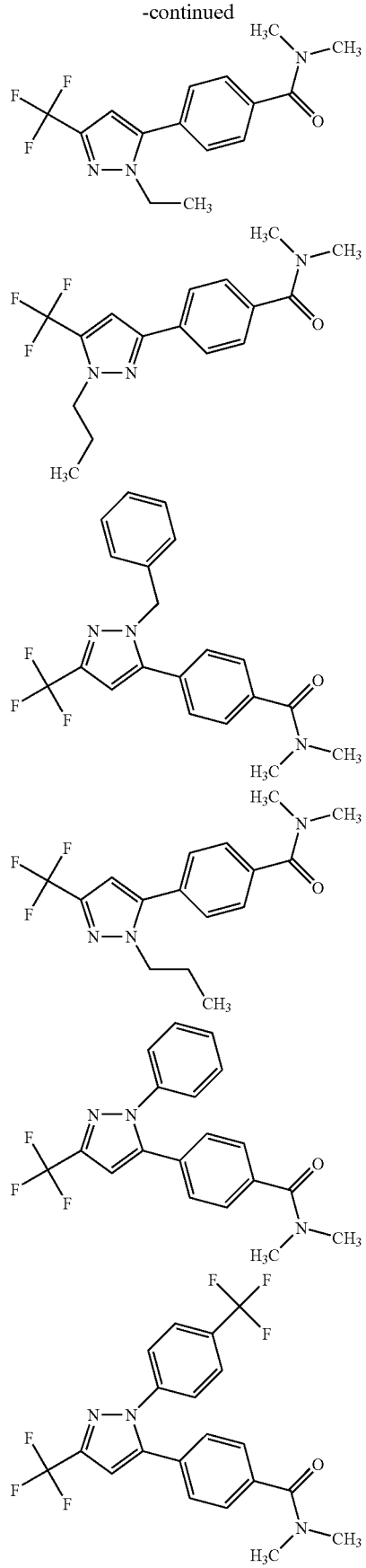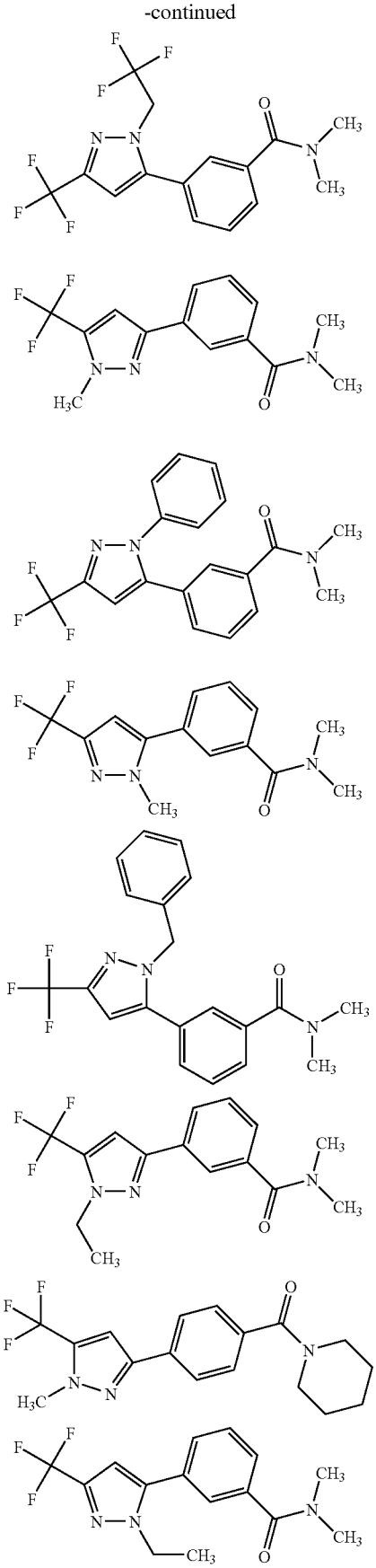

-continued

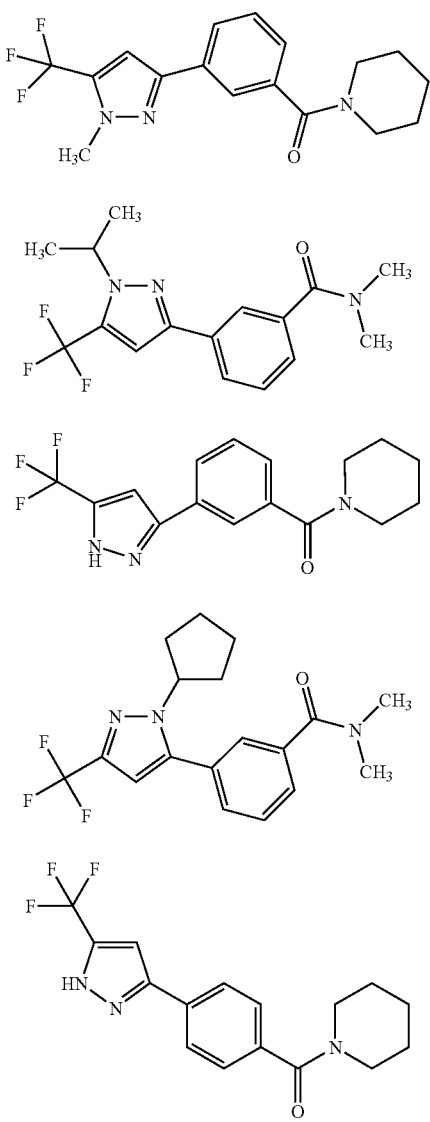

66. A compound of formula I:

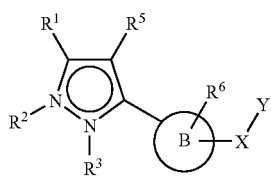

(I)

wherein:

R¹ is (C₁-C₆)alkyl, (C₁-C₆)haloalkyl, or aryl, unsubstituted or substituted with one or more R$_e$;

one of R² and R³ is absent and the other is hydrogen, (C₁-C₆)alkyl, halo(C₁-C₆)alkyl, hydroxy(C₁-C₆)alkyl, (C₃-C₈)cycloalkyl, amino(C₂-C₆)alkyl, or aryl, each unsubstituted or substituted with one or more groups selected from alkyl, halo, haloalkyl or nitro, Het, (C₃-C₈)cycloalkyl(C₁-C₆)alkyl, aryl(C₁-C₆)alkyl, (C₁-C₆) or Het(C₁-C₆)alkyl;

B is 6-12 membered monocyclic or bicyclic heteroaryl;

X is —C(=O), —C(=S), —C(R⁴)₂, or —S(O)$_z$;

each z is independently 0, 1, or 2;

Y is R⁴, —N(R⁴)₂, —SR⁴, or —C(R⁴)₃;

each R⁴ is independently selected from the group consisting of hydrogen, (C₁-C₆)alkyl, (C₂-C₆)alkenyl, (C₂-C₆)alkynyl, (C₁-C₆)alkoxy, (C₁-C₆)alkanoyl, (C₁-C₆)alkoxycarbonyl, (C₃-C₈)cycloalkyl, (C₃-C₈)cycloalkyl(C₁-C₆)alkyl, (C₁-C₆)alkoxy(C₂-C₆)alkyl, hydroxy(C₂-C₆)alkyl, cyano(C₁-C₆)alkyl, (C₁-C₆)alkthio(C₂-C₆)alkyl, aryl, aryl(C₁-C₆)alkyl, aryloxy(C₂-C₆)alkyl, halo(C₂-C₆)alkyl, (C₁-C₆)alkoxycarbonyl(C₁-C₆)alkyl, NR$_a$R$_b$, Het, or Het(C₁-C₆)alkyl, unsubstituted or substituted with one or more R$_d$; or two R⁴ groups are taken together with the atom to which they are attached to form aryl, Het, or a saturated or unsaturated 3-8 membered monocyclic or 8-12 membered bicyclic ring system comprising carbon atoms and optionally comprising one or more heteroatoms selected from O, S(O)$_z$, and NR$_C$, wherein each ring system is optionally substituted with one or more R$_d$;

each R$_a$ and R$_b$ is independently hydrogen or (C₁-C₆)alkyl;

each R$_c$ is independently hydrogen, aryl, S(O)₂, (C₁-C₆)alkanoyl, hydroxy(C₁-C₆)alkyl, alkoxy(C₁-C₆)alkyl, Het, (C₁-C₆)alkoxycabonyl or (C₁-C₆)alkyl, unsubstituted or substituted with one or more subtituents R$_e$;

each R$_d$ is independently halo, hydroxy, cyano, nitro, azido, amino, (C₁-C₆)alkylamino, amino(C₁-C₆)alkyl, amido, (C₁-C₆)alkyamido, aryl amido, carboxylic acid, (C₁-C₆)alkyl, hydroxy(C₁-C₆)alkyl, halo(C₁-C₆)alkyl, (C₁-C₆)alkoxy, halo(C₁-C₆)alkoxy, (C₁-C₆)alkanoyl, (C₁-C₆)alkoxycarbonyl, carboxy, (C₁-C₆)alkanoyloxy, Het, aryl, Het (C₁-C₆)alkyl, or aryl(C₁-C₆)alkyl, (C₁-C₆)alkylaryl, sulfonyl, sulfonamido, urea, carbamate, unsubstituted or substituted with one or more substituents R$_e$, or two R₄ come together with the atom to which they are attached to form a ketone or spirocyclic carbocyclic or heterocyclic ring, or two R$_d$ come together with the atoms to which they are attached to form a bicyclic carbocyclic or heterocyclic ring, wherein each spirocyclic or bicyclic ring is unsubstituted or substituted with one or more halo, hydroxy, cyano, nitro, azido, (C₁-C₆) alkyl, hydroxy(C₁-C₆)alkyl, halo(C₁-C₆)alkyl, (C₁-C₆) alkoxy, halo(C₁-C₆)alkoxy, (C₁-C₆)alkanoyl, (C₁-C₆) alkoxycarbonyl, carboxy, (C₁-C₆)alkanoyloxy, NR$_f$R$_g$, R$_f$R$_g$NC(=O)—, phenyl, or phenyl(C₁-C₆)alkyl, sulfonyl, sulfonamido, urea, carbamate, wherein R$_f$ and R$_g$ together with the nitrogen to which they are attached form a piperidino, pyrrolidino, morpholino, or thiomorpholino ring, unsubstituted or substituted with one or more substituents R$_e$;

each R$_e$ is independently selected from halo, hydroxy, cyano, nitro, azido, (C₁-C₆)alkyl, Het, aryl, (C₁-C₆)alkylHet, (C₁-C₆)alkylaryl, (C₁-C₆)alkylHet(C₁-C₆)alkyl, (C₁-C₆) alkylaryl(C₁-C₆)alkyl, (C₁-C₆)haloalkyl, (C₁-C₆)alkoxy, (C₁-C₆)haloalkoxy, (C₁-C₆)alkanoyl, (C₁-C₆)alkoxycarbonyl, carboxy, and (C₁-C₆)alkanoyloxy;

R⁵ is H, (C₁-C₆)alkyl, (C₁-C₆)alkenyl, (C₁-C₆)alkynyl, aryl(C₁-C₆)alkyl;

each R⁶ is H, (C₁-C₆)alkyl, amino, amido, keto, or aryl(C₁-C₆)alkyl;

or a pharmaceutically acceptable salt thereof.

67. The compound of any of the previous embodiments that is selected from the group consisting of

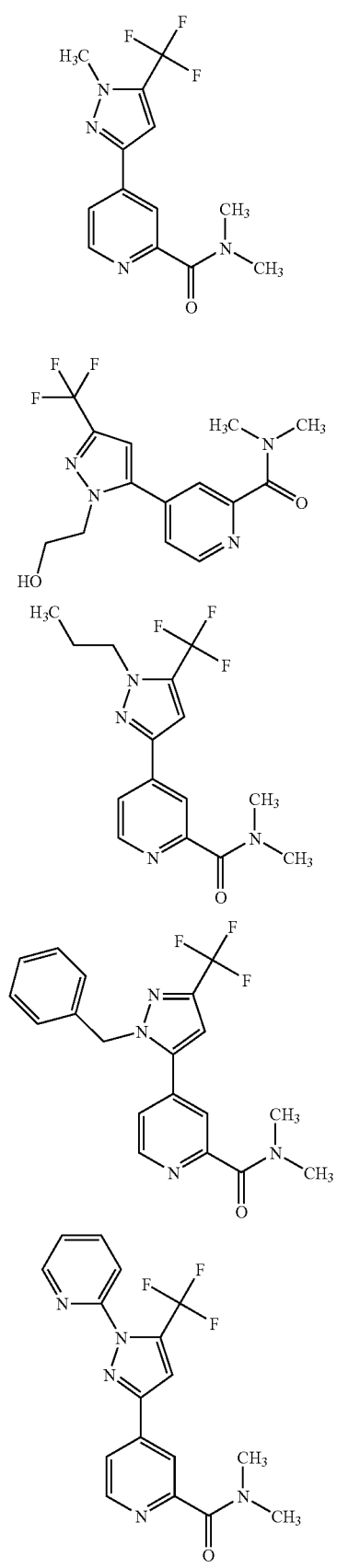
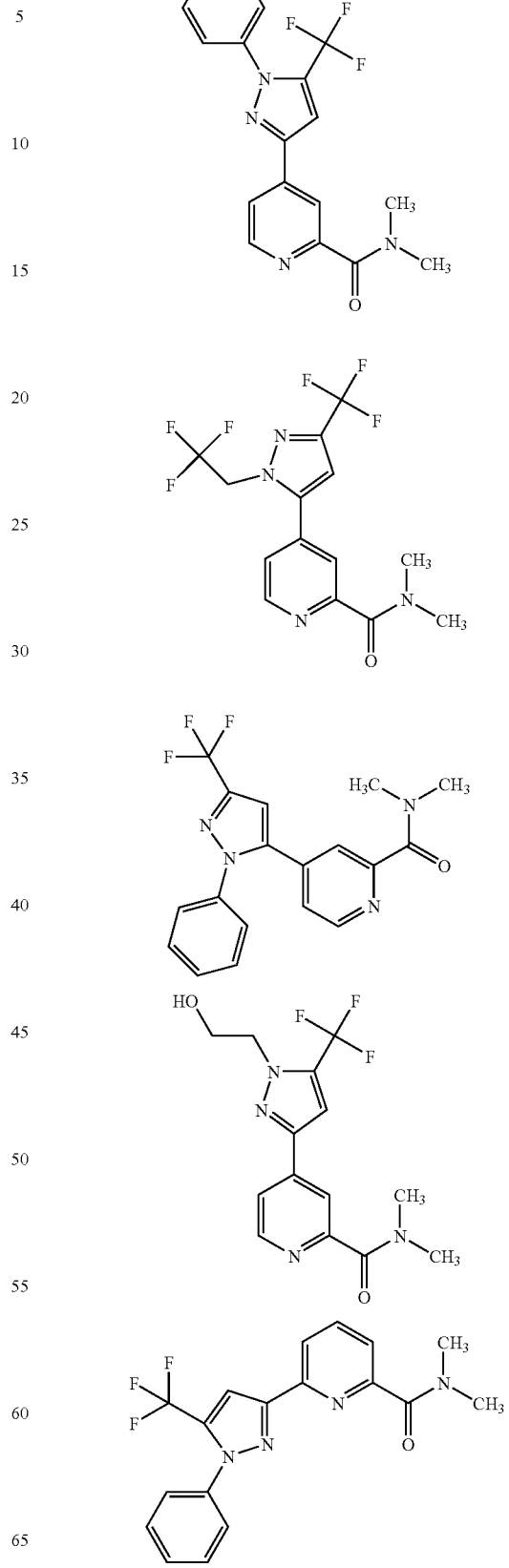

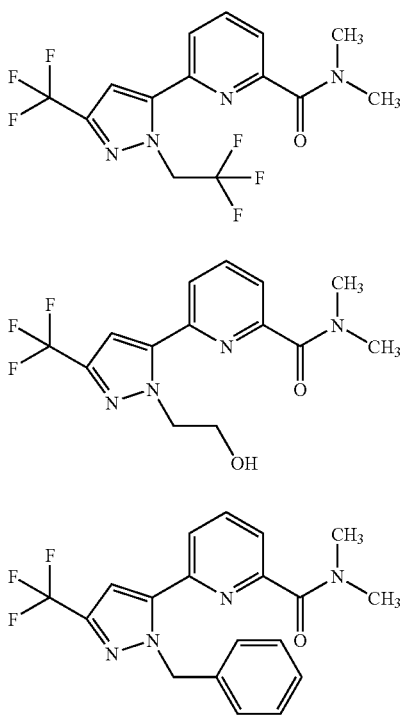

68. A compound of formula I:

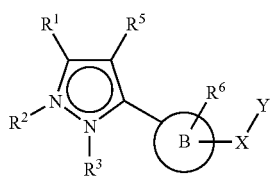

(I)

wherein:

R¹ is (C₁-C₆)alkyl, (C₁-C₆)haloalkyl, or aryl, unsubstituted or substituted with one or more R_e;

one of R² and R³ is absent and the other is hydrogen, (C₁-C₆)alkyl, halo(C₁-C₆)alkyl, hydroxy(C₁-C₆)alkyl, (C₃-C₈)cycloalkyl, amino(C₂-C₆)alkyl, or aryl, each unsubstituted or substituted with one or more groups selected from alkyl, halo, haloalkyl or nitro, Het, (C₃-C₈)cycloalkyl(C₁-C₆)alkyl, aryl(C₁-C₆)alkyl, (C₁-C₆) or Het(C₁-C₆)alkyl;

B is thiophene, furan, or pyrrole;

X is —C(═O), —C(═S), —C(R⁴)₂, or —S(O)_z;

each z is independently 0, 1, or 2;

Y is —N(R⁴)₂;

both R⁴ groups are taken together with the N to which they are attached to form a saturated or unsaturated 3-8 membered monocyclic or 8-12 membered bicyclic ring system comprising carbon atoms and optionally comprising one or more additional heteroatoms selected from O, S(O)_z, and NR_c, unsubstituted or substituted with one or more R_d, with the proviso that both R⁴ groups do not combine to form 2H-benzo[b][1,4]oxazine, wherein if the ring system is a monocyclic 5-7 membered ring system, it is substituted with one or more R_d other than halo or alkyl;

each R_c is independently hydrogen, aryl, S(O)₂, (C₁-C₆)alkanoyl, hydroxy(C₁-C₆)alkyl, alkoxy(C₁-C₆)alkyl, Het, (C₁-C₆)alkoxycabonyl or (C₁-C₆)alkyl, unsubstituted or substituted with one or more substituents R_e;

each R_d is independently halo, hydroxy, cyano, nitro, azido, amino, (C₁-C₆)alkylamino, amino(C₁-C₆)alkyl, amido, (C₁-C₆)alkyamido, aryl amido, carboxylic acid, (C₁-C₆)alkyl, hydroxy(C₁-C₆)alkyl, halo(C₁-C₆)alkyl, (C₁-C₆) alkoxy, halo(C₁-C₆)alkoxy, (C₁-C₆)alkanoyl, (C₁-C₆)alkoxycarbonyl, carboxy, (C₁-C₆)alkanoyloxy, Het, aryl, Het(C₁-C₆)alkyl, or aryl(C₁-C₆)alkyl, (C₁-C₆)alkylaryl, sulfonyl, sulfonamido, urea, carbamate, unsubstituted or substituted with one or more substituents R_e, or two R_d come together with the atom to which they are attached to form a ketone or spirocyclic carbocyclic or heterocyclic ring, or two R_d come together with the atoms to which they are attached to form a bicyclic carbocyclic or heterocyclic ring, wherein each spirocyclic or bicyclic ring is unsubstituted or substituted with one or more halo, hydroxy, cyano, nitro, azido, (C₁-C₆)alkyl, hydroxy(C₁-C₆)alkyl, halo(C₁-C₆)alkyl, (C₁-C₆)alkoxy, halo(C₁-C₆)alkoxy, (C₁-C₆)alkanoyl, (C₁-C₆)alkoxycarbonyl, carboxy, (C₁-C₆)alkanoyloxy, NR_fR_g, R_fR_gNC(═O)—, phenyl, or phenyl(C₁-C₆)alkyl, sulfonyl, sulfonamido, urea, carbamate, wherein R_f and R_g together with the nitrogen to which they are attached form a piperidino, pyrrolidino, morpholino, or thiomorpholino ring, unsubstituted or substituted with one or more substituents R_e;

each R_e is independently selected from halo, hydroxy, cyano, nitro, azido, (C₁-C₆)alkyl, Het, aryl, (C₁-C₆)alkylHet, (C₁-C₆)alkylaryl, (C₁-C₆)alkylHet(C₁-C₆)alkyl, (C₁-C₆)alkylaryl(C₁-C₆)alkyl, (C₁-C₆)haloalkyl, (C₁-C₆)alkoxy, (C₁-C₆)haloalkoxy, (C₁-C₆)alkanoyl, (C₁-C₆)alkoxycarbonyl, carboxy, and (C₁-C₆)alkanoyloxy;

R⁵ is H, (C₁-C₆)alkyl, (C₁-C₆)alkenyl, (C₁-C₆)alkynyl, aryl(C₁-C₆)alkyl;

each R⁶ is H, (C₁-C₆)alkyl, amino, amido, keto, or aryl(C₁-C₆)alkyl;

or a pharmaceutically acceptable salt thereof.

69. The compound of any of the previous embodiments that is selected from the group consisting of

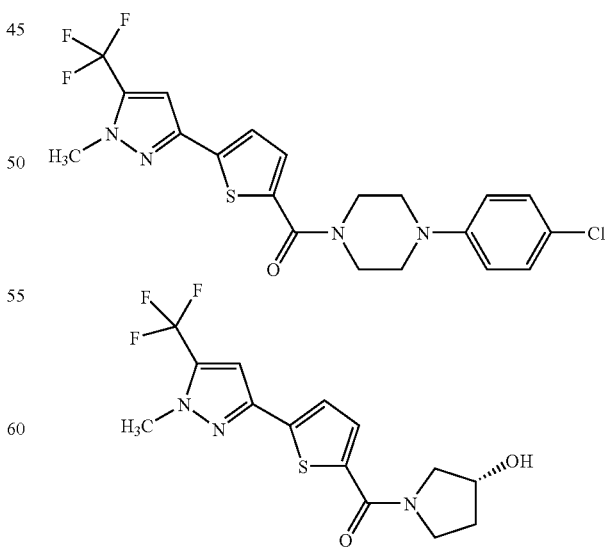

Chiral

-continued
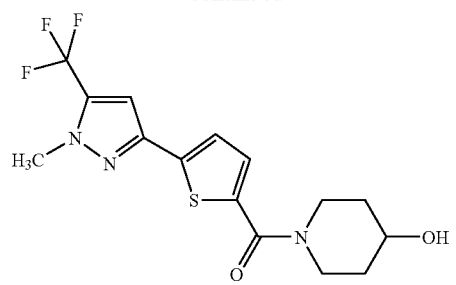
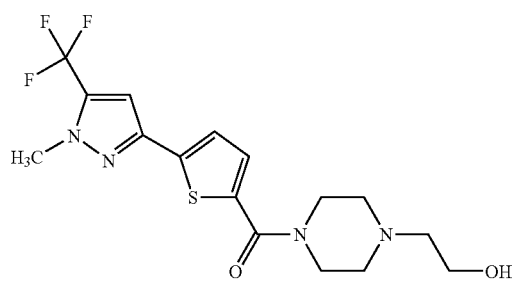
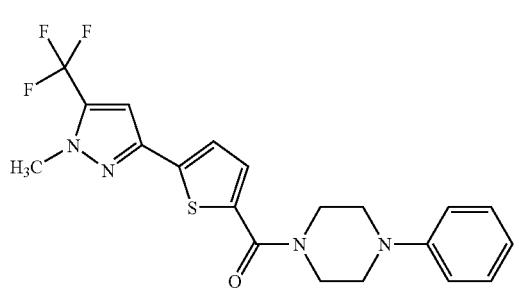
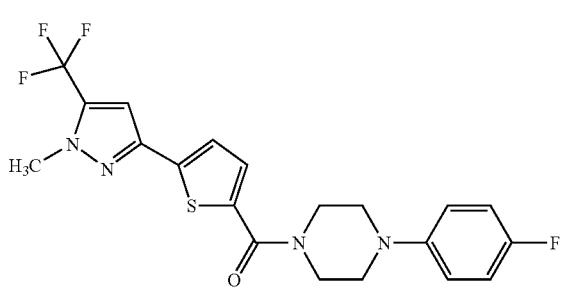
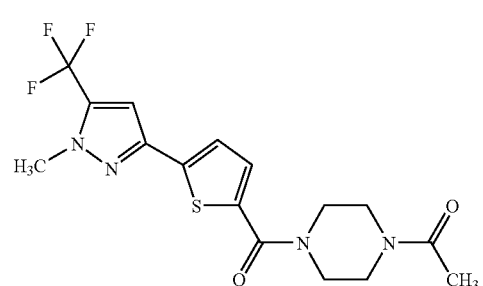
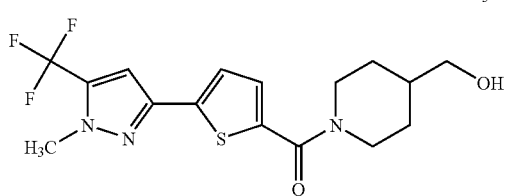
-continued
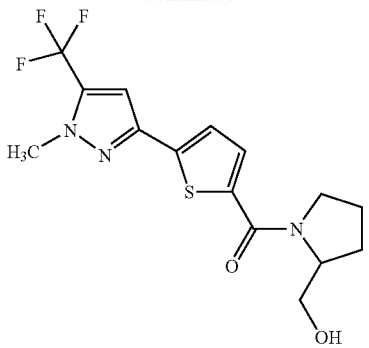
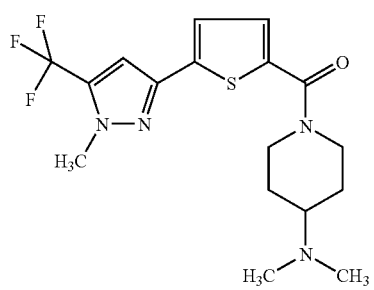
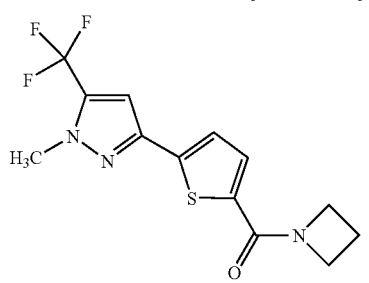
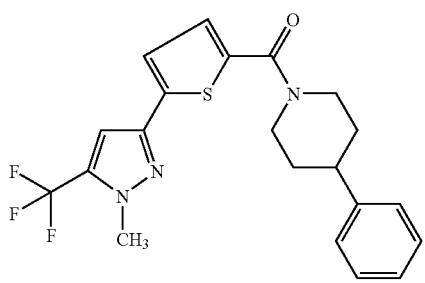
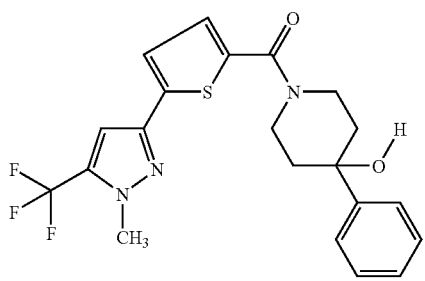
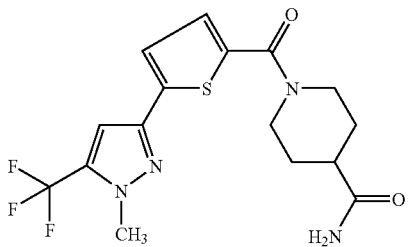

-continued

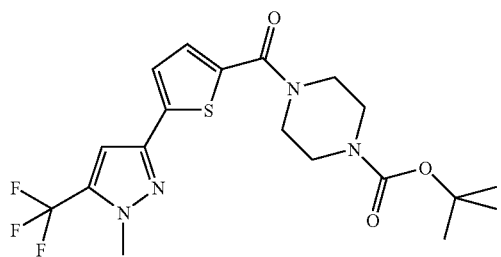

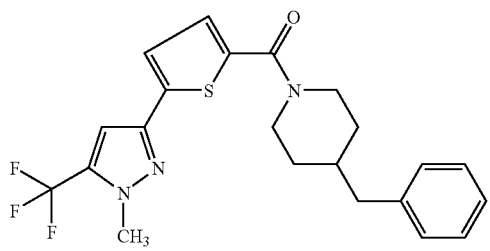

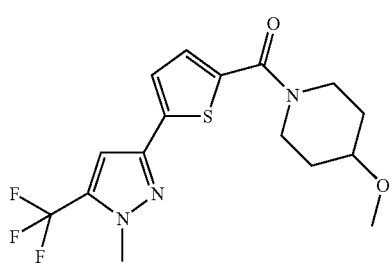

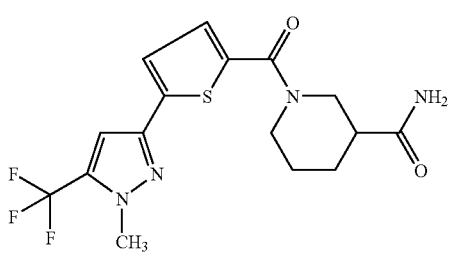

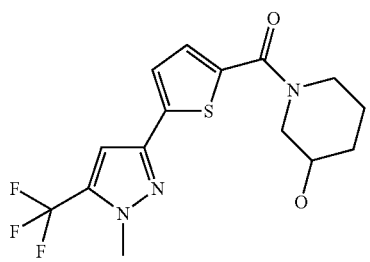

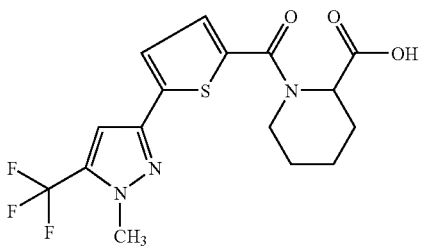

-continued

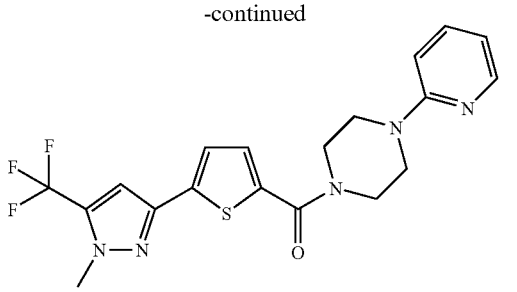

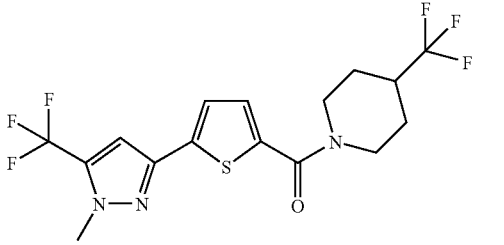

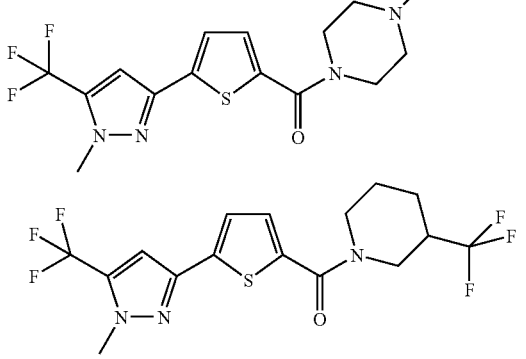

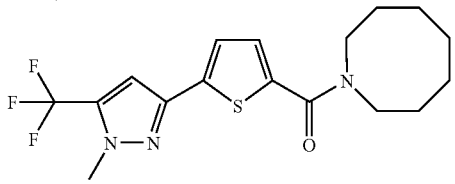

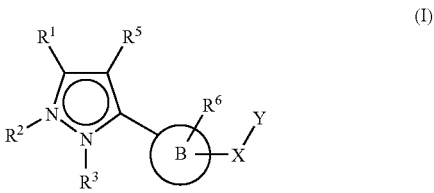

70. A compound of formula I:

(I)

$$\underset{R^3}{\overset{R^1}{\underset{R^2-N}{\bigvee}}} \underset{B}{\overset{R^5}{\bigvee}} \underset{X}{\overset{R^6}{\bigvee}} Y$$

wherein:
$R^1$ is $(C_1-C_6)$alkyl, $(C_1-C_6)$haloalkyl, or aryl, unsubstituted or substituted with one or more $R_e$;
one of $R^2$ and $R^3$ is absent and the other is hydrogen, $(C_1-C_6)$alkyl, halo$(C_1-C_6)$alkyl, hydroxy$(C_1-C_6)$alkyl, $(C_3-C_8)$cycloalkyl, amino$(C_2-C_6)$alkyl, or aryl, each unsubstituted or substituted with one or more groups selected from alkyl, halo, haloalkyl or nitro, Het, $(C_3-C_8)$cycloalkyl$(C_1-C_6)$alkyl, aryl$(C_1-C_6)$alkyl, $(C_1-C_6)$ or Het$(C_1-C_6)$alkyl;
B is thiophene, furan or pyrrole;
X is —C(=O), —C(=S), —C(R$^4$)$_2$, or —S(O)$_z$;
each z is independently 0, 1, or 2;

Y is R⁴, —N(R⁴)₂, —OR⁴, —SR⁴, —C(R⁴)₃;

each R⁴ is independently selected from the group consisting of hydrogen, (C₁-C₆)alkyl, (C₂-C₆)alkenyl, (C₂-C₆)alkynyl, amino, (C₁-C₆)alkoxy, (C₁-C₆)alkanoyl, (C₁-C₆)alkoxycarbonyl, (C₃-C₈)cycloalkyl, (C₃-C₈)cycloalkyl(C₁-C₆)alkyl, (C₁-C₆)alkoxy(C₂-C₆)alkyl, hydroxy(C₂-C₆)alkyl, cyano(C₁-C₆)alkyl, (C₁-C₆)alkthio(C₂-C₆)alkyl, aryl, aryl(C₁-C₆)alkyl, aryloxy(C₂-C₆)alkyl, halo(C₂-C₆)alkyl, (C₁-C₆)alkoxycarbonyl(C₁-C₆)alkyl, NR$_b$R$_c$, Het, or Het(C₁-C₆)alkyl, each unsubstituted or substituted with one or more R$_d$; with the proviso that at least one R⁴ is alkenyl, alkynyl, or amino;

each R$_b$ and R$_c$ is independently hydrogen or (C₁-C₆)alkyl;

each R$_d$ is independently halo, hydroxy, cyano, nitro, azido, amino, (C₁-C₆)alkylamino, amino(C₁-C₆)alkyl, amido, (C₁-C₆)alkyamido, aryl amido, carboxylic acid, (C₁-C₆)alkyl, hydroxy(C₁-C₆)alkyl, halo(C₁-C₆)alkyl, (C₁-C₆)alkoxy, halo(C₁-C₆)alkoxy, (C₁-C₆)alkanoyl, (C₁-C₆)alkoxycarbonyl, carboxy, (C₁-C₆)alkanoyloxy, Het, aryl, Het (C₁-C₆)alkyl, or aryl(C₁-C₆)alkyl, (C₁-C₆)alkylaryl, sulfonyl, sulfonamido, urea, carbamate, unsubstituted or substituted with one or more substituents R$_e$, or two R$_d$ come together with the atom to which they are attached to form a ketone or spirocyclic carbocyclic or heterocyclic ring, or two R$_d$ come together with the atoms to which they are attached to form a bicyclic carbocyclic or heterocyclic ring, wherein each spirocyclic or bicyclic ring is unsubstituted or substituted with one or more halo, hydroxy, cyano, nitro, azido, (C₁-C₆)alkyl, hydroxy(C₁-C₆)alkyl, halo(C₁-C₆)alkyl, (C₁-C₆)alkoxy, halo(C₁-C₆)alkoxy, (C₁-C₆)alkanoyl, (C₁-C₆)alkoxycarbonyl, carboxy, (C₁-C₆)alkanoyloxy, NR$_f$R$_g$, R$_f$R$_g$NC(=O)—, phenyl, or phenyl(C₁-C₆)alkyl, sulfonyl, sulfonamido, urea, carbamate, wherein R$_f$ and R$_g$ together with the nitrogen to which they are attached form a piperidino, pyrrolidino, morpholino, or thiomorpholino ring, unsubstituted or substituted with one or more substituents R$_e$;

each R$_e$ is independently selected from halo, hydroxy, cyano, nitro, azido, (C₁-C₆)alkyl, Het, aryl, (C₁-C₆)alkylHet, (C₁-C₆)alkylaryl, (C₁-C₆)alkylHet(C₁-C₆)alkyl, (C₁-C₆)alkylaryl(C₁-C₆)alkyl, (C₁-C₆)haloalkyl, (C₁-C₆)alkoxy, (C₁-C₆)haloalkoxy, (C₁-C₆)alkanoyl, (C₁-C₆)alkoxycarbonyl, carboxy, and (C₁-C₆)alkanoyloxy;

R⁵ is H, (C₁-C₆)alkyl, (C₁-C₆)alkenyl, (C₁-C₆)alkynyl, aryl(C₁-C₆)alkyl; and each R⁶ is H, (C₁-C₆)alkyl, amino, amido, keto, or aryl(C₁-C₆)alkyl;

or a pharmaceutically acceptable salt thereof.

71. A compound of formula I:

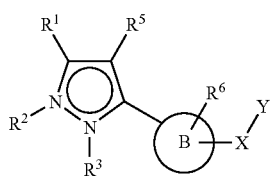

(I)

wherein:

R¹ is (C₁-C₆)alkyl, (C₁-C₆)haloalkyl, or aryl, unsubstituted or substituted with one or more R$_e$;

one of R² and R³ is absent and the other is hydrogen, (C₁-C₆)alkyl, halo(C₁-C₆)alkyl, hydroxy(C₁-C₆)alkyl, (C₃-C₈)cycloalkyl, amino(C₂-C₆)alkyl, or aryl, each unsubstituted or substituted with one or more groups selected from alkyl, halo, haloalkyl or nitro, Het, (C₃-C₈)cycloalkyl(C₁-C₆)alkyl, aryl(C₁-C₆)alkyl, (C₁-C₆) or Het(C₁-C₆)alkyl;

B is thiophene, furan, or pyrrole;

X is —C(=S) or —C(R⁴)₂;

Y is R⁴, —N(R⁴)₂, —SR⁴, or —C(R⁴)₃; wherein when X is —C(R⁴)₂, Y is —SR⁴;

each R⁴ is independently selected from the group consisting of hydrogen, (C₁-C₆)alkyl, (C₂-C₆)alkenyl, (C₂-C₆)alkynyl, (C₁-C₆)alkoxy, (C₁-C₆)alkanoyl, (C₁-C₆)alkoxycarbonyl, (C₃-C₈)cycloalkyl, (C₃-C₈)cycloalkyl(C₁-C₆)alkyl, (C₁-C₆)alkoxy(C₂-C₆)alkyl, hydroxy(C₂-C₆)alkyl, cyano(C₁-C₆)alkyl, (C₁-C₆)alkthio(C₂-C₆)alkyl, aryl, aryl(C₁-C₆)alkyl, aryloxy(C₂-C₆)alkyl, halo(C₂-C₆)alkyl, (C₁-C₆)alkoxycarbonyl(C₁-C₆)alkyl, NR$_a$R$_b$, Het, or Het(C₁-C₆)alkyl, unsubstituted or substituted with one or more R$_d$, or two R⁴ groups are taken together with the atom to which they are attached to form aryl, Het, or a saturated or unsaturated 3-8 membered monocyclic or 8-12 membered bicyclic ring system comprising carbon atoms and optionally comprising one or more heteroatoms selected from O, S(O)$_z$, and NR$_C$, wherein each ring system is optionally substituted with one or more R$_d$;

each z is independently 0, 1, or 2;

each R$_a$ and R$_b$ is independently hydrogen or (C₁-C₆)alkyl;

each R$_c$ is independently hydrogen, aryl, S(O)₂, (C₁-C₆)alkanoyl, hydroxy(C₁-C₆)alkyl, alkoxy(C₁-C₆)alkyl, Het, (C₁-C₆)alkoxycabonyl or (C₁-C₆)alkyl, unsubstituted or substituted with one or more subtituents R$_e$;

each R$_d$ is independently halo, hydroxy, cyano, nitro, azido, amino, (C₁-C₆)alkylamino, amino(C₁-C₆)alkyl, amido, (C₁-C₆)alkyamido, aryl amido, carboxylic acid, (C₁-C₆)alkyl, hydroxy(C₁-C₆)alkyl, halo(C₁-C₆)alkyl, (C₁-C₆)alkoxy, halo(C₁-C₆)alkoxy, (C₁-C₆)alkanoyl, (C₁-C₆)alkoxycarbonyl, carboxy, (C₁-C₆)alkanoyloxy, Het, aryl, Het (C₁-C₆)alkyl, or aryl(C₁-C₆)alkyl, (C₁-C₆)alkylaryl, sulfonyl, sulfonamido, urea, carbamate, unsubstituted or substituted with one or more substituents R$_e$, or two R$_d$ come together with the atom to which they are attached to form a ketone or spirocyclic carbocyclic or heterocyclic ring, or two R$_d$ come together with the atoms to which they are attached to form a bicyclic carbocyclic or heterocyclic ring, wherein each spirocyclic or bicyclic ring is unsubstituted or substituted with one or more halo, hydroxy, cyano, nitro, azido, (C₁-C₆)alkyl, hydroxy(C₁-C₆)alkyl, halo(C₁-C₆)alkyl, (C₁-C₆)alkoxy, halo(C₁-C₆)alkoxy, (C₁-C₆)alkanoyl, (C₁-C₆)alkoxycarbonyl, carboxy, (C₁-C₆)alkanoyloxy, NR$_f$R$_g$, R$_f$R$_g$NC(=O)—, phenyl, or phenyl(C₁-C₆)alkyl, sulfonyl, sulfonamido, urea, carbamate, wherein R$_f$ and R$_g$ together with the nitrogen to which they are attached form a piperidino, pyrrolidino, morpholino, or thiomorpholino ring, unsubstituted or substituted with one or more substituents R$_e$;

each R$_e$ is independently selected from halo, hydroxy, cyano, nitro, azido, (C₁-C₆)alkyl, Het, aryl, (C₁-C₆)alkylHet, (C₁-C₆)alkylaryl, (C₁-C₆)alkylHet(C₁-C₆)alkyl, (C₁-C₆)alkylaryl(C₁-C₆)alkyl, (C₁-C₆)haloalkyl, (C₁-C₆)alkoxy, (C₁-C₆)haloalkoxy, (C₁-C₆)alkanoyl, (C₁-C₆)alkoxycarbonyl, carboxy, and (C₁-C₆)alkanoyloxy;

R⁵ is H, (C₁-C₆)alkyl, (C₁-C₆)alkenyl, (C₁-C₆)alkynyl, aryl(C₁-C₆)alkyl;

each R⁶ is H, (C₁-C₆)alkyl, amino, amido, keto, or aryl(C₁-C₆)alkyl;

or a pharmaceutically acceptable salt thereof.

72. A compound, or a pharmaceutically acceptable salt thereof, of formula II

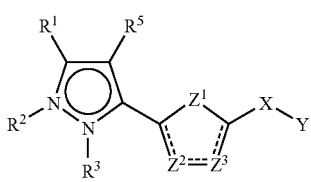

(II)

wherein:

$R^1$ is $(C_1-C_6)$alkyl, $(C_1-C_6)$haloalkyl, or aryl, unsubstituted or substituted with one or more $R_e$;

one of $R^2$ and $R^3$ is absent and the other is hydrogen, $(C_1-C_6)$alkyl, halo$(C_1-C_6)$alkyl, hydroxy$(C_1-C_6)$alkyl, $(C_3-C_8)$cycloalkyl, amino$(C_2-C_6)$alkyl, or aryl, each unsubstituted or substituted with one or more groups selected from alkyl, halo, haloalkyl or nitro, Het, $(C_3-C_8)$cycloalkyl$(C_1-C_6)$alkyl, aryl$(C_1-C_6)$alkyl, $(C_1-C_6)$ or Het$(C_1-C_6)$alkyl;

each of $Z^1$, $Z^2$, and $Z^3$ is independently $C(R^6)_p$, $N(R^6)_q$, O, or S, wherein if $Z^1$ is $N(R^6)_q$, O, or S, at least one of $Z^1$ or $Z^2$ must be $N(R^6)_q$, O, or S;

each p is independently 0, 1, or 2;

each q is independently 0 or 1;

X is —C(O), —C(=S), —C($R^4$)$_2$, or —S(O)$_z$;

each z is independently 0, 1, or 2;

Y is $R^4$, —N($R^4$)$_2$, —O$R^4$, —S$R^4$, or —C($R^4$)$_3$;

each $R^4$ is independently selected from the group consisting of hydrogen, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkoxycarbonyl, $(C_3-C_8)$cycloalkyl, $(C_3-C_8)$cycloalkyl$(C_1-C_6)$alkyl, $(C_1-C_6)$alkoxy$(C_2-C_6)$alkyl, hydroxy$(C_2-C_6)$alkyl, cyano$(C_1-C_6)$alkyl, $(C_1-C_6)$alkthio$(C_2-C_6)$alkyl, aryl, aryl$(C_1-C_6)$alkyl, aryloxy$(C_2-C_6)$alkyl, halo$(C_2-C_6)$alkyl, $(C_1-C_6)$alkoxycarbonyl$(C_1-C_6)$alkyl, $NR_aR_b$, Het, or Het$(C_1-C_6)$alkyl, wherein each alkyl, aryl, or Het is unsubstituted or substituted with one or more $R_d$, or two $R^4$ groups are taken together with the atom to which they are attached to form aryl, Het, or a saturated or unsaturated 3-8 membered monocyclic or 8-12 membered bicyclic ring system comprising carbon atoms and optionally comprising one or more additional heteroatoms selected from O, S(O)$_z$, and $NR_C$, wherein each ring system is optionally substituted with one or more $R_d$;

each $R_a$ and $R_b$ is independently hydrogen or $(C_1-C_6)$alkyl;

each $R_c$ is independently hydrogen, aryl, S(O)$_2$, $(C_1-C_6)$alkanoyl, hydroxy$(C_1-C_6)$alkyl, alkoxy$(C_1-C_6)$alkyl, Het, $(C_1-C_6)$alkoxycabonyl or $(C_1-C_6)$alkyl, unsubstituted or substituted with one or more subtituents $R_e$;

each $R_d$ is independently halo, hydroxy, cyano, nitro, azido, amino, $(C_1-C_6)$alkylamino, amino$(C_1-C_6)$alkyl, amido, $(C_1-C_6)$alkyamido, aryl amido, carboxylic acid, $(C_1-C_6)$alkyl, hydroxy$(C_1-C_6)$alkyl, halo$(C_1-C_6)$alkyl, $(C_1-C_6)$alkoxy, halo$(C_1-C_6)$alkoxy, $(C_1-C_6)$alkanoyl, $(C_1-C_6)$alkoxycarbonyl, carboxy, $(C_1-C_6)$alkanoyloxy, Het, aryl, Het$(C_1-C_6)$alkyl, or aryl$(C_1-C_6)$alkyl, $(C_1-C_6)$alkylaryl, sulfonyl, sulfonamido, urea, carbamate, unsubstituted or substituted with one or more subtituents $R_e$, or two $R_d$ come together with the atom to which they are attached to form a ketone or spirocyclic carbocyclic or heterocyclic ring, or two $R_d$ come together with the atoms to which they are attached to form a bicyclic carbocyclic or heterocyclic ring, wherein each spirocyclic or bicyclic ring is unsubstituted or substituted with one or more halo, hydroxy, cyano, nitro, azido, $(C_1-C_6)$alkyl, hydroxy$(C_1-C_6)$alkyl, halo$(C_1-C_6)$alkyl, $(C_1-C_6)$alkoxy, halo$(C_1-C_6)$alkoxy, $(C_1-C_6)$alkanoyl, $(C_1-C_6)$alkoxycarbonyl, carboxy, $(C_1-C_6)$alkanoyloxy, $NR_fR_g$, $R_fR_gNC(=O)$—, phenyl, or phenyl$(C_1-C_6)$alkyl, sulfonyl, sulfonamido, urea, carbamate, wherein $R_f$ and $R_g$ together with the nitrogen to which they are attached form a piperidino, pyrrolidino, morpholino, or thiomorpholino ring, unsubstituted or substituted with one or more substituents $R_e$;

each $R_e$ is independently selected from halo, hydroxy, cyano, nitro, azido, $(C_1-C_6)$alkyl, Het, aryl, $(C_1-C_6)$alkylHet, $(C_1-C_6)$alkylaryl, $(C_1-C_6)$alkylHet$(C_1-C_6)$alkyl, $(C_1-C_6)$alkylaryl$(C_1-C_6)$alkyl, $(C_1-C_6)$haloalkyl, $(C_1-C_6)$alkoxy, $(C_1-C_6)$haloalkoxy, $(C_1-C_6)$alkanoyl, $(C_1-C_6)$alkoxycarbonyl, carboxy, and $(C_1-C_6)$alkanoyloxy;

$R^5$ is H, $(C_1-C_6)$alkyl, aryl$(C_1-C_6)$alkyl; and each $R^6$ is H, $(C_1-C_6)$alkyl, amino, amido, keto, or aryl$(C_1-C_6)$alkyl; with the proviso that when X is —C(=O), Y is —N($R^4$)$_2$, $Z^1$ is O, $Z^2$ is N, and $Z^3$ is CH, both $R^4$ of Y are not H.

73. A pharmaceutical composition comprising a compound as described in any one of any of the previous embodiments, and a pharmaceutically acceptable diluent or carrier.

74. A method for preparing a compound of formula I or a salt thereof as described in any one of any of the previous embodiments comprising:

a) deprotecting a corresponding compound that comprises one or more protecting groups to provide the compound of formula I;

b) forming a pharmaceutically acceptable salt from a compound of formula I;

c) for a compound of formula I wherein X is —C(=O)—, reacting an intermediate acid of formula 100 with an amine of formula i:

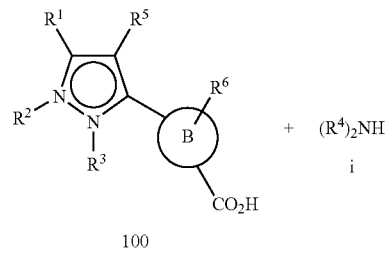

to provide the compound of formula I; or d) for a compound of formula I wherein $R^2$ is absent, reacting an intermediate diketone of formula 102 with a hydrazine of formula ii:

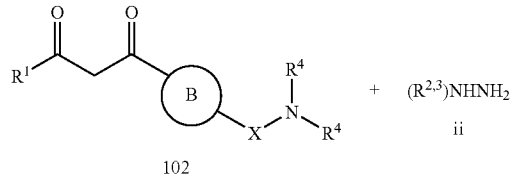

to provide the compound of formula I.

75. A compound as described in any one of any of the previous embodiments, or a pharmaceutically acceptable salt thereof, for use in medical therapy.

76. The use of a compound of formula I, or a pharmaceutically acceptable salt thereof, as described in any one of any of the previous embodiments for the manufacture of a medicament useful for improving cognitive function in an animal.

77. The use of any of the previous embodiments wherein the animal is a healthy animal.

78. The use of any of the previous embodiments wherein the animal is an aged animal.

79. The use of a compound of formula I, or a pharmaceutically acceptable salt thereof, as described in any one of any of the previous embodiments for the manufacture of a medicament useful for inhibiting MAO enzymes in an animal.

80. The use of a compound of formula I, or a pharmaceutically acceptable salt thereof, as described in any one of any of the previous embodiments for the manufacture of a medicament useful for activating the CREB pathway in an animal.

81. The use of a compound of formula I, or a pharmaceutically acceptable salt thereof, as described in any one of any of the previous embodiments for the manufacture of a medicament useful for treating a psychiatric disorder in an animal.

82. The use of a compound of formula I, or a pharmaceutically acceptable salt thereof, as described in any one of any of the previous embodiments for the manufacture of a medicament useful for treating Alzheimer's disease in an animal.

83. The use of a compound of formula I, or a pharmaceutically acceptable salt thereof, as described in any one of any of the previous embodiments for the manufacture of a medicament useful for treating Parkinson's disease in an animal.

84. A compound selected from the group consisting of

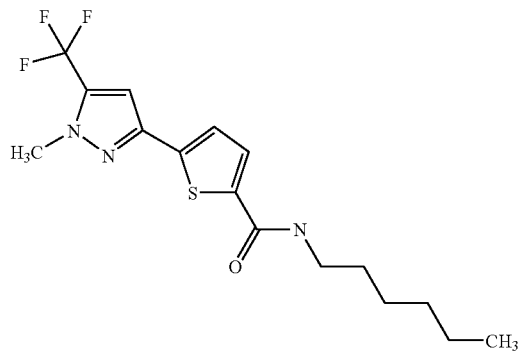

-continued

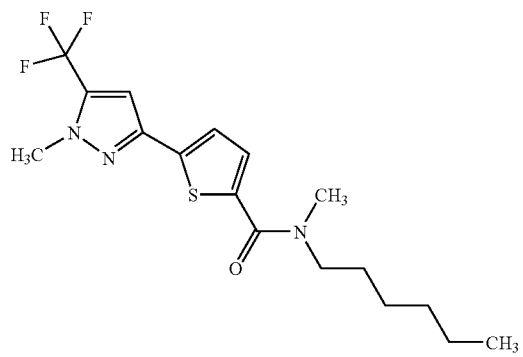

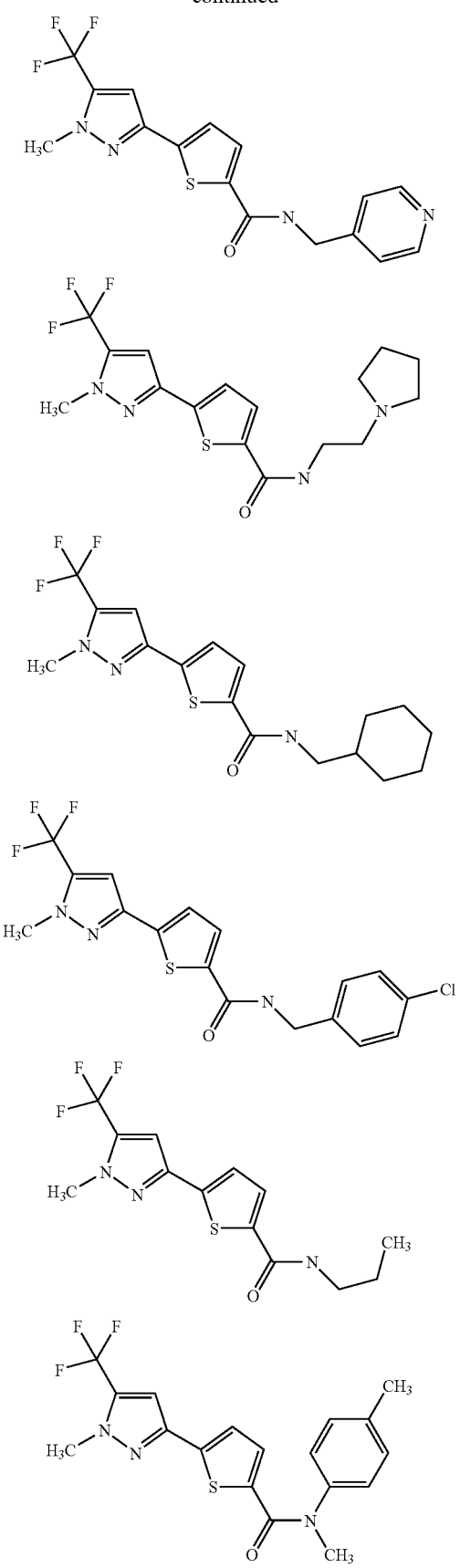
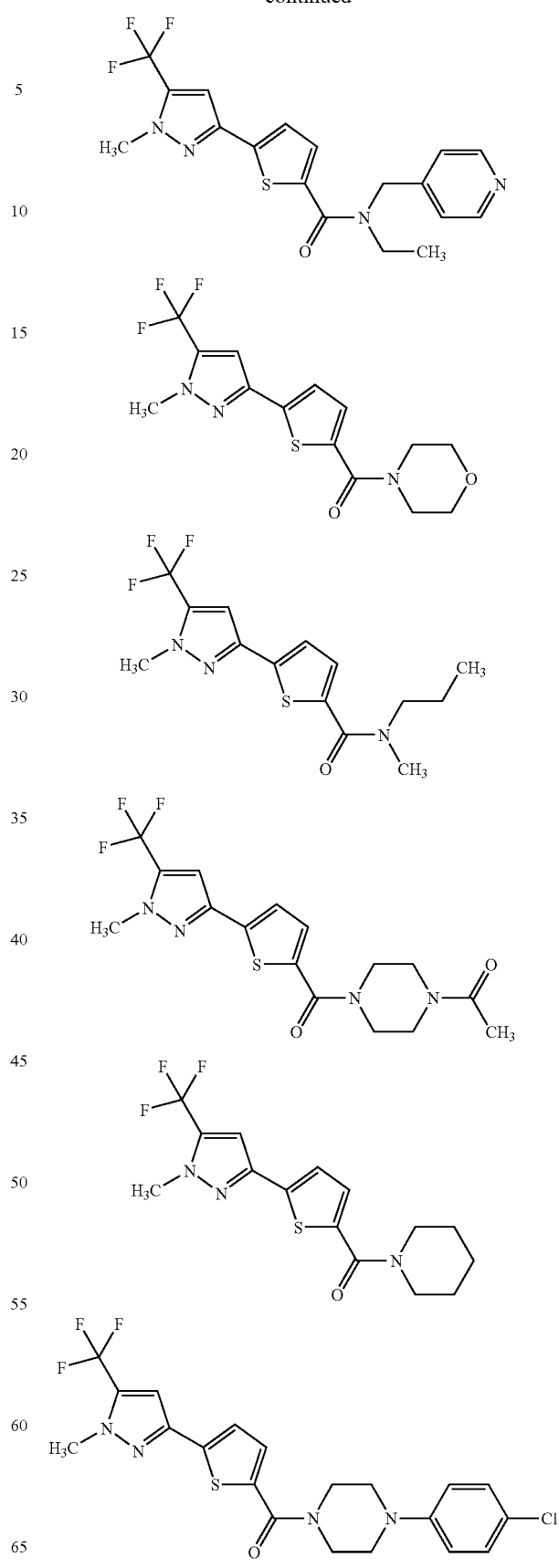

33
-continued
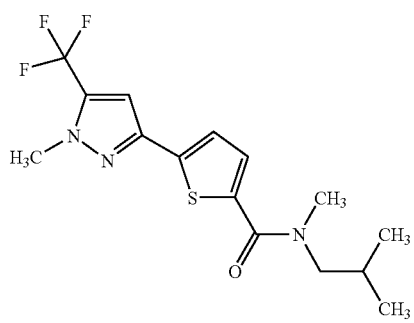
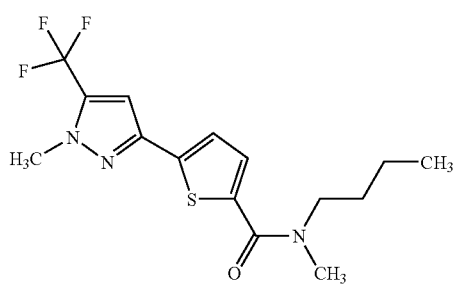
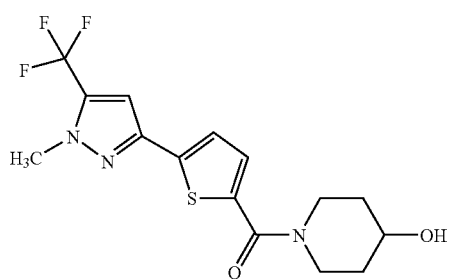
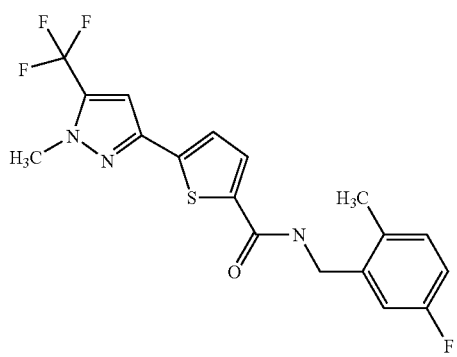
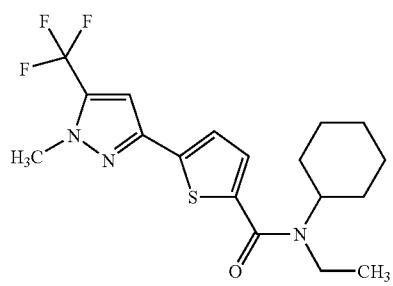
34
-continued
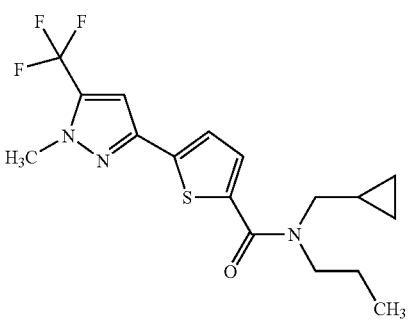
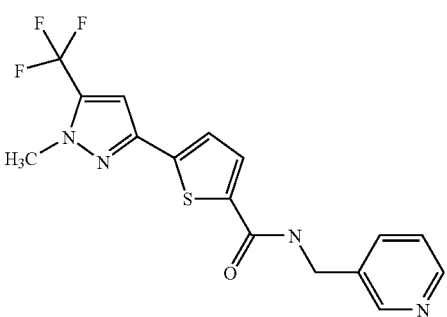
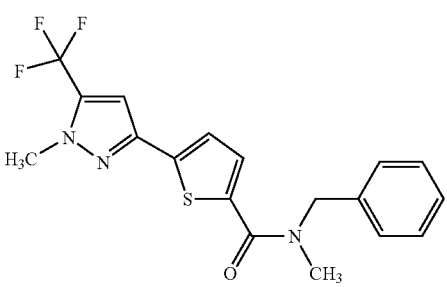
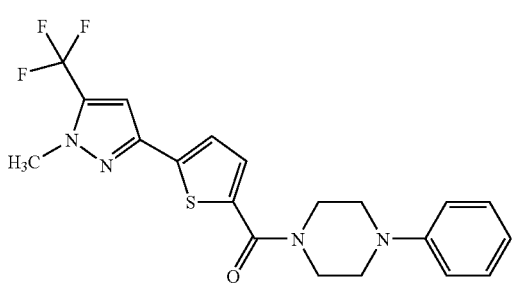
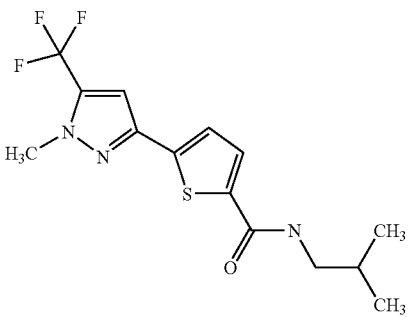

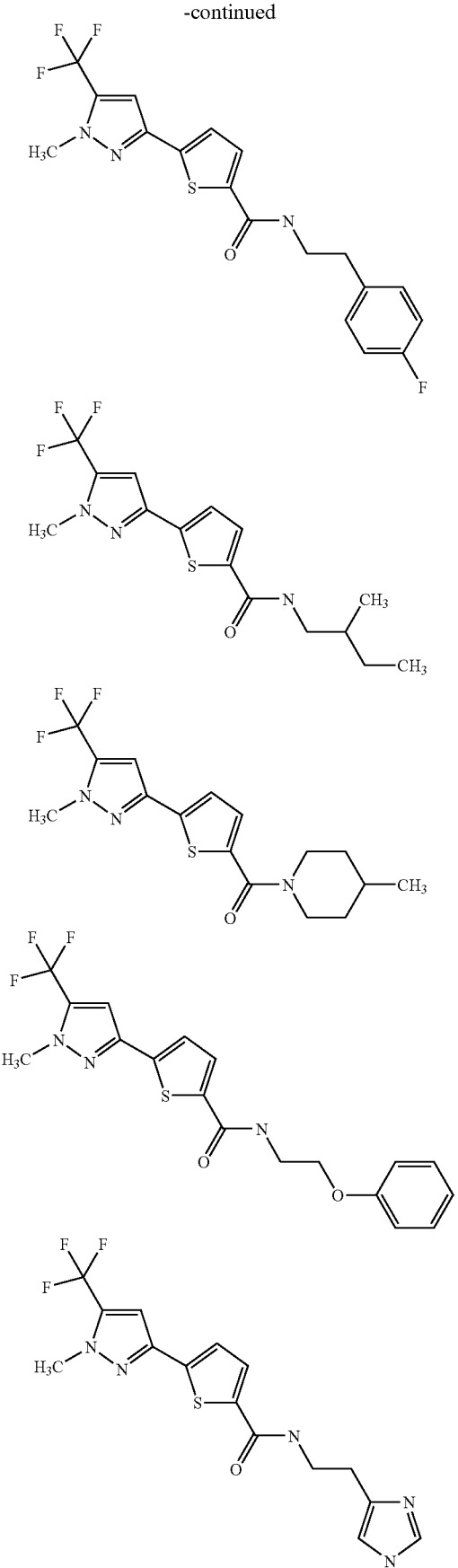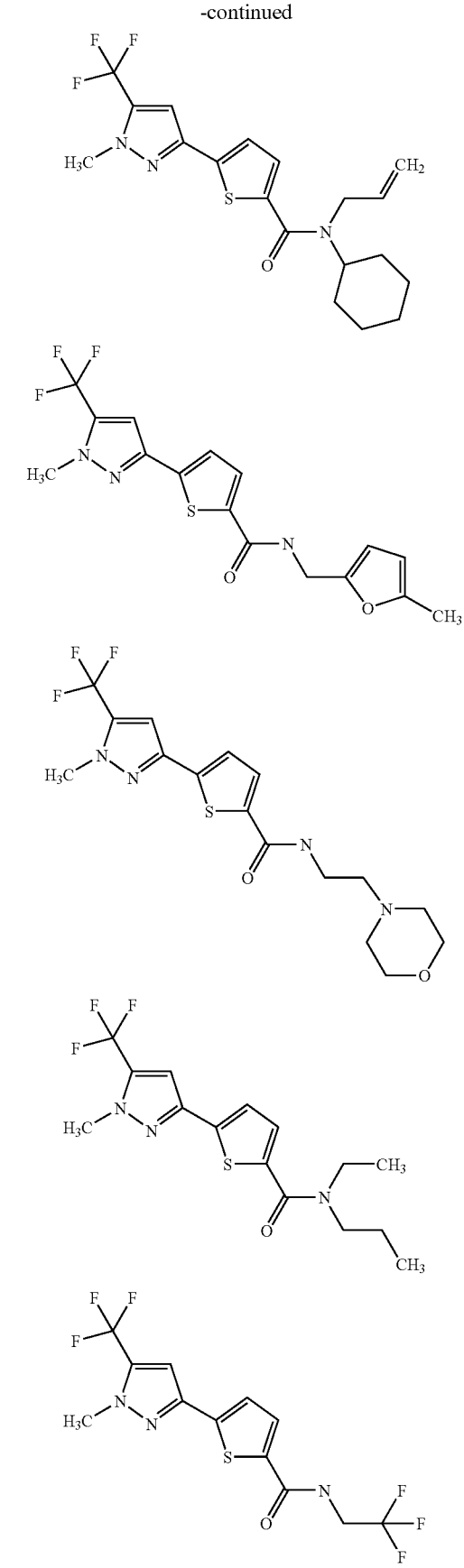

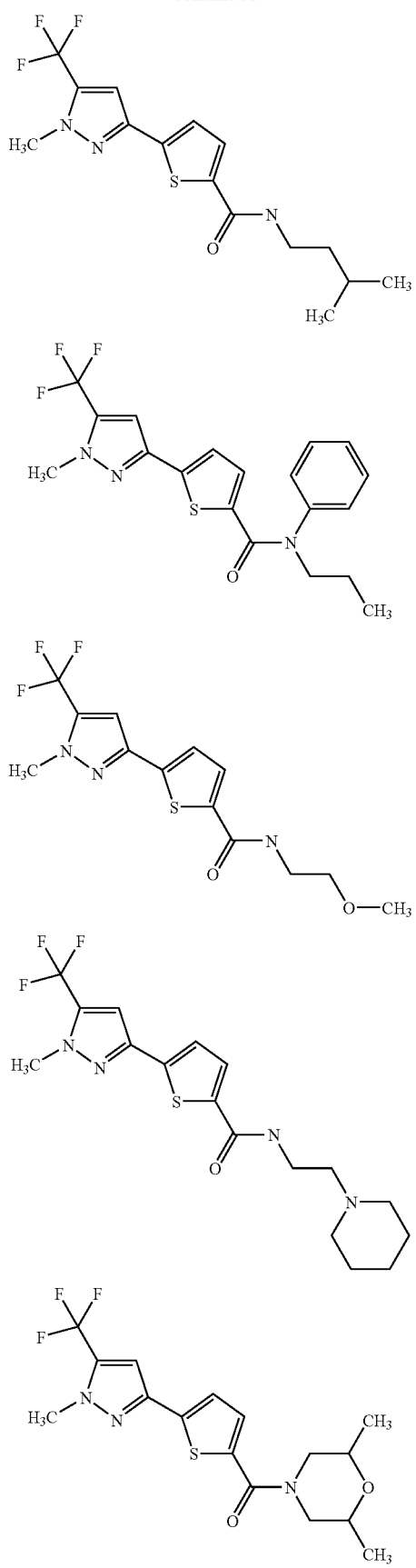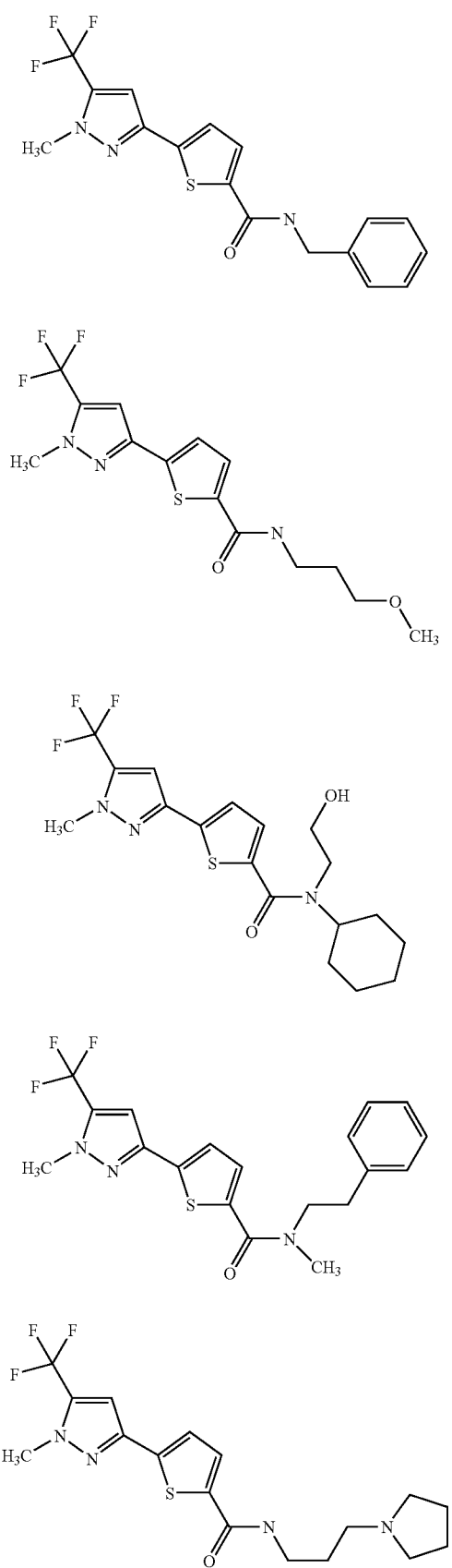

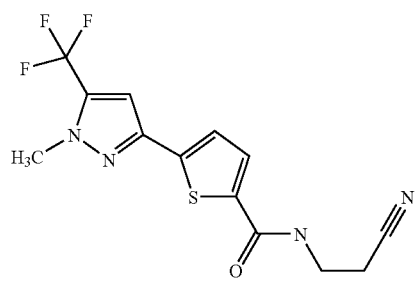
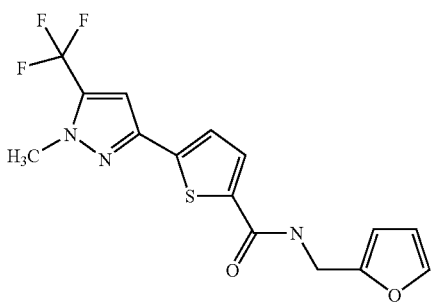
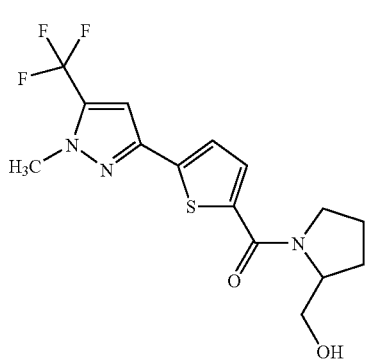
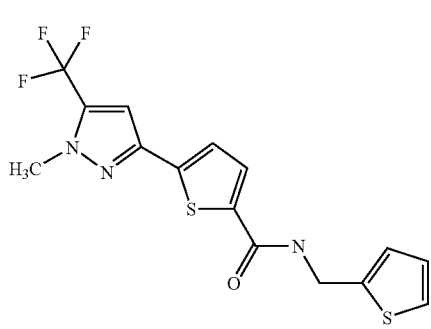
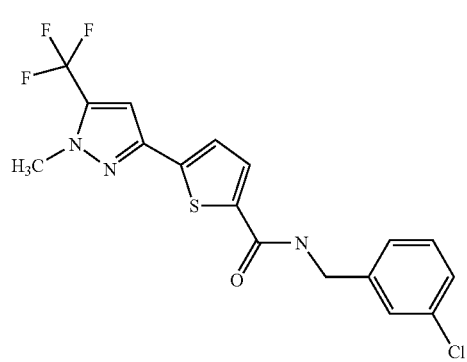
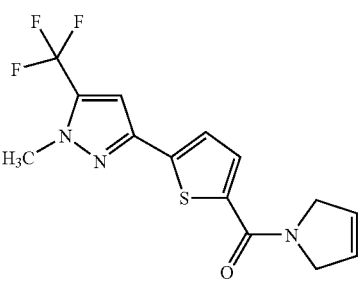
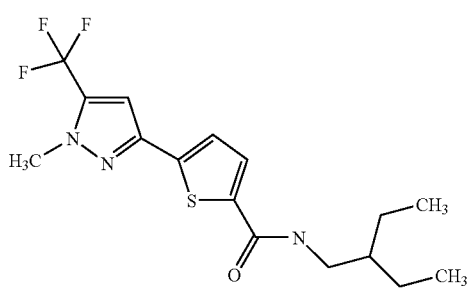
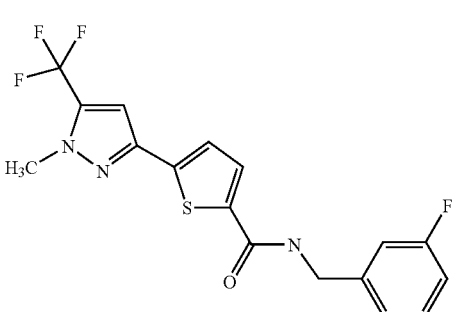
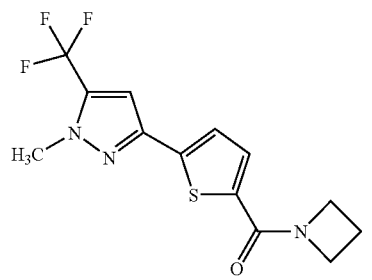
Chiral

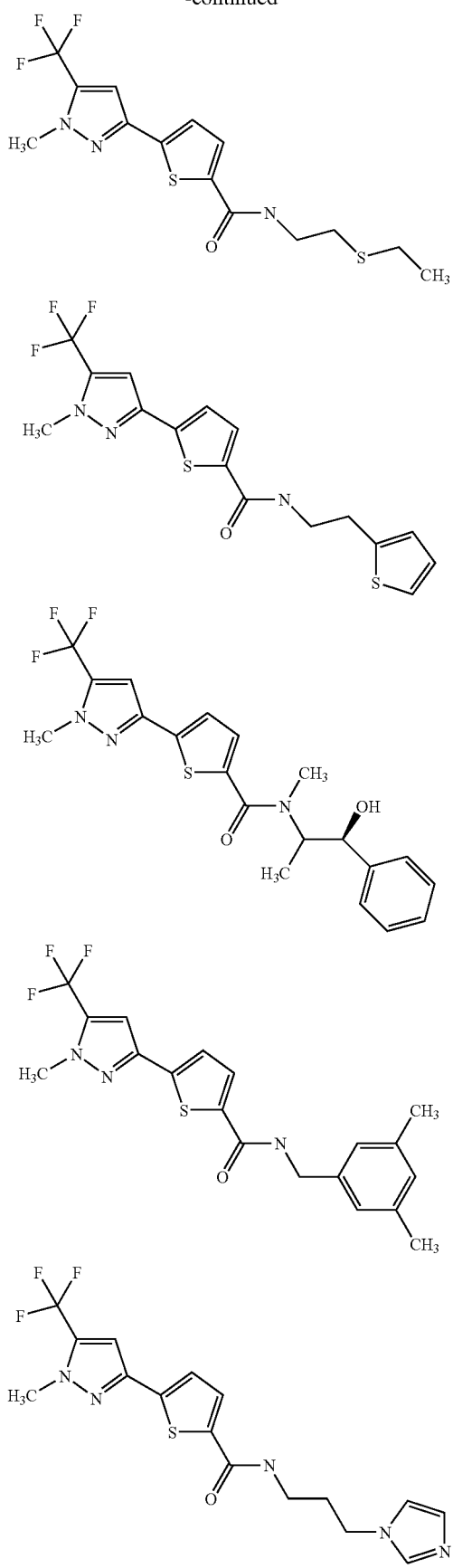
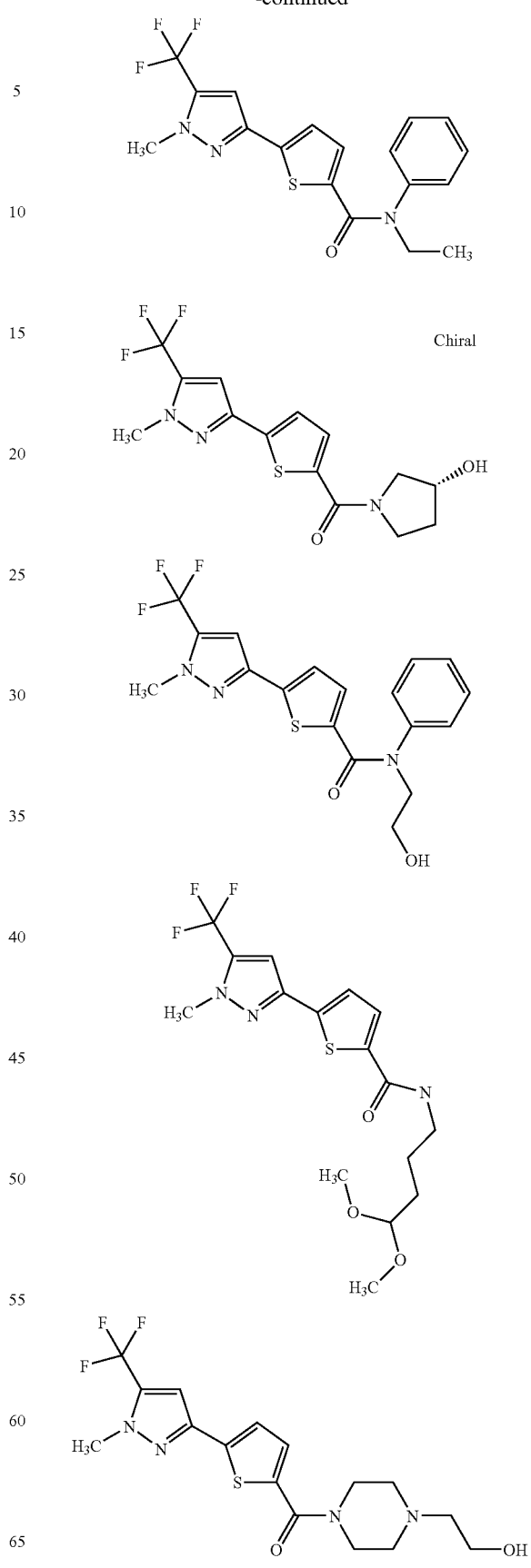

-continued

-continued
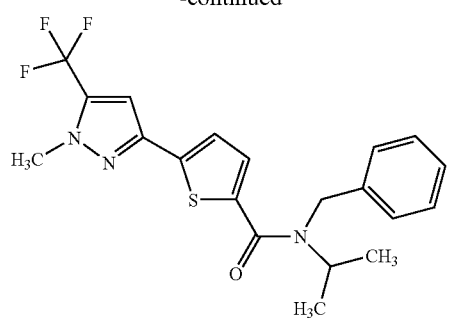
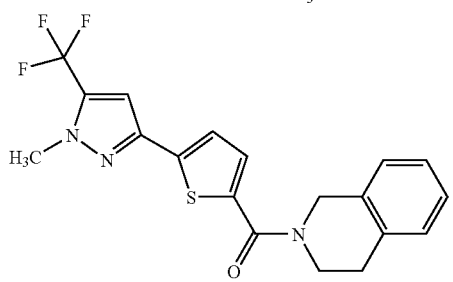
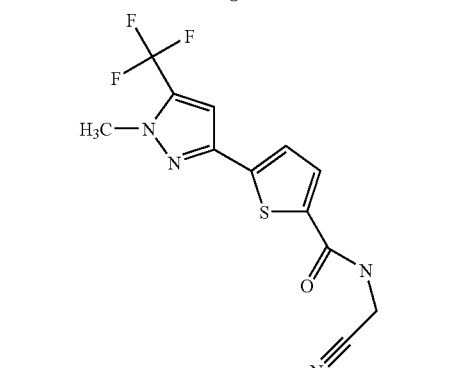
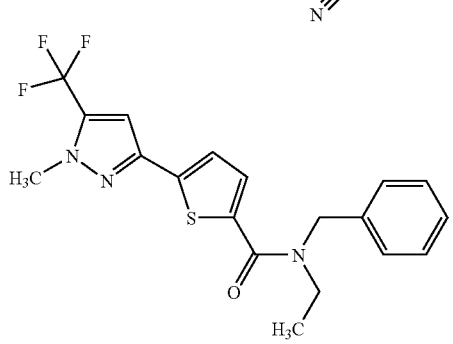
Chiral
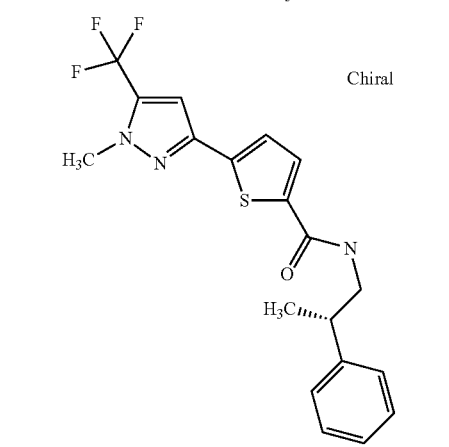
-continued
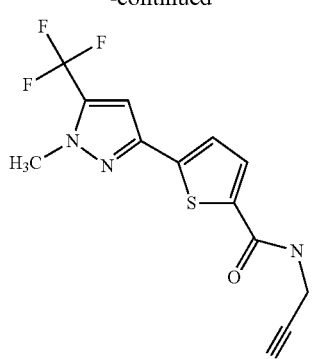
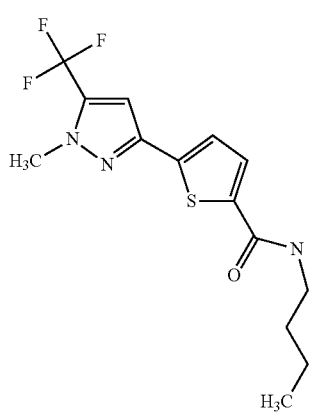
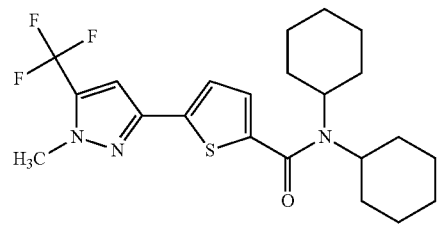
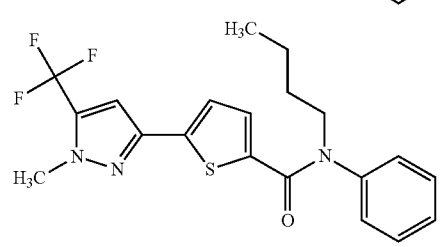
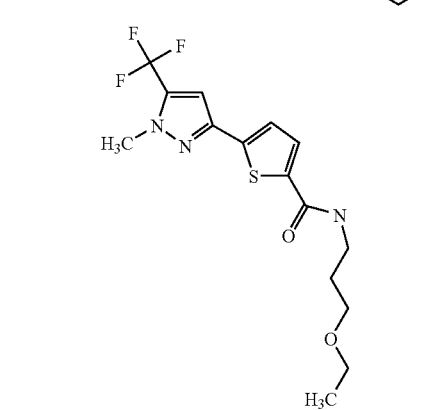

-continued
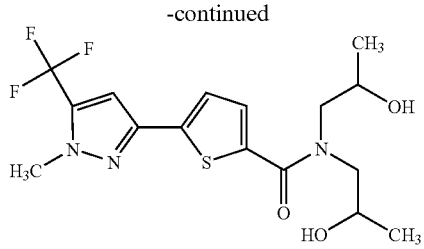
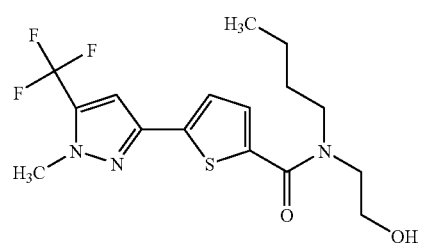
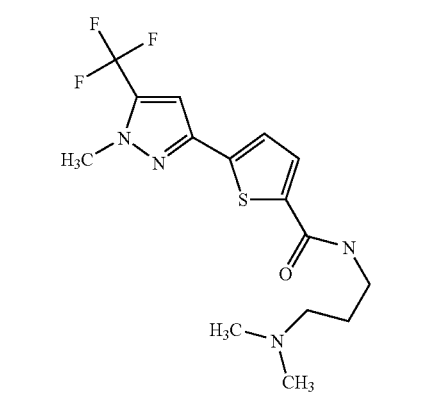
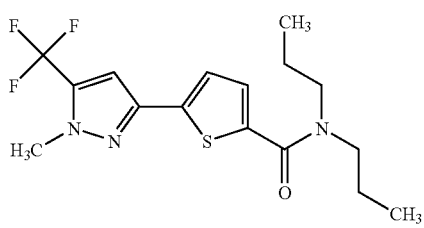
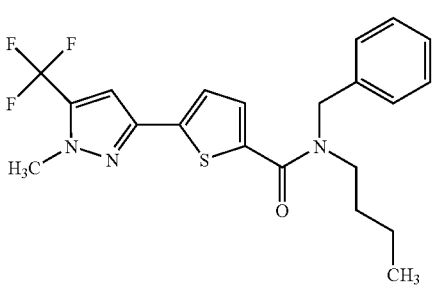
-continued
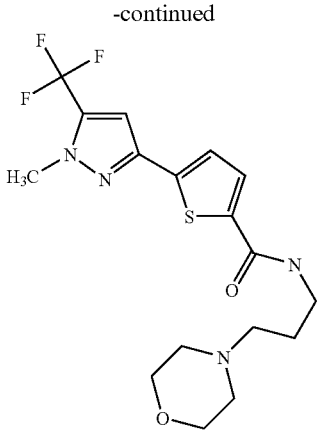
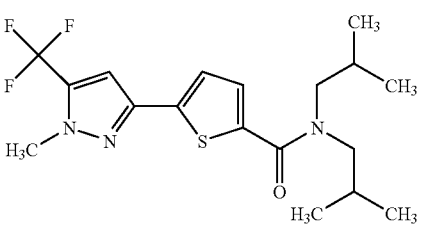
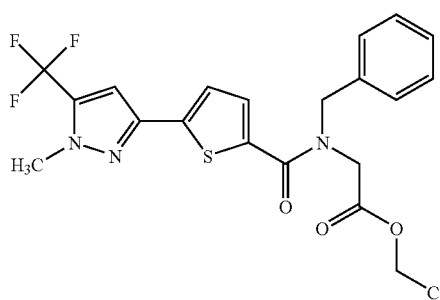
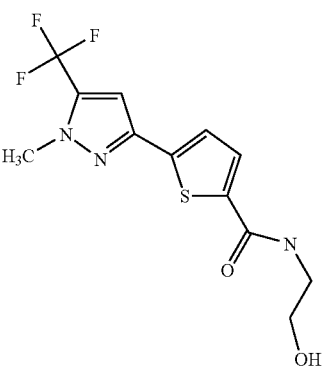
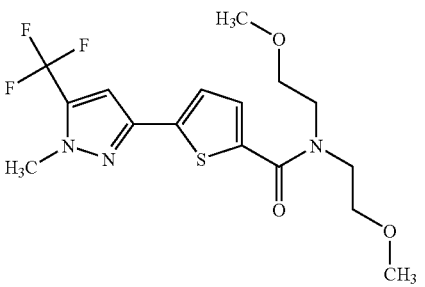

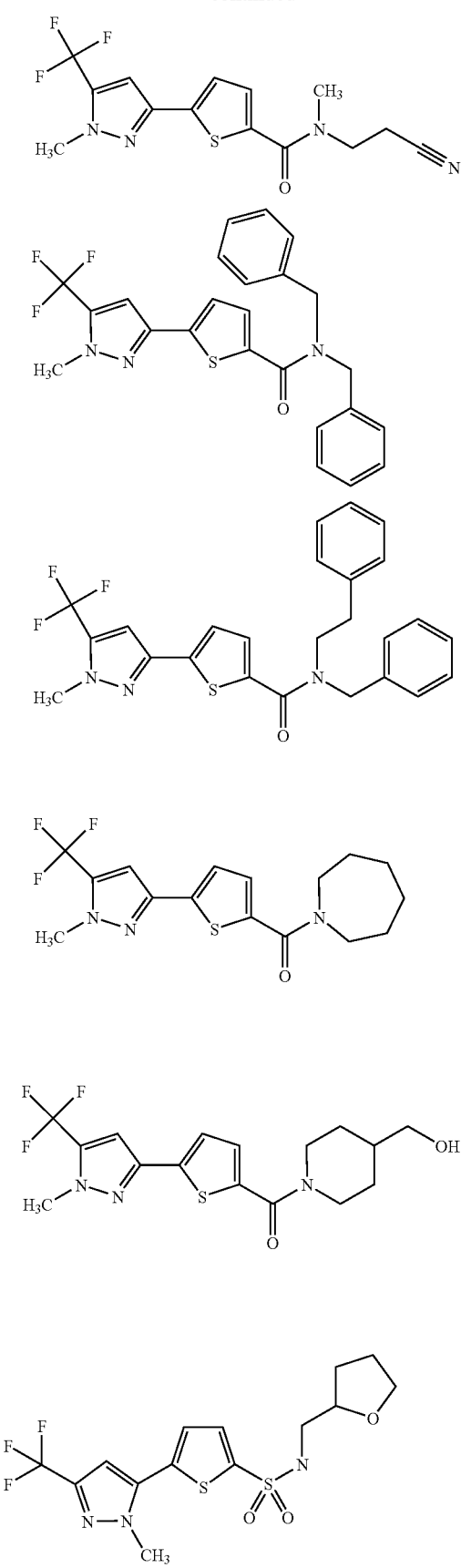
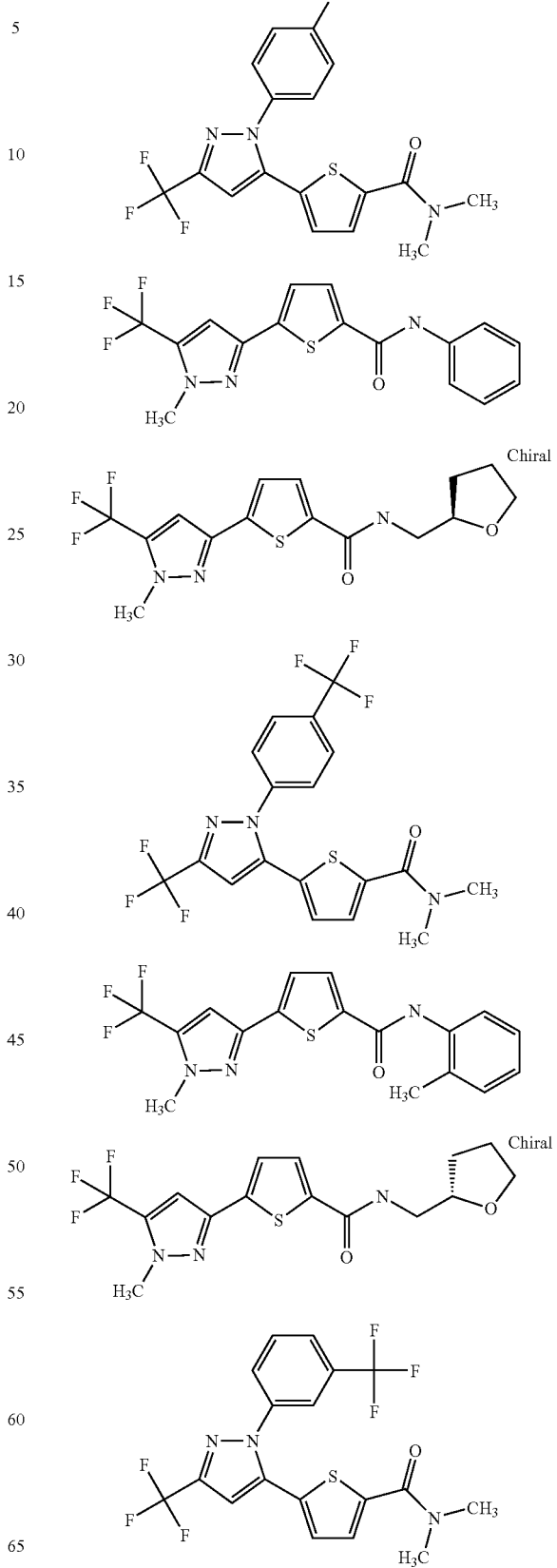

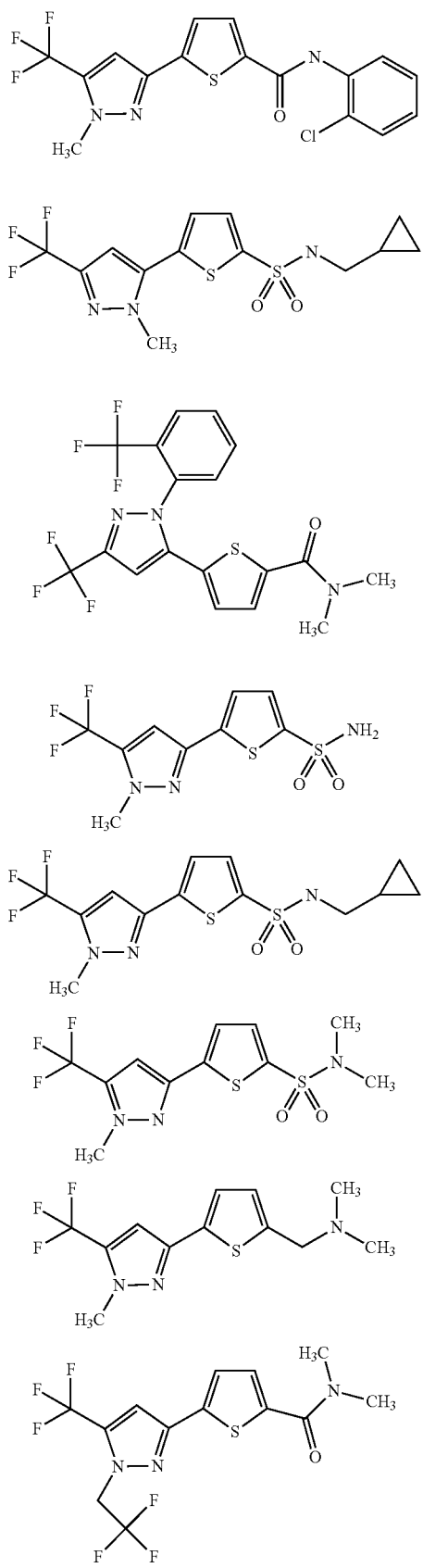
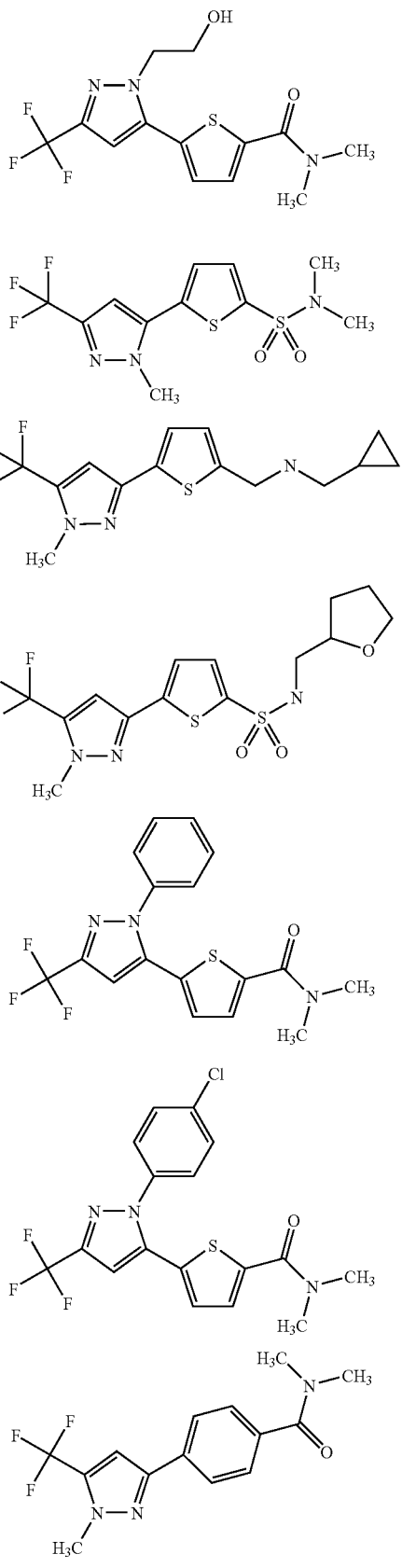

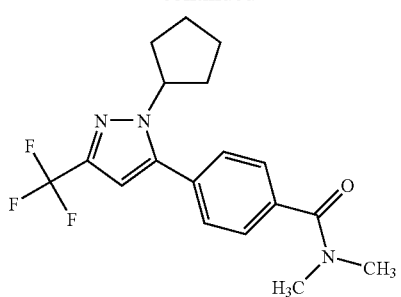
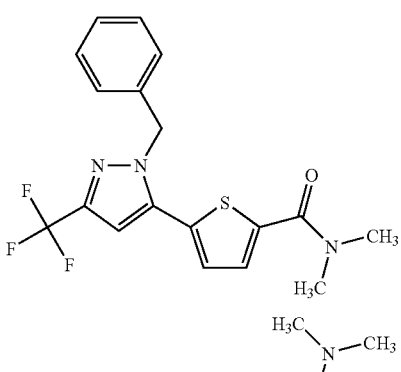
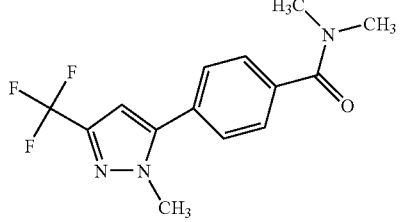
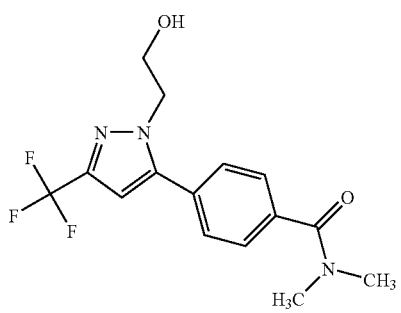
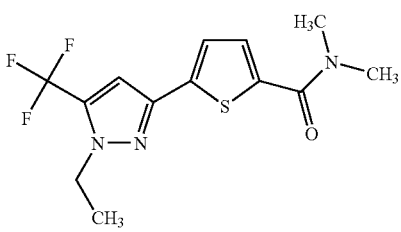
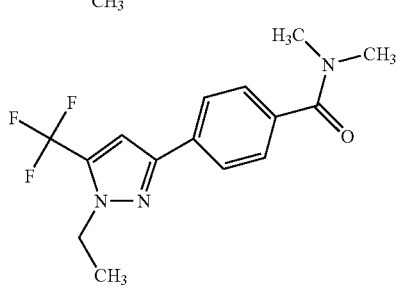
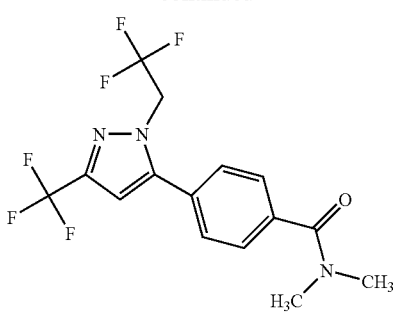
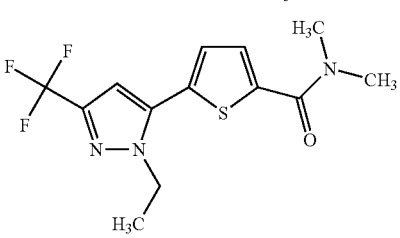
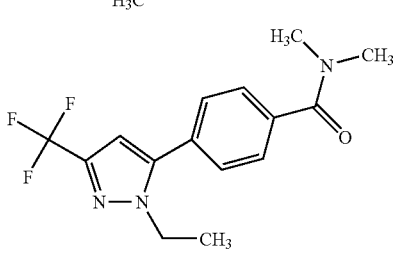
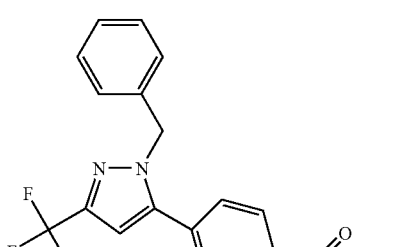
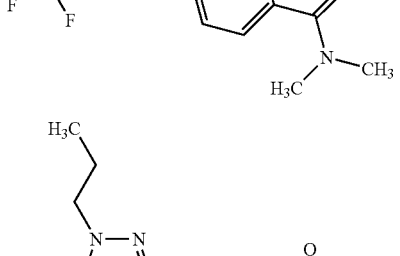
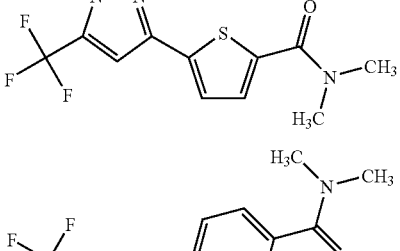
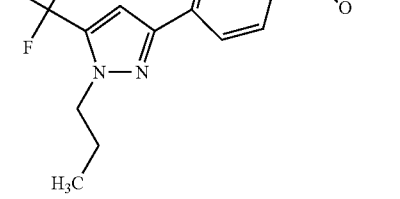

-continued
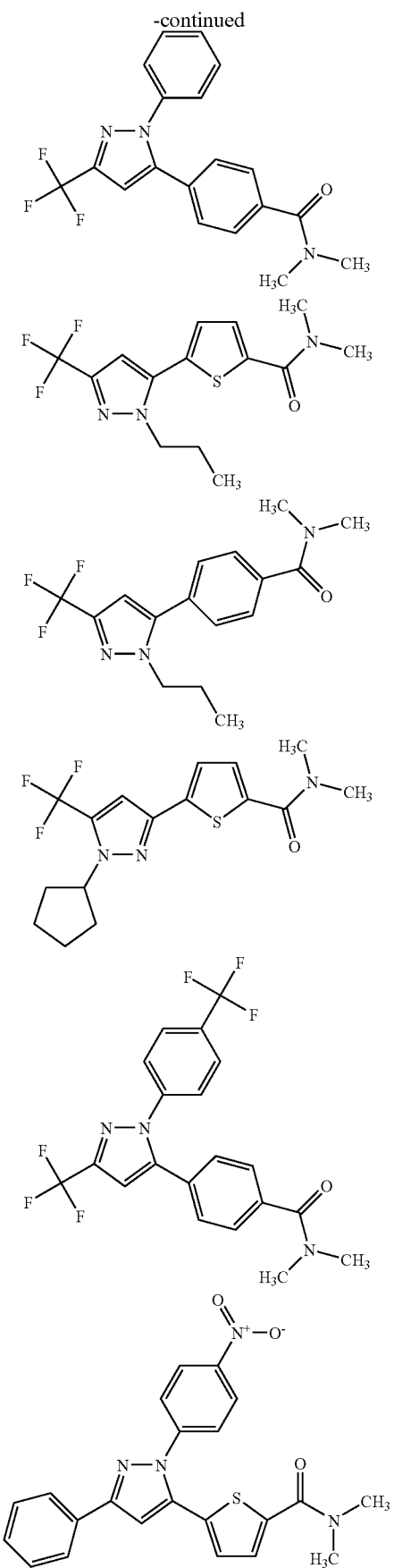
-continued
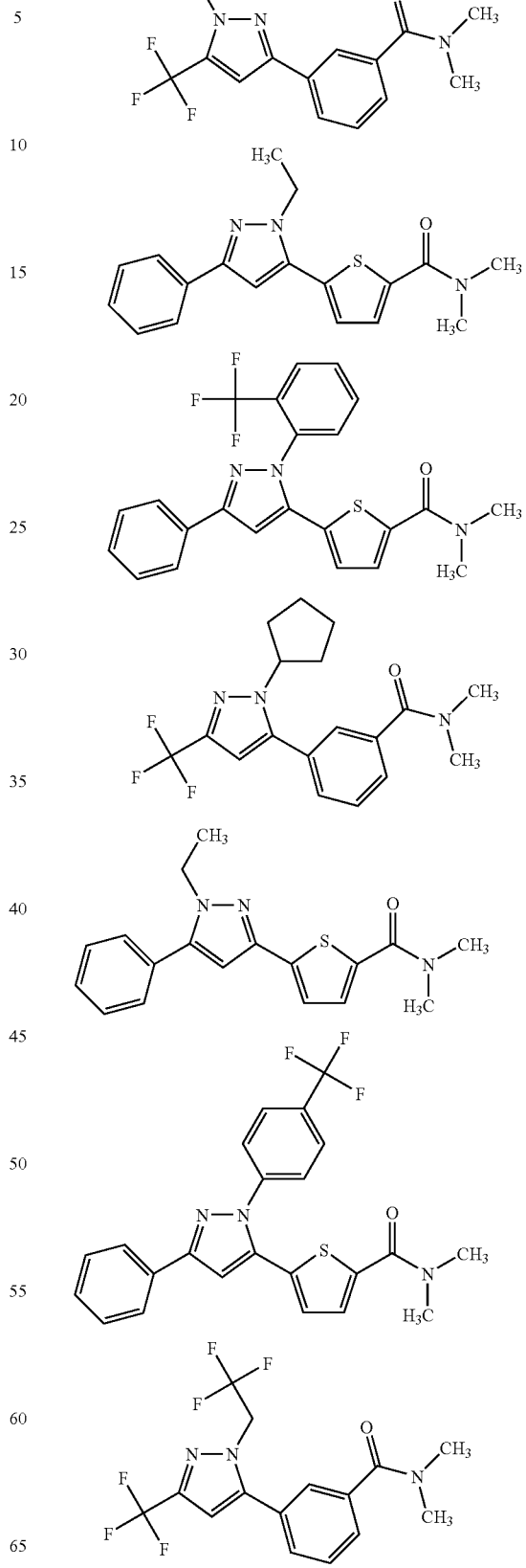

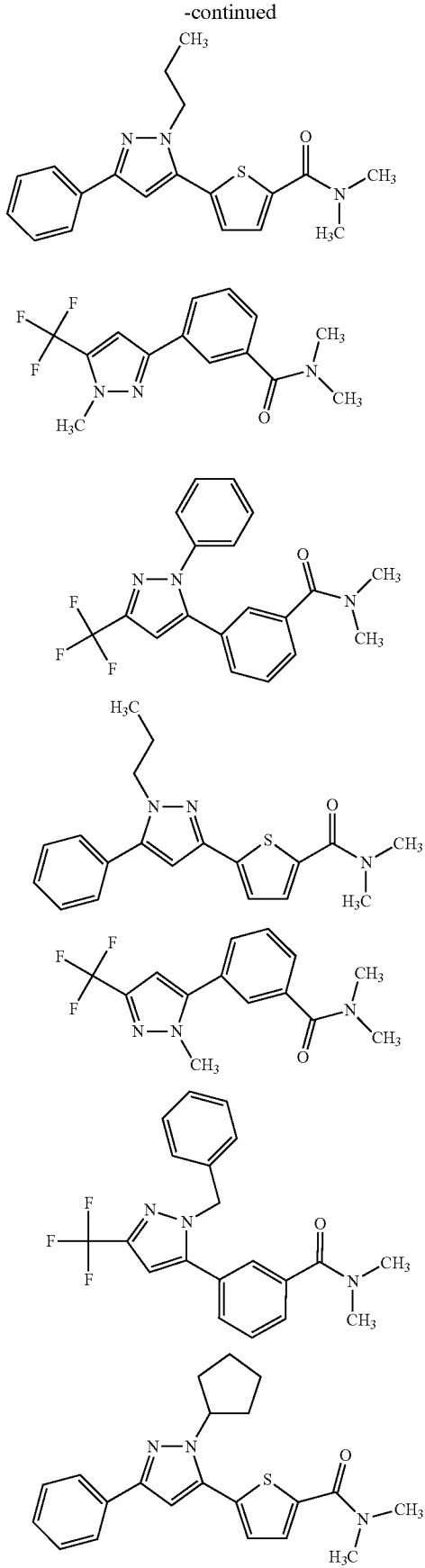
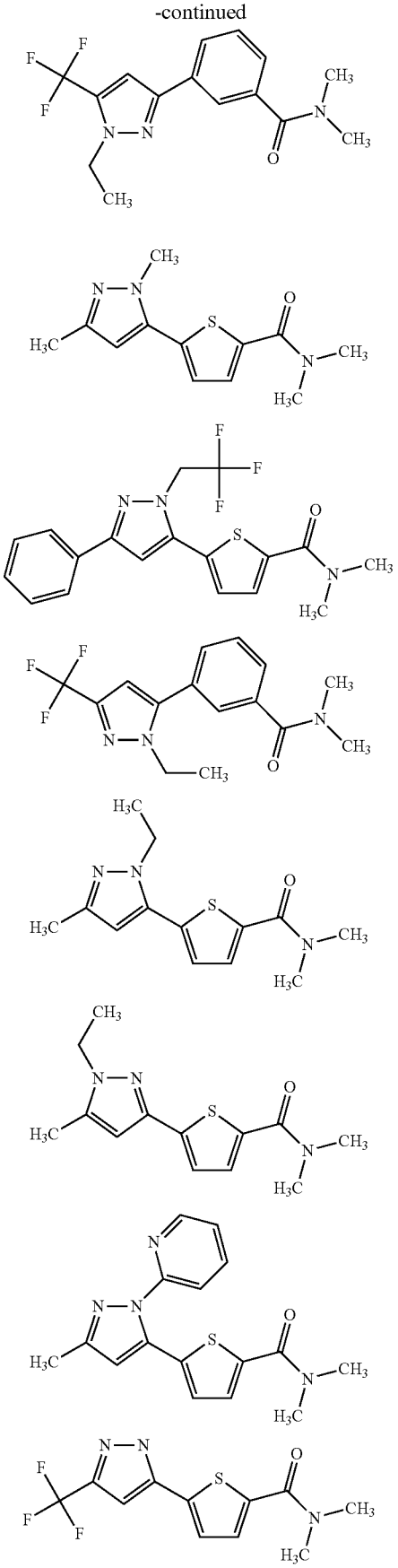

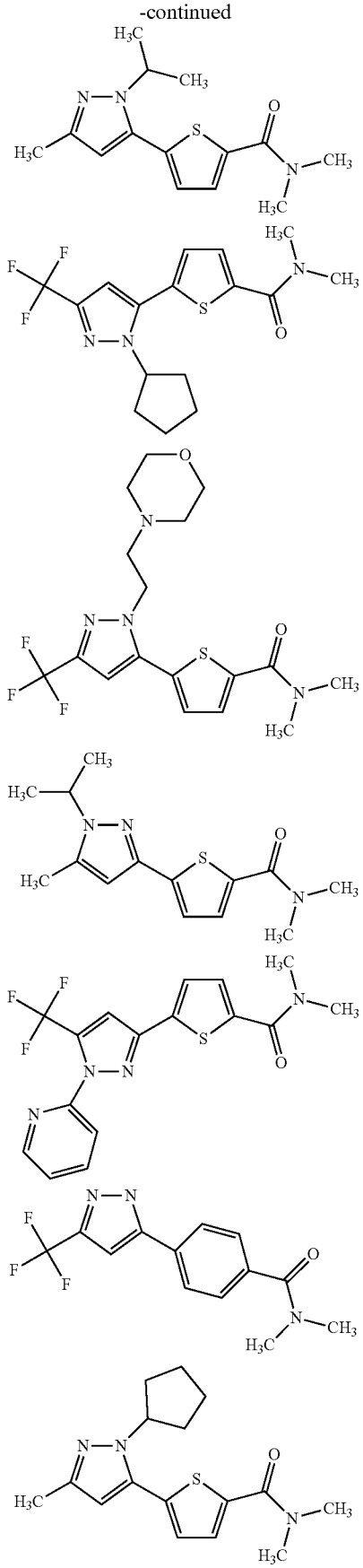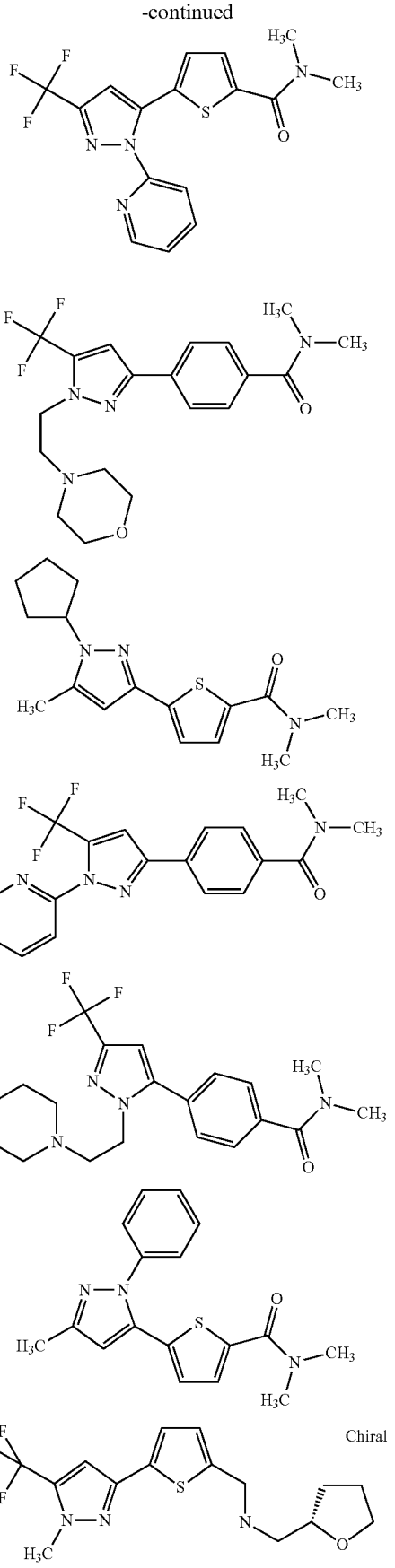

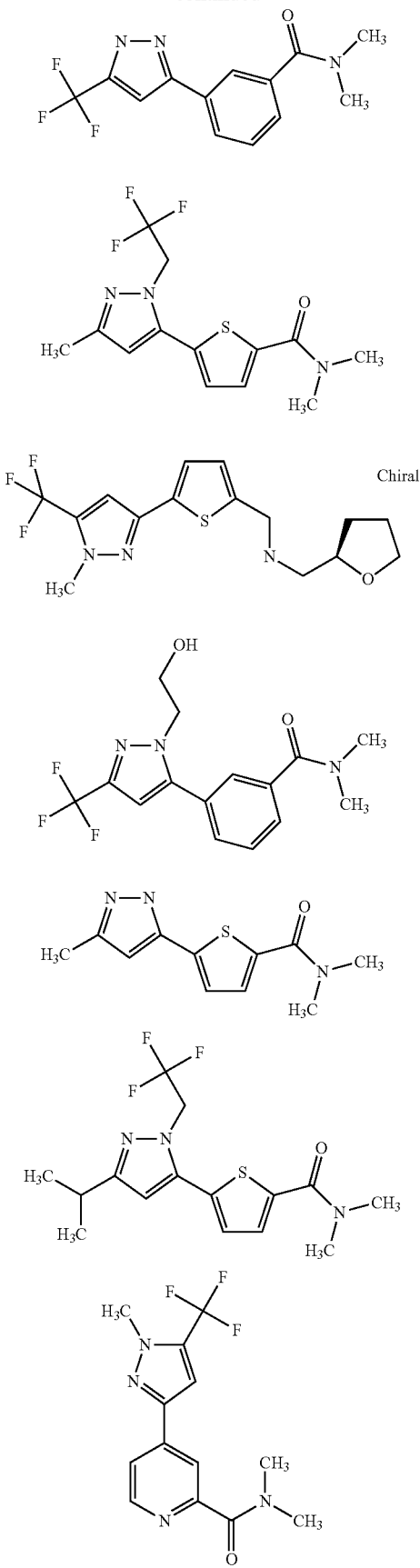
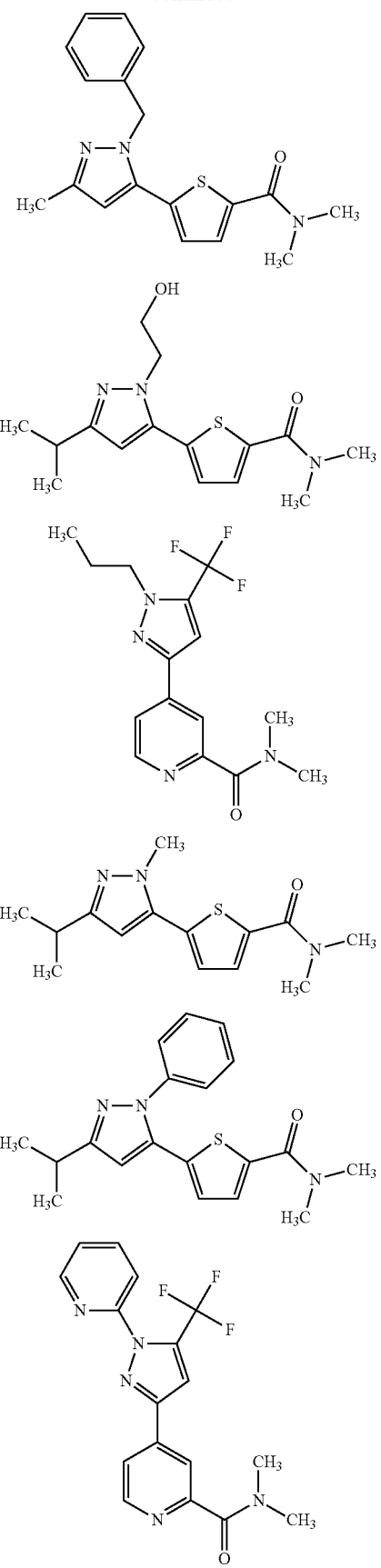

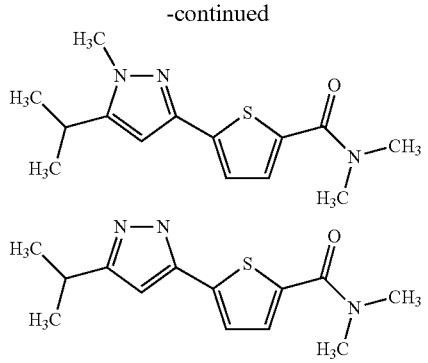
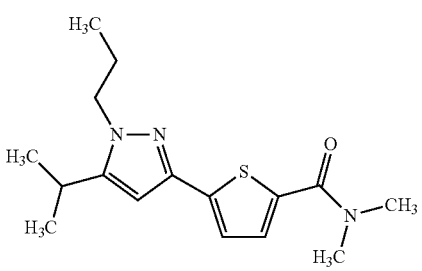
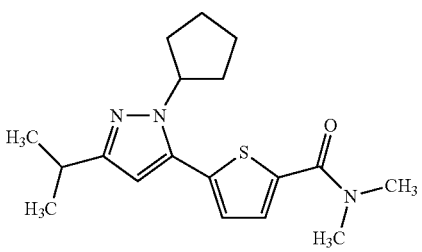
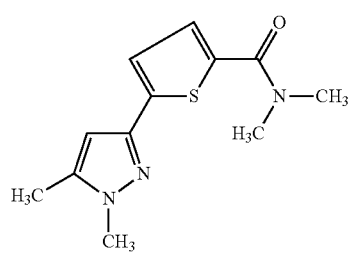
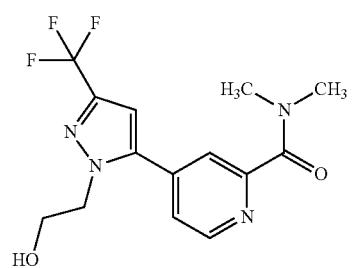
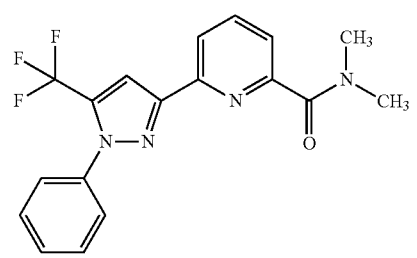
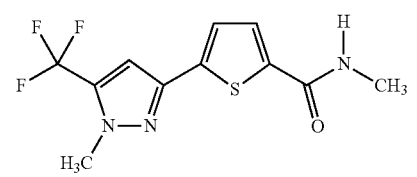

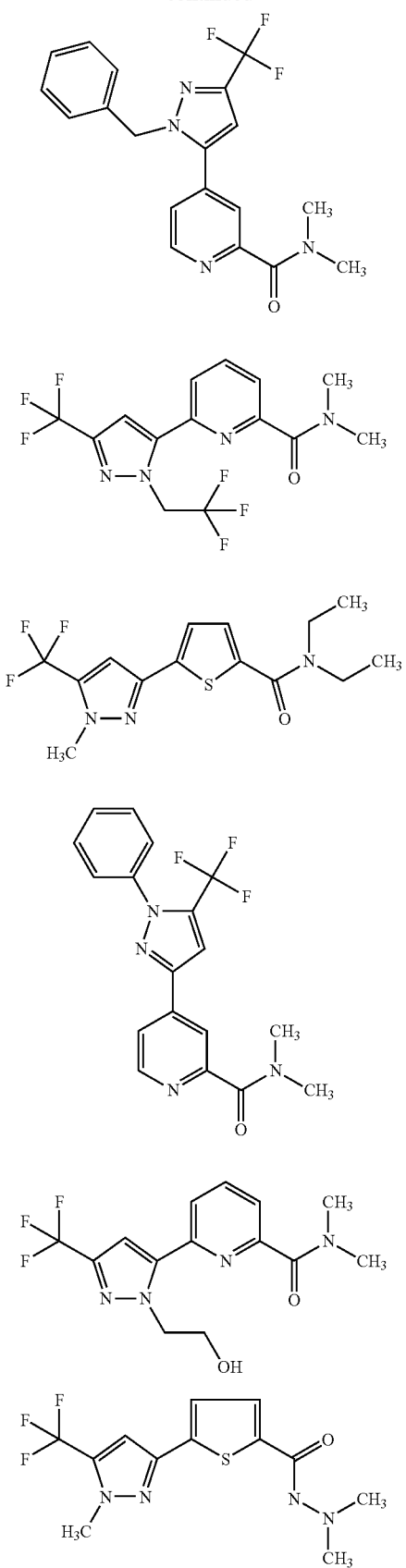
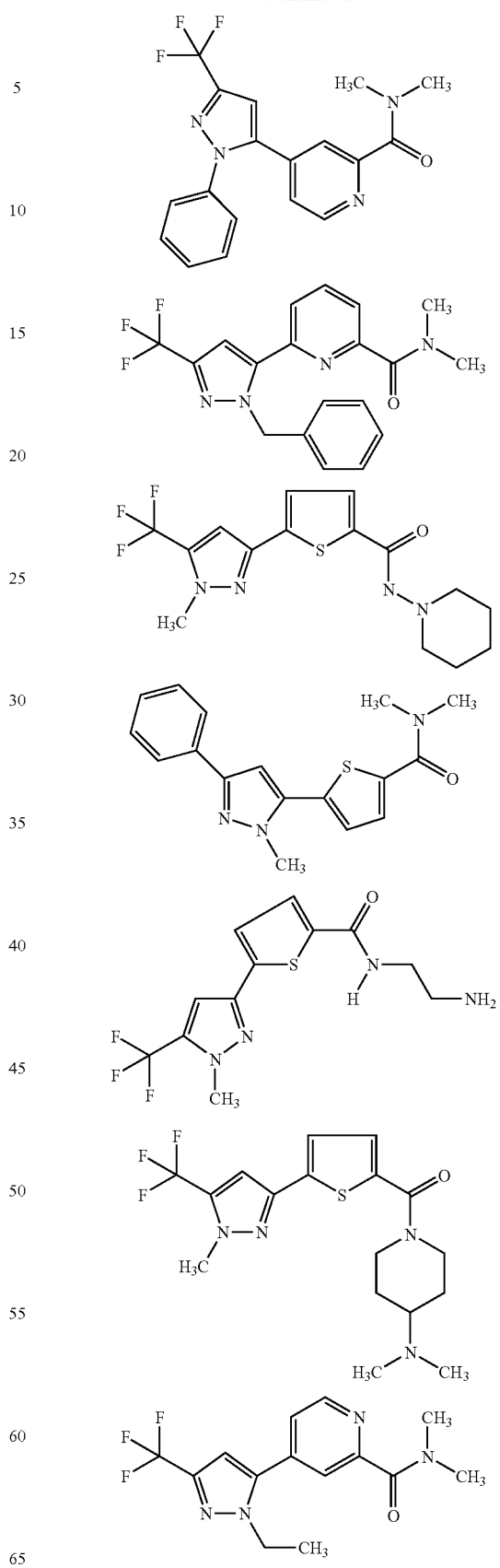

67
-continued

68
-continued

-continued
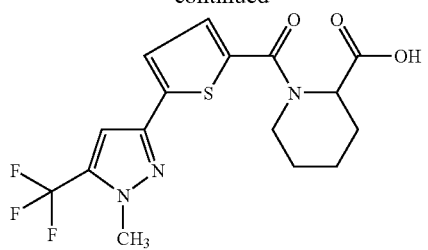
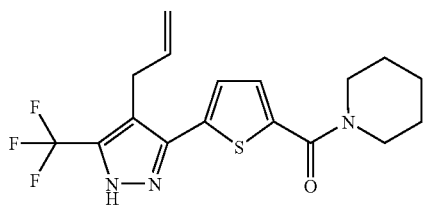
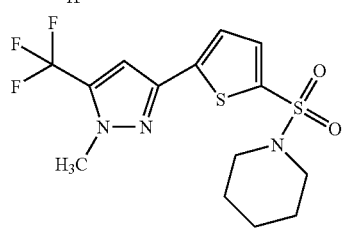
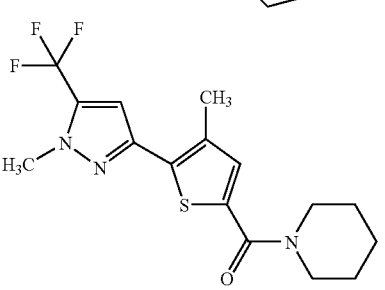
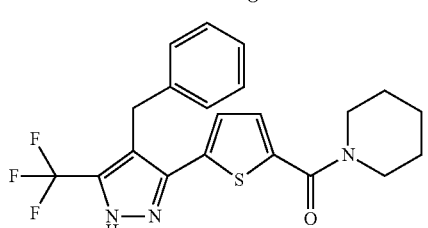
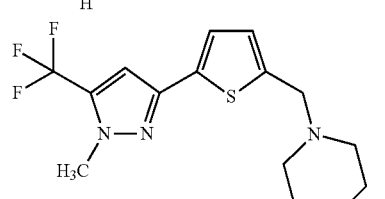
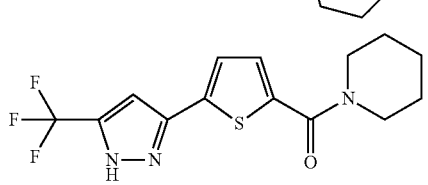
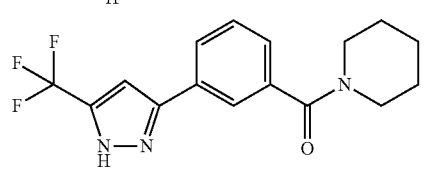
-continued
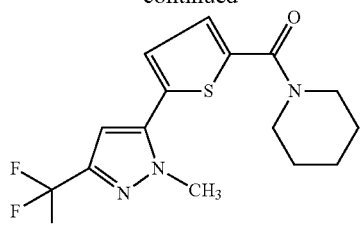
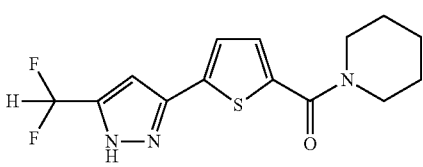
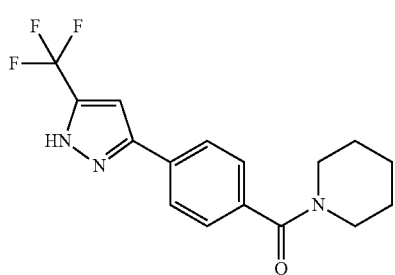
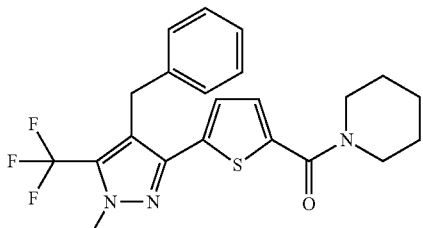
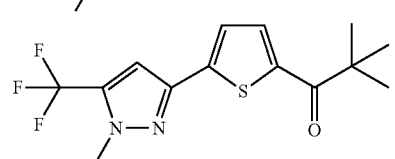
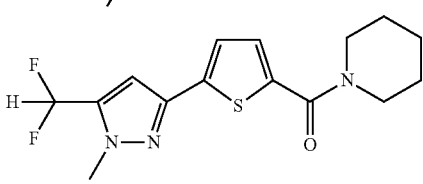
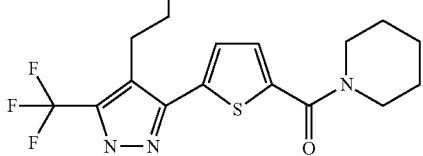
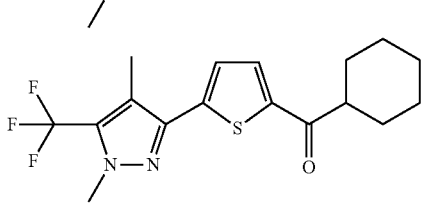

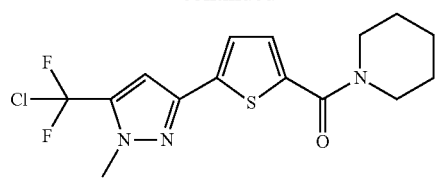
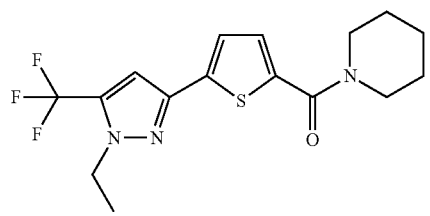
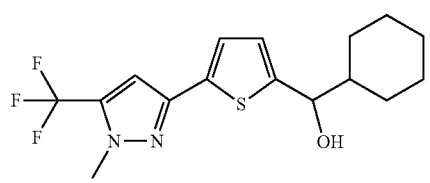
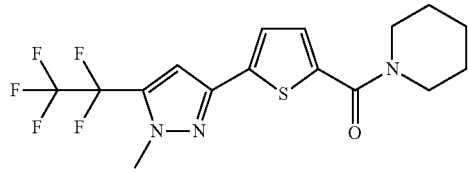
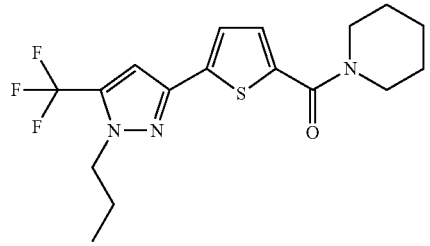
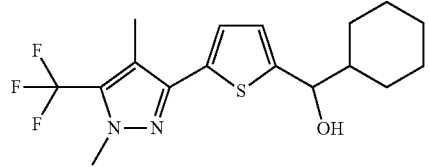
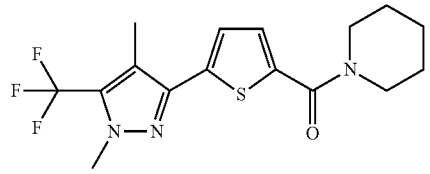
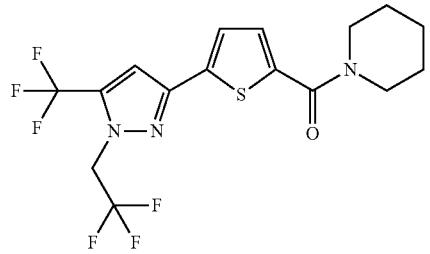
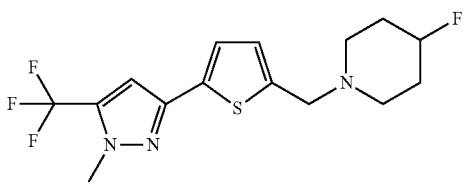
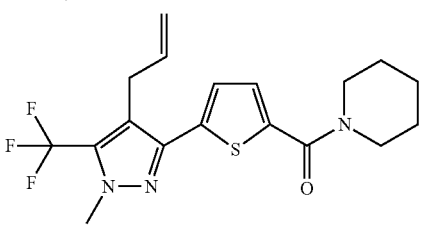
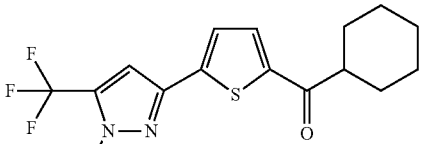
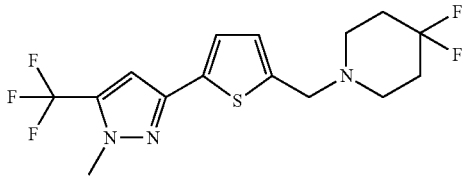
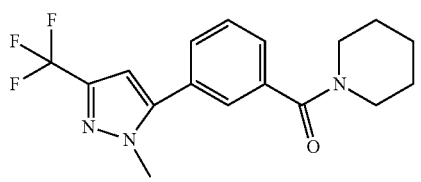
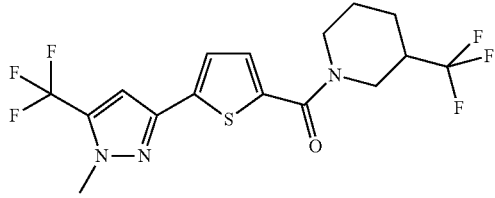
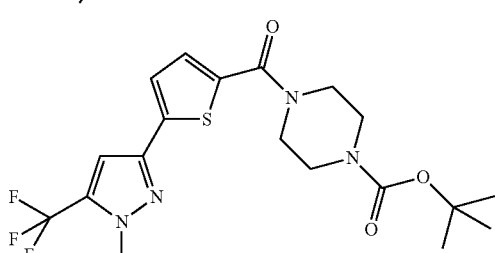
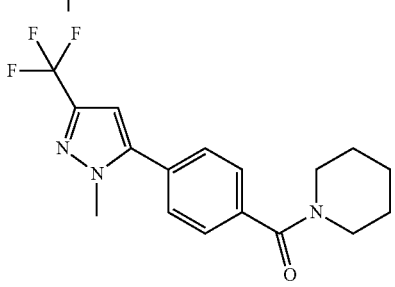

-continued
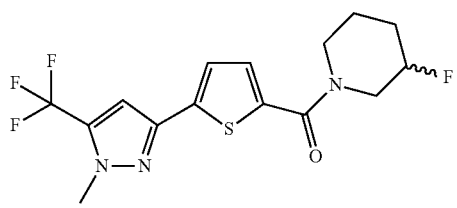
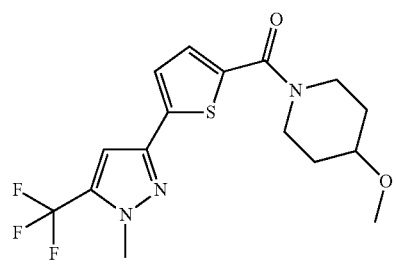
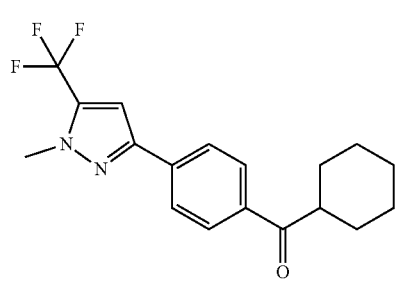
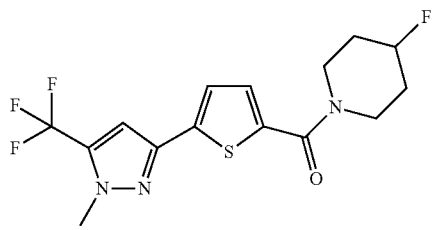
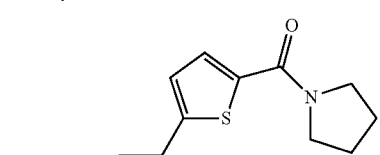
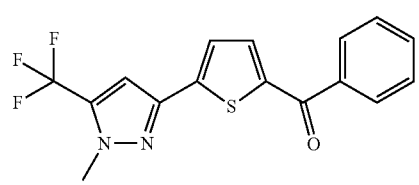
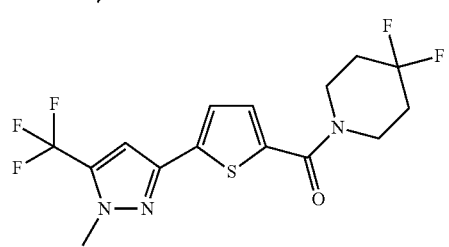
-continued
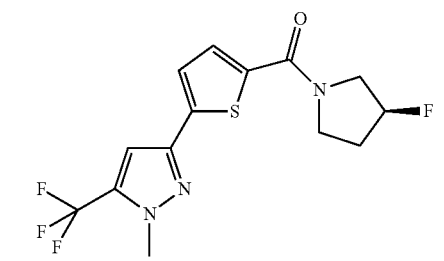
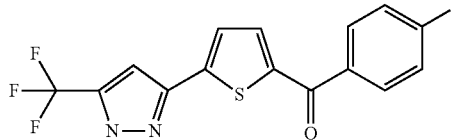
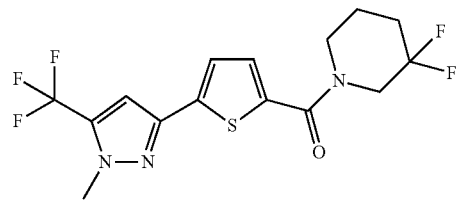
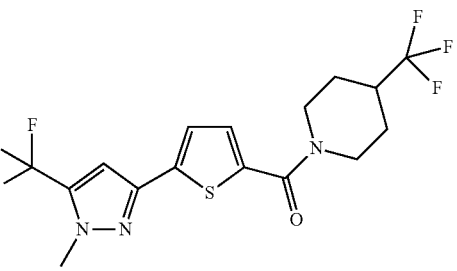
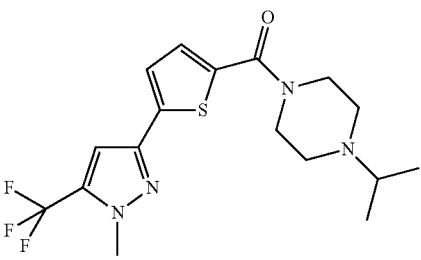

75
-continued
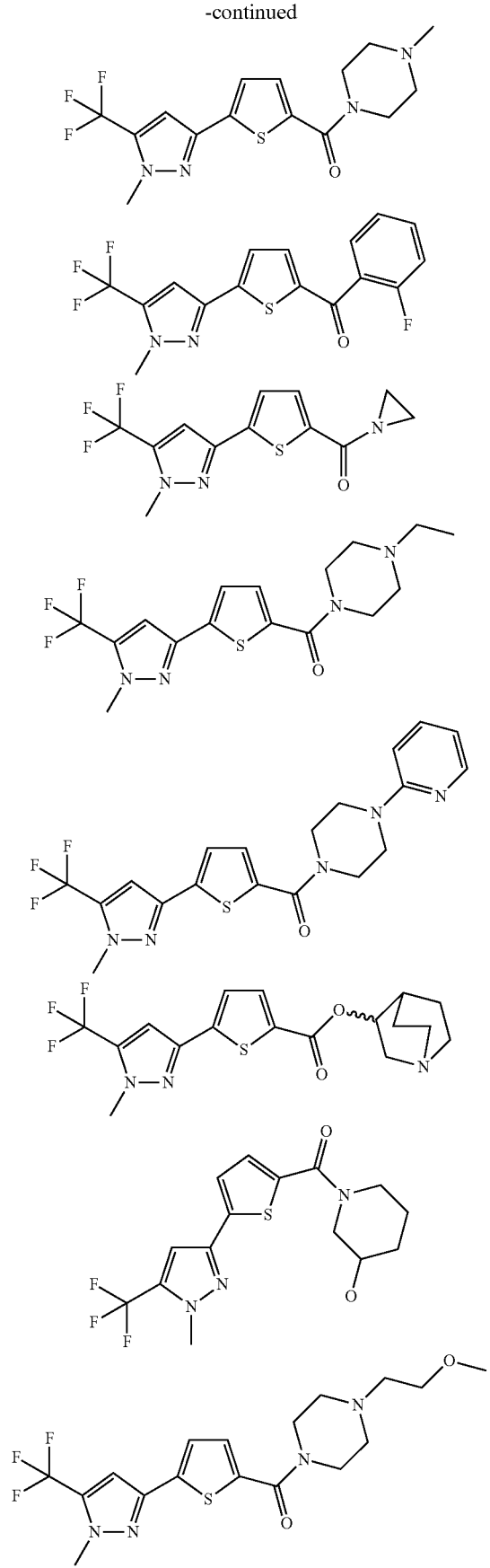
76
-continued
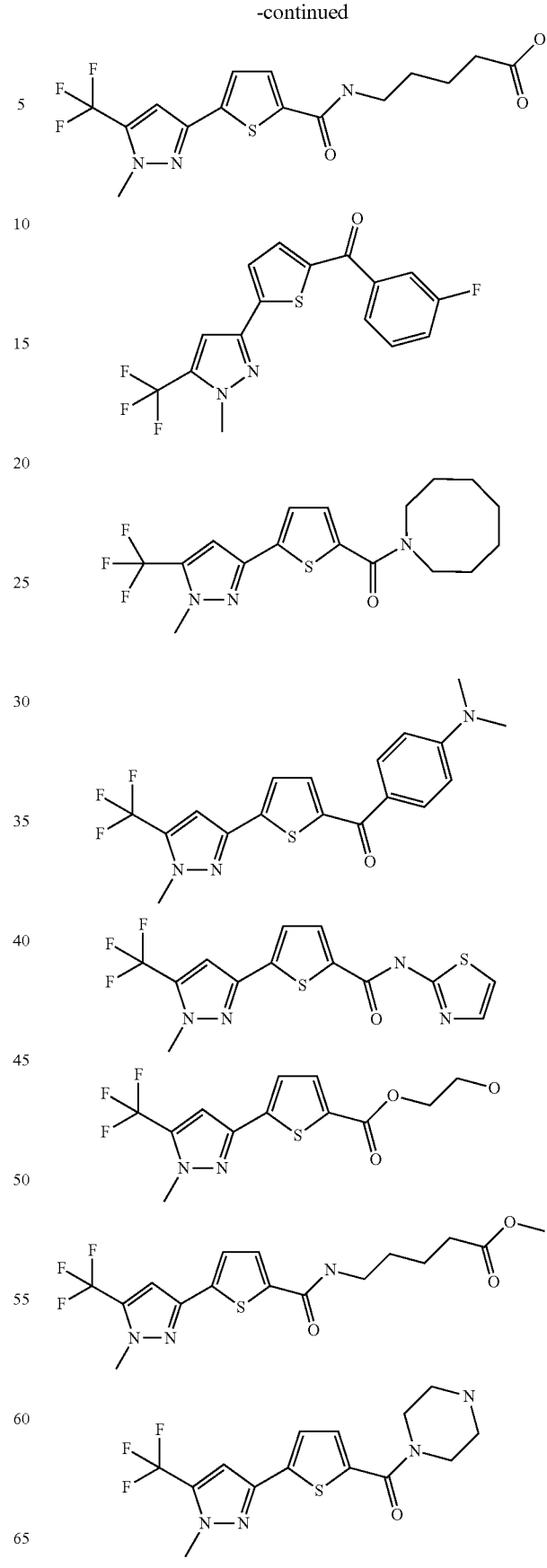

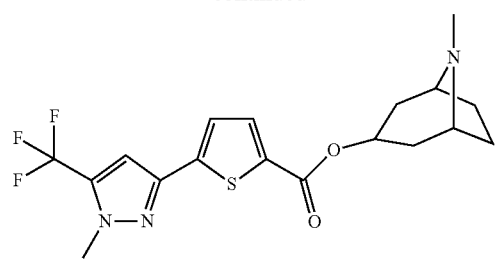
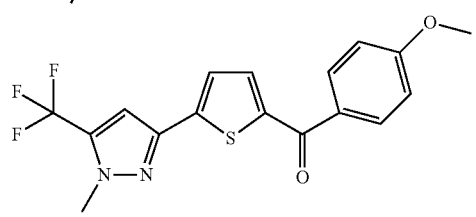
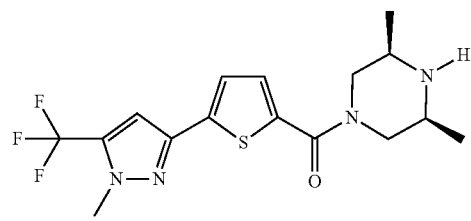
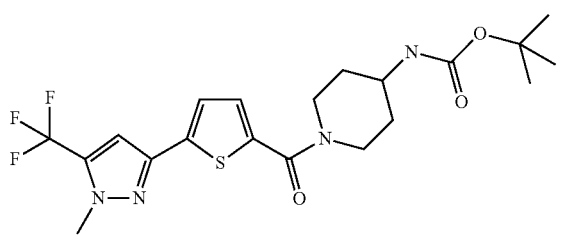
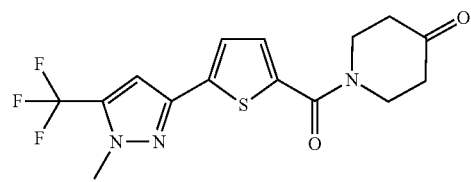
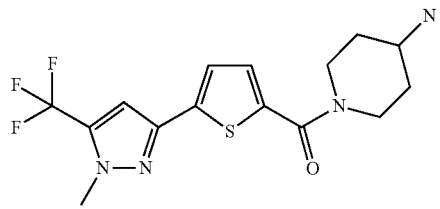
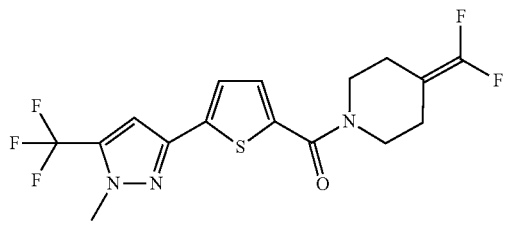
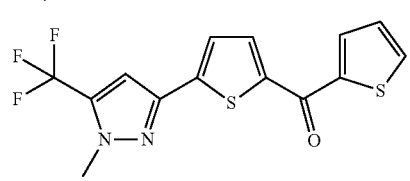
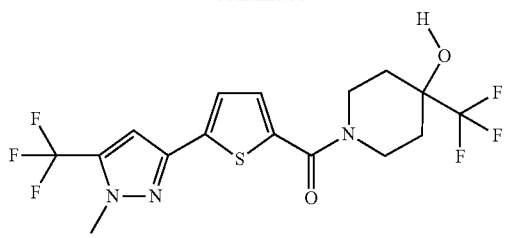
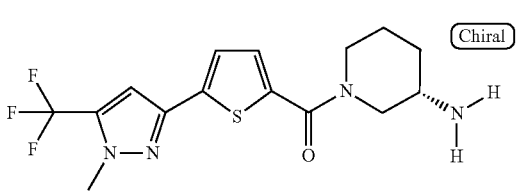
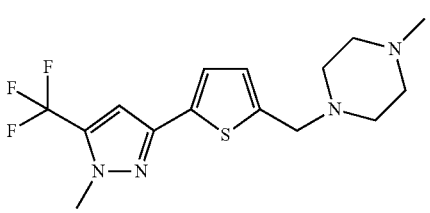
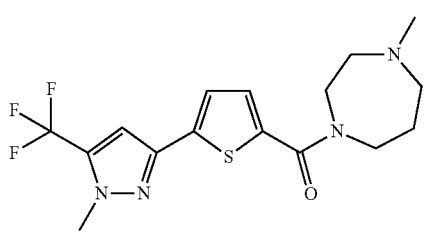
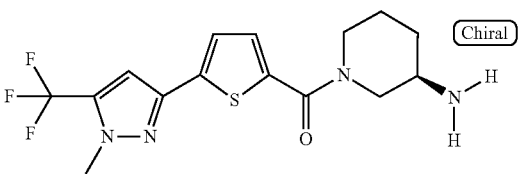
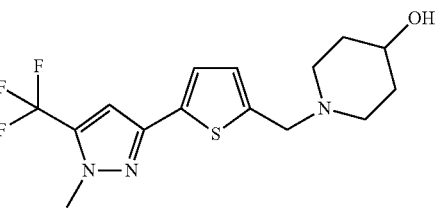
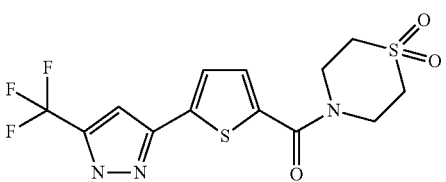
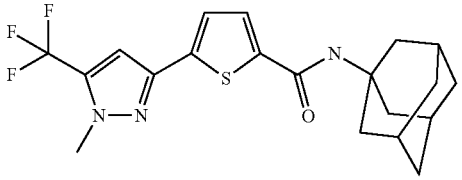

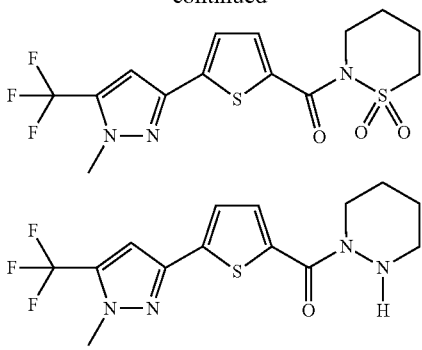

85 The method of any of the previous embodiments wherein the compound, or a pharmaceutically acceptable salt thereof, of formula I is the compound of any of the previous embodiments.

86. A compound of formula I

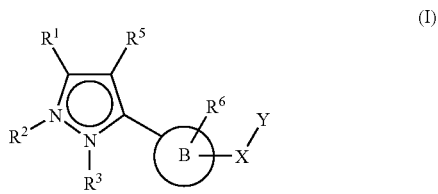

wherein:

$R^1$ is $(C_1-C_6)$alkyl, $(C_1-C_6)$haloalkyl, or aryl, unsubstituted or substituted with one or more $R_e$;

one of $R^2$ and $R^3$ is absent and the other is hydrogen, $(C_1-C_6)$alkyl, halo$(C_1-C_6)$alkyl, hydroxy$(C_1-C_6)$alkyl, $(C_3-C_8)$cycloalkyl, amino$(C_2-C_6)$alkyl, or aryl, each unsubstituted or substituted with one or more groups selected from alkyl, halo, haloalkyl or nitro, Het, $(C_3-C_8)$cycloalkyl$(C_1-C_6)$ alkyl, aryl$(C_1-C_6)$alkyl, $(C_1-C_6)$ or Het$(C_1-C_6)$alkyl;

B is 5- to 12-membered monocyclic or bicyclic Het;

X is —C(=O);

Y is —OR$^4$;

$R^4$ is an 8-12 membered bicyclic ring system comprising carbon atoms and optionally comprising one or more heteroatoms selected from O, S, and NR$_c$, wherein each ring system is optionally substituted with one or more $R_d$;

each $R_c$ is independently hydrogen, aryl, S(O)$_2$, $(C_1-C_6)$ alkanoyl, hydroxy$(C_1-C_6)$alkyl, alkoxy$(C_1-C_6)$alkyl, Het, $(C_1-C_6)$alkoxycabonyl or $(C_1-C_6)$alkyl, unsubstituted or substituted with one or more subtituents $R_e$;

each $R_d$ is independently halo, hydroxy, cyano, nitro, azido, amino, $(C_1-C_6)$alkylamino, amino$(C_1-C_6)$alkyl, amido, $(C_1-C_6)$alkyamido, aryl amido, carboxylic acid, $(C_1-C_6)$alkyl, hydroxy$(C_1-C_6)$alkyl, halo$(C_1-C_6)$alkyl, $(C_1-C_6)$ alkoxy, halo$(C_1-C_6)$alkoxy, $(C_1-C_6)$alkanoyl, $(C_1-C_6)$ alkoxycarbonyl, carboxy, $(C_1-C_6)$alkanoyloxy, Het, aryl, Het $(C_1-C_6)$alkyl, or aryl$(C_1-C_6)$alkyl, $(C_1-C_6)$alkylaryl, sulfonyl, sulfonamido, urea, carbamate, unsubstituted or substituted with one or more substituents $R_e$, or two $R_d$ come together with the atom to which they are attached to form a ketone or spirocyclic carbocyclic or heterocyclic ring, or two $R_d$ come together with the atoms to which they are attached to form a bicyclic carbocyclic or heterocyclic ring, wherein each spirocyclic or bicyclic ring is unsubstituted or substituted with one or more halo, hydroxy, cyano, nitro, azido, $(C_1-C_6)$ alkyl, hydroxy$(C_1-C_6)$alkyl, halo$(C_1-C_6)$alkyl, $(C_1-C_6)$ alkoxy, halo$(C_1-C_6)$alkoxy, $(C_1-C_6)$alkanoyl, $(C_1-C_6)$ alkoxycarbonyl, carboxy, $(C_1-C_6)$alkanoyloxy, NR$_f$R$_g$, R$_f$R$_g$NC(=O)—, phenyl, or phenyl$(C_1-C_6)$alkyl, sulfonyl, sulfonamido, urea, carbamate, wherein R$_f$ and R$_g$ together with the nitrogen to which they are attached form a piperidino, pyrrolidino, morpholino, or thiomorpholino ring, unsubstituted or substituted with one or more substituents $R_e$;

each $R_e$ is independently selected from halo, hydroxy, cyano, nitro, azido, $(C_1-C_6)$alkyl, Het, aryl, $(C_1-C_6)$alkylHet, $(C_1-C_6)$alkylaryl, $(C_1-C_6)$alkylHet$(C_1-C_6)$alkyl, $(C_1-C_6)$ alkylaryl$(C_1-C_6)$alkyl, $(C_1-C_6)$halo alkyl, $(C_1-C_6)$alkoxy, $(C_1-C_6)$haloalkoxy, $(C_1-C_6)$alkanoyl, $(C_1-C_6)$alkoxycarbonyl, carboxy, and $(C_1-C_6)$alkanoyloxy;

$R^5$ is H, $(C_1-C_6)$alkyl, $(C_1-C_6)$alkenyl, $(C_1-C_6)$alkynyl, aryl$(C_1-C_6)$alkyl; and each $R^6$ is H, $(C_1-C_6)$alkyl, amino, amido, keto, or aryl$(C_1-C_6)$alkyl;

or a pharmaceutically acceptable salt thereof.

87. The compound of any of the previous embodiments that is selected from the group consisting of

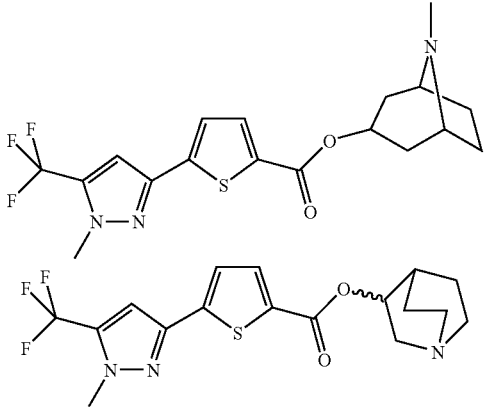

88. The compound of any of the previous embodiments wherein Y=R$^4$.

BRIEF DESCRIPTION OF THE FIGURES

FIG. 1 shows data for two representative compounds of the invention in the Contextual Memory Assay described herein below. Specifically, compounds 162 and 177, injected 20 minutes before training, significantly enhanced contextual memory in mice ("N" indicates number of subjects used in experiments)

DETAILED DESCRIPTION

The following definitions are used, unless otherwise described: Halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic; Het encompasses a radical of a monocyclic, bicyclic, or tricyclic ring system containing a total of 3-20 atoms, including carbon atoms and one or more heteroatoms selected from oxygen, sulfur, and N(X) wherein X is absent or is H, O, $(C_1-C_4)$alkyl, phenyl or benzyl, wherein one or more ring carbons of Het can optionally be substituted with oxo (=O); Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. The term Het encompasses Heteroaryl. Where a dashed line (————) appears in a structure either, a single or double bond can be present.

The term "animal" as used herein includes birds, reptiles, and mammals (e.g. domesticated mammals and humans).

The term "selectively inhibiting" as used herein means that a compound inhibits the activity of MAO-B to a greater extent than it inhibits the activity of MAO-A (in vitro or in vivo). In one embodiment of the invention, the compound of formula I inhibits the activity of MAO-B two times more than it inhibits the activity of MAO-A. In another embodiment of the invention, the compound of formula I inhibits the activity of MAO-B five times more than it inhibits the activity of MAO-A. In another embodiment of the invention, the compound of formula I inhibits the activity of MAO-B ten times more than it inhibits the activity of MAO-A. In another embodiment of the invention, the compound of formula I inhibits the activity of MAO-B one hundred times more than it inhibits the activity of MAO-A.

The term "psychiatric disorder" as used herein includes psychotic disorders, neurological disorders and neurotic disorders. The term includes schizophrenia, age-associated memory impairment (AAMI); mild cognitive impairment (MCI), delirium (acute confusional state); depression, dementia (sometimes further classified as Alzheimer's or non-Alzheimer's type dementia); Alzheimer's disease; Parkinson's disease; Huntington's disease (chorea); mental retardation; (e.g., Rubenstein-Taybi and Downs Syndrome); cerebrovascular disease (e.g., vascular dementia, post-cardiac surgery); affective disorders; psychotic disorders; autism (Kanner's Syndrome); neurotic disorders; attention deficit disorder (ADD); subdural hematoma; normal-pressure hydrocephalus; brain tumor; head trauma (postconcussional disorder) or brain trauma.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, stereoisomeric, or regioisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine MAO-B inhibiting activity using the standard tests described herein, or using other similar tests which are well known in the art.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_3-C_8)$cycloalkyl can be cyclopropyl, cyclobutyl, cyclopentyl, or cyclohexyl; $(C_3-C_8)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; cyano$(C_2-C_6)$alkyl can be 2-cyanoethyl, 3-cyanopropyl, 2-cuanopropyl, or 4-cyanobutyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 2-hydroxyethyl, 2-hydroxypropyl, or 2,4-hydroxybutyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; $(C_1-C_6)$alkoxy$(C_2-C_6)$alkyl can be 2-methoxyethyl, 2-ethoxyethyl, 2,2-dimethoxyethyl, 3-ethoxypropyl, 4,4-dimethoxybutyl; cyano$(C_1-C_6)$alkyl can be cyanomethyl or cyanoethyl; $(C_1-C_6)$alkoxycarbonyl$(C_1-C_6)$alkyl can be methoxycarbonylmethyl, ethoxycarbonylmethyl, methoxycarbonylethyl, or ethoxycarbonylethyl; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl or its N-oxide).

A specific value for $R^1$ is trifluoromethyl, phenyl, methyl, isopropyl, difluoromethyl, chloro-difluoromethyl, or pentafluoroethyl.

A specific value for $R^2$ is methyl, ethyl, propyl, isopropyl, phenyl, cyclopentyl, 2-pyridyl, 2-morpholinoethyl, or 2-hydroxyethyl.

A specific value for $R^3$ is methyl, ethyl, propyl, isopropyl, 2-pyridyl, cyclopentyl, phenyl, 4-trifluoromethylphenyl, 2-pyridyl, 3-trifluoromethylphenyl, 2-trifluoromethylphenyl, 2,2,2-trifluoroethyl, 2-hydroxyethyl, 4-chlorophenyl, benzyl, 4-nitrophenyl, hydrogen, 2-morpholinoethyl, or cyclohexyl.

In a preferred embodiment, $R^3$ is absent.

A specific value for B is 2,5-thiophenediyl, 1,4-benzenediyl, 1,3-benzenediyl, 2,4-pyridinediyl, or 2,6-pyridinediyl.

A specific value for X is —C(=O)Y, —C(=S)Y, —C(R$^4$)$_2$Y, or —S(O)$_2$Y.

A specific value for Y is $R^4$, —N(R$^4$)$_2$, —OR$^4$, —SR$^4$, or —C(R$^4$)$_3$.

A specific value for $R^4$ is hydrogen, methyl, ethyl, butyl, propyl, isopropyl, 2-fluorophenethyl, 2-pyrrolidinoethyl, 2-furylmethyl, 4-methylbenzyl, cyclopropylmethyl, cyclohexylmethyl, 4-methoyxbenzyl, 4-fluorobenzyl, 4-pyridylmethyl, 4-chlorobenzyl, cyclohexyl, benzyl, 4-methylphenyl, 3-pyrrolidin-1-ylpropyl, 3-chlorobenzyl, 3,5-dimethylbenzyl, 2-(ethylthio)ethyl, isobutyl, allyl, 2-hydroxyethyl, phenyl, 3-fluoro-6-methylbenzyl, 3-pyridylmethyl, 4-fluorophenethyl, 2-phenoxyethyl, 5-methyl-fur-2-ylmethyl, 2,2,2-trifluoroethyl, 2-methoxyethyl, 2-methylbutyl, 2-imidazol-4-ylethyl, phenethyl, 2-morpholinoethyl, 3-methylbutyl, 2-piperidinoethyl, 3-methoxypropyl, 3-chlorobenzyl, 2-furylmethyl, 3,5-difluorobenzyl, 2-(2-furyl)ethyl, 3-imidazol-1-ylpropyl, 2-cyanoethyl, 2-ethylbutyl, 2-pyrid-3-ylethyl, S-α-hydroxy-β-methylphenethyl, S-α-methylphenethyl, 4,4-dimethoxybutyl, 3-(2-oxopyrrolidin-1-yl)propyl, 2,2-dimethoxyethyl, 4-methylphenethyl, cyanomethyl, 3-ethoxypropyl, 3-(N,N-dimethylamino)propyl, 3-morpholinopropyl, 2-hydroxypropyl, 2-methylpropyl, ethoxycarbonylmethyl, 2-methylphenyl, 2-hydroxyphenyl, tetrahydrofuran-2-ylmethyl, R-tetrahydrofuran-2-ylmethyl, S-tetrahydrofuran-2-ylmethyl, 2-aminoethyl, 5-aminopentyl, 4-(4-chlorophenyl)piperazine, or N-piperidinyl.

A specific value for both $R^4$ taken together with Y to which they are attached is morpholine, piperidine, 4-methylpiperidine, 2,6-dimethylmorpholine, 2-hydroxymethylpyrrolidine, pyrrolidine, azetidine, 3-pyrroline, 4-(4-fluorophenyl)piperazine, 3,5-dimethylmorpholine, 4-(2-hydroxyethyl)piperazine, 3,5-dimethylpiperidine, indoline, R-3-hydroxypyrrolidine, 1,4-Dioxa-8-aza-spiro[4.5]decane, 1,2,3,4-tetrahydroisoquinoline, 2,3,4,5,6,7-hexahydroazepine, 4-hydroxymethylpiperidine, 4-(N,N-dimethylamino)piperidine, 4-(1-pyrrolidinyl)piperidine, 4-phenylpiperidine, 4-hydroxy-4-phenylpiperidine, 4-(carboxamide)piperidine, 4-hydroxypiperidino, 4-phenylpiperazine, 4-acetylpiperazine, 4-benzylpiperidine, 4-trifluoromethylpiperidine, 3-trifluoromethyl piperidine, 3-fluoropiperidine, 4-fluoropiperidine, 4,4 difluoropiperidine, 3,3-difluoropiperidine, 4-isopropylpiperizine, 4-tbutoxycarbonyl-piperizine, 4-methoxy piperidine, pyrrolidine, or 3-fluoropyrrolidine.

A specific value for both $R^4$ taken together with Y=carbon to which they are attached is cyclohexyl, phenyl, 4-fluorophenyl or 4-trifluoromethylphenyl.

A specific group of compounds are compounds wherein one $R^4$ is hydrogen and the other is hydrogen, methyl, ethyl, butyl, propyl, isopropyl, 2-fluorophenethyl, 2-pyrrolidinoethyl, 2-furylmethyl, 4-methylbenzyl, cyclopropylmethyl, cyclohexylmethyl, 4-methoyxbenzyl, 4-fluorobenzyl, 4-pyridylmethyl, 4-chlorobenzyl, cyclohexyl, benzyl, 4-methylphenyl, 3-pyrrolidin-1-ylpropyl, 3-chlorobenzyl, 2-furylmethyl, 3,5-dimethylbenzyl, 2-(ethylthio)ethyl, isobutyl, allyl, 2-hydroxyethyl, phenyl, 3-fluoro-6-methylbenzyl, 3-pyridylmethyl, 4-fluorophenethyl, 2-phenoxyethyl, 5-methyl-fur-2-ylmethyl, 2,2,2-trifluoroethyl, 2-methoxyethyl, 2-methylbutyl, 2-imidazol-4-ylethyl, phenethyl, 2-morpholinoethyl, 3-methylbutyl, 2-piperidinoethyl, 3-methoxypropyl, 3-chlorobenzyl, 2-furylmethyl, 2-ethylthioethyl, 3,5-difluorobenzyl, 2-(2-furyl)ethyl, 3-imidazol-1-ylethyl, 2-cyanoethyl, 2-ethylbutyl, 2-pyrid-3-ylethyl, S-α-hydroxy-β-methylphenethyl, S-α-methylphenethyl, 4,4-dimethoxybutyl, 3-(2-oxopyrrolidin-1-yl)propyl, 2,2-dimethoxyethyl, 4-methylphenethyl, cyanomethyl, 3-ethoxypropyl, 3-(N,N-dimethyl)propyl, 3-morpholinopropyl, 2-hydroxypropyl, 2-methylpropyl, ethoxycarbonylmethyl, 2-methylphenyl, 2-hydroxyphenyl, tetrahydrofuran-2-ylmethyl, R-tetrahydrofuran-2-ylmethyl, S-tetrahydrofuran-2-ylmethyl, 2-aminoethyl, 5-aminopentyl, 4-(4-chlorophenyl)piperazine, or N-piperidinyl.

A specific value for $R^5$ is methyl, ethyl, benzyl, propyl, and allyl.

A specific value for $R^6$ is methyl.

A specific value for Het is a radical of a monocyclic or bicyclic ring system containing a total of 3-12 atoms, including one or more carbon atoms, and one or two heteroatoms selected from oxygen, sulfur, and N(X) wherein X is absent or is H, O, (C1-C4)alkyl, phenyl or benzyl. Specific values for Het include piperidine, morpholine, thiomorpholine, pyrrolidine, imidazole, furan, pyridine, 2-oxopyrrolidine, furan, tetrahydrofuran, piperazine, and azetidine.

Processes for preparing compounds of formula I are provided as further embodiments of the invention and are illustrated by the following procedures in which the meanings of the generic radicals are as given above unless otherwise qualified.

A compound of formula I can be prepared using the general synthetic schemes illustrated below. Bis aryl or Het. For example, a compound of formula I wherein X is —C(=O)— can be prepared by reacting an intermediate acid of formula 100 with an amine of formula 101.

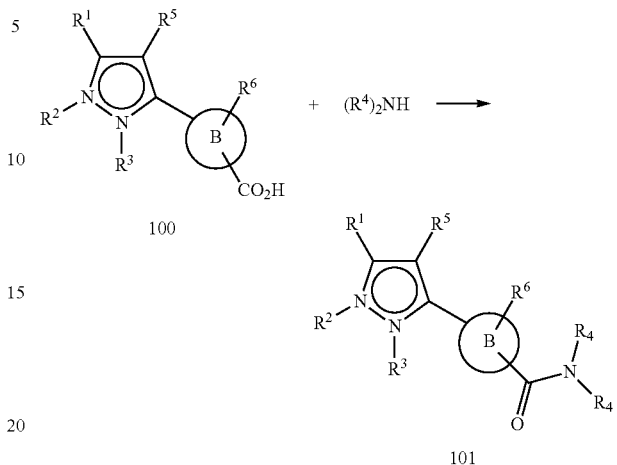

A solution of the acid 100 in a suitable solvent (e.g. DMF) is treated with EDC-HCl, HOBT hydrate, and Hunig's base to activate the acid; the requsite amine is added to the activated acid to provide an amide of formula 101. Standard aqueous work-up followed by normal phase, flash chromatography provides the purified amide. The amine can also be coupled to acid 100 via activation with oxalyl chloride or thionyl chloride.

A compound of formula 103a/b can be prepared by reacting an intermediate diketone of formula 102 with a hydrazine of formula ii, as illustrated below.

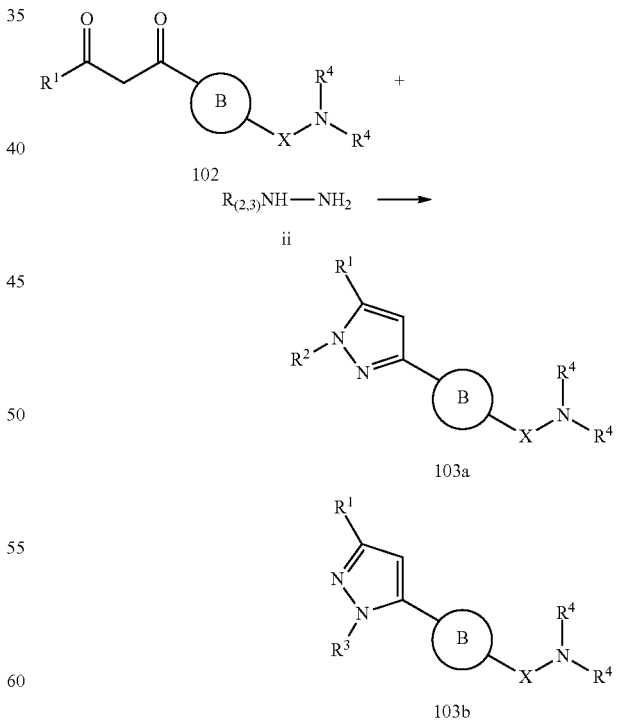

It will be understood that the above reaction, as well as other reactions that are useful for preparing or modifying pyrazole rings may provide a single regioisomer or a mixture of regioisomers (e.g. a mixture of compounds of formula I wherein $R^2$ is absent and compounds of formula I wherein $R^3$ is absent). When a mixture results, the regioisomers can be separated using a number of standard techniques (e.g. chromatography) that are well known.

Intermediate acids of formula 100a and 100b can be prepared as illustrated below.

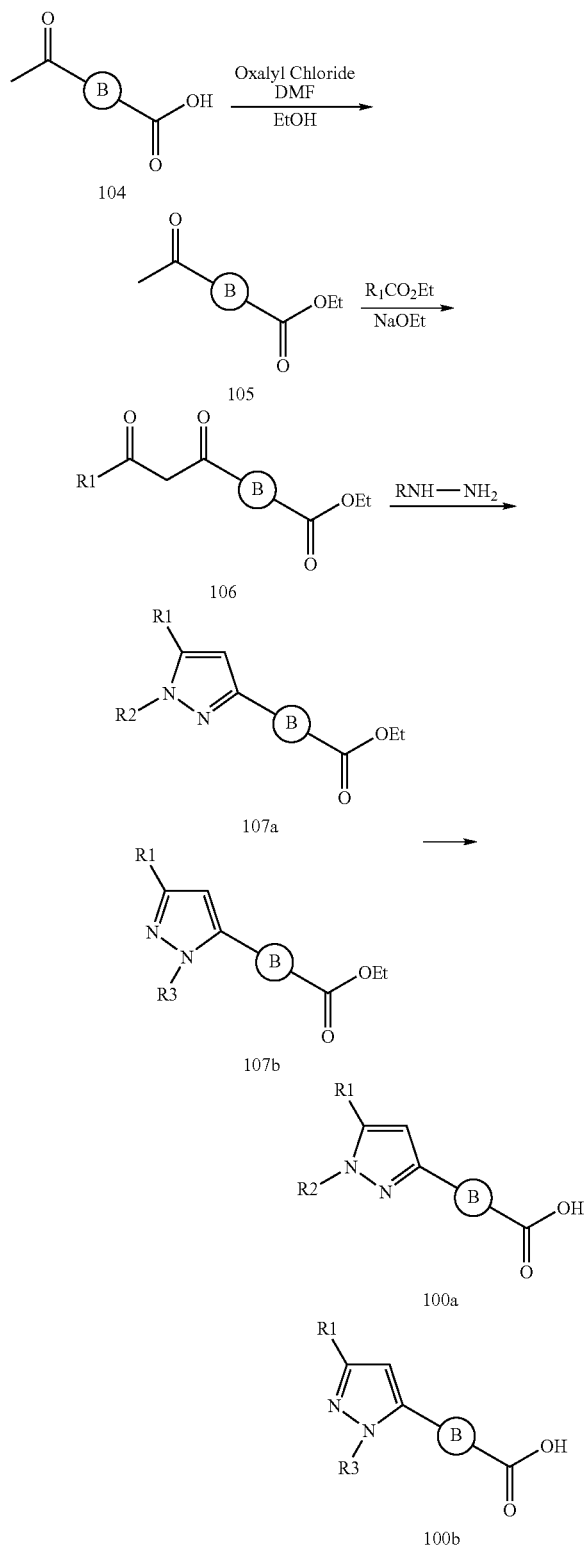

An acid of formula 104 can be converted to the corresponding ester using any suitable conditions (e.g. by treatment with oxalyl chloride in a suitable solvent followed by treatment with an alcohol). Conversion of the ester 105 to the diketone 106 followed by treatment with the requisite hydrazine provides the pyrazoles 107a/b. Subsequent hydrolysis of the ester under standard conditions provides the acids of formula 100a/b. An intermediate diketone of formula 102 can be prepared from a keto-acid of formula 108 as illustrated below.

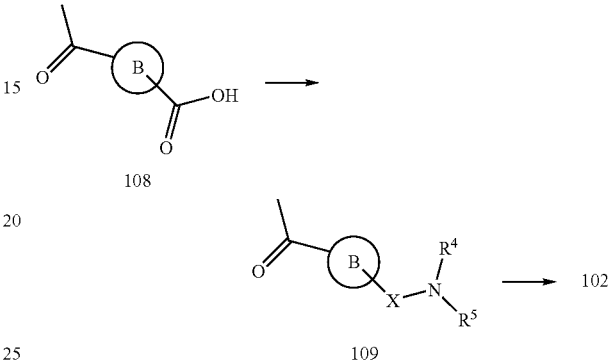

The acid functionality of 108 can be converted to the group —XN($R^4$)$_2$ of compound 109 under standard conditions. The ketone 109 can be converted to the diketone 102 under standard conditions, for example, by treatment with an ester of formula $R^1$COOEt.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.15 to about 100 mg/kg, e.g., from about 1 to about 75 mg/kg of body weight per day, such as 0.75 to about 50 mg per kilogram body weight of the recipient per day, preferably in the range of 1 to 90 mg/kg/day, most preferably in the range of 1 to 60 mg/kg/day.

The compound is conveniently administered in unit dosage form; for example, containing 1 to 1000 mg, conveniently 10 to 750 mg, most conveniently, 5 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds of the invention can also optionally be administered in combination with one or more other therapeutic agents that are effective to improve cognition and/or one or more therapeutic agents that are effective to treat schizophrenia, age-associated memory impairment (AAMI); mild cognitive impairment (MCI), delirium (acute confusional state); depression, dementia (sometimes further classified as Alzheimer's or non-Alzheimer's type dementia); Alzheimer's disease; Parkinson's disease; Huntington's disease (chorea); mental retardation; (e.g., Rubenstein-Taybi and Downs Syndrome); cerebrovascular disease (e.g., vascular dementia, post-cardiac surgery); affective disorders; psychotic disorders; autism (Kanner's Syndrome); neurotic disorders; attention deficit disorder (ADD); subdural hematoma; normal-pressure hydrocephalus; brain tumor; head trauma (postconcussional disorder) or brain trauma (see DSM-IV, APA 1994).

The ability of a compound of the invention to act as an inhibitor of MAO-B can be determined using pharmacological models which are well known to the art, or using the following assay.

MAO Inhibition Assay

MAO enzymatic assay was performed according to the fluorometric method described by Matsumoto and colleagues (Matsumoto, et. al., *Clin. Biochem.*, 1985 18, 126-129). with the following modifications. Human recombinant MAO-A and MAO-B expressed in insect cells were used. For both assays, test compound and/or vehicle was preincubated with purified enzyme in phosphate buffer pH 7.4 for 15 minutes at 37° C. The reaction was initiated by addition of 50 µM kynuramine. Following a 60 minute incubation period, the reaction was terminated by the addition of 6 N NaOH. The amount of 4-hydroxyquinoline formed was determined spectrofluorimetrically at 325 nm/465 nm. Results were converted to percent inhibition and $IC_{50}$'s were determined using the XLfit program from IDBS (ID Business Solutions Ltd., 2 Occam Court, Surrey Research Park, Guildford, Surrey, GU2 7QB UK). Representative compounds of the invention were evaluated in this assay. Typically, the compounds of the invention showed MAO-B inhibitory properties at 0.1-10 µM, typically at 5-100%. Preferred compounds also demonstrated selectivity for MAO-B over MAO-A.

The ability of a compound to activate CREB can be determined using the following assay (see WO 2004/016227).

CREB Activation Assay

The following CRE-Luci assay is a high throughput, well-based method for identifying compounds that enhance cognition by increasing CREB pathway function. The assay enables the identification of cognitive enhancers that do not affect CREB pathway function alone, but act to increase (enhance) CREB pathway function in combination with a CREB function stimulating agent.

The assay is carried out by (a) contacting host cells (particularly cells of neural origin (e.g. human neuroblastoma SK-N-MC cells) having a luciferase gene operably linked to a CRE promoter with a test compound and a suboptimal dose of a CREB function stimulating agent (e.g., forskolin); (b) determining luciferase activity in the host cells which have been contacted with the test compound and with the CREB function stimulating agent; and (c) comparing the luciferase activity determined in step (b) with the luciferase activity in control cells which have been contacted with the CREB function stimulating agent and which have not been contacted with the test compound (i.e., control cells which have been contacted with the CREB function stimulating agent alone).

Host cells comprising luciferase gene operably linked to a CRE-promoter can be manufactured by introducing into cells a DNA construct comprising a luciferase gene operably linked to a CRE promoter. DNA constructs can be introduced into cells according to methods known in the art (e.g., transformation, direct uptake, calcium phosphate precipitation, electroporation, projectile bombardment, using liposomes). Such methods are described in more detail, for example, in Sambrooke et al., Molecular cloning: A laboratory Manual, $2^{nd}$ edition (New York: Cold Spring Harbor University Press) (1989); and Ausubel, et al., Current Protocols in Molecular Biology (New York: John Wiley & Sons) (1998).

SK-N-MC cells stably transfected with CRE-luc construct are seeded in 96-well, white assay plates (PerkinElmer) at a concentration of 20,000 cells/well in 100 µL MEM complete media. These cells are incubated in a $CO_2$ incubator under standard cell culture condition. After 18 to 24 hours of incubation, cells are treated with either a vehicle control (DMSO, Sigma), the test compounds (5 µM final concentration), or a positive control (HT-0712, 5 µM final concentration) (16 wells for each treatment) for 2 hours. Forskolin (5 µM final concentration, Sigma) is then added to 8 wells of each treatment group and an equivalent amount of DMSO is added to the other 8 wells. Six hours after forskolin addition, luciferase activity is measured by adding 25 µL of assay reagent (BritLite kit, PerkinElmer) to each well. After incubation at room temperature for 3 minutes, luminescence is detected using a Wallac Victor 5 plate reader (PerkinElmer). The transcription induction ratio is derived by normalizing the luciferase activity of the compound or positive control in the presence of forskolin over forskolin treatment alone. The compound treatment alone serves as control to determine whether compound can active CRE promoter by itself.

Representative compounds of the invention were found to increase CREB pathway function using this assay.

The ability of a compound to modulate cognitive behavior can be evaluated using the following assay to measure memory after contextual fear conditioning.

Contextual Memory Assay: Fear Conditioning

Contextual memory is a form of Pavlovian fear conditioning in which a naïve mouse is placed into a novel chamber (context) containing distinct visual, olfactory and tactile cues. After a couple of minutes of acclimation, the mouse receives a brief, mild electric shock to its feet. From this negative experience, the mouse will remember for months that that chamber is dangerous. When placed back into the same context at some later time after training, the mouse's natural response to danger is to "freeze," sitting stone still for many seconds. This is similar to what happens to humans when they experience fear. The percent of time during an observation period that the mouse spends frozen represents a quantitative measure (memory score) of its memory of the context.

Contextual conditioning has been extensively used to investigate the neural substrates mediating fear-motivated learning (Phillips, R. G., LeDoux, J. E., *Behav Neurosci,* 1992, 106, 274-285; Kim, J. J., et. al., *Behav Neurosci,* 1993, 107, 1093-1098; Bourtchouladze, R., et. al., *Learn Mem,* 1998, 5, 365-374; and Bourtchouladze, R et. al., *Cell,* 1994, 79, 59-68). Contextual conditioning has been also used to study the impact of various mutations on hippocampus-dependent memory (Bourtchouladze, R., et. al., *Learn Mem,* 1998, 5, 365-374; Bourtchouladze, R., et. al., *Cell,* 1994, 79, 59-68.; Silva, A. J., et. al., *Curr Biol,* 1996, 6, 1509-1518; Kogan J. L. et al., *Curr Biol,* 1997, 7, 1-11; Abel, T., et. al., *Cell,* 1997, 88, 615-626; and Giese K. P., et al., *Science,* 1998, 279, 870-873); and strain and genetic background differences in mice (Logue, S. F., et. al., *Behav Neurosci,* 1997, 111, 104-113; and Nguyen, P. V., et. al., *Learn Mem,* 2000, 7, 170-179). Because robust memory can be triggered with a few minutes training session, contextual conditioning has been especially useful to study biology of temporally distinct processes of short- and long-term memory (Kim, J. J., et. al., *Behav Neurosci,* 1993, 107, 1093-1098; Bourtchouladze, R., et. al., *Learn Mem,* 1998, 5, 365-374; Bourtchouladze, R., et. al., *Cell,* 1994, 79, 59-68; and Abel, T., et. al., *Cell,* 1997, 88, 615-626). As such, contextual conditioning is an excellent model to evaluate the role of various novel drug-compounds in hippocampus-dependent memory.

Young-adult (10-12 weeks old) C57BL/6 male mice and Sprague Dawley male rats of 250-300 g (Taconic, N.Y.) were used. Mice were group-housed (5 mice) in standard laboratory cages while rats were housed in pairs and maintained on a 12:12 light-dark cycle. The experiments were always conducted during the light phase of the cycle. With the exception of testing times, the mice had ad lib access to food and water. The experiments were conducted according with the Animal Welfare assurance #A3280-01 and animals were maintained in accordance with the animal Welfare Act and Department of Health and Human Services guide.

To assess contextual memory, a modified contextual fear conditioning task originally developed for evaluation of memory in CREB knock-out mice was used (Bourtchouladze, R., et. al., *Cell,* 1994, 79, 59-68). On the training day, the mouse was placed into the conditioning chamber (Med Associates, Inc., VA) for 2 minutes before the onset of unconditioned stimulus (US), 0.5 mA, of 2 sec foot shock. The US was repeated two times with a 1 min inter-trial interval between shocks. Training was performed by automated software package (Med Associates, Inc., VA). After the last training trial, the mice were left in the conditioning chamber for another 30 sec and were then placed back in their home cages. 24 hours after training, the mouse was placed into the same training chamber and contextual memory was assessed by scoring freezing behavior ('freezing' serves as memory score). Freezing was defined as the complete lack of movement in intervals of 5 seconds (Kim, J. J., et. al., *Behav Neurosci,* 1993, 107, 1093-1098; Phillips, R. G., LeDoux, J. E., *Behav Neurosci,* 1992, 106, 274-285; Bourtchouladze, R., et. al., *Learn Mem,* 1998, 5, 365-374; Bourtchouladze, R., et. al., *Cell,* 1994, 79, 59-68; and Abel, T., et. al., *Cell,* 1997, 88, 615-626). Total testing time lasted 3 minutes. After each experimental subject, the experimental apparatus was thoroughly cleaned with 75% ethanol, water, dried, and ventilated for a few minutes.

All experiments were designed and performed in a balanced fashion, meaning that (i) for each experimental condition (e.g. a specific dose-effect) an equal number of experimental and control mice was used; and (ii) each experimental condition was replicated 2-3 independent times, and replicate days were added to generate final number of subjects. The proceeding of each experiment was filmed. In each experiment, the experimenter was unaware (blind) to the treatment of the subjects during training and testing. Data were analyzed by Student's unpaired t test using a software package (Statview 5.0.1; SAS Institute, Inc). All values in the text and figures are expressed as mean±SEM.

Compounds were dissolved in 1% DMSO/PBS and administered intraperitonially (I.P.) in a volume of 8 ml/kg 20 min before training. Control animals received vehicle alone (1% DMSO/PBS). For oral administration the compounds were dissolved in 30% DMSO/70% CMC. Consequently, control animals received 30% DMSO/70% CMC. For each training and drug-injecting procedure, an experimentally naïve group of animals were used.

To evaluate the effects of Compound 162 and Compound 177 on contextual memory, mice were injected with a compound or vehicle 20 minutes before training and trained with 2 training trials (US). Mice were than tested in the same context 24 hours after training (FIG. 1). I.P. administration of 0.01 mg/kg of each compound significantly facilitated freezing to context 24 hr after training. Representative compounds of the invention were also tested and found to produce behavioral effects when administered orally.

The ability of a compound to modulate cognitive behavior can also be evaluated using the following Object Recognition Assay.

Object Recognition Assay

Object recognition is an ethologically relevant task for rodents, which does not result from negative reinforcement (foot shock). This task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one (Bourtchouladze, R., et. al., *Proc Natl Acad Sci USA,* 2003, 100, 10518-10522). Recent neuroimaging studies in humans demonstrated that memory in object recognition depends on prefrontal cortex (PFC) (Deibert, et. al., *Neurology,* 1999, 52, 1413-1417). Consistent with these findings, rats with the PFC lesions show poor working memory when they are required to discriminate between familiar and novel objects (Mitchell, J. B., Laiacona, J., *Behav Brain Res,* 1998, 97, 107-113). Other studies on monkeys and rodents suggest that the hippocampus is important for novel object recognition (Teng, E., et. al., *J. Neurosci,* 2000, 20, 3853-3863; and Mumby, D. G., *Brain Res,* 2001, 127, 159-181). Hence, object recognition provides an excellent behavioral model to evaluate drug-compound effects on cognitive task associated with function of hippocampus and cortex.

Prior to initiation of training, animals were handled for 3-5 minutes for 5 days. Training and testing were performed identically for mice and rats with an exception of training apparatus dimensions (for mice: a Plexiglas box of L=48 cm; W=38 cm and H=20 cm; for rats: a Plexiglas box of L=70 cm; W=60 cm and H=35 cm). The day before training, an individual animal was placed into a training apparatus located in a dimly lit room and allowed to habituate to the environment for 15 minutes (also see Pittenger, C., et. al., *Neuron,* 2002, 34, 447-462; and Bourtchouladze, R., et. al., *Proc Natl Acad Sci USA,* 2003, 100, 10518-10522). Training was initiated 24 h hours after habituation. An animal was placed back into the training box, which contained two identical objects (e.g. a small conus-shape object), and was allowed to explore these objects. The objects were placed into the central area of the box and the spatial position of objects (left-right sides) was counterbalanced between subjects. Animals were trained for 15 minutes. To test for memory retention, animals were observed for 10 minutes 24 hours after training. A rodent was presented with two objects, one of which was used during training, and thus was 'familiar' and the other of which was novel (e.g. a small pyramid-shape object). To insure that the discrimination targets do not differ in smell, after each experimental subject, the apparatus and the objects were thoroughly cleaned with 90% ethanol, dried and ventilated for a few minutes.

The experiments were videotaped via an overhead video camera system. Types were then reviewed by a blinded observer and the following behavioral parameters were determined: time of exploration of an each object; the total time of exploration of the objects; number of approaches to the objects; and time (latency) to first approach to an object. The discrimination index—memory score—was determined as described previously (Ennaceur, A., Aggleton, J. P., *Behav*

*Brain Res,* 1997, 88, 181-193; and Bourtchouladze, R., et. al., *Proc Natl Acad Sci USA,* 2003, 100, 10518-10522). This Data was analyzed by Student's unpaired t test using a software package (Statview 5.0.1; SAS Institute, Inc). All values in the text and figures are expressed as mean±SEM.

The following Examples illustrate methods that are generally useful for preparing compounds of the invention.

EXAMPLES

Example 1

Preparation of a Compound Wherein $R^1$ is $CF_3$, X is —C(=O)— and B is a Thiophene Ring

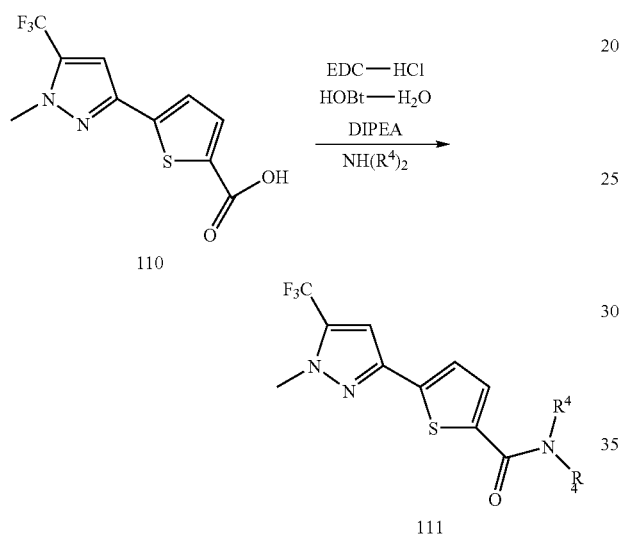

A solution of the commercially available acid was mixed in DMF. To the solution were added EDC-HCl, HOBT hydrate, and Hunig's base to activate the acid; to the activated acid was added the desired amine to produce the final product. The reactions underwent standard aqueous work-up and the crude products were subsequently purified by normal phase, flash chromatography. The final products were confirmed for purity and identity by LC/MS.

Example 2

Preparation of a Compound wherein $R^1$ is $CF_3$, X is —C(=O)— and B is a Phenyl Ring

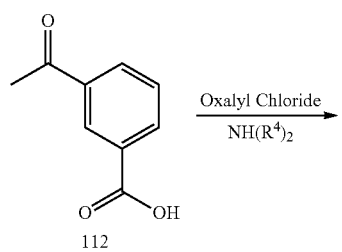

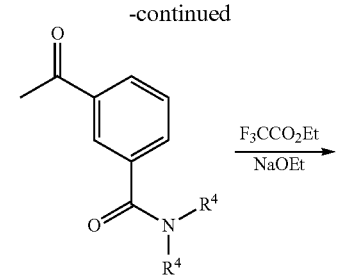

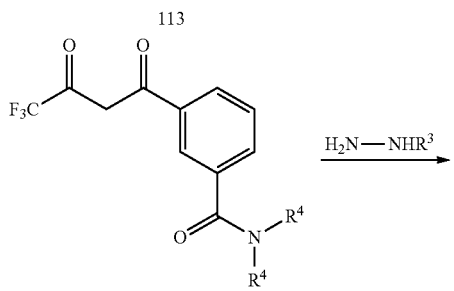

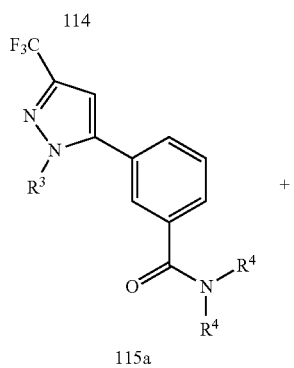

Oxalyl Chloride was added to 3-acetyl-benzoic acid (112) in dichloromethane below 20° C. After completion of the reaction, the mixture was concentrated to remove excess reagent. The residue was dissolved in fresh dichloromethane, cooled below 20° C., then followed by the addition of secondary amine and triethyl amine. The reaction stirred for 1 hour, was quenched with water, then washed with 5% HCl to remove excess triethyl amine. The organic layer was subsequently washed with 5% sodium bicarbonate to remove unreacted starting material, then washed with water, dried and concentrated to give 3-acetyl-N,N-dialkyl benzamide (113) in 75-80% yield.

Treatment of the 3-acetyl-benzamide 113 with a preformed solution of sodium ethyl methyl-ortho-trifluoroacetate, prepared by the mixture of NaOMe and ethyl trifluoroacetate in benzene, efficiently converted the material to diketo compound. Subsequent acidification of the crude reaction followed by extraction into organic solvent gave compound 114 in yields of 85-90%

The final pyrazole compounds (115a/b) were synthesize by the addition of the appropriate substituted hydrazine to compound 114 in ethanol, acidified ethanol, or acetic acid, depending on the specific hydrazine used.

Example 3

Preparation of a Compound Wherein $R^1$ is $CF_3$, X is —C(=O)— and B is a Phenyl Ring

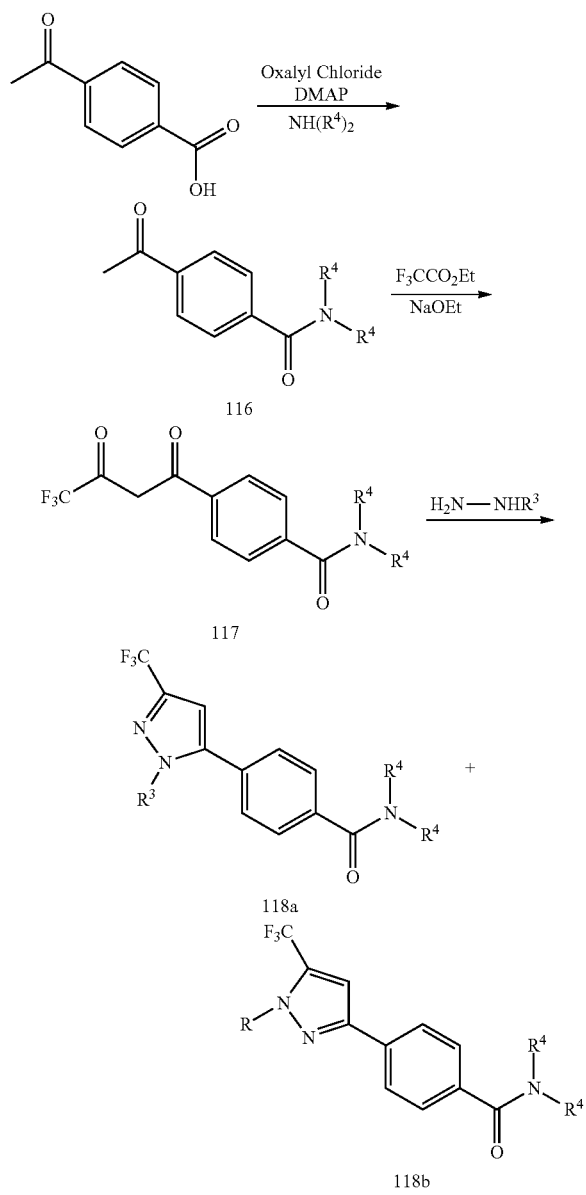

Oxalyl Chloride was added to 4-acetyl-benzoic acid in dichloromethane and DMF below 20° C., and the reaction mass concentrated to remove excess reagent. The residue was dissolved in fresh dichloromethane and the secondary amine was then added. Still below 20° C., triethyl amine was added and stirred for an hour. The reaction was quenched with water, washed with 5% HCl to remove excess triethyl amine, and then washed with 5% sodium bicarbonate to remove unreacted starting material. The organic layer was washed with water, dried and concentrated to give 4-acetyl-dialkyl benzamide 116 in yields of 85-90%.

Treatment of the benzamide with pre-forming sodium ethyl methyl-ortho-trifluoroacetate from NaOMe and ethyl trifluoroacetate in benzene and reacting the preformed orthoalkoxide with 4-acetyl-N,N-dialkyl benzamide and subsequent acidification followed by extraction gave compounds 117 in yields of 50-55%.

The final pyrazole compounds 118a/b were synthesize by the addition of the appropriate substituted hydrazine to compound 117 in ethanol, acidified ethanol, or acetic acid, depending on the specific hydrazine used.

Example 4

Preparation of a Compound Wherein $R^1$ is $CF_3$, X is —C(=O)— and B is a Pyridine Ring Two methods (A and B) were used for the synthesis of 2,4 disubstituted pyridine compounds.

Method A: ($R^3$=2,2,2 Trifluoroethyl, phenyl, 2-hydroxyethyl, benzyl, 2-pyridyl)

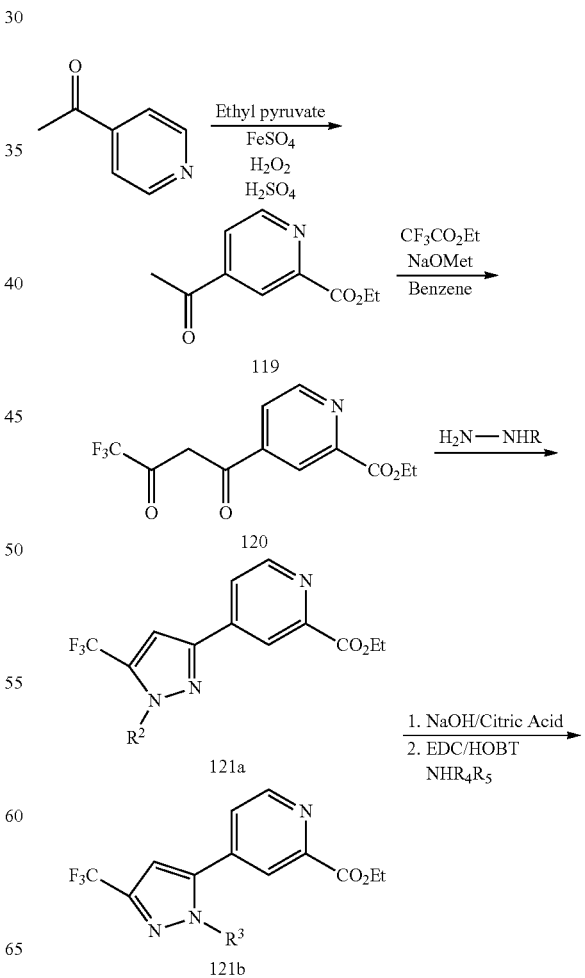

Method B: ($R^2$ or $R^3$=alkyl)

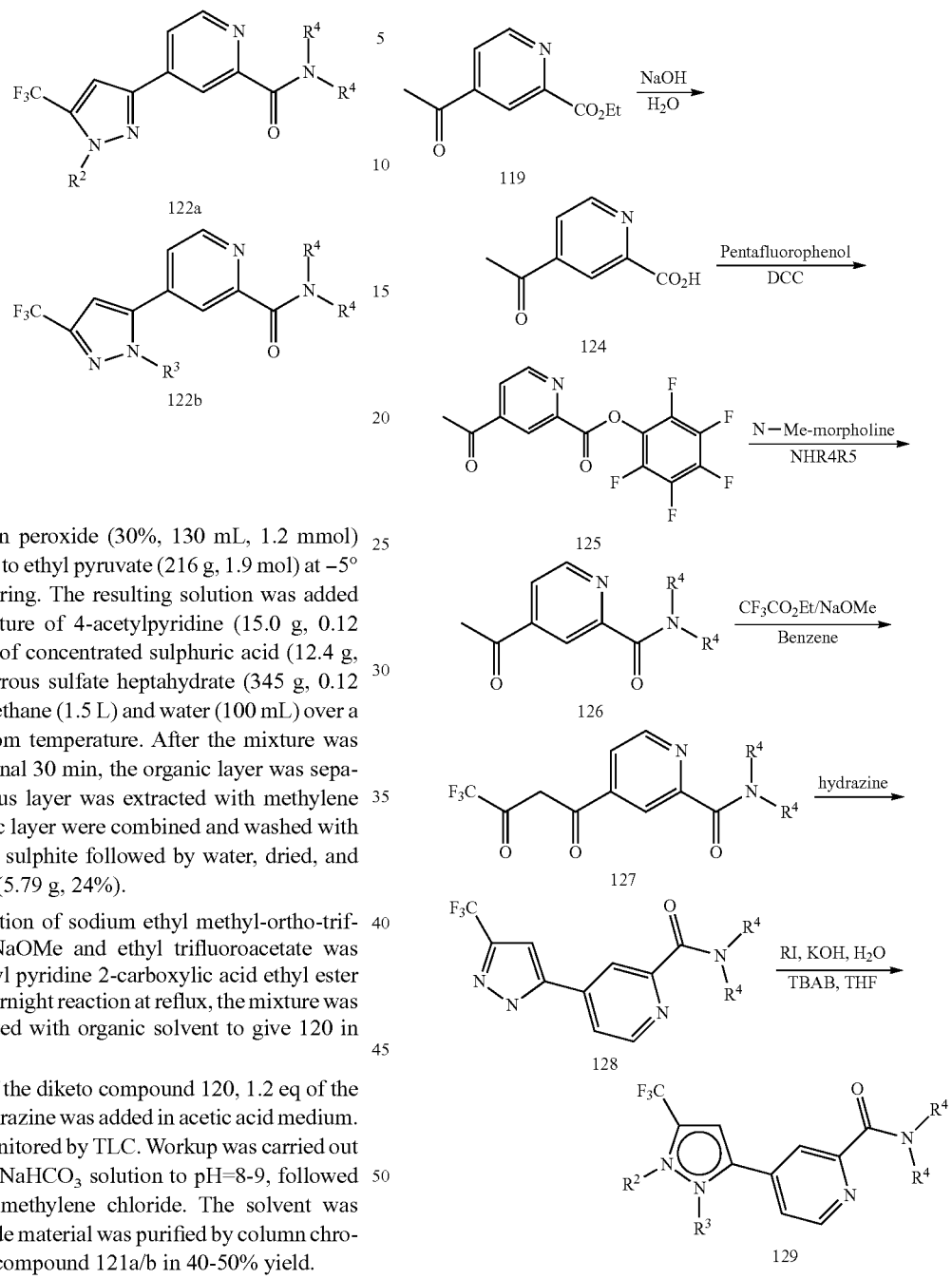

Aqueous hydrogen peroxide (30%, 130 mL, 1.2 mmol) was added drop wise to ethyl pyruvate (216 g, 1.9 mol) at −5° C. to 5° C. with stirring. The resulting solution was added drop wise to a mixture of 4-acetylpyridine (15.0 g, 0.12 mmol) to a mixture of concentrated sulphuric acid (12.4 g, 0.12 mmol), and ferrous sulfate heptahydrate (345 g, 0.12 mmol) in dichloromethane (1.5 L) and water (100 mL) over a 2 hour period at room temperature. After the mixture was stirred for an additional 30 min, the organic layer was separated and the aqueous layer was extracted with methylene chloride. The organic layer were combined and washed with 5% aqueous sodium sulphite followed by water, dried, and purified to give 119 (5.79 g, 24%).

A preformed solution of sodium ethyl methyl-ortho-trifluoroacetate from NaOMe and ethyl trifluoroacetate was reacted with 4-Acetyl pyridine 2-carboxylic acid ethyl ester in benzene. After overnight reaction at reflux, the mixture was acidified and extracted with organic solvent to give 120 in yields of 65-70%

To 1 equivalent of the diketo compound 120, 1.2 eq of the monosubstituted hydrazine was added in acetic acid medium. The reaction was monitored by TLC. Workup was carried out by adding saturated $NaHCO_3$ solution to pH=8-9, followed by extraction with methylene chloride. The solvent was removed and the crude material was purified by column chromatography to give compound 121a/b in 40-50% yield.

Compound 121a/b was dissolved in 1.5 eq of NaOH in water and stirred at room temperature for 2 h. To the mixture was added 20% citric acid solution to about pH 2. The product was extraction into ethyl acetate and concentrated. To the acid intermediate in DMF was added 1.5 eq of EDCI, 1.3 eq of HOBT, 1.3 eq dialkyl amine, and 4 eq of diisopropyl ethylamine and stirred at room temperature overnight. The completion of reaction was monitored by TLC. To the mixture was added water and ethyl, the ethyl acetate layer was concentrated to give the crude product, which was purified by column chromatography to yield compounds of the general structure of 122a/b.

Compound 119 was dissolved in 1.5 eq of NaOH in water and stirred at room temperature for 2 hours. The solution was acidified with 20% citric acid solution to pH=2 and extracted into ethyl acetate. Concentration of solvent gave product 124 in 45-50% yield.

Compound 124 was dissolved in 5 volumes of THF and 5 volumes of dichloromethane. To the solution was added 1.1 eq of pentafluorophenol followed by 1.1 eq of DCC. The reaction was stirred at room temperature for 2 hrs. The mixture was then filtered through a bed of Celite and washed with THF and dichloromethane. The filtrate was concentrated under vacuum to get a brown solid, which was recrystallized from ethyl acetate/Hexane to give the pure pentafluorophenyl ester 125.

To a solution of the pentafluorophenyl ester 125 in dichloromethane was added 1.2 eq of dialkyl amine and 1.5 eq of N-methyl morpholine; this solution stirred at room temperature overnight. After confirming the completion of the reaction by TLC, water was added to the reaction the layers separated. The aqueous layer extracted once more with dichloromethane. The organic layers were combined and washed with brine solution, then concentrated to give compound 126 in 45-50% yield.

Sodium ethylmethylorthotrifluoroacetate, formed by the mixture of NaOMe and ethyl trifluoroacetate in benzene, was reacted with compound 126 in benzene at reflux overnight. The resulting mixture was acidified and extracted into organic solvent to give compound 127 in good yields (65-70%).

To compound 127, in 10 volumes ethanol, was added a few drops of acetic acid followed by 6-7 eq of hydrazine hydrate (80%). This mixture was stirred at room temperature for 3-4 hours while monitoring the reaction by TLC. After complete reaction, the ethanol was completely removed under vacuum and water was added and stirred vigorously at room temperature to precipitate the product as a solid. The material was filtered and washed with copious amounts of water, then dried to give compound 128.

To a sample of 200 mg of the compound 128 in 2-3 mL of THF was added alkyl iodide and 1 mL of 6N KOH followed by tetrabutyl ammonium bromide (25 mg). The reaction was stirred at room temperature for 2-3 h. After completion of the reaction as determined by TLC, the phases were separated. The THF layer was concentrated and spotted on a Prep TLC plate. Elution was done with 30% ethyl acetate in hexane. After 10-15 elutions, the two geometric isomers (one wherein $R^2$ was absent and one wherein $R^3$ was absent) were separable. The silica gel was scrapped and extracted with ethyl acetate and dichloromethane, then concentrated to give the pure regioisomers of compound 129 (wherein $R^2$ or $R^3$=Methyl or Ethyl).

Example 5

Preparation of a Compound Wherein $R^1$ is $CF_3$, X is —C(=O)— and B is a Pyridine Ring

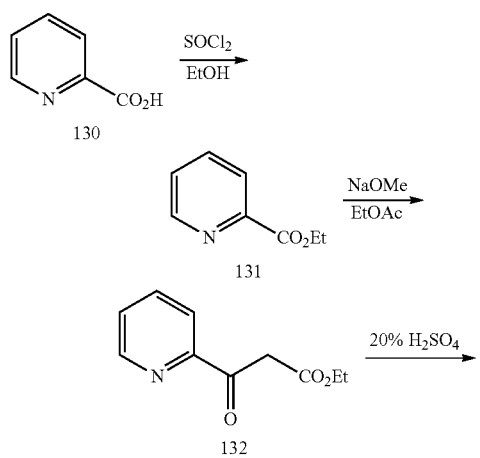

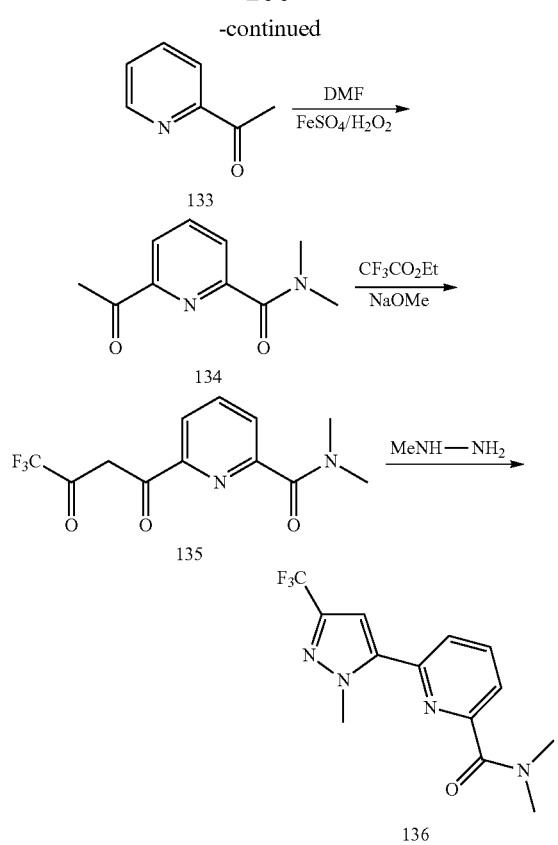

To 8 g of compound 130 in 30 mL of methanol. 11.8 ml of thionyl chloride was added slowly at 5° C. The mixture was allowed to stir for 30 min at room temperature, and was refluxed overnight. The reaction mixture was concentrated under high vacuum, then dissolve in sodium bicarbonate solution. Then compound was extracted into dichloromethane, then dried and concentrated to give a 70% yield of compound 131.

To 6 g of compound 131 in 100 mL benzene, 2.6 g of NaOMe was added. The reaction mass was heated to 80° C. and 5 ml of ethyl acetate was added to the reaction and further refluxed for an additional one hour. The reaction was neutralized with citric acid and extracted with dichloromethane. Removal of solvent afforded a 60% yield of compound 132.

To 4 g of compound 132 was added 40 mL of 20% sulphuric acid, which was then refluxed for two hours. Then reaction mixture was neutralized with the sodium hydroxide, extracted into dichloromethane, and concentrated to give a yield of 60% of desired compound 133.

To a 1 liter round bottom flask with 150 mL of DMF was added compound 133 added at 0° C. To the reaction mixture was added hydrogen peroxide and ferrous sulphate heptahydrate simultaneously at 0° C. The reaction mixture was allowed to stir overnight. The reaction mixture was poured in the water, then extracted with dichloromethane. The organic layer was dried over sodium sulphate and concentrated to afford 2% of desired compound 134.

To 1 g of compound 134 in 10 mL benzene was added 0.8 g of sodium methoxide. The reaction mixture was heated gently to reflux, and allowed to stir for two hours. The reaction mixture was neutralized with citric acid then extracted with ethyl acetate. The organic layer was dried and concentrated to give 80% yield of the compound 135.

To 200 mg of compound 135 in ethanol was added methyl hydrazine. The mixture was allowed to stir for six hours at room temperature. Then reaction mixture was neutralized with sodium bicarbonate and extracted with ethyl acetate. The organic layer was then dried and concentrated to afford a 50% yield of the final compound 136.

Example 6

Preparation of a Compound Wherein $R^1$ is Phenyl, X is —C(=O)—Y=N, and B is a Thiophene Ring

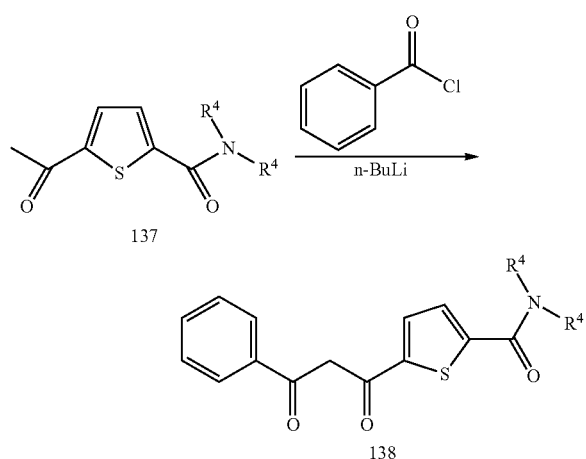

To the stirred solution of diisopropyl ethylamine (3.69 g, 36.51 mmol) in THF (60 mL) cooled to −70° C. was added n-BuLi (2.33 g, 36.51 mmol) over 40 minutes. The mixture was stirred at −70° C. for 2 hours. The amide 137, dissolved in a minimum amount of THF, was added slowly to the reaction mixture and stirring was continued for 2 hours at −70° C. The reaction was warmed to −30° C. and stirred for an additional 30 min. The mixture was cooled back to −70° C., followed by the addition of benzoyl chloride (5.13 g, 36.51 mmols), added slowly over 20 min. The reaction was stirred for 3 hours at 70° C., and quenched with 23 mL of 1.5 N HCl. Product was extracted with dichloromethane, then concentrated to afford the crude product, which was purified by column chromatography over silica gel to give the desired product 138 in 20-25% yield.

The diketone 138 was converted to a compound of formula I using the procedures described in Example 9 below.

Example 7

Preparation of a Compound Wherein $R^1$ is Methyl, X is —C(=O)—Y=N, and B is a Thiophene Ring

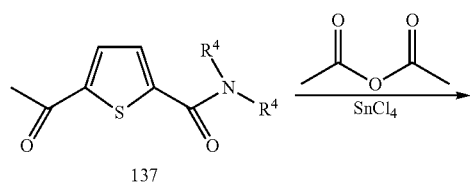

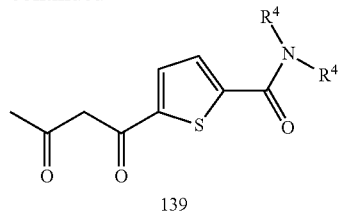

Stannic chloride (1.32 g, 5.07 mmol) was added drop wise over a period of 50 min to a stirred mixture of amide 137 (0.5 g, 2.53 mmol) and acetic anhydride (1.03 g, 10.14 mmol), which was pre-cooled to 20° C. During the addition, temperature did not exceed 100° C. After standing overnight at room temperature, the reaction mixture was again cooled to 0-20° C. and hydrolyzed by stirring for 7 hours with 30% HCl (1 mL). Water (20 mL) was added into the mixture and stirred for an additional 30 min at room temperature. The solid was filtered off and crude brownish yellow solid was purified by column chromatography using chloroform and methanol. The product 139 was isolated in 40-45% yield.

The diketone 139 was converted to a compound of formula I using the procedures described in Example 9 below.

Example 8

Preparation of a Compound Wherein $R^1$ is Isopropyl, X is —C(=O)—, Y=N, and B is a Thiophene Ring

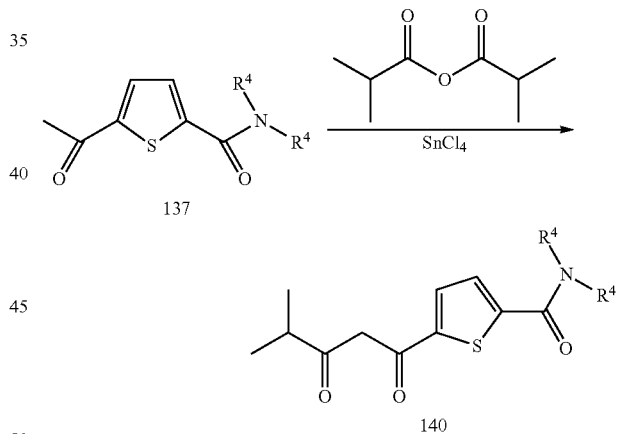

Stannic chloride (19.8 g, 76.06 mmol) was added drop wise over a period of 1 hour to a stirred mixture of amide 139 (5 g, 25.35 mmol) and isobutyric anhydride (24.06 g, 152.12 mmol) which was cooled to below 20° C. During this addition, temperature never exceeded 100° C. After standing overnight at room temperature, the reaction mixture was again cooled to 0-20° C. and hydrolyzed by stirring for 7 h with 30% HCl (25 mL). Water (100 mL) was added and the mixture was stirred for 30 min at room temperature. The solids were filtered off and a crude, brownish yellow solid was purified by column chromatography over silica gel using chloroform and methanol to give 45-50% yield of product 140.

The diketone 140 was converted to a compound of formula I using the procedures described in Example 10 below.

The acylating agent, isobutyric anhydride, was prepared in the following fashion. Isobutyric acid (50 g, 562.4 mmol was added thionyl chloride (85 g, 703.03 mmols) slowly over 45 minutes. The mixture was refluxed for 30 min and the acid chloride was isolated by distillation. To a mixture of pyridine (40 g, 506 mmol) and dry benzene (50 mL), was added isobutyryl chloride (27 g, 253 mmol). Isobutyric acid (22.32 g, 253 mmol) was then added slowly over 10 minutes and the reaction was stirred for 3 h at room temperature. The solids were filtered off and washed with dry benzene. The filtrate was concentrated to give a crude reddish colored product.

Example 9

Preparation of a Compound Wherein $R^1$ is Phenyl, Methyl, Trifluoromethyl, Chloro-difluoromethyl, Pentafluoroethyl, or Isopropyl; X is —C(=O)—; Y=N; and B is a Thiophene Ring The following methods (1-4) were used for the construction of the pyrazole moiety when the B ring was a thiophene Cyclization with Substituted Hydrazines

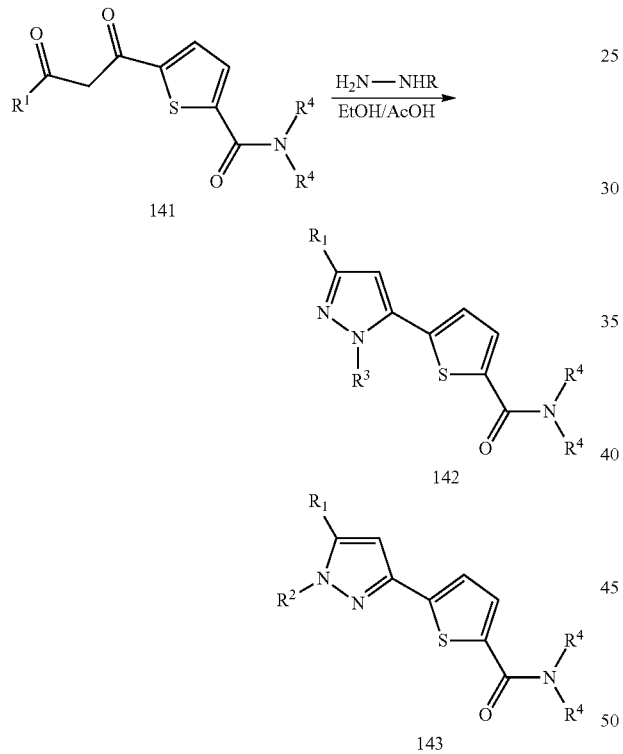

$R^1$ = Phenyl, methyl, trifluoromethyl or isopropyl

Cyclization Methods:—

Equimolar mixture of scaffold 141 and mono substituted hydrazine were mixed together in ethanol containing few drops of acetic acid. The reaction mass was stirred for more than 12 h at room temperature and monitored by TLC.

Equimolar amounts of scaffold 141 and mono substituted hydrazine hydrochloride (for benzyl, cyclopentyl and 4-chlorophenyl hydrazines which are present as HCl salts) were mixed together in ethanol and the reaction mass was stirred at room temperature and monitored by TLC.

Equimolar amounts of scaffold 141 and 2-hydrazino pyridine were mixed together in acetic acid. The reaction was stirred at reflux and reaction progress was monitored by TLC.

Equimolar mixture of scaffold 141 and mono alkyl hydrazines were mixed together in acetic acid. The reaction mass was stirred at room temperature and monitored by TLC.

N-alkylation of 1-H Pyrazoles Using Microwave

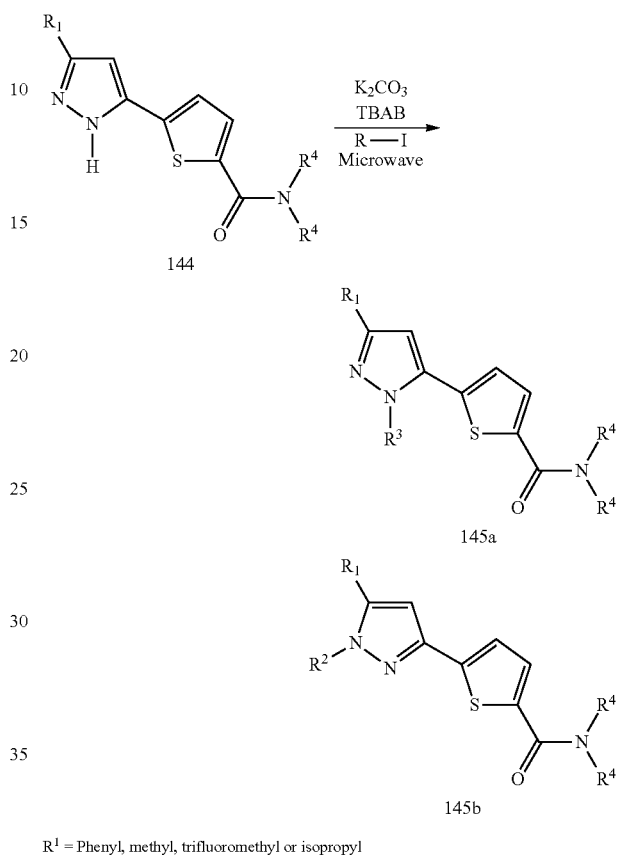

$R^1$ = Phenyl, methyl, trifluoromethyl or isopropyl

The synthesis were carried out by mixing compound 144 with excess of alkyl iodide and a catalytic amount of tetrabutyl ammonium bromide (TBAB). The mixtures were adsorbed on potassium carbonate and irradiated in an open glass bottle (15 mL) in a domestic microwave oven for 2-3 min to provide compounds 145a/b.

Phase Transfer Method for N-Alkylation of 1-H-Pyrazoles

In certain cases the utility microwave assisted alkylation was limited due to the volatility of certain alkyl iodides, such as methyl and ethyl iodides, which prevented complete conversion to desired product. The following procedure was used in such cases.

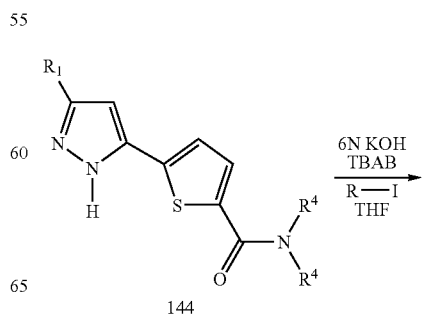

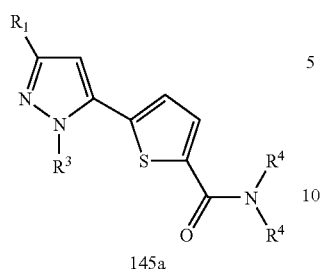

145a

R¹ = Phenyl, methyl, trifluoromethyl or isopropyl

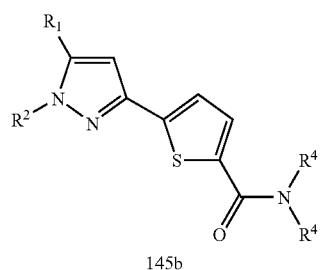

145b

To a solution of 1 mL of THF and 1 mL of 6N KOH solution were added 200 mg of N-1-H pyrazole 144 and a catalytic amount of tetrabutyl ammonium bromide (TBAB). The mixture was stirred for 15 min at room temperature. To this mixture was added 2 equivalents of the requisite alkyl halide, which was subsequently stirred at room temperature until the reaction was complete as determined by TLC.

Dialkyl Sulfate Method for N-Alkylation of 1-H-Pyrazoles

Pyrazoles may be alkylated with good regiospecifically favouring the product 111 under non-basic conditions using dialkyl sulfates. Generally, ratios of >9:1 (111:111a) are obtained.

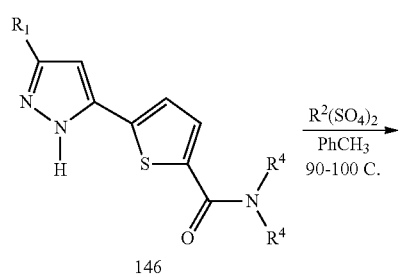

146

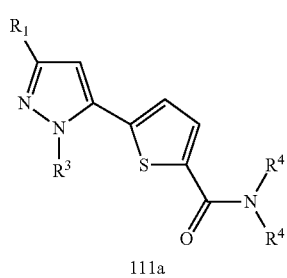

111a

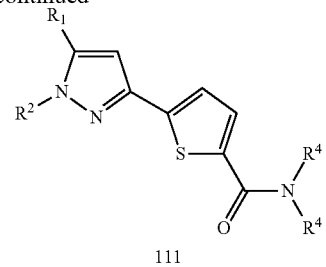

111

R¹ = CF₃, CHF₂, CF₃CF₂

A suspension of pyrazole 146 in toluene (~10 mL/g) was treated with dimethyl sulfate (1.5 eq) and heated at 90-100° C. for 24 h at which time an additional 0.125 eq of dimethyl sulfate was added follow by 10 h of heating. The reaction mixture was then cooled and diluted with EtOAc, washed with water, a saturated NaHCO₃ solution, and brine. The organic layer was dried over MgSO₄, filtered and evaporated in vacuo to afford a crude solid. The two regioisomer products, 111 and 111a could be purified and separated by chromatography on silica gel utilizing EtOAc/hexanes as eluant or recrystallized from EtOAc/hexanes.

Example 10

Preparation of a Compound Wherein R¹ is Trifluoromethyl; X is —CH₂—; Y═N; and B is a Thiophene Ring

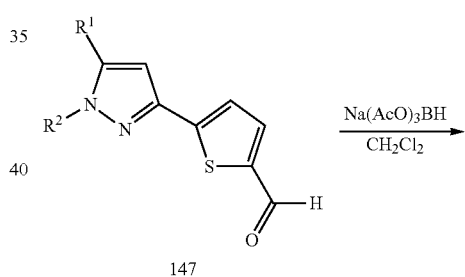

147

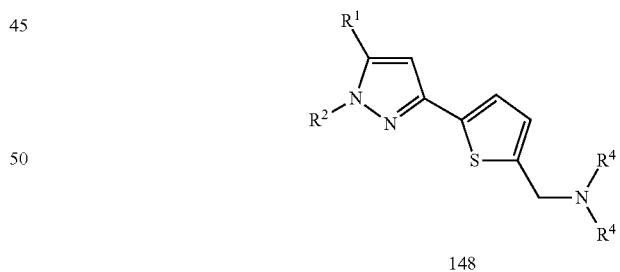

148

R¹ = CF₃

A solution of aldehdye 147 in dichloromethane (~20 mL/g) was treated with amine (1.1 eq) followed by triacetoxyborohydride and stirred for 16 h. The reaction mixture was then treated with a saturated NaHCO₃ solution and allowed to stir for 15 min after which time the reaction mixture was partitioned between EtOAc and water. The organic layer was further washed with a brine solution and dried over MgSO₄, filtered, and evaporated in vacuo. The crude product could be purified by chromatography on silica gel utilizing EtOAc/hexanes as eluant.

Example 11

Preparation of a Compound Wherein $R^1$ is Trifluoromethyl; X is —C(O)—Y═C; and B is a Thiophene or Phenyl Ring;

Acylation Methods:—

Formylation of scaffold 152 and subsequent treatment of product 153 with 2-4 eq of Grignard reagent at 0-10° C. followed by oxidation of the resulting alcohol 154 to ketone 155.

Treatment of Weinreb amide scaffold 158 and 2-4 eq of Grignard reagent at 0-10° C.

Friedel-Crafts acylation of scaffold 160 with an excess of acyl halide.

1.

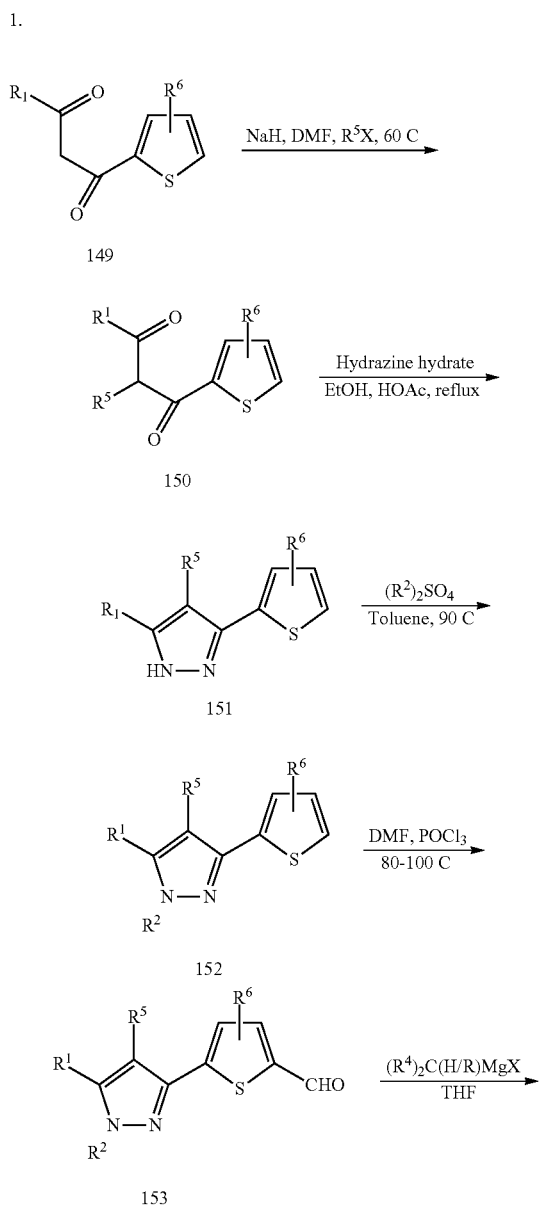

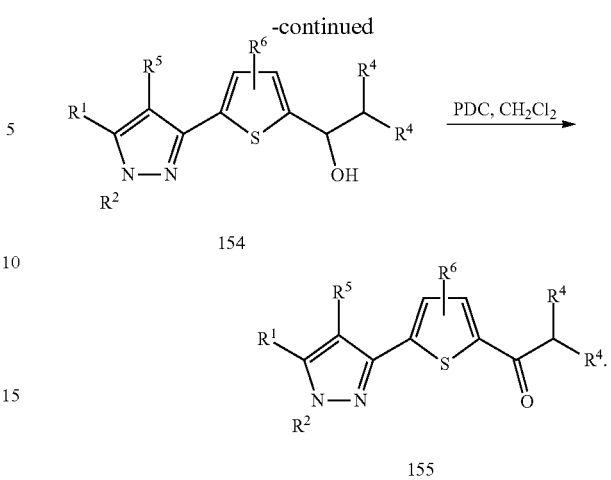

General Procedure for Alkylation of Scaffold 149

A solution of NaH (1.1 eq) in DMF (5 mL/g NaH) was treated portionwise with diketone 149 and stirred until gas evolution had seized. The reaction was then treated with alkylhalide (2.0 eq) and heated at 50-60° C. for 16 h with additional amounts of alkyl halide and heating if the reaction is not complete. On completion, the reaction mixture was partitioned between EtOAc (50 mL/g NaH) and a 5% sulphuric acid solution (50 mL/g NaH). The organic layer was further washed with water and brine, then dried over $MgSO_4$, filtered, and evaporated in vacuo to afford product 150. The crude product is generally of sufficient purity for use, but may be purified by chromatography on silica gel utilizing EtOAc/hexanes as eluant.

General Procedure for Carbonylation of Scaffold 152

A solution of DMF (10 ml/g of 152) at 5-10° C. was treated with phosphorous oxychloride (10 eq) and allowed to warm to room temperature after which time thiophene 152 was added. The resulting solution was heated at 80-100° C. for 16-24 h until the reaction reached completion. The reaction was then cooled to 0-5° C. and carefully treated with a saturated aqueous solution of $K_2CO_3$ and EtOAc. The organic layer was further washed with water and brine then dried over $MgSO_4$, filtered, and evaporated in vacuo to afford product 153. The crude product may be purified by chromatography on silica gel utilizing EtOAc/hexanes as eluant.

General Procedure for Grignard Addition of Scaffold 153

A solution of aldehyde 153 in THF (20 mL/g) was treated with a 1M THF solution of Grignard reagent (1.5 eq) and stirred for 1 h. The reaction was then treated with a saturated aqueous solution of ammonium chloride and EtOAc. The organic layer was further washed with brine, dried over $MgSO_4$, filtered, and evaporated in vacuo to afford product 154. The crude product may be purified by chromatography on silica gel utilizing EtOAc/hexanes as eluant.

General Procedure for the Oxidation of Scaffold 154

A solution of carbinol 154 in dichloromethane (20 mL/g) was treated with pyridinium dichlorochromate (1.5 eq) and stirred for 3 h. The reaction was then evaporated to ¼ volume, diluted with EtOAc, and filtered through a plug of Celite. The organic layer was then evaporated in vacuo to afford crude product 155. The crude product may be purified by chromatography on silica gel utilizing EtOAc/hexanes as eluant.

2.

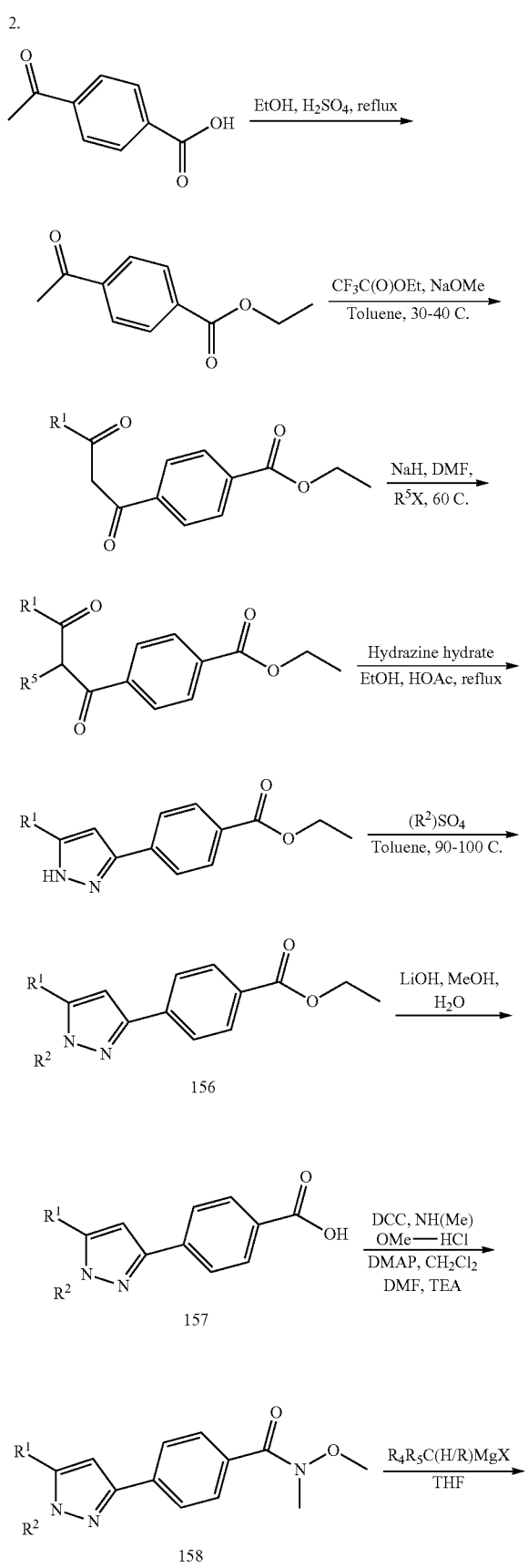

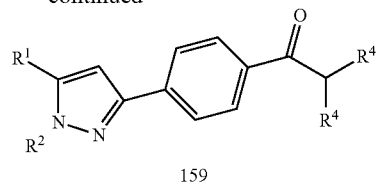
159

General Procedure for the Coupling of 157 with N,O-Dimethylhydroxylamine Hydrochloride to Provide Scaffold 158

A mixture of acid 157, N,O-Dimethylhydroxylamine hydrochloride (1.2 eq), triethylamine (1.2 eq), and DMAP (cat.), in dichloromethane (1 mL/g) and DMF (0.1 mL/g) at 0-5° C., was treated with DCC (1.2 eq). The reaction mixture was allowed to warm to room temperature and stir 16 h after which time, the reaction was filtered through Celite with the aid of EtOAc and evaporated in vacuo to afford crude product 158. The crude product may be purified by chromatography on silica gel utilizing EtOAc/hexanes as eluant.

General Procedure for Grignard Addition to 158 to Provide Scaffold 159

A solution of Weinreb amide 158 in THF (20 mL/g) was treated with a 1M THF solution of Grignard reagent (4.0 eq) and stirred for 2 h. The reaction was then treated with a saturated aqueous solution of ammonium chloride and EtOAc. The organic layer was further washed with brine, dried over $MgSO_4$, filtered, and evaporated in vacuo to afford crude product 159. The crude product may be purified by chromatography on silica gel utilizing EtOAc/hexanes as eluant.

3.

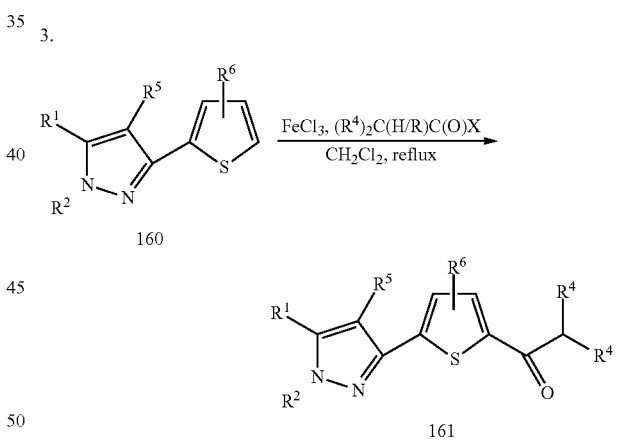

A solution of 160 in dichloromethane (100 ml/g) was treated with $FeCl_3$ (1.6 eq) followed by carboxylic acid chloride (1.6 eq). The reaction was heated at reflux for 16 hours followed by partitioning with water. The dichloromethane portion was then dried over $Na_2SO_4$, filtered, and concentrated in vacuo to afford crude product 161. The crude product may be purified by chromatography on silica gel utilizing EtOAc/hexanes as eluant.

Example 12

Preparation of Compounds of the Invention

Using the general procedures identified above, the following compounds of the invention were prepared.

| Comp. # | Structure | Compound Name | MW | LC/MS (ES+) |
|---|---|---|---|---|
| 162 | 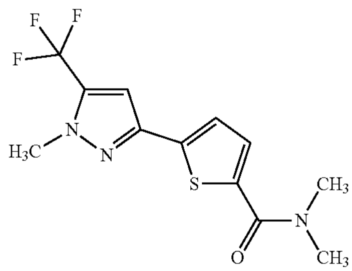 [SMILES: CN(C)C(=O)c1ccc(-c2cc(C(F)(F)F)n(C)n2)s1] | 5-(1-Methyl-5-trifluoromethyl-1H-pyrazol-3-yl)-thiophene-2-carboxylic acid dimethylamide | 303.30 | 304.5 |
| 163 | 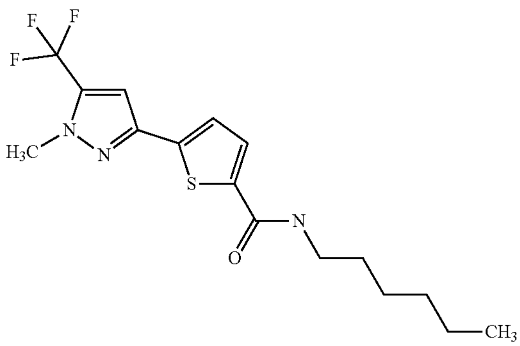 [SMILES: CCCCCCNC(=O)c1ccc(-c2cc(C(F)(F)F)n(C)n2)s1] | 5-(1-Methyl-5-trifluoromethyl-1H-pyrazol-3-yl)-thiophene-2-carboxylic acid hexylamide | 359.41 | 360.5 |
| 164 | 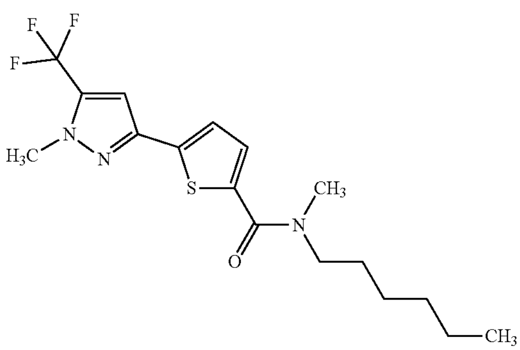 [SMILES: CCCCCCN(C)C(=O)c1ccc(-c2cc(C(F)(F)F)n(C)n2)s1] | 5-(1-Methyl-5-trifluoromethyl-1H-pyrazol-3-yl)-thiophene-2-carboxylic acid hexyl-methyl-amide | 373.44 | 374.5 |
| 165 | 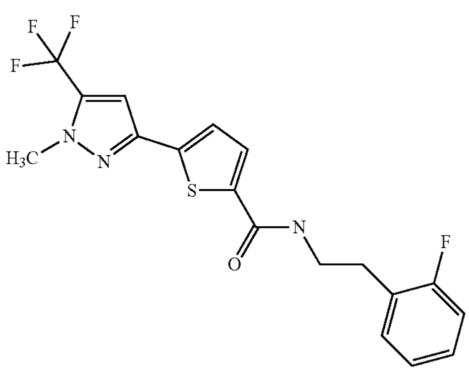 [SMILES: Cn1nc(-c2ccc(C(=O)NCCc3ccccc3F)s2)cc1C(F)(F)F] | 5-(1-Methyl-5-trifluoromethyl-1H-pyrazol-3-yl)-thiophene-2-carboxylic acid [2-(2-fluoro-phenyl)-ethyl]-amide | 397.39 | 398.5 |
| 166 | 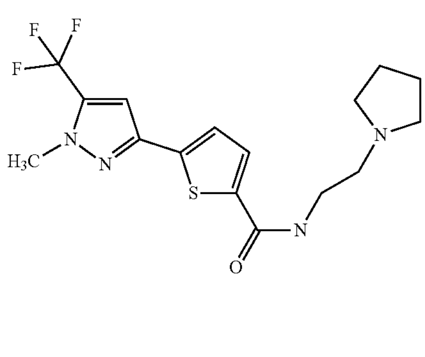 [SMILES: Cn1nc(-c2ccc(C(=O)NCCN3CCCC3)s2)cc1C(F)(F)F] | 5-(1-Methyl-5-trifluoromethyl-1H-pyrazol-3-yl)-thiophene-2-carboxylic acid (2-pyrrolidin-1-ethyl)-amide | 372.41 | 373.1 |

-continued

| Comp. # | Structure | Compound Name | MW | LC/MS (ES+) |
|---|---|---|---|---|
| 167 | 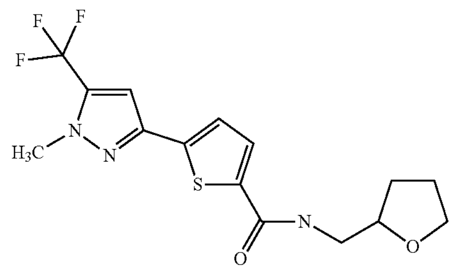 [SMILES: Cn1nc(-c2ccc(C(=O)NCC3CCCO3)s2)cc1C(F)(F)F] | 5-(1-Methyl-5-trifluoromethyl-1H-pyrazol-3-yl)-thiophene-2-carboxylic acid (tetrahydro-furan-2-ylmethyl)-amide | 359.37 | 360.5 |
| 168 | 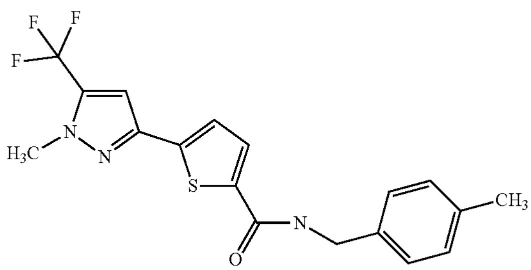 [SMILES: Cc1ccc(CNC(=O)c2ccc(-c3cc(C(F)(F)F)n(C)n3)s2)cc1] | 5-(1-Methyl-5-trifluoromethyl-1H-pyrazol-3-yl)-thiophene-2-carboxylic acid 4-methyl-benzylamide | 379.40 | 380.5 |
| 169 | 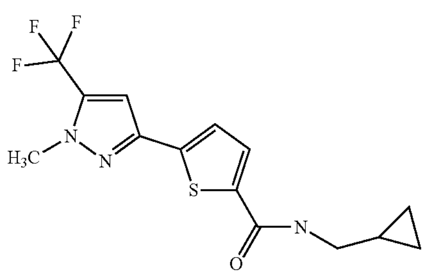 [SMILES: Cn1nc(-c2ccc(C(=O)NCC3CC3)s2)cc1C(F)(F)F] | 5-(1-Methyl-5-trifluoromethyl-1H-pyrazol-3-yl)-thiophene-2-carboxylic acid cyclopropylmethyl-amide | 329.34 | 330.5 |
| 170 | 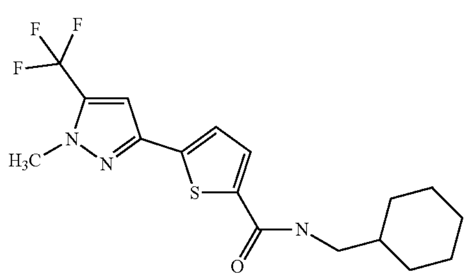 [SMILES: Cn1nc(-c2ccc(C(=O)NCC3CCCCC3)s2)cc1C(F)(F)F] | 5-(1-Methyl-5-trifluoromethyl-1H-pyrazol-3-yl)-thiophene-2-carboxylic acid cyclohexylmethyl-amide | 371.42 | 372.5 |
| 171 | 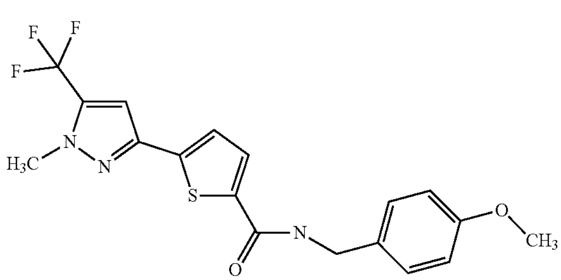 [SMILES: COc1ccc(CNC(=O)c2ccc(-c3cc(C(F)(F)F)n(C)n3)s2)cc1] | 5-(1-Methyl-5-trifluoromethyl-1H-pyrazol-3-yl)-thiophene-2-carboxylic acid 4-methoxy-benzylamide | 395.40 | 396.5 |

| Comp. # | Structure | Compound Name | MW | LC/MS (ES+) |
|---|---|---|---|---|
| 172 | 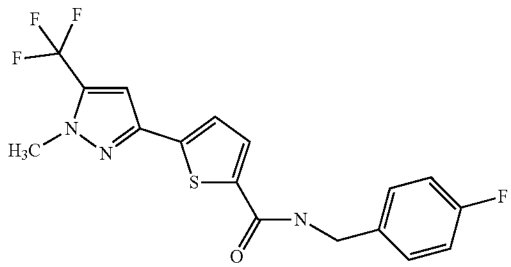 [SMILES: Cn1nc(-c2ccc(C(=O)NCc3ccc(F)cc3)s2)cc1C(F)(F)F] | 5-(1-Methyl-5-trifluoromethyl-1H-pyrazol-3-yl)-thiophene-2-carboxylic acid 4-fluoro-benzylamide | 383.36 | 384.5 |
| 173 | 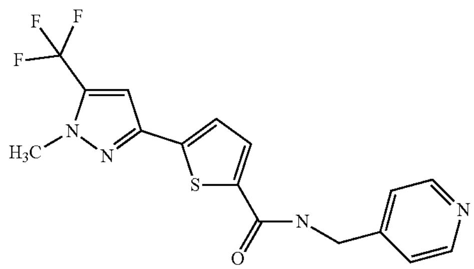 [SMILES: Cn1nc(-c2ccc(C(=O)NCc3ccncc3)s2)cc1C(F)(F)F] | 5-(1-Methyl-5-trifluoromethyl-1H-pyrazol-3-yl)-thiophene-2-carboxylic acid (pyridin-4-ylmethyl)-amide | 366.36 | 367.4 |
| 174 | 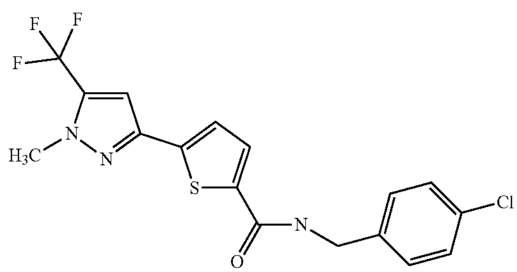 [SMILES: Cn1nc(-c2ccc(C(=O)NCc3ccc(Cl)cc3)s2)cc1C(F)(F)F] | 5-(1-Methyl-5-trifluoromethyl-1H-pyrazol-3-yl)-thiophene-2-carboxylic acid (pyridin-4-ylmethyl)-amide | 399.82 | 400.5 |
| 175 | 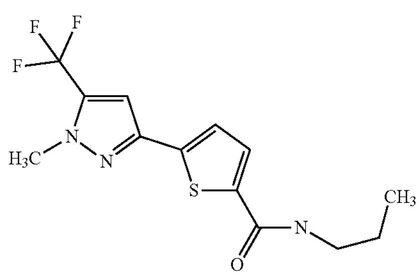 [SMILES: CCCNC(=O)c1ccc(-c2cc(C(F)(F)F)n(C)n2)s1] | 5-(1-Methyl-5-trifluoromethyl-1H-pyrazol-3-yl)-thiophene-2-carboxylic acid propylamide | 317.33 | 318.5 |
| 176 | 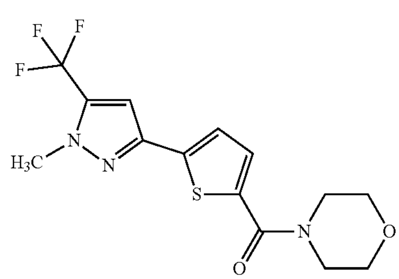 [SMILES: Cn1nc(-c2ccc(C(=O)N3CCOCC3)s2)cc1C(F)(F)F] | [5-(1-Methyl-5-trifluoromethyl-1H-pyrazol-3-yl)-thiophen-2-yl]-morpholin-4-yl-methanone | 345.34 | 346.5 |

| Comp. # | Structure | Compound Name | MW | LC/MS (ES+) |
|---|---|---|---|---|
| 177 | 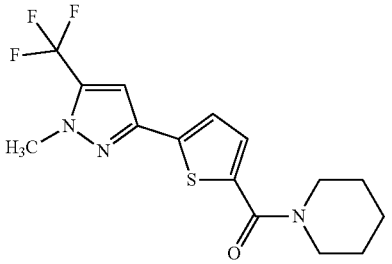 [SMILES: Cn1nc(-c2ccc(C(=O)N3CCCCC3)s2)cc1C(F)(F)F] | [5-(1-Methyl-5-trifluoromethyl-1H-pyrazol-3-yl)-thiophen-2-yl]-piperidin-1-yl-methanone | 343.37 | 344.6 |
| 178 | 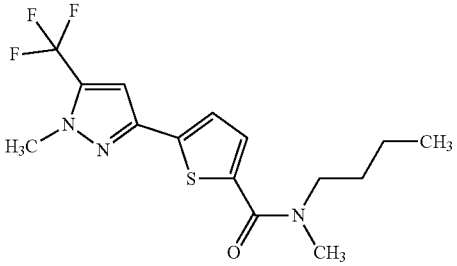 [SMILES: CCCCN(C)C(=O)c1ccc(-c2cc(C(F)(F)F)n(C)n2)s1] | 5-(1-Methyl-5-trifluoromethyl-1H-pyrazol-3-yl)-thiophene-2-carboxylic acid butyl-methyl-amide | 345.38 | 346.5 |
| 179 | 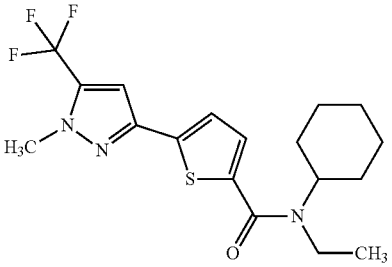 [SMILES: CCN(C(=O)c1ccc(-c2cc(C(F)(F)F)n(C)n2)s1)C1CCCCC1] | 5-(1-Methyl-5-trifluoromethyl-1H-pyrazol-3-yl)-thiophene-2-carboxylic acid cyclohexyl-ethyl-amide | 385.45 | 386.6 |
| 180 | 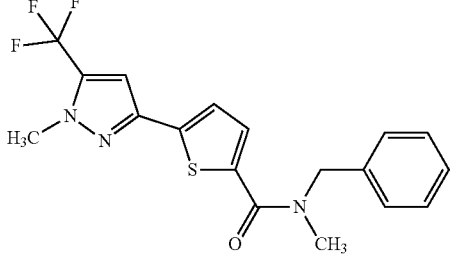 [SMILES: CN(Cc1ccccc1)C(=O)c1ccc(-c2cc(C(F)(F)F)n(C)n2)s1] | 5-(1-Methyl-5-trifluoromethyl-1H-pyrazol-3-yl)-thiophene-2-carboxylic acid benzyl-methyl-amide | 379.40 | 380.5 |
| 181 | 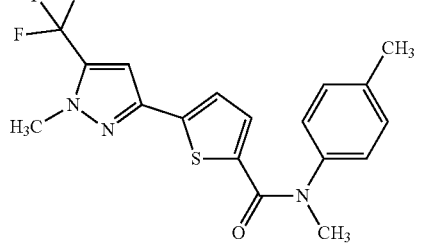 | 5-(1-Methyl-5-trifluoromethyl-1H-pyrazol-3-yl)-thiophene-2-carboxylic acid methyl-p-tolyl-amide | 379.40 | 380.5 |

-continued

| Comp. # | Structure | Compound Name | MW | LC/MS (ES+) |
|---|---|---|---|---|
| 182 | 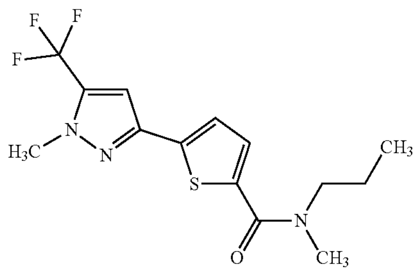 [SMILES: CCCN(C)C(=O)c1ccc(-c2cc(C(F)(F)F)n(C)n2)s1] | 5-(1-methyl-5-trifluoromethyl-1H-pyrazol-3-yl)-thiophene-2-carboxylic acid methyl-propyl-amide | 331.36 | 332.5 |
| 183 | 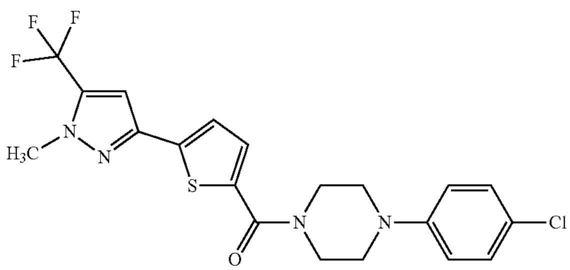 [SMILES: Cn1nc(-c2ccc(C(=O)N3CCN(c4ccc(Cl)cc4)CC3)s2)cc1C(F)(F)F] | [4-(4-Chloro-phenyl)-piperazin-1-yl]-[5-(1-methyl-5-trifluoromethyl-1H-pyrazol-3-yl)-thiophen-2-yl]-methanone | 454.90 | 455.6 |
| 184 | 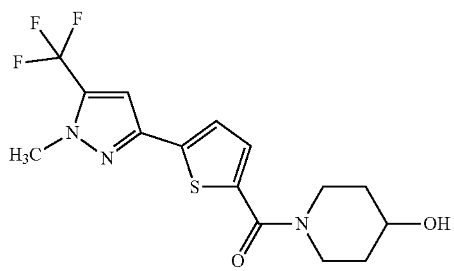 [SMILES: Cn1nc(-c2ccc(C(=O)N3CCC(O)CC3)s2)cc1C(F)(F)F] | (4-Hydroxy-piperidin-1-yl)-[5-(1-methyl-5-trifluoromethyl-1H-pyrazol-3-yl)-thiophen-2-yl]-methanone | 359.37 | 360.5 |
| 185 | 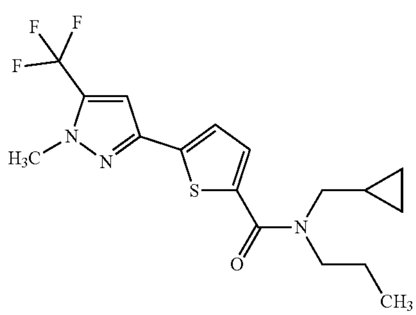 [SMILES: CCCN(CC1CC1)C(=O)c1ccc(-c2cc(C(F)(F)F)n(C)n2)s1] | 5-(1-Methyl-5-trifluoromethyl-1H-pyrazol-3-yl)-thiophene-2-carboxylic acid cyclopropylmethyl-propyl-amide | 371.42 | 372.5 |
| 186 | 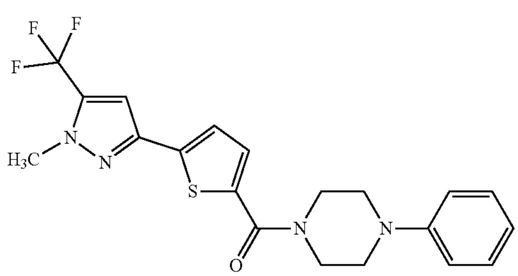 [SMILES: Cn1nc(-c2ccc(C(=O)N3CCN(c4ccccc4)CC3)s2)cc1C(F)(F)F] | [5-(1-Methyl-5-trifluoromethyl-1H-pyrazol-3-yl)-thiophen-2-yl]-(4-phenyl-piperazin-1-yl)-methanone | 420.45 | 421.5 |

-continued

| Comp. # | Structure | Compound Name | MW | LC/MS (ES+) |
|---|---|---|---|---|
| 187 | 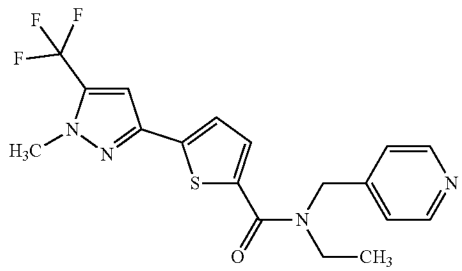 [SMILES: CCN(Cc1ccncc1)C(=O)c1ccc(-c2cc(C(F)(F)F)n(C)n2)s1] | 5-(1-Methyl-5-trifluoromethyl-1H-pyrazol-3-yl)-thiophene-2-carboxylic acid ethyl-pyridin-4-ylmethyl-amide | 394.42 | 395.5 |
| 188 | 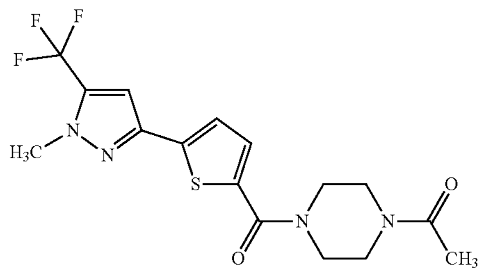 [SMILES: CC(=O)N1CCN(C(=O)c2ccc(-c3cc(C(F)(F)F)n(C)n3)s2)CC1] | 1-{4-[5-(1-Methyl-5-trifluoromethyl-1H-pyrazol-3-yl)-thiophene-2-carbonyl]-piperazin-1-yl}-ethanone | 386.39 | 387.5 |
| 189 | 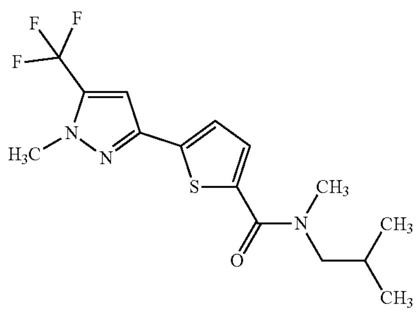 [SMILES: CC(C)CN(C)C(=O)c1ccc(-c2cc(C(F)(F)F)n(C)n2)s1] | 5-(1-methyl-5-trifluoromethyl-1H-pyrazol-3-yl)-thiophene-2-carboxylic acid isobutyl-methyl-amide | 345.38 | 346.5 |
| 190 | 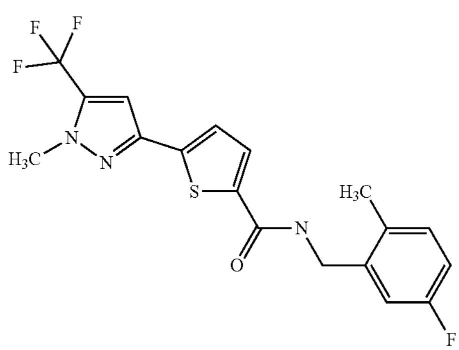 [SMILES: Cc1ccc(F)cc1CNC(=O)c1ccc(-c2cc(C(F)(F)F)n(C)n2)s1] | 5-(1-Methyl-5-trifluoromethyl-1H-pyrazol-3-yl)-thiophene-2-carboxylic acid 5-fluoro-2-methyl-benzylamide | 397.39 | 398.5 |
| 191 | 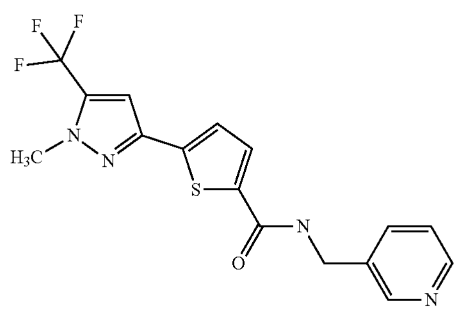 [SMILES: Cn1nc(-c2ccc(C(=O)NCc3cccnc3)s2)cc1C(F)(F)F] | 5-(1-Methyl-5-trifluoromethyl-1H-pyrazol-3-yl)-thiophene-2-carboxylic acid (pyridin-3-ylmethyl)-amide | 366.36 | 367.4 |

| Comp. # | Structure | Compound Name | MW | LC/MS (ES+) |
|---|---|---|---|---|
| 192 | 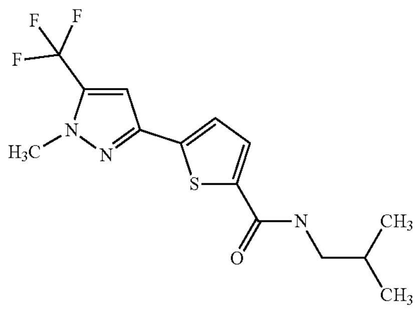 [SMILES: CC(C)CNC(=O)c1ccc(-c2cc(C(F)(F)F)n(C)n2)s1] | 5-(1-Methyl-5-trifluoromethyl-1H-pyrazol-3-yl)-thiophene-2-carboxylic acid isobutyl-amide | 331.36 | 332 |
| 193 | 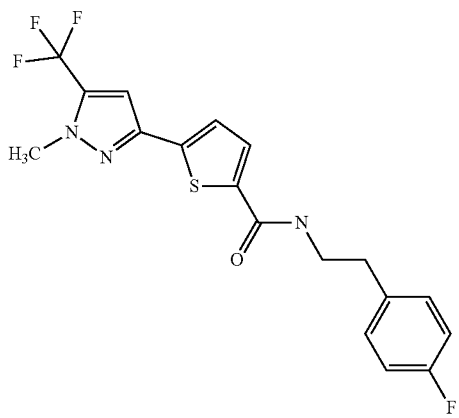 [SMILES: Cn1nc(-c2ccc(C(=O)NCCc3ccc(F)cc3)s2)cc1C(F)(F)F] | 5-(1-Methyl-5-trifluoromethyl-1H-pyrazol-3-yl)-thiophene-2-carboxylic acid [2-(4-fluoro-phenyl)-ethyl]-amide | 397.39 | 398 |
| 194 | 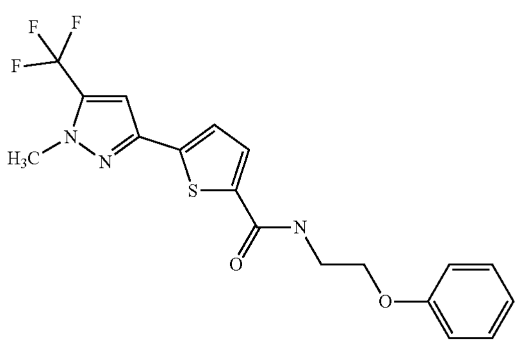 [SMILES: Cn1nc(-c2ccc(C(=O)NCCOc3ccccc3)s2)cc1C(F)(F)F] | 5-(1-methyl-5-trifluoromethyl-1H-pyrazol-3-yl)-thiophene-2-carboxylic acid (2-phenoxy-ethyl)-amide | 395.40 | 396 |
| 195 | 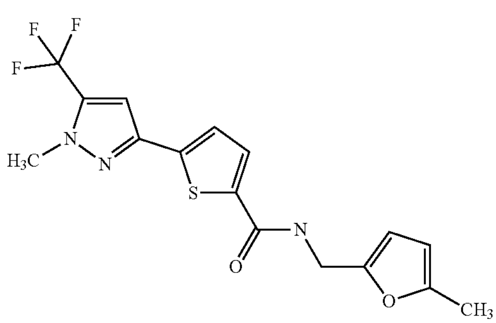 [SMILES: Cc1ccc(CNC(=O)c2ccc(-c3cc(C(F)(F)F)n(C)n3)s2)o1] | 5-(1-Methyl-5-trifluoromethyl-1H-pyrazol-3-yl)-thiophene-2-carboxylic acid (5-methyl-furan-2-ylmethyl)-amide | 369.36 | 370.5 |

-continued

| Comp. # | Structure | Compound Name | MW | LC/MS (ES+) |
|---|---|---|---|---|
| 196 | 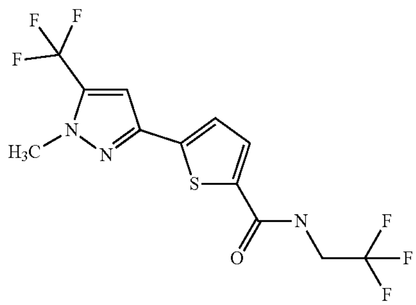 [SMILES: Cn1nc(-c2ccc(C(=O)NCC(F)(F)F)s2)cc1C(F)(F)F] | 5-(1-Methyl-5-trifluoromethyl-1H-pyrazol-3-yl)-thiophene-2-carboxylic acid (2,2,2-trifluoro-ethyl)-amide | 357.28 | 358.1 |
| 197 | 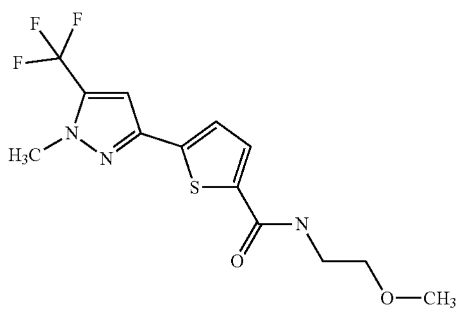 [SMILES: COCCNC(=O)c1ccc(-c2cc(C(F)(F)F)n(C)n2)s1] | 5-(1-Methyl-5-trifluoromethyl-1H-pyrazol-3-yl)-thiophene-2-carboxylic acid (2-methoxy-ethyl)-amide | 333.33 | 334 |
| 198 | 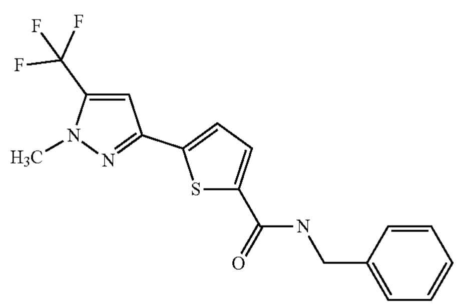 [SMILES: Cn1nc(-c2ccc(C(=O)NCc3ccccc3)s2)cc1C(F)(F)F] | 5-(1-Methyl-5-trifluoromethyl-1H-pyrazol-3-yl)-thiophene-2-carboxylic acid benzylamide | 365.37 | 366.1 |
| 199 | 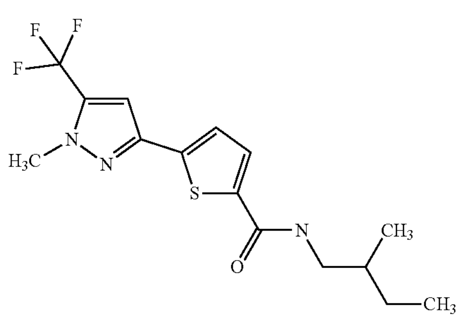 [SMILES: CCC(C)CNC(=O)c1ccc(-c2cc(C(F)(F)F)n(C)n2)s1] | 5-(1-Methyl-5-trifluoromethyl-1H-pyrazol-3-yl)-thiophene-2-carboxylic acid (2-methyl-butyl)-amide | 345.38 | 346.1 |

| Comp. # | Structure | Compound Name | MW | LC/MS (ES+) |
|---|---|---|---|---|
| 200 | 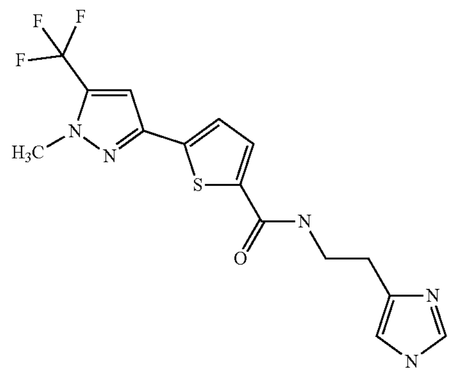 [SMILES: Cn1nc(-c2ccc(C(=O)NCCc3c[nH]cn3)s2)cc1C(F)(F)F] | 5-(1-methyl-5-trifluoromethyl-1H-pyrazol-3-yl)-thiophene-2-carboxylic acid [2-(1H-imidazol-4-yl)-ethyl]-amide | 369.37 | 370.1 |
| 201 | 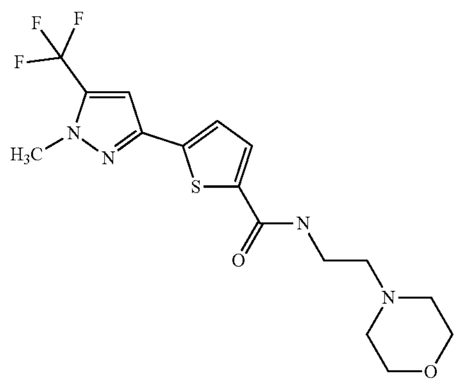 [SMILES: Cn1nc(-c2ccc(C(=O)NCCN3CCOCC3)s2)cc1C(F)(F)F] | 5-(1-Methyl-5-trifluoromethyl-1H-pyrazol-3-yl)-thiophene-2-carboxylic acid (2-morpholin-4-yl-ethyl)-amide | 388.41 | 389.5 |
| 202 | 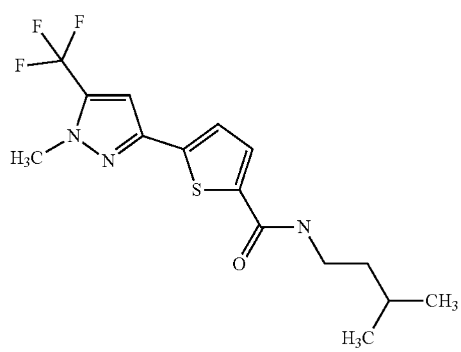 [SMILES: CC(C)CCNC(=O)c1ccc(-c2cc(C(F)(F)F)n(C)n2)s1] | 5-(1-Methyl-5-trifluoromethyl-1H-pyrazol-3-yl)-thiophene-2-carboxylic acid (3-methyl-butyl)-amide | 345.38 | 346.5 |
| 203 | 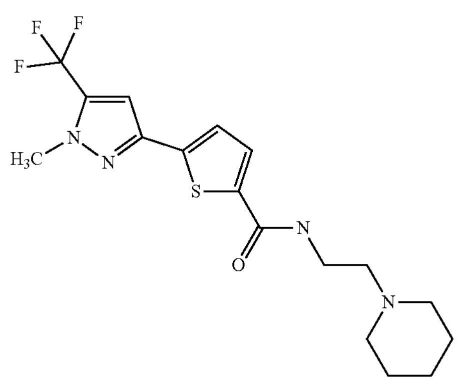 [SMILES: Cn1nc(-c2ccc(C(=O)NCCN3CCCCC3)s2)cc1C(F)(F)F] | 5-(1-Methyl-5-trifluoromethyl-1H-pyrazol-3-yl)-thiophene-2-carboxylic acid (2-piperidin-1-yl-ethyl)-amide | 386.44 | 387 |

| Comp. # | Structure | Compound Name | MW | LC/MS (ES+) |
|---|---|---|---|---|
| 204 | 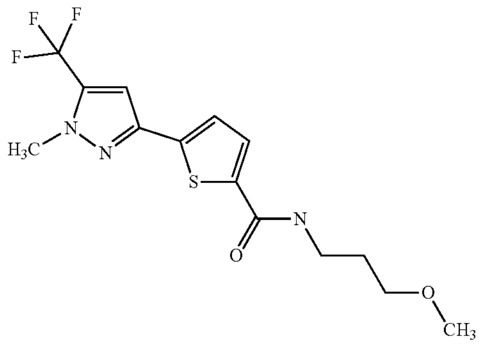 [SMILES: COCCCNC(=O)c1ccc(-c2cc(C(F)(F)F)n(C)n2)s1] | 5-(1-Methyl-5-trifluoromethyl-1H-pyrazol-3-yl)-thiophene-2-carboxylic acid (3-methoxy-propyl)-amide | 347.36 | 348 |
| 205 | 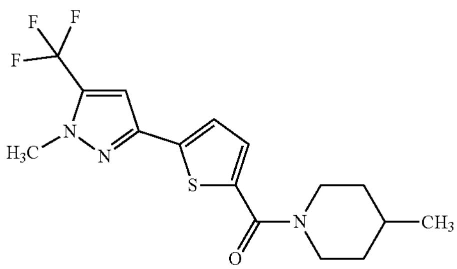 [SMILES: CC1CCN(C(=O)c2ccc(-c3cc(C(F)(F)F)n(C)n3)s2)CC1] | (4-Methyl-piperidin-1-yl)-[5-(1-methyl-5-trifluoromethyl-1H-pyrazol-3-yl)-thiophen-2-yl]-methanone | 357.39 | 358.1 |
| 206 | 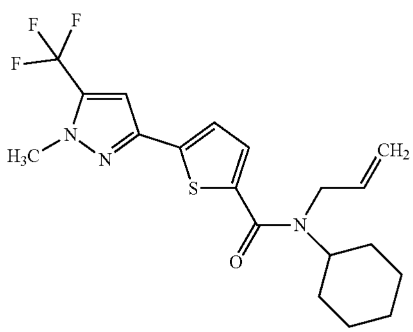 [SMILES: C=CCN(C(=O)c1ccc(-c2cc(C(F)(F)F)n(C)n2)s1)C1CCCCC1] | 5-(1-Methyl-5-trifluoromethyl-1H-pyrazol-3-yl)-thiophene-2-carboxylic acid allyl-cyclohexyl-amide | 397.46 | 398 |
| 207 | 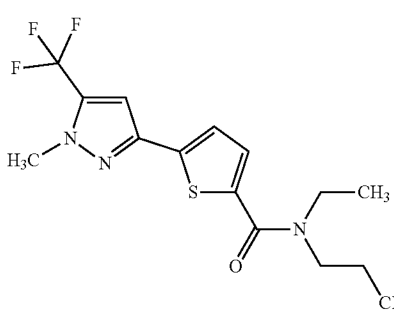 | 5-(1-Methyl-5-trifluoromethyl-1H-pyrazol-3-yl)-thiophene-2-carboxylic acid ethyl-propyl-amide | 345.38 | 346.5 |
| 208 | 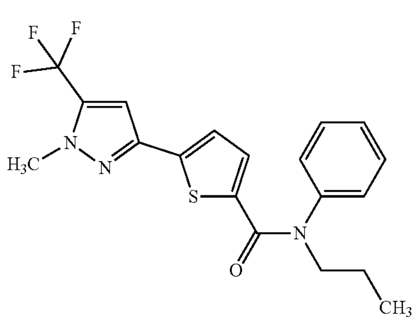 [SMILES: CCCN(C(=O)c1ccc(-c2cc(C(F)(F)F)n(C)n2)s1)c1ccccc1] | 5-(1-methyl-5-trifluoromethyl-1H-pyrazol-3-yl)-thiophene-2-carboxylic acid phenyl-propyl-amide | 393.43 | 394.5 |

-continued

| Comp. # | Structure | Compound Name | MW | LC/MS (ES+) |
|---|---|---|---|---|
| 209 | 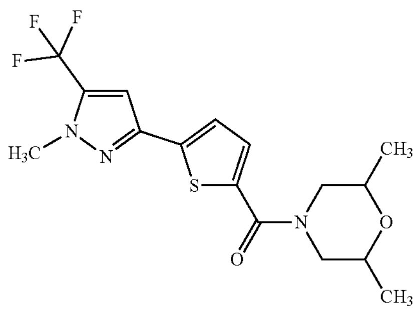 [SMILES: CC1CN(C(=O)c2ccc(-c3cc(C(F)(F)F)n(C)n3)s2)CC(C)O1] | (2,6-Dimethyl-morpholin-4-yl)-[5-(1-methyl-5-trifluoromethyl-1H-pyrazol-3-yl)-thiophen-2-yl]-methanone | 373.39 | 374.6 |
| 210 | 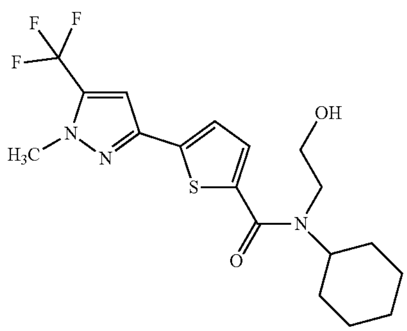 [SMILES: Cn1nc(-c2ccc(C(=O)N(CCO)C3CCCCC3)s2)cc1C(F)(F)F] | 5-(1-Methyl-5-trifluoromethyl-1H-pyrazol-3-yl)-thiophene-2-carboxylic acid cyclohexyl-(2-hydroxy-ethyl)-amide | 401.45 | 402.3 |
| 211 | 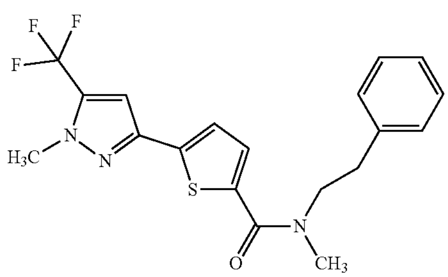 [SMILES: CN(CCc1ccccc1)C(=O)c1ccc(-c2cc(C(F)(F)F)n(C)n2)s1] | 5-(1-Methyl-5-trifluoromethyl-1H-pyrazol-3-yl)-thiophene-2-carboxylic acid methyl-phenethyl-amide | 393.43 | 394.1 |
| 212 | 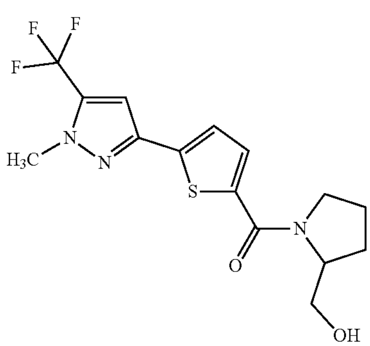 [SMILES: Cn1nc(-c2ccc(C(=O)N3CCCC3CO)s2)cc1C(F)(F)F] | (2-Hydroxymethyl-pyrrolidin-1-yl)-[5-(1-methyl-5-trifluoromethyl-1H-pyrazol-3-yl)-thiophen-2-yl]-methanone | 359.37 | 360.4 |
| 213 | 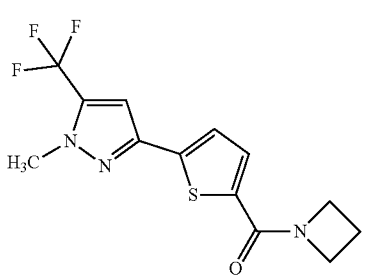 [SMILES: Cn1nc(-c2ccc(C(=O)N3CCC3)s2)cc1C(F)(F)F] | Azetidin-1-yl-[5-(1-methyl-5-trifluoromethyl-1H-pyrazol-3-yl)-thiophen-2-yl]-methanone | 315.32 | 316.5 |

-continued

| Comp. # | Structure | Compound Name | MW | LC/MS (ES+) |
|---|---|---|---|---|
| 214 | 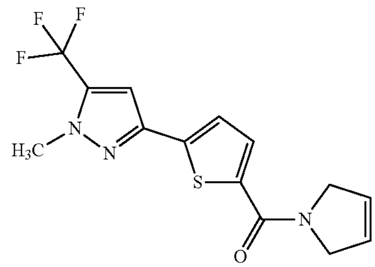 [SMILES: Cn1nc(-c2ccc(C(=O)N3CC=CC3)s2)cc1C(F)(F)F] | (2,5-Dihydro-pyrrol-1-yl)-[5-(1-methyl-5-trifluoromethyl-1H-pyrazol-3-yl)-thiophen-2-yl]-methanone | 327.33 | 328.6 |
| 215 | 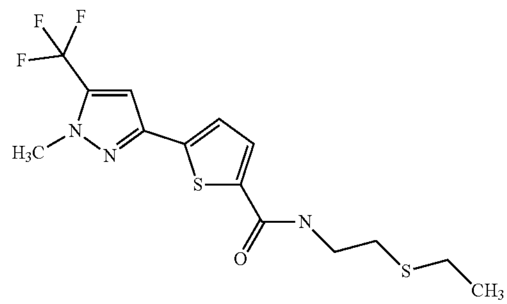 [SMILES: CCSCCNC(=O)c1ccc(-c2cc(C(F)(F)F)n(C)n2)s1] | 5-(1-Methyl-5-trifluoromethyl-1H-pyrazol-3-yl)-thiophene-2-carboxylic acid (2-ethylsulfanyl-ethyl)-amide | 363.42 | 364.3 |
| 216 | 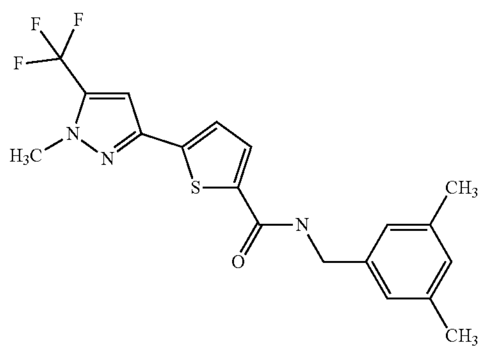 [SMILES: Cc1cc(C)cc(CNC(=O)c2ccc(-c3cc(C(F)(F)F)n(C)n3)s2)c1] | 5-(1-Methyl-5-trifluoromethyl-1H-pyrazol-3-yl)-thiophene-2-carboxylic acid 3,5-dimethyl-benzylamide | 393.43 | 394.5 |
| 217 | 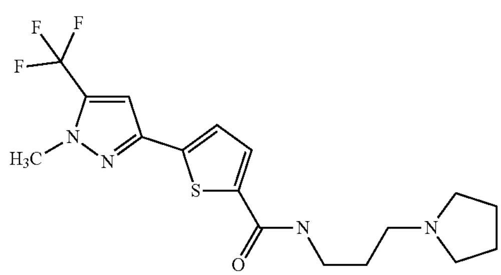 [SMILES: Cn1nc(-c2ccc(C(=O)NCCCN3CCCC3)s2)cc1C(F)(F)F] | 5-(1-Methyl-5-trifluoromethyl-1H-pyrazol-3-yl)-thiophene-2-carboxylic acid (3-pyrrolidin-1-yl-propyl)-amide | 386.44 | 387 |
| 218 | 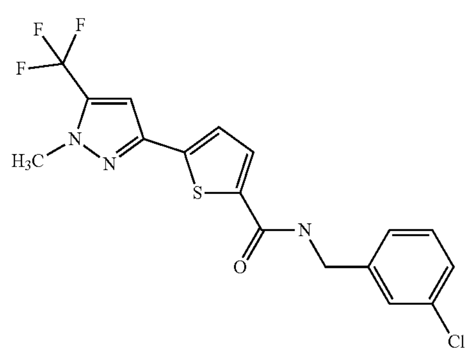 [SMILES: Cn1nc(-c2ccc(C(=O)NCc3cccc(Cl)c3)s2)cc1C(F)(F)F] | 5-(1-Methyl-5-trifluoromethyl-1H-pyrazol-3-yl)-thiophene-2-carboxylic acid 3-chloro-benzylamide | 399.82 | 400.5 |

| Comp. # | Structure | Compound Name | MW | LC/MS (ES+) |
|---|---|---|---|---|
| 219 | 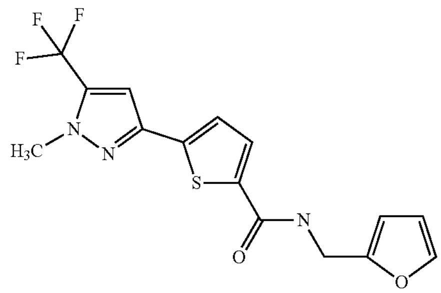 [SMILES: Cn1nc(-c2ccc(C(=O)NCc3ccco3)s2)cc1C(F)(F)F] | 5-(1-Methyl-5-trifluoromethyl-1H-pyrazol-3-yl)-thiophene-2-carboxylic acid (furan-2-ylmethyl)-amide | 355.34 | 356.5 |
| 220 | 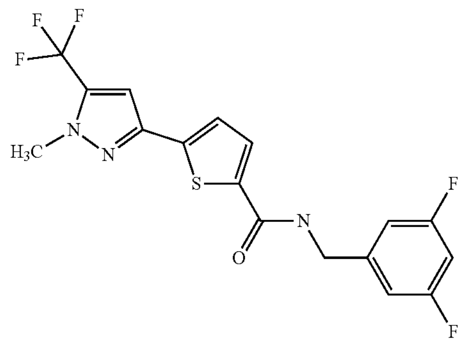 [SMILES: Cn1nc(-c2ccc(C(=O)NCc3cc(F)cc(F)c3)s2)cc1C(F)(F)F] | 5-(1-Methyl-5-trifluoromethyl-1H-pyrazol-3-yl)-thiophene-2-carboxylic acid 3,5-difluoro-benzylamide | 401.35 | 402 |
| 221 | 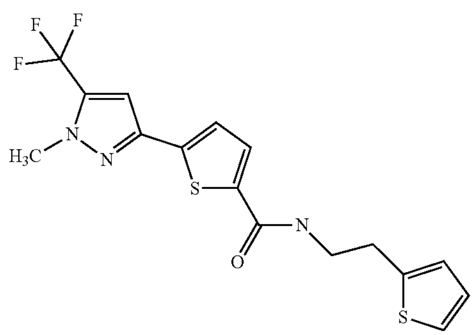 [SMILES: Cn1nc(-c2ccc(C(=O)NCCc3cccs3)s2)cc1C(F)(F)F] | 5-(1-Methyl-5-trifluoromethyl-1H-pyrazol-3-yl)-thiophene-2-carboxylic acid (2-thiophen-2-yl-ethyl)-amide | 385.43 | 386.3 |
| 222 | 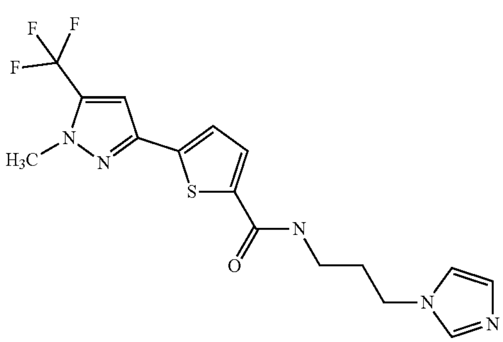 [SMILES: Cn1nc(-c2ccc(C(=O)NCCCn3ccnc3)s2)cc1C(F)(F)F] | 5-(1-methyl-5-trifluoromethyl-1H-pyrazol-3-yl)-thiophene-2-carboxylic acid (3-imidazol-1-yl-propyl)-amide | 383.39 | 384.5 |
| 223 | 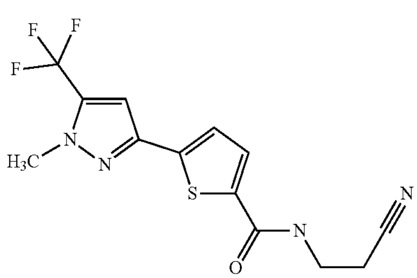 [SMILES: Cn1nc(-c2ccc(C(=O)NCCC#N)s2)cc1C(F)(F)F] | 5-(1-Methyl-5-trifluoromethyl-1H-pyrazol-3-yl)-thiophene-2-carboxylic acid (2-cyano-ethyl)-amide | 328.31 | 329 |

| Comp. # | Structure | Compound Name | MW | LC/MS (ES+) |
|---|---|---|---|---|
| 224 | 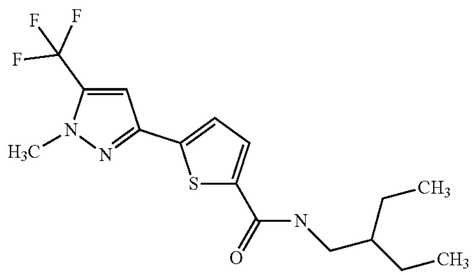 [SMILES: CCC(CC)CNC(=O)c1ccc(-c2cc(C(F)(F)F)n(C)n2)s1] | 5-(1-Methyl-5-trifluoromethyl-1H-pyrazol-3-yl)-thiophene-2-carboxylic acid (2-ethyl-butyl)-amide | 359.41 | 360.3 |
| 225 | 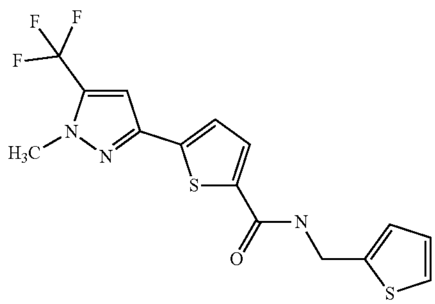 [SMILES: Cn1nc(-c2ccc(C(=O)NCc3cccs3)s2)cc1C(F)(F)F] | 5-(1-Methyl-5-trifluoromethyl-1H-pyrazol-3-yl)-thiophene-2-carboxylic acid (thiophen-2-ylmethyl)-amide | 371.40 | 372 |
| 226 | 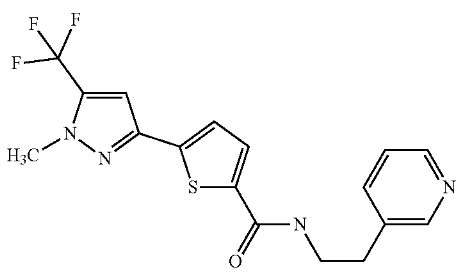 [SMILES: Cn1nc(-c2ccc(C(=O)NCCc3cccnc3)s2)cc1C(F)(F)F] | 5-(1-Methyl-5-trifluoromethyl-1H-pyrazol-3-yl)-thiophene-2-carboxylic acid (2-pyridin-3-yl-ethyl)-amide | 380.39 | 381.5 |
| 227 | Chiral | 5-(1-Methyl-5-trifluoromethyl-1H-pyrazol-3-yl)-thiophene-2-carboxylic acid ((S)-2-hydroxy-1-methyl-2-phenyl-ethyl)-methyl-amide | 423.45 | 424.5 |
| 228 | 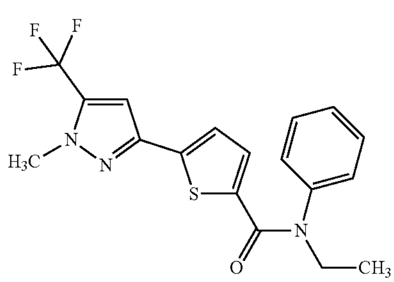 [SMILES: CCN(C(=O)c1ccc(-c2cc(C(F)(F)F)n(C)n2)s1)c1ccccc1] | 5-(1-methyl-5-trifluoromethyl-1H-pyrazol-3-yl)-thiophene-2-carboxylic acid ethyl-phenyl-amide | 379.40 | 380.5 |

| Comp. # | Structure | Compound Name | MW | LC/MS (ES+) |
|---|---|---|---|---|
| 229 | Chiral | ((R)-3-Hydroxy-pyrrolidin-1-yl)-[5-(1-methyl-5-trifluoromethyl-1H-pyrazol-3-yl)-thiophen-2-yl]-methanone | 345.34 | 346.6 |
| 230 | 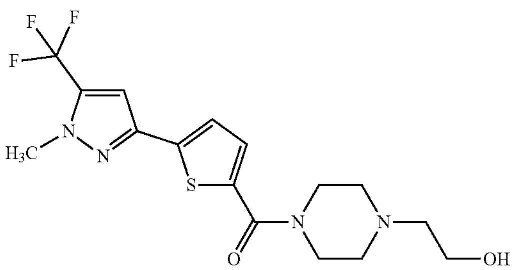 [SMILES: Cn1nc(-c2ccc(C(=O)N3CCN(CCO)CC3)s2)cc1C(F)(F)F] | [4-(2-Hydroxy-ethyl)-piperazin-1-yl]-[5-(1-methyl-5-trifluoromethyl-1H-pyrazol-3-yl)-thiophen-2-yl]-methanone | 388.41 | 389.6 |
| 231 | 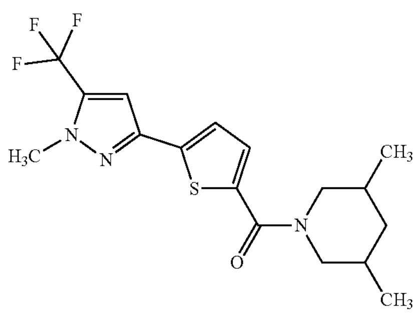 [SMILES: CC1CC(C)CN(C(=O)c2ccc(-c3cc(C(F)(F)F)n(C)n3)s2)C1] | (3,5-Dimethyl-piperidin-1-yl)-[5-(1-methyl-5-trifluoromethyl-1H-pyrazol-3-yl)-thiophen-2-yl]-methanone | 371.42 | 372.6 |
| 232 | 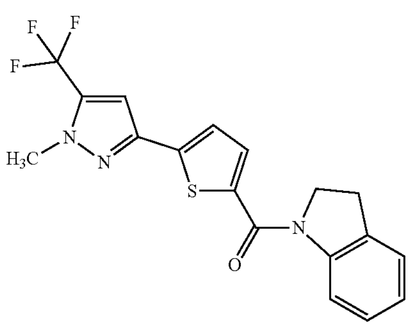 [SMILES: Cn1nc(-c2ccc(C(=O)N3CCc4ccccc43)s2)cc1C(F)(F)F] | (2,3-Dihydro-indol-1-yl)-[5-(1-methyl-5-trifluoromethyl-1H-pyrazol-3-yl)-thiophen-2-yl]-methanone | 377.38 | 378.6 |
| 233 | 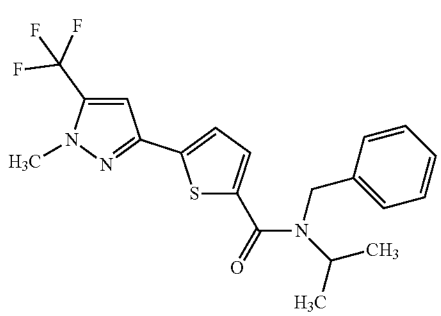 [SMILES: CC(C)N(Cc1ccccc1)C(=O)c1ccc(-c2cc(C(F)(F)F)n(C)n2)s1] | 5-(1-Methyl-5-trifluoromethyl-1H-pyrazol-3-yl)-thiophene-2-carboxylic acid benzyl-isopropyl-amide | 407.45 | 408 |

-continued

| Comp. # | Structure | Compound Name | MW | LC/MS (ES+) |
|---|---|---|---|---|
| 234 | 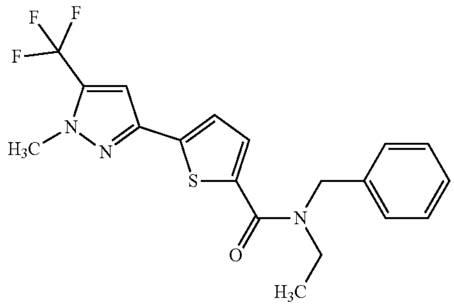 [SMILES: CCN(Cc1ccccc1)C(=O)c1ccc(-c2cc(C(F)(F)F)n(C)n2)s1] | 5-(1-methyl-5-trifluoromethyl-1H-pyrazol-3-yl)-thiophene-2-carboxylic acid benzyl-ethyl-amide | 393.43 | 394 |
| 235 | 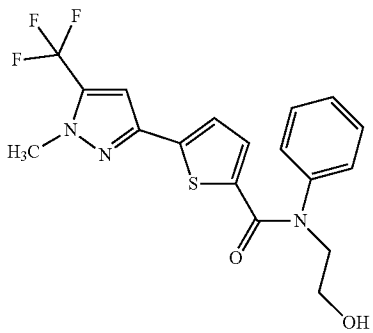 [SMILES: Cn1nc(-c2ccc(C(=O)N(CCO)c3ccccc3)s2)cc1C(F)(F)F] | 5-(1-methyl-5-trifluoromethyl-1H-pyrazol-3-yl)-thiophene-2-carboxylic acid (2-hydroxy-ethyl)-phenyl-amide | 395.40 | 396 |
| 236 | 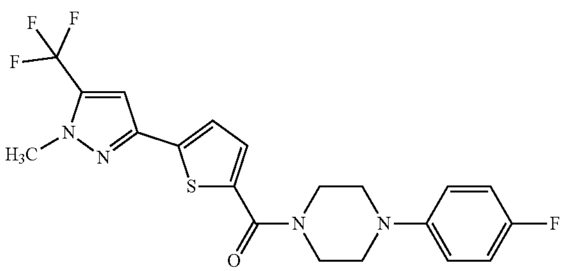 [SMILES: Cn1nc(-c2ccc(C(=O)N3CCN(c4ccc(F)cc4)CC3)s2)cc1C(F)(F)F] | [4-(4-Fluoro-phenyl)-piperazin-1-yl]-[5-(1-methyl-5-trifluoromethyl-1H-pyrazol-3-yl)-thiophen-2-yl]-methanone | 438.44 | 439.6 |
| 237 | 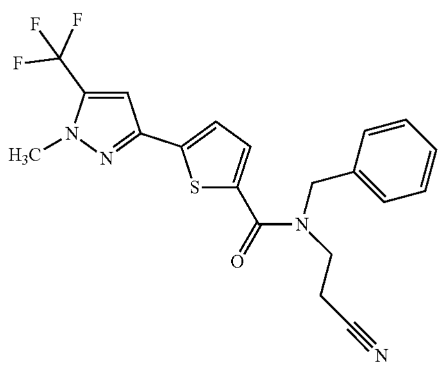 [SMILES: Cn1nc(-c2ccc(C(=O)N(CCC#N)Cc3ccccc3)s2)cc1C(F)(F)F] | 5-(1-Methyl-5-trifluoromethyl-1H-pyrazol-3-yl)-thiophene-2-carboxylic acid benzyl-(2-cyano-ethyl)-amide | 418.44 | 419 |
| 238 | 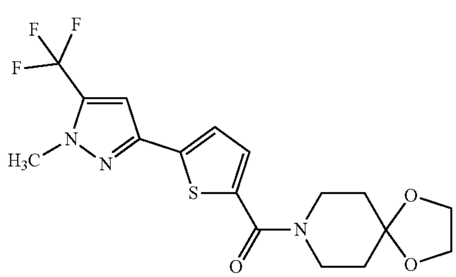 [SMILES: Cn1nc(-c2ccc(C(=O)N3CCC4(CC3)OCCO4)s2)cc1C(F)(F)F] | (1,4-Dioxa-8-aza-spiro[4.5]dec-8-yl)-[5-(1-methyl-5-trifluoromethyl-1H-pyrazol-3-yl)-thiophen-2-yl]-methanone | 401.40 | 402.6 |

| Comp. # | Structure | Compound Name | MW | LC/MS (ES+) |
|---|---|---|---|---|
| 239 | 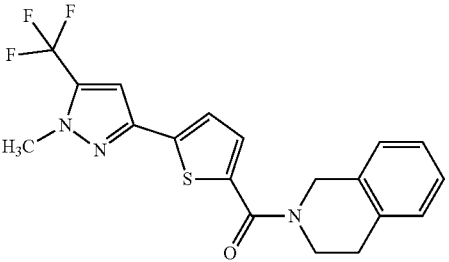 [SMILES: Cn1nc(-c2ccc(C(=O)N3CCc4ccccc4C3)s2)cc1C(F)(F)F] | (3,4-Dihydro-1H-isoquinolin-2-yl)-[5-(1-methyl-5-trifluoromethyl-1H-pyrazol-3-yl)-thiophen-2-yl]-methanone | 391.41 | 392.6 |
| 240 | 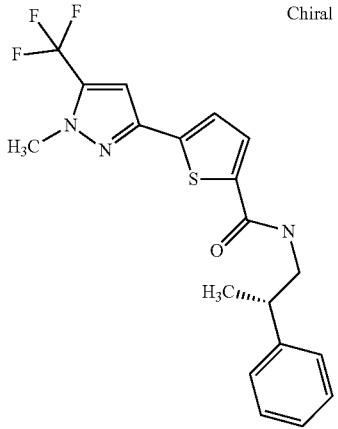 [SMILES: C[C@H](CNC(=O)c1ccc(-c2cc(C(F)(F)F)n(C)n2)s1)c1ccccc1] Chiral | 5-(1-Methyl-5-trifluoromethyl-1H-pyrazol-3-yl)-thiophene-2-carboxylic acid ((S)-2-phenyl-propyl)-amide | 393.43 | 394.4 |
| 241 | 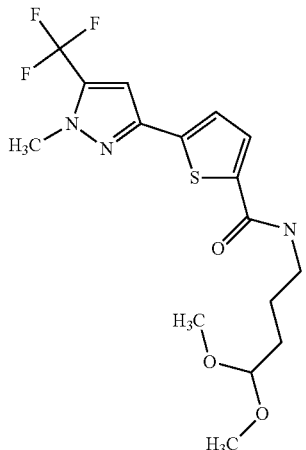 [SMILES: COC(CCCNC(=O)c1ccc(-c2cc(C(F)(F)F)n(C)n2)s1)OC] | 5-(1-Methyl-5-trifluoromethyl-1H-pyrazol-3-yl)-thiophene-2-carboxylic acid (4,4-dimethoxy-butyl)-amide | 391.41 | 392.4 |
| 242 | 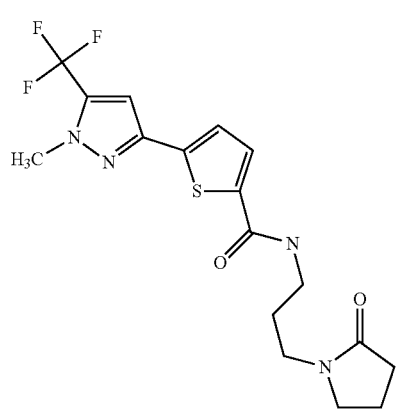 [SMILES: Cn1nc(-c2ccc(C(=O)NCCCN3CCCC3=O)s2)cc1C(F)(F)F] | 5-(1-Methyl-5-trifluoromethyl-1H-pyrazol-3-yl)-thiophene-2-carboxylic acid [3-(2-oxo-pyrrolidin-1-yl)-propyl]-amide | 400.42 | 401.6 |

-continued

| Comp. # | Structure | Compound Name | MW | LC/MS (ES+) |
|---|---|---|---|---|
| 243 | 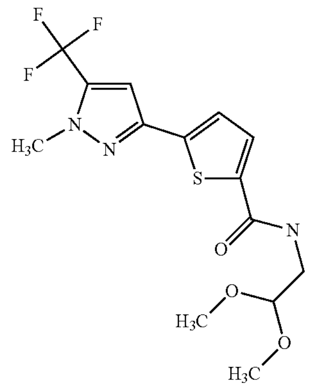 [SMILES: COC(CNC(=O)c1ccc(-c2cc(C(F)(F)F)n(C)n2)s1)OC] | 5-(1-Methyl-5-trifluoromethyl-1H-pyrazol-3-yl)-thiophene-2-carboxylic acid (2,2-dimethoxy-ethyl)-amide | 363.26 | 364.3 |
| 244 | 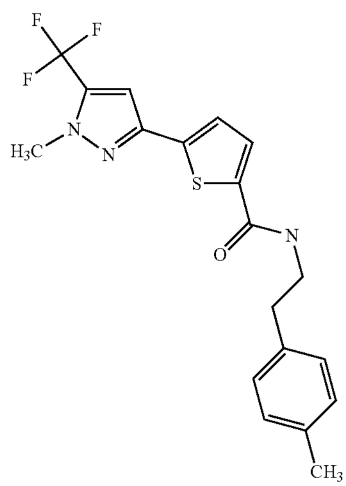 [SMILES: Cc1ccc(CCNC(=O)c2ccc(-c3cc(C(F)(F)F)n(C)n3)s2)cc1] | 5-(1-Methyl-5-trifluoromethyl-1H-pyrazol-3-yl)-thiophene-2-carboxylic acid (2-p-tolyl-ethyl)-amide | 393.43 | 394 |
| 245 | 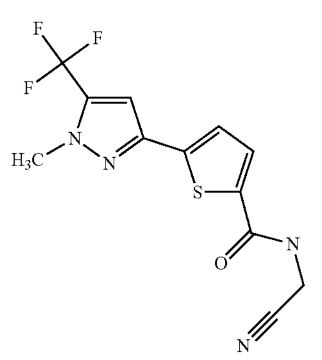 [SMILES: Cn1nc(-c2ccc(C(=O)NCC#N)s2)cc1C(F)(F)F] | 5-(1-Methyl-5-trifluoromethyl-1H-pyrazol-3-yl)-thiophene-2-carboxylic acid cyanomethyl-amide | 314.29 | 315.1 |

-continued

| Comp. # | Structure | Compound Name | MW | LC/MS (ES+) |
|---|---|---|---|---|
| 246 | 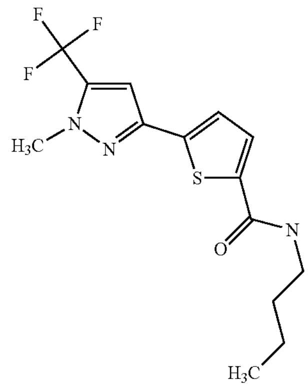 [SMILES: CCCCNC(=O)c1ccc(-c2cc(C(F)(F)F)n(C)n2)s1] | 5-(1-Methyl-5-trifluoromethyl-1H-pyrazol-3-yl)-thiophene-2-carboxylic acid butylamide | 331.36 | 332.5 |
| 247 | 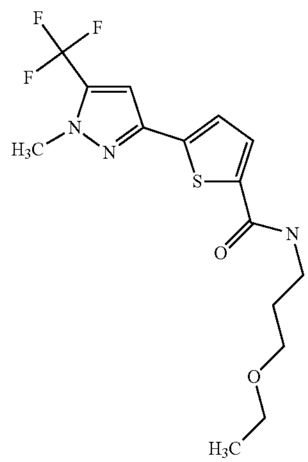 [SMILES: CCOCCCNC(=O)c1ccc(-c2cc(C(F)(F)F)n(C)n2)s1] | 5-(1-Methyl-5-trifluoromethyl-1H-pyrazol-3-yl)-thiophene-2-carboxylic acid (3-ethoxy-propyl)-amide | 361.38 | 362.1 |
| 248 | 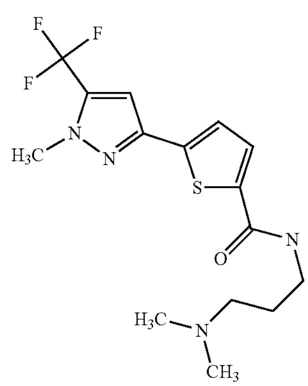 [SMILES: CN(C)CCCNC(=O)c1ccc(-c2cc(C(F)(F)F)n(C)n2)s1] | 5-(1-Methyl-5-trifluoromethyl-1H-pyrazol-3-yl)-thiophene-2-carboxylic acid (3-dimethylamino-propyl)-amide | 360.40 | 361 |

| Comp. # | Structure | Compound Name | MW | LC/MS (ES+) |
|---|---|---|---|---|
| 249 | 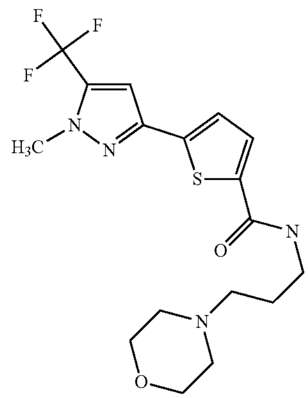 [SMILES: Cn1nc(-c2ccc(C(=O)NCCCN3CCOCC3)s2)cc1C(F)(F)F] | 5-(1-Methyl-5-trifluoromethyl-1H-pyrazol-3-yl)-thiophene-2-carboxylic acid (3-morpholin-4-yl-propyl)-amide | 402.44 | 403 |
| 250 | 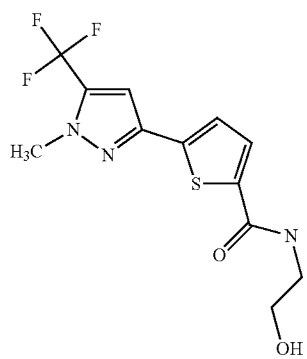 [SMILES: Cn1nc(-c2ccc(C(=O)NCCO)s2)cc1C(F)(F)F] | 5-(1-Methyl-5-trifluoromethyl-1H-pyrazol-3-yl)-thiophene-2-carboxylic acid (2-hydroxy-ethyl)-amide | 319.30 | 320.3 |
| 251 | 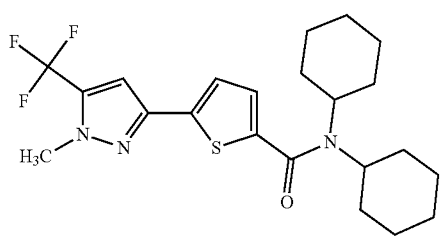 [SMILES: Cn1nc(-c2ccc(C(=O)N(C3CCCCC3)C3CCCCC3)s2)cc1C(F)(F)F] | 5-(1-Methyl-5-trifluoromethyl-1H-pyrazol-3-yl)-thiophene-2-carboxylic acid dicyclohexylamide | 439.54 | 440.6 |
| 252 | 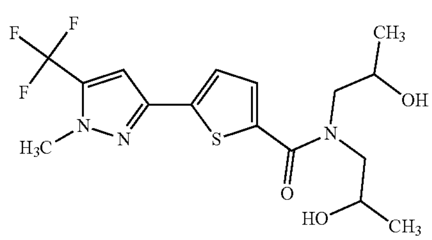 [SMILES: CC(O)CN(CC(C)O)C(=O)c1ccc(-c2cc(C(F)(F)F)n(C)n2)s1] | 5-(1-Methyl-5-trifluoromethyl-1H-pyrazol-3-yl)-thiophene-2-carboxylic acid bis(2-hydroxy-propyl)-amide | 391.41 | 392.5 |
| 253 | 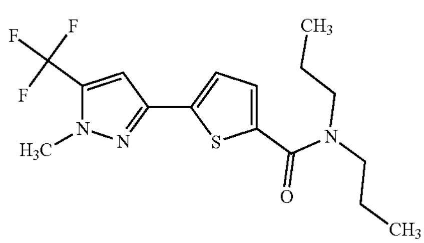 [SMILES: CCCN(CCC)C(=O)c1ccc(-c2cc(C(F)(F)F)n(C)n2)s1] | 5-(1-Methyl-5-trifluoromethyl-1H-pyrazol-3-yl)-thiophene-2-carboxylic acid dipropylamide | 359.41 | 360.5 |

-continued

| Comp. # | Structure | Compound Name | MW | LC/MS (ES+) |
|---|---|---|---|---|
| 254 | 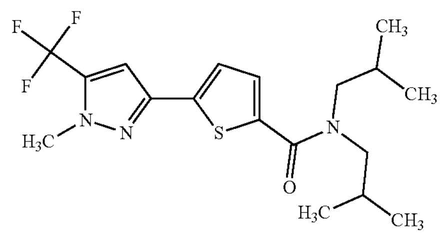 [SMILES: CC(C)CN(CC(C)C)C(=O)c1ccc(-c2cc(C(F)(F)F)n(C)n2)s1] | 5-(1-Methyl-5-trifluoromethyl-1H-pyrazol-3-yl)-thiophene-2-carboxylic acid diisobutylamide | 387.46 | 388 |
| 255 | 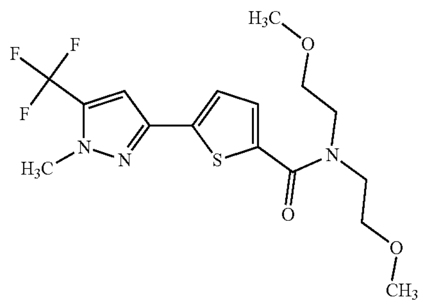 [SMILES: COCCN(CCOC)C(=O)c1ccc(-c2cc(C(F)(F)F)n(C)n2)s1] | 5-(1-Methyl-5-trifluoromethyl-1H-pyrazol-3-yl)-thiophene-2-carboxylic acid bis(2-methoxy-ethyl)-amide | 391.41 | 392.5 |
| 256 | 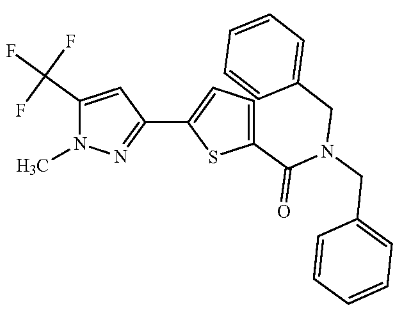 [SMILES: Cn1nc(-c2ccc(C(=O)N(Cc3ccccc3)Cc3ccccc3)s2)cc1C(F)(F)F] | 5-(1-Methyl-5-trifluoromethyl-1H-pyrazol-3-yl)-thiophene-2-carboxylic acid dibenzylamide | 455.50 | 456.5 |
| 257 | 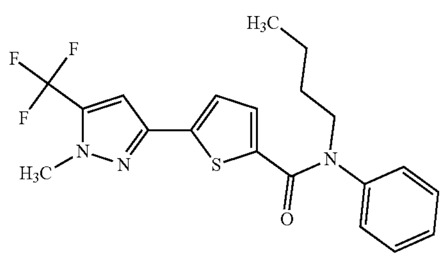 [SMILES: CCCCN(C(=O)c1ccc(-c2cc(C(F)(F)F)n(C)n2)s1)c1ccccc1] | 5-(1-Methyl-5-trifluoromethyl-1H-pyrazol-3-yl)-thiophene-2-carboxylic acid butyl-phenyl-amide | 407.45 | 408.6 |
| 258 | 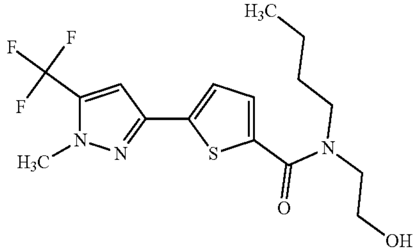 [SMILES: CCCCN(CCO)C(=O)c1ccc(-c2cc(C(F)(F)F)n(C)n2)s1] | 5-(1-Methyl-5-trifluoromethyl-1H-pyrazol-3-yl)-thiophene-2-carboxylic acid butyl-(2-hydroxy-ethyl)-amide | 375.41 | 376 |

-continued

| Comp. # | Structure | Compound Name | MW | LC/MS (ES+) |
|---|---|---|---|---|
| 259 | 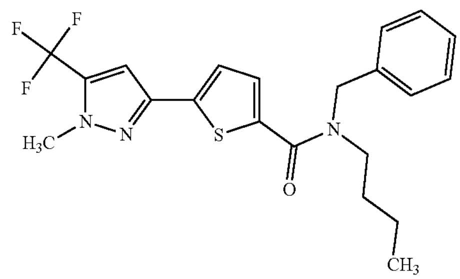 [SMILES: CCCCN(Cc1ccccc1)C(=O)c1ccc(-c2cc(C(F)(F)F)n(C)n2)s1] | 5-(1-Methyl-5-trifluoromethyl-1H-pyrazol-3-yl)-thiophene-2-carboxylic acid benzyl-butyl-amide | 421.48 | 422.6 |
| 260 | 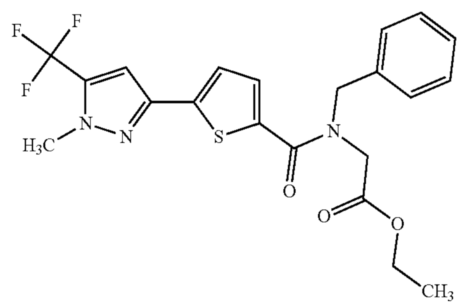 [SMILES: CCOC(=O)CN(Cc1ccccc1)C(=O)c1ccc(-c2cc(C(F)(F)F)n(C)n2)s1] | {Benzyl-[5-(1-methyl-5-trifluoromethyl-1H-pyrazol-3-yl)-thiophene-2-carbonyl]-amino}-acetic acid ethyl ester | 451.46 | 452.6 |
| 261 | 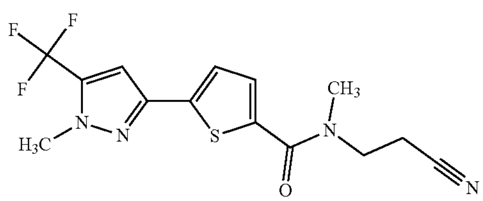 [SMILES: CN(CCC#N)C(=O)c1ccc(-c2cc(C(F)(F)F)n(C)n2)s1] | 5-(1-Methyl-5-trifluoromethyl-1H-pyrazol-3-yl)-thiophene-2-carboxylic acid (2-cyano-ethyl)-methyl-amide | 342.34 | 343.5 |
| 262 | 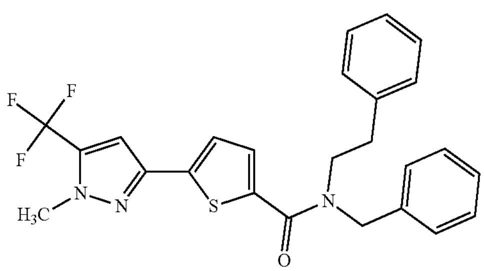 [SMILES: Cn1nc(-c2ccc(C(=O)N(CCc3ccccc3)Cc3ccccc3)s2)cc1C(F)(F)F] | 5-(1-Methyl-5-trifluoromethyl-1H-pyrazol-3-yl)-thiophene-2-carboxylic acid benzyl-phenethyl-amide | 469.52 | 470.6 |
| 263 | 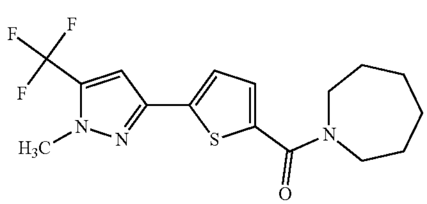 [SMILES: Cn1nc(-c2ccc(C(=O)N3CCCCCC3)s2)cc1C(F)(F)F] | [5-(1-Methyl-5-trifluoromethyl-1H-pyrazol-3-yl)-thiophen-2-yl]-perhydro-azepin-1-yl-methanone | 357.39 | 358.4 |
| 264 | 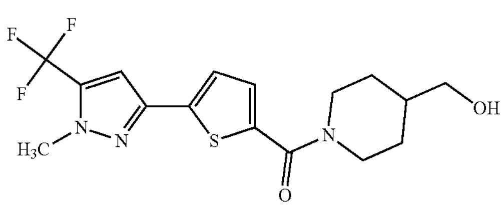 [SMILES: Cn1nc(-c2ccc(C(=O)N3CCC(CO)CC3)s2)cc1C(F)(F)F] | (4-Hydroxymethyl-piperidin-1-yl)-[5-(1-methyl-5-trifluoromethyl-1H-pyrazol-3-yl)-thiophen-2-yl]-methanone | 373.39 | 374.5 |

-continued

| Comp. # | Structure | Compound Name | MW | LC/MS (ES+) |
|---|---|---|---|---|
| 265 | 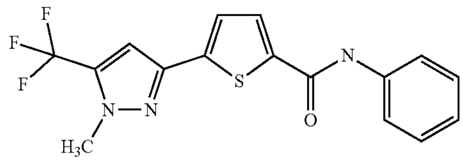 [SMILES: Cn1nc(-c2ccc(C(=O)Nc3ccccc3)s2)cc1C(F)(F)F] | 5-(1-Methyl-5-trifluoromethyl-1H-pyrazol-3-yl)-thiophen-2-carboxylic acid phenylamide | 351.35 | 352.5 |
| 266 | 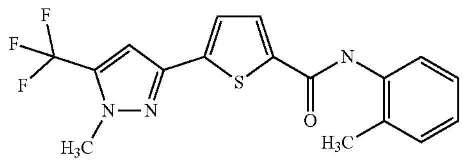 [SMILES: Cc1ccccc1NC(=O)c1ccc(-c2cc(C(F)(F)F)n(C)n2)s1] | 5-(1-Methyl-5-trifluoromethyl-1H-pyrazol-3-yl)-thiophene-2-carboxylic acid o-tolylamide | 365.37 | 366 |
| 267 | 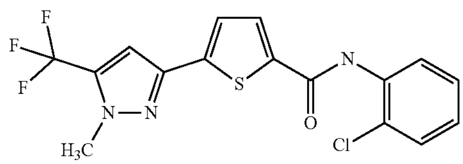 [SMILES: Cn1nc(-c2ccc(C(=O)Nc3ccccc3Cl)s2)cc1C(F)(F)F] | 5-(1-Methyl-5-trifluoromethyl-1H-pyrazol-3-yl)-thiophene-2-carboxylic acid (2-chloro-phenyl)-amide | 385.79 | 386 |
| 268 | 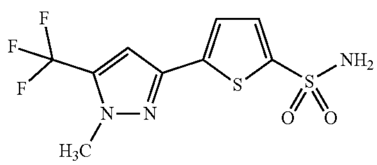 [SMILES: Cn1nc(-c2ccc(S(N)(=O)=O)s2)cc1C(F)(F)F] | 5-(1-Methyl-5-trifluoromethyl-1H-pyrazol-3-yl)-thiophene-2-sulfonic acid amide | 311.31 | 312.5 |
| 269 | 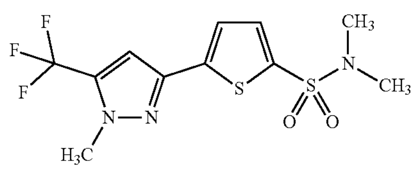 [SMILES: CN(C)S(=O)(=O)c1ccc(-c2cc(C(F)(F)F)n(C)n2)s1] | 5-(1-Methyl-5-trifluoromethyl-1H-pyrazol-3-yl)-thiophene-2-sulfonic acid dimethylamide | 339.36 | 340.5 |
| 270 | 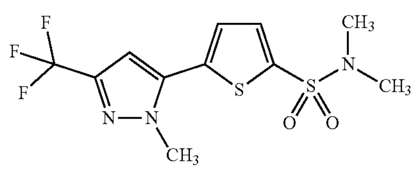 [SMILES: CN(C)S(=O)(=O)c1ccc(-c2cc(C(F)(F)F)nn2C)s1] | 5-(1-Methyl-5-trifluoromethyl-1H-pyrazol-5-yl)-thiophene-2-sulfonic acid dimethylamide | 339.36 | 340.5 |
| 271 | 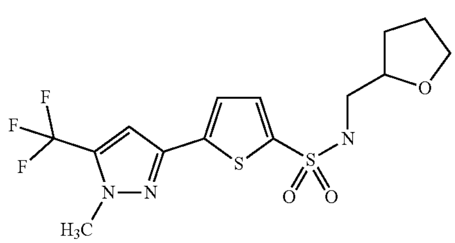 [SMILES: Cn1nc(-c2ccc(S(=O)(=O)NCC3CCCO3)s2)cc1C(F)(F)F] | 5-(1-Methyl-5-trifluoromethyl-1H-pyrazol-3-yl)-thiophene-2-sulfonic acid (tetrahydro-furan-2-ylmethyl)-amide | 395.42 | 396.5 |
| 272 | 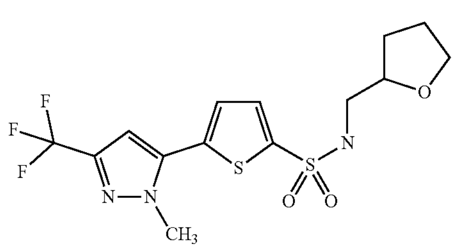 [SMILES: Cn1nc(C(F)(F)F)cc1-c1ccc(S(=O)(=O)NCC2CCCO2)s1] | 5-(1-Methyl-3-trifluoromethyl-1H-pyrazol-5-yl)-thiophene-2-sulfonic acid (tetrahydro-furan-2-ylmethyl)-amide | 395.42 | 396.5 |

-continued

| Comp. # | Structure | Compound Name | MW | LC/MS (ES+) |
|---|---|---|---|---|
| 273 | Chiral | 5-(1-Methyl-5-trifluoromethyl-1H-pyrazol-3-yl)-thiophene-2-carboxylic acid [(R)-1-(tetrahydro-furan-2-yl)methyl]-amide | 359.37 | 360.6 |
| 274 | Chiral | 5-(1-Methyl-5-trifluoromethyl-1H-pyrazol-3-yl)-thiophene-2-carboxylic acid [(S)-1-(tetrahydro-furan-2-yl)methyl]-amide | 359.37 | 360.4 |
| 275 | 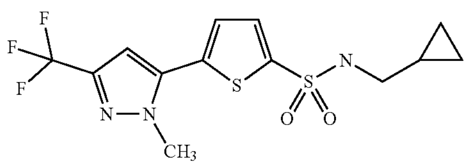 [SMILES: Cn1nc(C(F)(F)F)cc1-c1ccc(S(=O)(=O)NCC2CC2)s1] | 5-(1-Methyl-3-trifluoromethyl-1H-pyrazol-5-yl)-thiophene-2-sulfonic acid cyclopropylmethyl-amide | 365.40 | 366.5 |
| 276 | 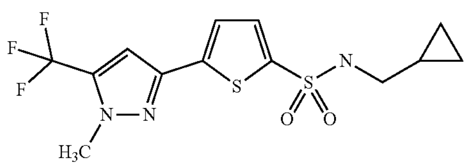 [SMILES: Cn1nc(-c2ccc(S(=O)(=O)NCC3CC3)s2)cc1C(F)(F)F] | 5-(1-Methyl-5-trifluoromethyl-1H-pyrazol-3-yl)-thiophene-2-sulfonic acid cyclopropylmethyl-amide | 365.40 | 366.5 |
| 277 | 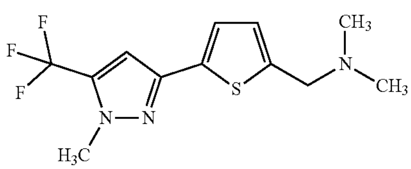 [SMILES: CN(C)Cc1ccc(-c2cc(C(F)(F)F)n(C)n2)s1] | Dimethyl-[5-(1-methyl-5-trifluoromethyl-1H-pyrazol-3-yl)-thiophen-2-ylmethyl]-amine | 289.32 | 290.5 |
| 278 | 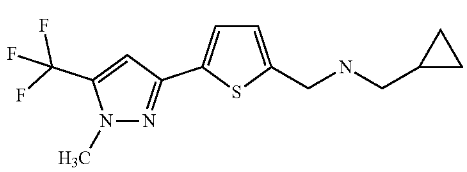 [SMILES: Cn1nc(-c2ccc(CNCC3CC3)s2)cc1C(F)(F)F] | Cyclopropylmethyl-[5-(1-methyl-6-trifluoromethyl-1H-pyrazol-3-yl)-thiophen-2-ylmethyl]-amine | 315.36 | 316.6 |
| 279 | 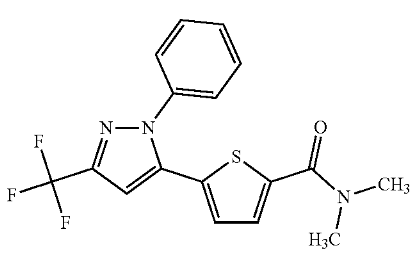 [SMILES: CN(C)C(=O)c1ccc(-c2cc(C(F)(F)F)nn2-c2ccccc2)s1] | 5-(1-Phenyl-3-trifluoromethyl-1H-pyrazol-5-yl)-thiophene-2-carboxylic acid dimethylamide | 365.37 | 366 |

| Comp. # | Structure | Compound Name | MW | LC/MS (ES+) |
|---|---|---|---|---|
| 280 | 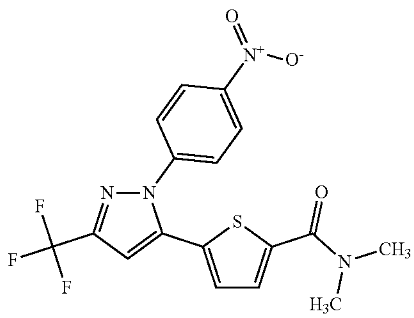 [SMILES: CN(C)C(=O)c1ccc(-c2cc(C(F)(F)F)nn2-c2ccc([N+](=O)[O-])cc2)s1] | 5-[1-(4-Nitro-phenyl)-3-trifluoromethyl-1H-pyrazol-5-yl]-thiophene-2-carboxylic acid dimethylamide | 410.37 | 411 |
| 281 | 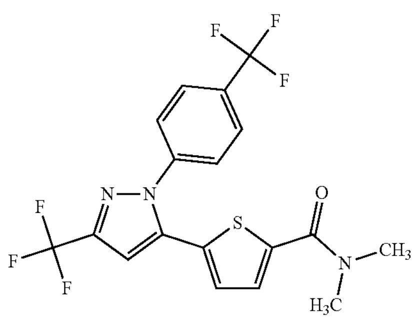 [SMILES: CN(C)C(=O)c1ccc(-c2cc(C(F)(F)F)nn2-c2ccc(C(F)(F)F)cc2)s1] | 5-[3-Trifluoromethyl-1-(4-trifluoromethyl-phenyl)-1H-pyrazol-5-yl]-thiophene-2-carboxylic acid dimethylamide] | 433.37 | 434 |
| 282 | 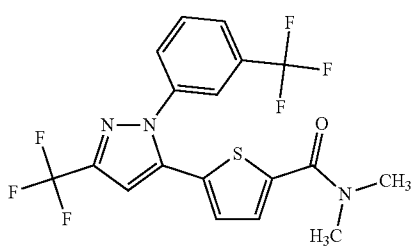 [SMILES: CN(C)C(=O)c1ccc(-c2cc(C(F)(F)F)nn2-c2cccc(C(F)(F)F)c2)s1] | 5-[3-Trifluoromethyl-1-(3-trifluoromethyl-phenyl)-1H-pyrazol-5-yl]-thiophene-2-carboxylic acid dimethylamide | 433.37 | 434 |
| 283 | 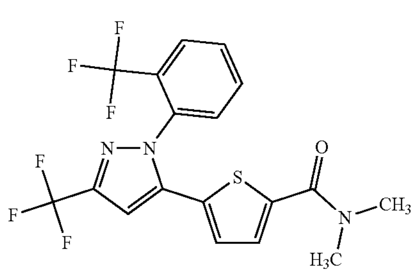 [SMILES: CN(C)C(=O)c1ccc(-c2cc(C(F)(F)F)nn2-c2ccccc2C(F)(F)F)s1] | 5-[3-Trifluoromethyl-1-(2-trifluoromethyl-phenyl)-2H-pyrazol-5-yl]-thiophene-2-carboxylic acid dimethylamide | 433.37 | 434.5 |
| 284 | 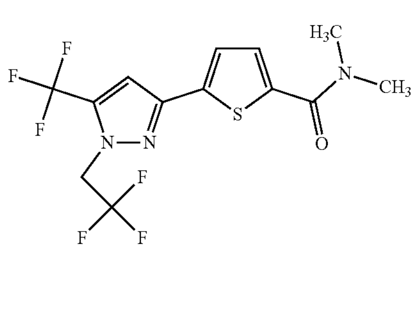 [SMILES: CN(C)C(=O)c1ccc(-c2cc(C(F)(F)F)n(CC(F)(F)F)n2)s1] | 5-[1-(2,2,2-Trifluoro-ethyl)-5-trifluoromethyl-1H-pyrazol-3-yl]-thiophene-2-carboxylic acid dimethylamide | 371.30 | 372 |

-continued

| Comp. # | Structure | Compound Name | MW | LC/MS (ES+) |
|---|---|---|---|---|
| 285 | 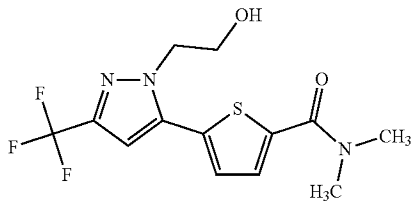 [SMILES: CN(C)C(=O)c1ccc(-c2cc(C(F)(F)F)nn2CCO)s1] | 5-[2-(2-Hydroxy-ethyl)-5-trifluoromethyl-2H-pyrazol-3-yl]-thiophene-2-carboxylic acid dimethylamide | 333.33 | 334.5 |
| 286 | 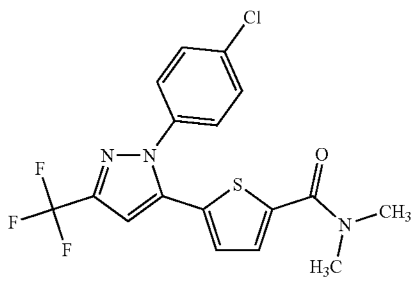 [SMILES: CN(C)C(=O)c1ccc(-c2cc(C(F)(F)F)nn2-c2ccc(Cl)cc2)s1] | 5-[1-(4-Chlorophenyl)-3-trifluoromethyl-1H-pyrazol-5-yl]-thiophene-2-carboxylic acid dimethylamide | 399.82 | 400.5 |
| 287 | 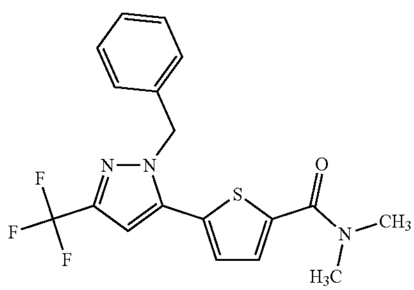 [SMILES: CN(C)C(=O)c1ccc(-c2cc(C(F)(F)F)nn2Cc2ccccc2)s1] | 5-(1-Benzyl-3-trifluoromethyl-1H-pyrazol-5-yl)-thiophene-2-carboxylic acid dimethylamide | 379.40 | 380 |
| 288 | 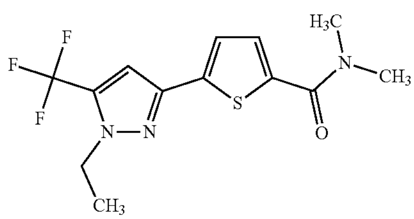 [SMILES: CCn1nc(-c2ccc(C(=O)N(C)C)s2)cc1C(F)(F)F] | 5-(1-Ethyl-5-trifluoromethyl-1H-pyrazol-3-yl)-thiophene-2-carboxylic acid dimethylamide | 317.33 | 318.5 |
| 289 | 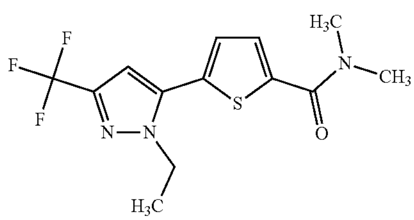 [SMILES: CCn1nc(C(F)(F)F)cc1-c1ccc(C(=O)N(C)C)s1] | 5-(1-Ethyl-3-trifluoromethyl-1H-pyrazol-5-yl)-thiophene-2-carboxylic acid dimethylamide | 317.33 | 318.5 |
| 290 | 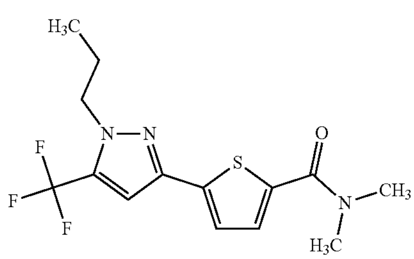 [SMILES: CCCn1nc(-c2ccc(C(=O)N(C)C)s2)cc1C(F)(F)F] | 5-(1-Propyl-5-trifluoromethyl-1H-pyrazol-3-yl)-thiophene-2-carboxylic acid dimethylamide | 331.36 | 332.5 |

| Comp. # | Structure | Compound Name | MW | LC/MS (ES+) |
|---|---|---|---|---|
| 291 | 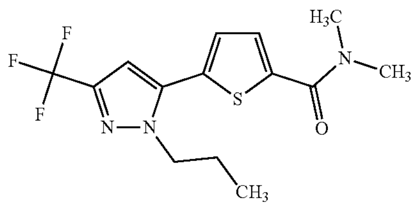 [SMILES: CCCn1nc(C(F)(F)F)cc1-c1ccc(C(=O)N(C)C)s1] | 5-(1-Propyl-3-trifluoromethyl-1H-pyrazol-5-yl)-thiophene-2-carboxylic acid dimethylamide | 331.36 | 332.1 |
| 292 | 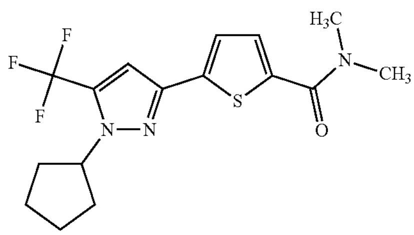 [SMILES: CN(C)C(=O)c1ccc(-c2cc(C(F)(F)F)n(C3CCCC3)n2)s1] | 5-(1-Cyclopentyl-5-trifluoromethyl-1H-pyrazol-3-yl)-thiophene-2-carboxylic acid dimethylamide | 357.39 | 358.6 |
| 293 | 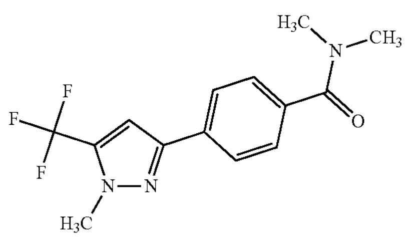 [SMILES: CN(C)C(=O)c1ccc(-c2cc(C(F)(F)F)n(C)n2)cc1] | N,N-Dimethyl-4-(1-methyl-5-trifluoromethyl-1H-pyrazol-3-yl)-benzamide | 297.28 | 298.9 |
| 294 | 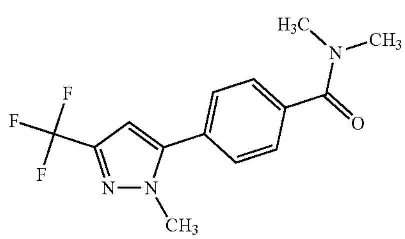 [SMILES: CN(C)C(=O)c1ccc(-c2cc(C(F)(F)F)nn2C)cc1] | N,N-Dimethyl-4-(1-methyl-3-trifluoromethyl-1H-pyrazol-5-yl)-benzamide | 297.28 | 298.5 |
| 295 | 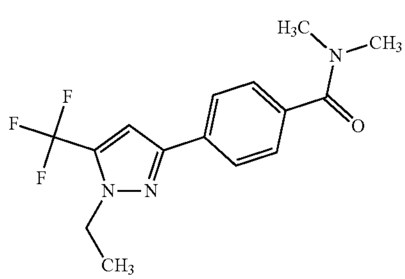 [SMILES: CCn1nc(-c2ccc(C(=O)N(C)C)cc2)cc1C(F)(F)F] | 4-(1-Ethyl-5-trifluoromethyl-1H-pyrazol-3-yl)-N,N-dimethyl-benzamide | 311.30 | 312.9 |
| 296 | 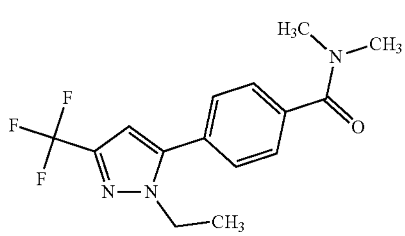 [SMILES: CCn1nc(C(F)(F)F)cc1-c1ccc(C(=O)N(C)C)cc1] | 4-(1-Ethyl-3-trifluoromethyl-1H-pyrazol-5-yl)-N,N-dimethyl-benzamide | 311.30 | 312.5 |

-continued

| Comp. # | Structure | Compound Name | MW | LC/MS (ES+) |
|---|---|---|---|---|
| 297 | 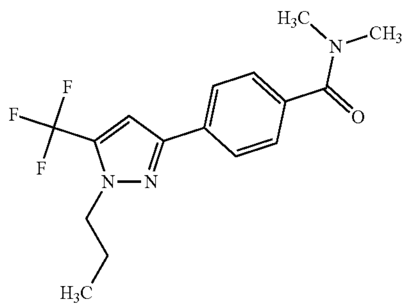 [SMILES: CCCn1nc(-c2ccc(C(=O)N(C)C)cc2)cc1C(F)(F)F] | N,N-Dimethyl-4-(1-propyl-5-trifluoromethyl-1H-pyrazol-3-yl)-benzamide | 325.33 | 326.6 |
| 298 | 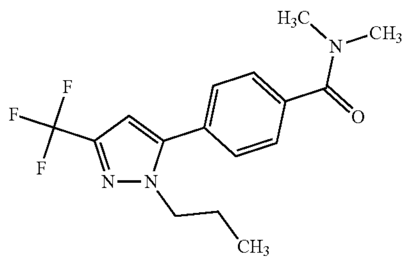 [SMILES: CCCn1nc(C(F)(F)F)cc1-c1ccc(C(=O)N(C)C)cc1] | N,N-Dimethyl-4-(1-propyl-3-trifluoromethyl-1H-pyrazol-5-yl)-benzamide | 325.33 | 326.9 |
| 299 | 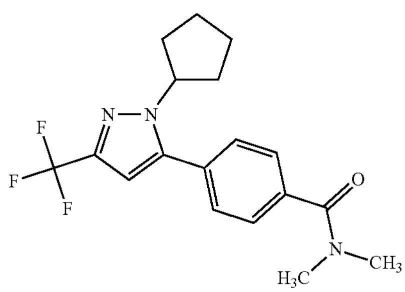 [SMILES: CN(C)C(=O)c1ccc(-c2cc(C(F)(F)F)nn2C2CCCC2)cc1] | 4-(1-Cyclopentyl-3-trifluoromethyl-1H-pyrazol-5-yl)-N,N-dimethyl-benzamide | 351.37 | 352.5 |
| 300 | 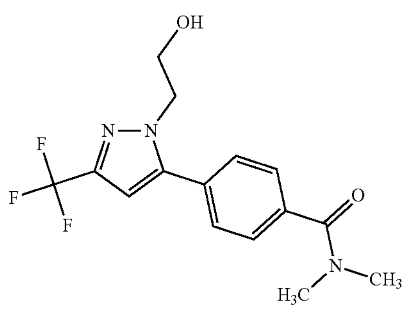 [SMILES: CN(C)C(=O)c1ccc(-c2cc(C(F)(F)F)nn2CCO)cc1] | 4-[1-(2-Hydroxy-ethyl)-3-trifluoromethyl-1H-pyrazol-5-yl]-N,N-dimethyl-benzamide | 327.30 | 328.1 |
| 301 | 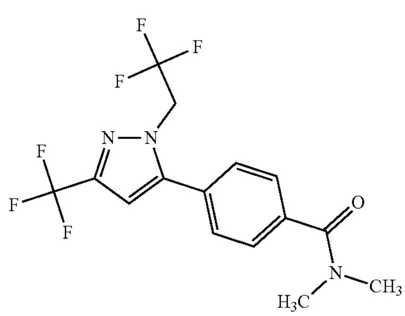 [SMILES: CN(C)C(=O)c1ccc(-c2cc(C(F)(F)F)nn2CC(F)(F)F)cc1] | N,N-Dimethyl-4-[1-(2,2,2-trifluoro-ethyl)-3-trifluoromethyl-1H-pyrazol-5-yl]-benzamide | 365.27 | 366.4 |

-continued

| Comp. # | Structure | Compound Name | MW | LC/MS (ES+) |
|---|---|---|---|---|
| 302 | 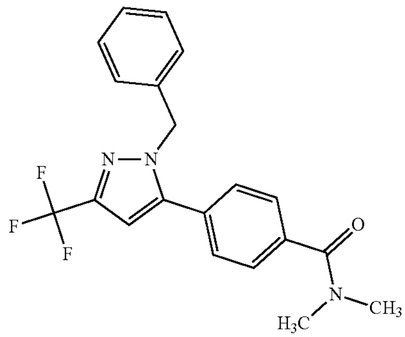 [SMILES: CN(C)C(=O)c1ccc(-c2cc(C(F)(F)F)nn2Cc2ccccc2)cc1] | 4-(1-Benzyl-3-trifluoromethyl-1H-pyrazol-5-yl)-N,N-dimethyl-benzamide | 373.37 | 374.5 |
| 303 | 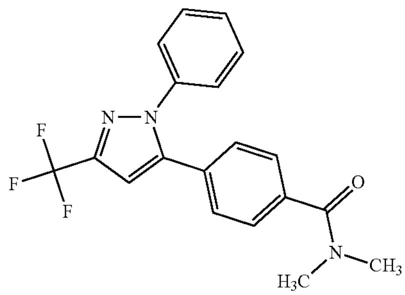 [SMILES: CN(C)C(=O)c1ccc(-c2cc(C(F)(F)F)nn2-c2ccccc2)cc1] | N,N-Dimethyl-4-(1-phenyl-3-trifluoromethyl-1H-pyrazol-5-yl)-benzamide | 359.35 | 360.6 |
| 304 | 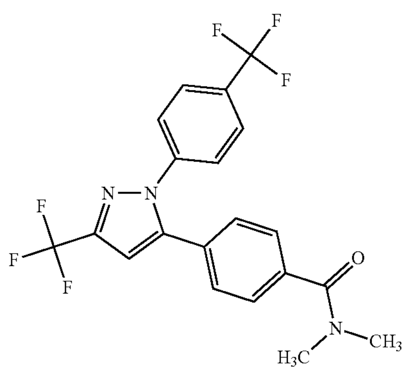 [SMILES: CN(C)C(=O)c1ccc(-c2cc(C(F)(F)F)nn2-c2ccc(C(F)(F)F)cc2)cc1] | N,N-Dimethyl-4-[5-trifluoromethyl-2-(4-trifluoromethyl-phenyl)-2H-pyrazol-3-yl]-benzamide | 427.34 | 428.4 |
| 305 | 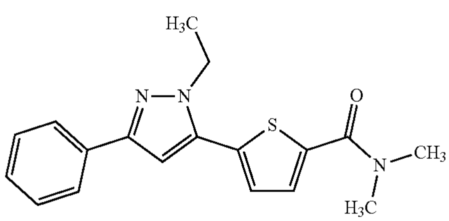 [SMILES: CCn1nc(-c2ccccc2)cc1-c1ccc(C(=O)N(C)C)s1] | 5-(2-Ethyl-5-phenyl-2H-pyrazol-3-yl)-thiophene-2-carboxylic acid dimethylamide | 325.43 | 326.6 |
| 306 | 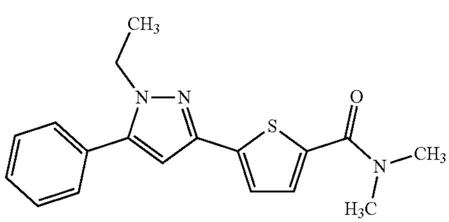 [SMILES: CCn1nc(-c2ccc(C(=O)N(C)C)s2)cc1-c1ccccc1] | 5-(1-Ethyl-5-phenyl-1H-pyrazol-3-yl)-thiophene-2-carboxylic acid dimethylamide | 325.43 | 326.6 |

| Comp. # | Structure | Compound Name | MW | LC/MS (ES+) |
|---|---|---|---|---|
| 307 | 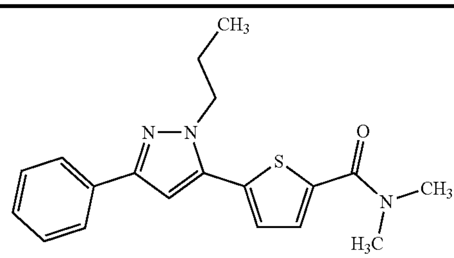 | 5-(3-Phenyl-1-propyl-1H-pyrazol-5-yl)-thiophene-2-carboxylic acid dimethylamide | 339.46 | 340.5 |
| 308 | 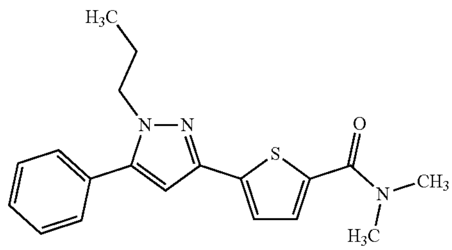 [SMILES: CCCn1nc(-c2ccc(C(=O)N(C)C)s2)cc1-c1ccccc1] | 5-(5-Phenyl-1-propyl-1H-pyrazol-3-yl)-thiophene-2-carboxylic acid dimethylamide | 339.46 | 340 |
| 309 | 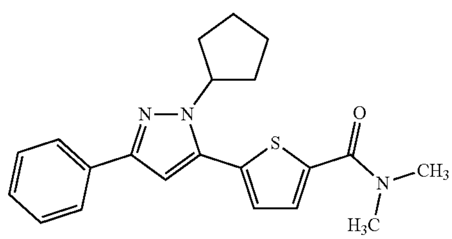 [SMILES: CN(C)C(=O)c1ccc(-c2cc(-c3ccccc3)nn2C2CCCC2)s1] | 5-(1-Cyclopentyl-3-phenyl-1H-pyrazol-5-yl)-thiophene-2-carboxylic acid dimethylamide | 365.49 | 366.5 |
| 310 | 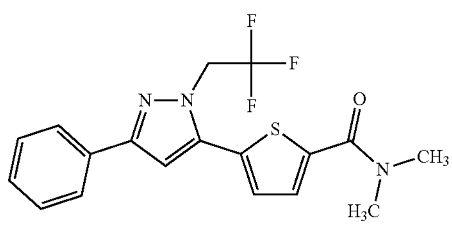 [SMILES: CN(C)C(=O)c1ccc(-c2cc(-c3ccccc3)nn2CC(F)(F)F)s1] | 5-[3-Phenyl-1-(2,2,2-trifluoro-ethyl)-1H-pyrazol-5-yl]-thiophene-2-carboxylic acid dimethylamide | 379.40 | 380.5 |
| 311 | 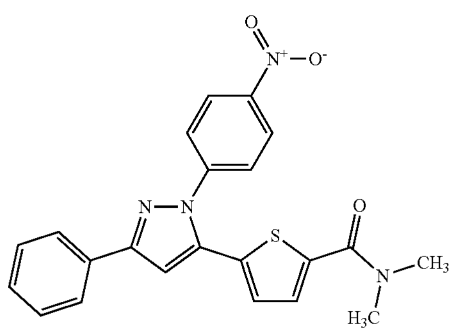 [SMILES: CN(C)C(=O)c1ccc(-c2cc(-c3ccccc3)nn2-c2ccc([N+](=O)[O-])cc2)s1] | 5-[1-(4-Nitro-phenyl)-3-phenyl-1H-pyrazol-5-yl]-thiophene-2-carboxylic acid dimethylamide | 418.47 | 419 |
| 312 | 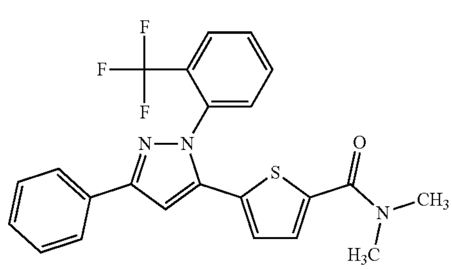 [SMILES: CN(C)C(=O)c1ccc(-c2cc(-c3ccccc3)nn2-c2ccccc2C(F)(F)F)s1] | 5-[3-Phenyl-1-(2-trifluoromethyl-phenyl)-1H-pyrazol-5-yl]-thiophene-2-carboxylic acid dimethylamide | 441.47 | 442.5 |

-continued

| Comp. # | Structure | Compound Name | MW | LC/MS (ES+) |
|---|---|---|---|---|
| 313 | 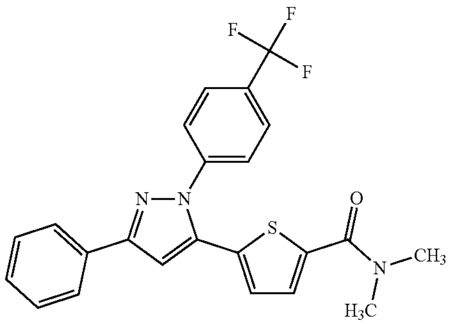 [SMILES: CN(C)C(=O)c1ccc(-c2cc(-c3ccccc3)nn2-c2ccc(C(F)(F)F)cc2)s1] | 5-[3-Phenyl-1-(4-trifluoromethyl-phenyl)-1H-pyrazol-5-yl]-thiophene-2-carboxylic acid dimethylamide | 441.47 | 442.5 |
| 314 | 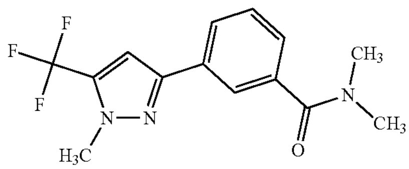 [SMILES: CN(C)C(=O)c1cccc(-c2cc(C(F)(F)F)n(C)n2)c1] | N,N-Dimethyl-3-(1-methyl-5-trifluoromethyl-1H-pyrazol-3-yl)-benzamide | 297.28 | 298.5 |
| 315 | 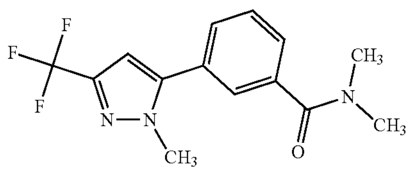 | N,N-Dimethyl-3-(1-methyl-3-trifluoromethyl-1H-pyrazol-5-yl)-benzamide | 297.28 | 298.4 |
| 316 | 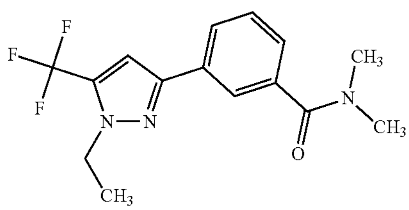 [SMILES: CCn1nc(-c2cccc(C(=O)N(C)C)c2)cc1C(F)(F)F] | 3-(1-Ethyl-5-trifluoromethyl-1H-pyrazol-3-yl)-N,N-dimethyl-benzamide | 311.30 | 312.5 |
| 317 | 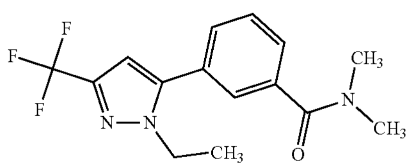 [SMILES: CCn1nc(C(F)(F)F)cc1-c1cccc(C(=O)N(C)C)c1] | 3-(1-Ethyl-3-trifluoromethyl-1H-pyrazol-5-yl)-N,N-dimethyl-benzamide | 311.30 | 312.5 |
| 318 | 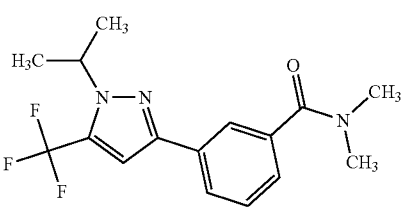 [SMILES: CC(C)n1nc(-c2cccc(C(=O)N(C)C)c2)cc1C(F)(F)F] | 3-(1-Isopropyl-5-trifluoromethyl-1H-pyrazol-3-yl)-N,N-dimethyl-benzamide | 325.33 | 326.5 |
| 319 | 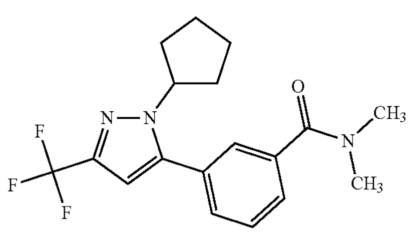 [SMILES: CN(C)C(=O)c1cccc(-c2cc(C(F)(F)F)nn2C2CCCC2)c1] | 3-(1-Cyclopentyl-3-trifluoromethyl-1H-pyrazol-5-yl)-N,N-dimethyl-benzamide | 351.37 | 352.6 |

-continued

| Comp. # | Structure | Compound Name | MW | LC/MS (ES+) |
|---|---|---|---|---|
| 320 | 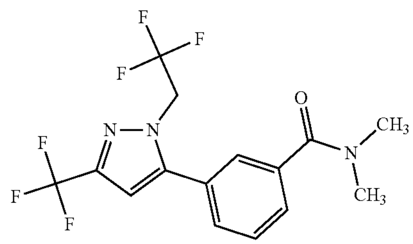 [SMILES: CN(C)C(=O)c1cccc(-c2cc(C(F)(F)F)nn2CC(F)(F)F)c1] | N,N-dimethyl-3-[1-(2,2,2-trifluoro-ethyl)-3-trifluoromethyl-1H-pyrazol-5-yl]-benzamide | 365.27 | 366 |
| 321 | 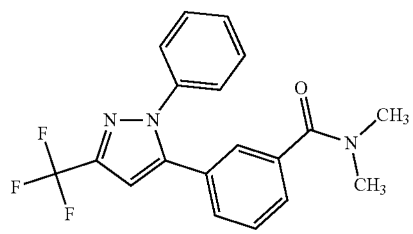 [SMILES: CN(C)C(=O)c1cccc(-c2cc(C(F)(F)F)nn2-c2ccccc2)c1] | N,N-Dimethyl-3-(1-phenyl-3-trifluoromethyl-1H-pyrazol-5-yl)-benzamide | 359.35 | 360.1 |
| 322 | 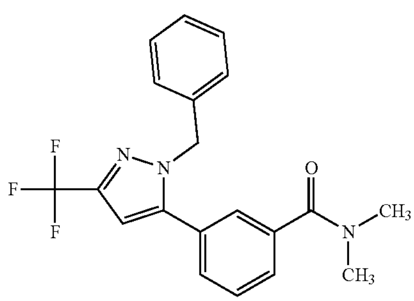 [SMILES: CN(C)C(=O)c1cccc(-c2cc(C(F)(F)F)nn2Cc2ccccc2)c1] | 3-(1-Benzyl-3-trifluoromethyl-1H-pyrazol-5-yl)-N,N-dimethyl-benzamide | 373.37 | 374.2 |
| 323 | 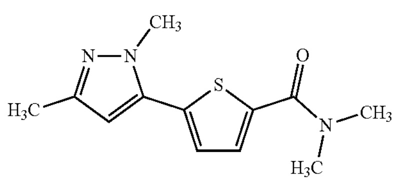 | 5-(1,3-Dimethyl-1H-pyrazol-5-yl)-thiophene-2-carboxylic acid dimethylamide | 249.33 | 250.5 |
| 324 | 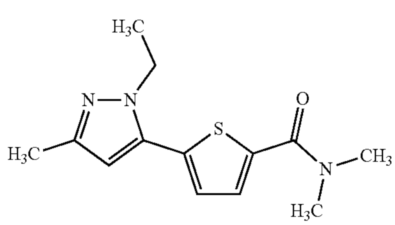 | 5-(1-Ethyl-3-methyl-1H-pyrazol-5-yl)-thiophene-2-carboxylic acid dimethylamide | 263.36 | 264.6 |
| 325 | 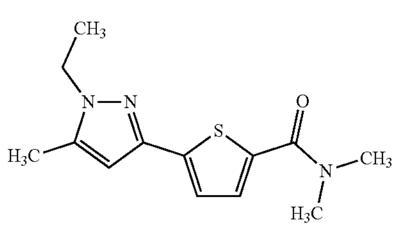 | 5-(1-Ethyl-5-methyl-1H-pyrazol-3-yl)-thiophene-2-carboxylic acid dimethylamide | 263.36 | 264.5 |

-continued

| Comp. # | Structure | Compound Name | MW | LC/MS (ES+) |
|---|---|---|---|---|
| 326 | 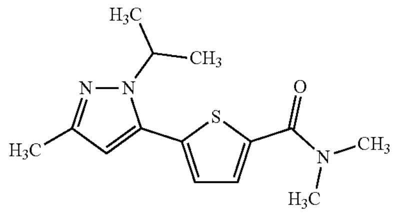 | 5-(1-Isopropyl-3-methyl-1H-pyrazol-5-yl)-thiophene-2-carboxylic acid dimethylamide | 277.39 | 278.6 |
| 327 | 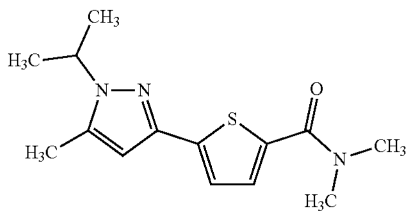 [SMILES: Cc1cc(-c2ccc(C(=O)N(C)C)s2)nn1C(C)C] | 5-(1-Isopropyl-5-methyl-1H-pyrazol-3-yl)-thiophene-2-carboxylic acid dimethylamide | 277.39 | 278.1 |
| 328 | 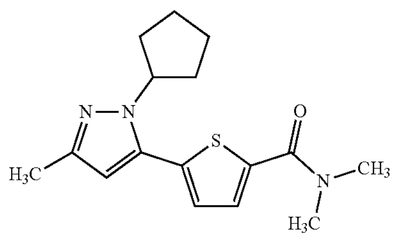 | 5-(1-Cyclopentyl-3-methyl-1H-pyrazol-5-yl)-thiophene-2-carboxylic acid dimethylamide | 303.42 | 304.6 |
| 329 | 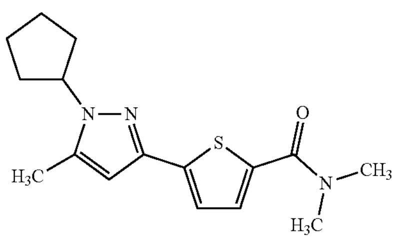 [SMILES: Cc1cc(-c2ccc(C(=O)N(C)C)s2)nn1C1CCCC1] | 5-(1-Cyclopentyl-5-methyl-1H-pyrazol-3-yl)-thiophene-2-carboxylic acid dimethylamide | 303.42 | 304.2 |
| 330 | 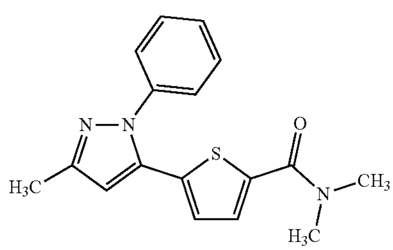 | 5-(3-Methyl-1-phenyl-1H-pyrazol-5-yl)-thiophene-2-carboxylic acid dimethylamide | 311.40 | 312 |
| 331 | 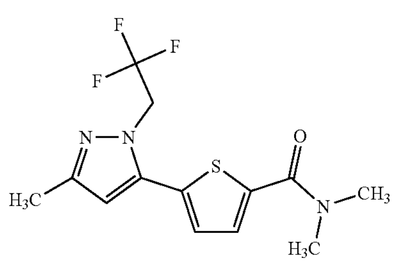 | 5-[3-Methyl-1-(2,2,2-trifluoro-ethyl)-1H-pyrazol-5-yl]-thiophene-2-carboxylic acid dimethylamide | 317.33 | 318.1 |

| Comp. # | Structure | Compound Name | MW | LC/MS (ES+) |
|---|---|---|---|---|
| 332 | 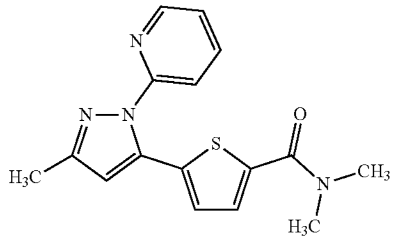 | 5-(3-Methyl-1-pyridin-2-yl-1H-pyrazol-5-yl)-thiophene-2-carboxylic acid dimethylamide | 312.39 | 313.9 |
| 333 | 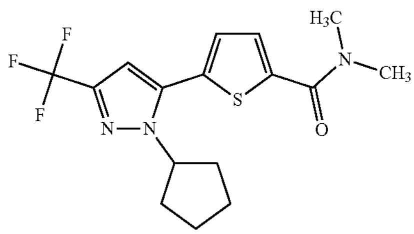 [SMILES: CN(C)C(=O)c1ccc(-c2cc(C(F)(F)F)nn2C2CCCC2)s1] | 5-(1-Cyclopentyl-3-trifluoromethyl-1H-pyrazol-5-yl)-thiophene-2-carboxylic acid dimethylamide | 357.39 | 358.5 |
| 334 | 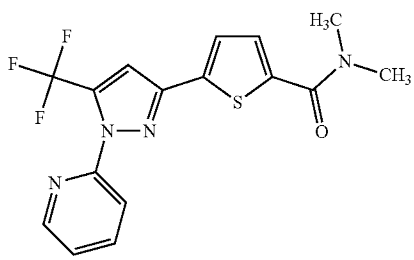 [SMILES: CN(C)C(=O)c1ccc(-c2cc(C(F)(F)F)n(-c3ccccn3)n2)s1] | 5-(1-Pyridin-2-yl-5-trifluoromethyl-1H-pyrazol-3-yl)-thiophene-2-carboxylic acid dimethylamide | 366.36 | 367.5 |
| 335 | 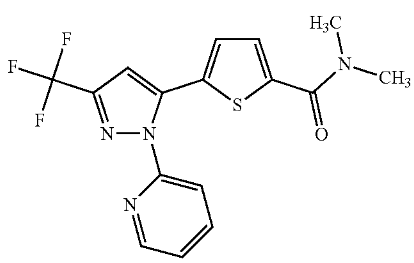 [SMILES: CN(C)C(=O)c1ccc(-c2cc(C(F)(F)F)nn2-c2ccccn2)s1] | 5-(1-Pyridin-2-yl-3-trifluoromethyl-1H-pyrazol-5-yl)-thiophene-2-carboxylic acid dimethylamide | 366.36 | 367.5 |
| 336 | 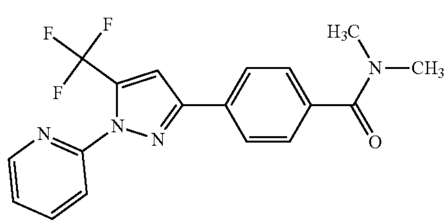 [SMILES: CN(C)C(=O)c1ccc(-c2cc(C(F)(F)F)n(-c3ccccn3)n2)cc1] | N,N-Dimethyl-4-(1-pyridin-2-yl-5-trifluoromethyl-1H-pyrazol-3-yl)-benzamide | 360.33 | 361.6 |
| 337 | Chiral | [5-(1-Methyl-5-trifluoromethyl-1H-pyrazol-3-yl)-thiophen-2-ylmethyl]-[(S)-1-(tetrahydro-furan-2-yl)methyl]-amine | 345.38 | 346.6 |

-continued

| Comp. # | Structure | Compound Name | MW | LC/MS (ES+) |
|---|---|---|---|---|
| 338 | Chiral | [5-(1-Methyl-5-trifluoromethyl-1H-pyrazol-3-yl)-thiophen-2-ylmethyl]-[(R)-1-(tetrahydro-furan-2-yl)methyl]-amine | 345.38 | 346.6 |
| 339 | 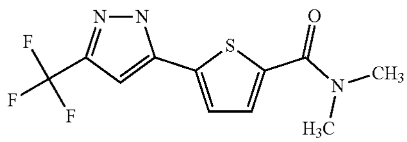 [SMILES: CN(C)C(=O)c1ccc(-c2cc(C(F)(F)F)n[nH]2)s1] | 5-(5-Trifluoromethyl-2H-pyrazol-3-yl)-thiophene-2-carboxylic acid dimethylamide | 289.28 | 290.5 |
| 340 | 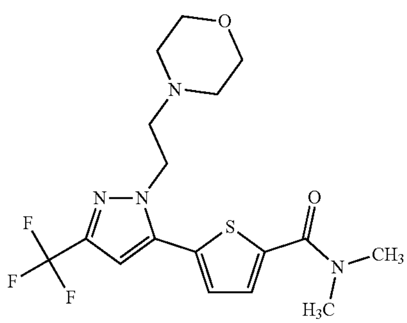 [SMILES: CN(C)C(=O)c1ccc(-c2cc(C(F)(F)F)nn2CCN2CCOCC2)s1] | 5-[1-(2-Morpholin-4-yl-ethyl)-3-trifluoromethyl-1H-pyrazol-5-yl]-thiophene-2-carboxylic acid dimethylamide | 402.44 | 403.5 |
| 341 | 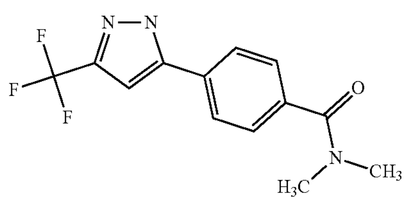 [SMILES: CN(C)C(=O)c1ccc(-c2cc(C(F)(F)F)n[nH]2)cc1] | N,N-Dimethyl-4-(5-trifluoromethyl-2H-pyrazol-3-yl)-benzamide | 283.25 | 284.5 |
| 342 | 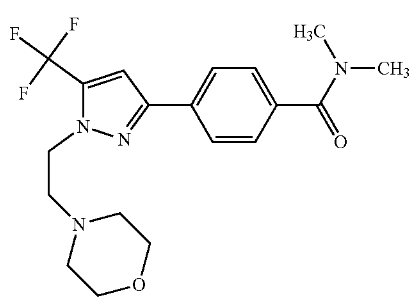 [SMILES: CN(C)C(=O)c1ccc(-c2cc(C(F)(F)F)n(CCN3CCOCC3)n2)cc1] | N,N-Dimethyl-4-[1-(2-morpholin-4-yl-ethyl)-5-trifluoromethyl-1H-pyrazol-3-yl]-benzamide | 396.41 | 397.6 |
| 343 | 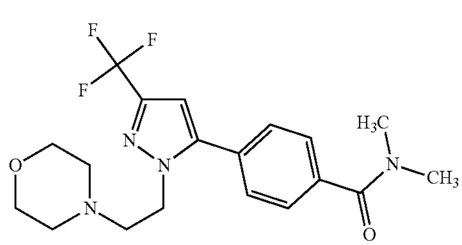 [SMILES: CN(C)C(=O)c1ccc(-c2cc(C(F)(F)F)nn2CCN2CCOCC2)cc1] | N,N-Dimethyl-4-[1-(2-morpholin-4-yl-ethyl)-3-trifluoromethyl-1H-pyrazol-5-yl]-benzamide | 396.41 | 397.2 |

| Comp. # | Structure | Compound Name | MW | LC/MS (ES+) |
|---|---|---|---|---|
| 344 | 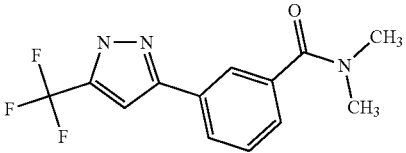 [SMILES: CN(C)C(=O)c1cccc(-c2cc(C(F)(F)F)[nH]n2)c1] | N,N-Dimethyl-3-(5-trifluoromethyl-1H-pyrazol-3-yl)-benzamide | 283.25 | 284.9 |
| 345 | 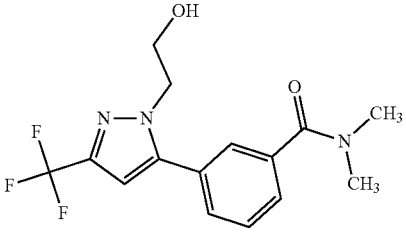 [SMILES: CN(C)C(=O)c1cccc(-c2cc(C(F)(F)F)nn2CCO)c1] | 3-[1-(2-Hydroxy-ethyl)-3-trifluoromethyl-1H-pyrazol-5-yl]-N,N-dimethyl-benzamide | 327.30 | 328.9 |
| 346 | 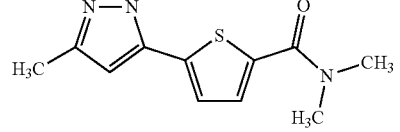 | 5-(5-Methyl-2H-pyrazol-3-yl)-thiophene-2-carboxylic acid dimethylamide | 235.31 | 236.6 |
| 347 | 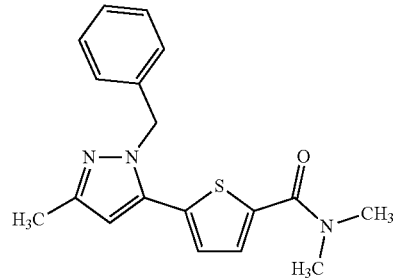 | 5-(1-Benzyl-3-methyl-1H-pyrazol-5-yl)-thiophene-2-carboxylic acid dimethylamide | 325.43 | 326.5 |
| 348 | 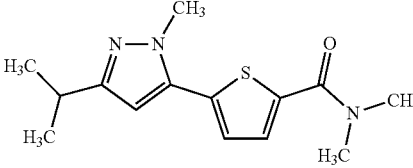 | 5-(3-Isopropyl-1-methyl-1H-pyrazol-5-yl)-thiophene-2-carboxylic acid dimethylamide | 277.39 | 278.5 |
| 349 | 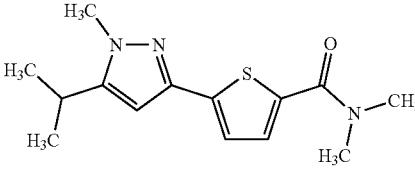 | 5-(5-Isopropyl-1-methyl-1H-pyrazol-3-yl)-thiophene-2-carboxylic acid dimethylamide | 277.39 | 278.6 |
| 350 | 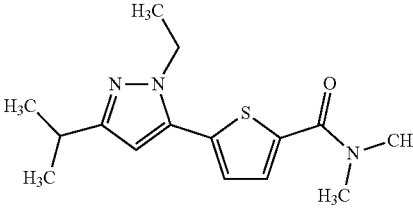 | 5-(1-Ethyl-3-isopropyl-1H-pyrazol-5-yl)-thiophene-2-carboxylic acid dimethylamide | 291.41 | 292.5 |

| Comp. # | Structure | Compound Name | MW | LC/MS (ES+) |
|---|---|---|---|---|
| 351 | 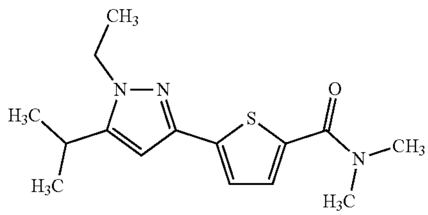 [SMILES: CCn1nc(-c2ccc(C(=O)N(C)C)s2)cc1C(C)C] | 5-(1-Ethyl-5-isopropyl-1H-pyrazol-3-yl)-thiophene-2-carboxylic acid dimethylamide | 291.41 | 292.5 |
| 352 | 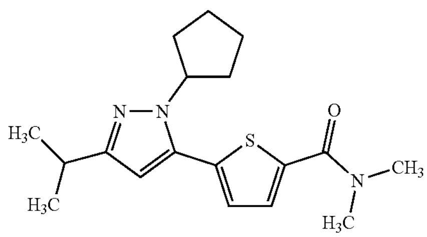 [SMILES: CC(C)c1cc(-c2ccc(C(=O)N(C)C)s2)n(C2CCCC2)n1] | 5-(1-Cyclopropyl-3-isopropyl-1H-pyrazol-5-yl)-thiophene-2-carboxylic acid dimethylamide | 331.48 | 332.5 |
| 353 | 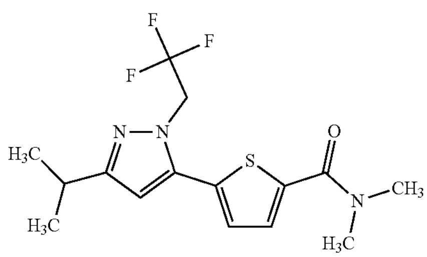 [SMILES: CC(C)c1cc(-c2ccc(C(=O)N(C)C)s2)n(CC(F)(F)F)n1] | 5-[3-Isopropyl-1-(2,2,2-trifluoro-ethyl)-1H-pyrazol-5-yl]-thiophene-2-carboxylic acid dimethylamide | 345.38 | 346.9 |
| 354 | 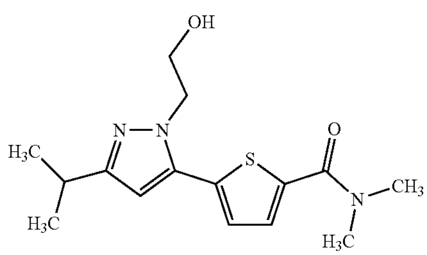 [SMILES: CC(C)c1cc(-c2ccc(C(=O)N(C)C)s2)n(CCO)n1] | 5-[1-(2-Hydroxy-ethyl)-3-isopropyl-1H-pyrazol-5-yl]-thiophene-2-carboxylic acid dimethylamide | 307.41 | 308.6 |
| 355 | 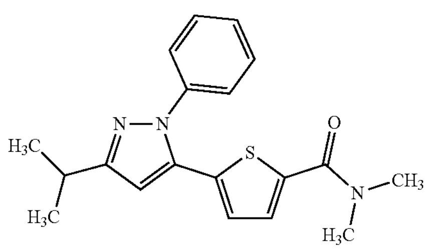 [SMILES: CC(C)c1cc(-c2ccc(C(=O)N(C)C)s2)n(-c2ccccc2)n1] | 5-(3-Isopropyl-5-phenyl-1H-pyrazol-5-yl)-thiophene-2-carboxylic acid dimethylamide | 339.46 | 340.5 |
| 356 | 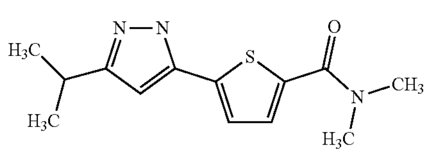 [SMILES: CC(C)c1cc(-c2ccc(C(=O)N(C)C)s2)[nH]n1] | 5-(5-Isopropyl-2H-pyrazol-3-yl)-thiophene-2-carboxylic acid dimethylamide | 263.36 | 264.6 |

| Comp. # | Structure | Compound Name | MW | LC/MS (ES+) |
|---|---|---|---|---|
| 357 | 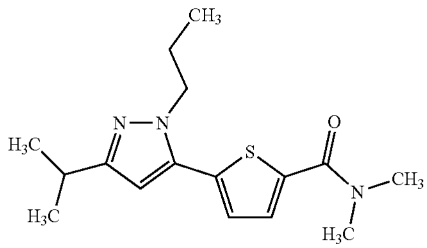 [SMILES: CCCn1nc(C(C)C)cc1-c1ccc(C(=O)N(C)C)s1] | 5-(3-Isopropyl-1-propyl-1H-pyrazol-5-yl)-thiophene-2-carboxylic acid dimethylamide | 305.44 | 306.2 |
| 358 | 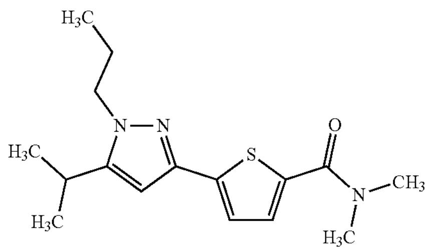 [SMILES: CCCn1nc(-c2ccc(C(=O)N(C)C)s2)cc1C(C)C] | 5-(5-Isopropyl-1-propyl-1H-pyrazol-3-yl)-thiophene-2-carboxylic acid dimethylamide | 305.44 | 306 |
| 359 | 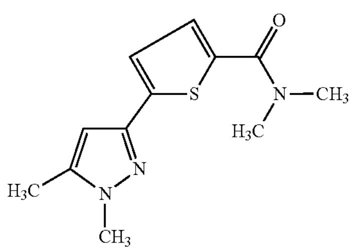 | 5-(1,5-Dimethyl-1H-pyrazol-3-yl)-thiophene-2-carboxylic acid dimethylamide | 249.33 | 250.2 |
| 360 | 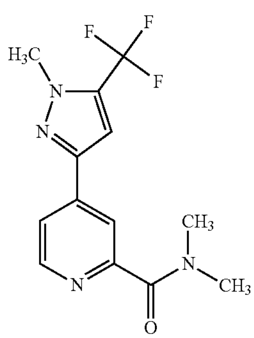 | 4-(1-Methyl-5-trifluoromethyl-1H-pyrazol-3-yl)-pyridine-2-carboxylic acid dimethylamide | 298.26 | 299.2 |
| 361 | 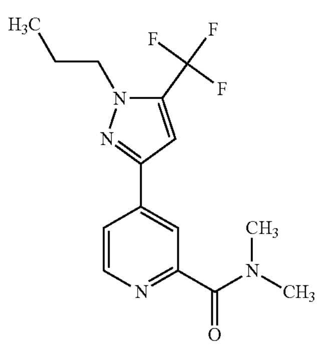 [SMILES: CCCn1nc(-c2ccnc(C(=O)N(C)C)c2)cc1C(F)(F)F] | 4-(1-Propyl-5-trifluoromethyl-1H-pyrazol-3-yl)-pyridine-2-carboxylic acid dimethylamide | 326.32 | 327.5 |

-continued

| Comp. # | Structure | Compound Name | MW | LC/MS (ES+) |
|---|---|---|---|---|
| 362 | 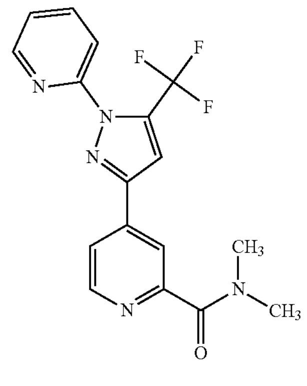 [SMILES: CN(C)C(=O)c1cc(-c2cc(C(F)(F)F)n(-c3ccccn3)n2)ccn1] | 4-(1-Pyridin-2-yl-5-trifluoromethyl-1H-pyrazol-3-yl)-pyridine-2-carboxylic acid dimethylamide | 361.32 | 362.1 |
| 363 | 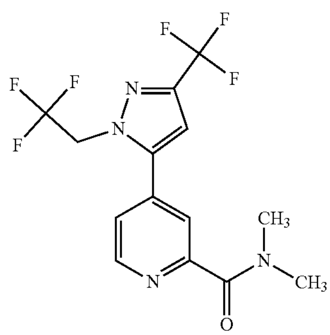 [SMILES: CN(C)C(=O)c1cc(-c2cc(C(F)(F)F)nn2CC(F)(F)F)ccn1] | 4-[1-(2,2,2-Trifluoro-ethyl)-3-trifluoromethyl-1H-pyrazol-5-yl]-pyridine-2-carboxylic acid dimethylamide | 366.26 | 367.2 |
| 364 | 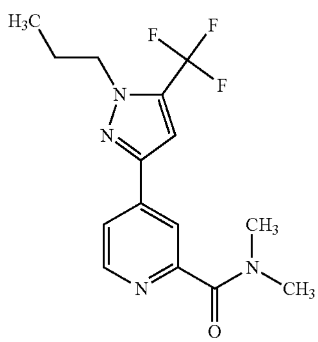 [SMILES: CCCn1nc(-c2ccnc(C(=O)N(C)C)c2)cc1C(F)(F)F] | 4-[1-(2-Hydroxy-ethyl)-5-trifluoromethyl-1H-pyrazol-3-yl]-pyridine-2-carboxylic acid dimethylamide | 328.29 | 329.2 |
| 365 | 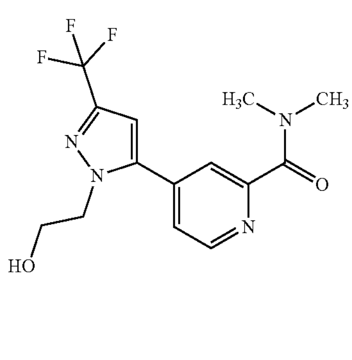 [SMILES: CN(C)C(=O)c1cc(-c2cc(C(F)(F)F)nn2CCO)ccn1] | 4-[1-(2-Hydroxy-ethyl)-3-trifluoromethyl-1H-pyrazol-5-yl]-pyridine-2-carboxylic acid dimethylamide | 328.29 | 329.3 |

| Comp. # | Structure | Compound Name | MW | LC/MS (ES+) |
|---|---|---|---|---|
| 366 | 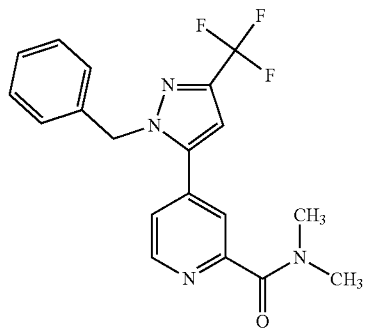 [SMILES: CN(C)C(=O)c1cc(-c2cc(C(F)(F)F)nn2Cc2ccccc2)ccn1] | 4-(1-Benzyl-3-trifluoromethyl-1H-pyrazol-5-yl)-pyridine-2-carboxylic acid dimethylamide | 374.36 | 375 |
| 367 | 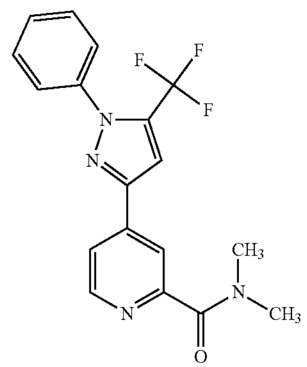 [SMILES: CN(C)C(=O)c1cc(-c2cc(C(F)(F)F)n(-c3ccccc3)n2)ccn1] | 4-(1-Phenyl-5-trifluoromethyl-1H-pyrazol-3-yl)-pyridine-2-carboxylic acid dimethylamide | 360.33 | 361.1 |
| 368 | 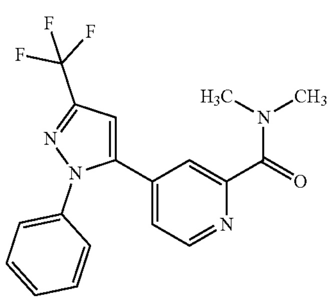 [SMILES: CN(C)C(=O)c1cc(-c2cc(C(F)(F)F)nn2-c2ccccc2)ccn1] | 4-(1-Phenyl-3-trifluoromethyl-1H-pyrazol-5-yl)-pyridine-2-carboxylic acid dimethylamide | 360.33 | 361 |
| 369 | 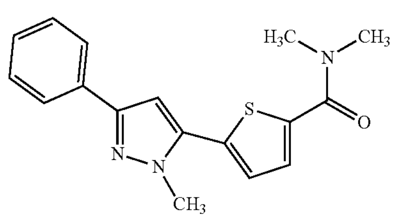 [SMILES: CN(C)C(=O)c1ccc(-c2cc(-c3ccccc3)nn2C)s1] | 5-(1-Methyl-3-phenyl-1H-pyrazol-5-yl)-thiophene-2-carboxylic acid dimethylamide | 311.40 | 312.1 |
| 370 | 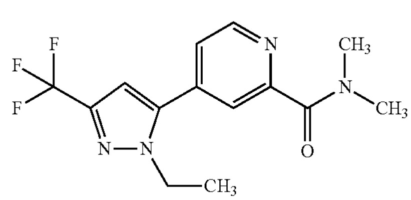 [SMILES: CCn1nc(C(F)(F)F)cc1-c1ccnc(C(=O)N(C)C)c1] | 4-(1-Ethyl-3-trifluoromethyl-1H-pyrazol-5-yl)-pyridine-2-carboxylic acid dimethylamide | 312.29 | 313.5 |

| Comp. # | Structure | Compound Name | MW | LC/MS (ES+) |
|---|---|---|---|---|
| 371 | 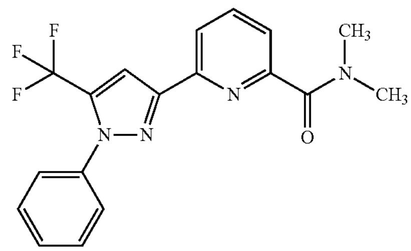 [SMILES: CN(C)C(=O)c1cccc(-c2cc(C(F)(F)F)n(-c3ccccc3)n2)n1] | 6-(1-Phenyl-5-trifluoromethyl-1H-pyrazol-3-yl)-pyridine-2-carboxylic acid dimethylamide | 360.33 | 361.6 |
| 372 | 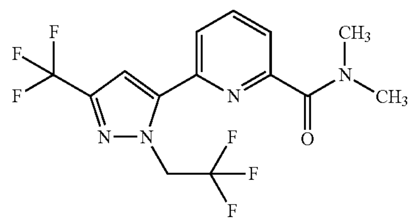 [SMILES: CN(C)C(=O)c1cccc(-c2cc(C(F)(F)F)nn2CC(F)(F)F)n1] | 6-[1-(2,2,2-Trifluoro-ethyl)-3-trifluoromethyl-1H-pyrazol-5-yl]-pyridine-2-carboxylic acid dimethylamide | 366.26 | 367.5 |
| 373 | 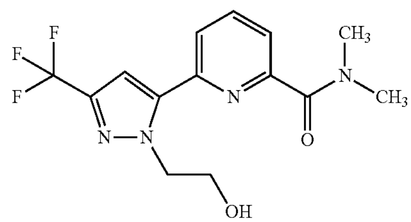 [SMILES: CN(C)C(=O)c1cccc(-c2cc(C(F)(F)F)nn2CCO)n1] | 6-[2-(2-Hydroxy-ethyl)-3-trifluoromethyl-1H-pyrazol-5-yl]-pyridine-2-carboxylic acid dimethylamide | 328.29 | 329.5 |
| 374 | 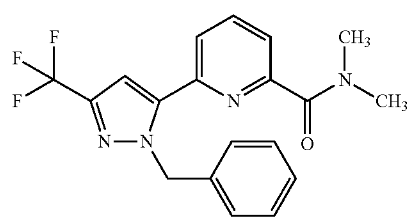 [SMILES: CN(C)C(=O)c1cccc(-c2cc(C(F)(F)F)nn2Cc2ccccc2)n1] | 6-(1-Benzyl-3-trifluoromethyl-1H-pyrazol-5-yl)-pyridine-2-carboxylic acid dimethylamide | 373.46 | 375.6 |
| 375 | 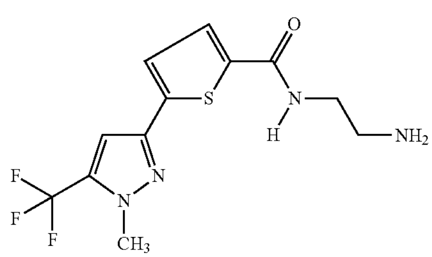 [SMILES: Cn1nc(-c2ccc(C(=O)NCCN)s2)cc1C(F)(F)F] | 5-(1-Methyl-5-trifluoromethyl-1H-pyrazol-3-yl)-thiophene-2-carboxylic acid (2-amino-ethyl)-amide | 318.32 | 319.3 |
| 376 | 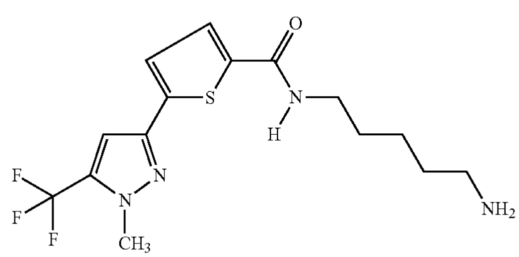 [SMILES: Cn1nc(-c2ccc(C(=O)NCCCCCN)s2)cc1C(F)(F)F] | 5-(1-Methyl-5-trifluoromethyl-1H-pyrazol-3-yl)-thiophene-2-carboxylic acid (5-amino-pentyl)-amide | 360.40 | 361.4 |

-continued

| Comp. # | Structure | Compound Name | MW | LC/MS (ES+) |
|---|---|---|---|---|
| 377 | 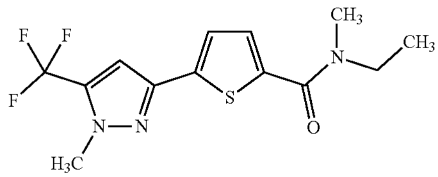 [SMILES: CCN(C)C(=O)c1ccc(-c2cc(C(F)(F)F)n(C)n2)s1] | 5-(1-Methyl-5-trifluoromethyl-1H-pyrazol-3-yl)-thiophene-2-carboxylic acid ethyl-methyl-amide | 317.33 | 318.4 |
| 378 | 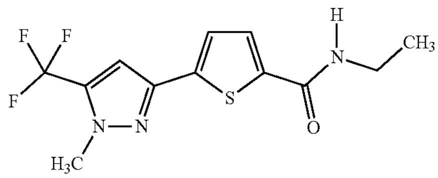 [SMILES: CCNC(=O)c1ccc(-c2cc(C(F)(F)F)n(C)n2)s1] | 5-(1-Methyl-5-trifluoromethyl-1H-pyrazol-3-yl)-thiophene-2-carboxylic acid methylamide | 289.28 | 290.3 |
| 379 | 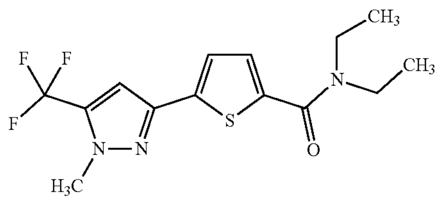 [SMILES: CCN(CC)C(=O)c1ccc(-c2cc(C(F)(F)F)n(C)n2)s1] | 5-(1-Methyl-5-trifluoromethyl-1H-pyrazol-3-yl)-thiophene-2-carboxylic acid diethylamide | 331.36 | 332.3 |
| 380 | 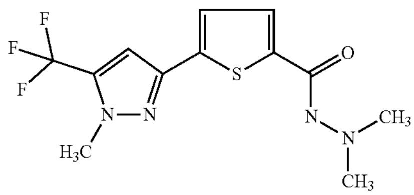 [SMILES: CN(C)NC(=O)c1ccc(-c2cc(C(F)(F)F)n(C)n2)s1] | 5-(1-Methyl-5-trifluoromethyl-1H-pyrazol-3-yl)-thiophene-2-carboxylic acid N',N'-dimethyl-hydrazide | 318.22 | 319.5 |
| 381 | 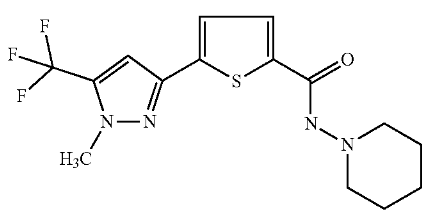 [SMILES: Cn1nc(-c2ccc(C(=O)NN3CCCCC3)s2)cc1C(F)(F)F] | 5-(1-Methyl-5-trifluoromethyl-1H-pyrazol-3-yl)-thiophene-2-carboxylic acid piperidin-1-ylamide | 358.38 | 359.6 |
| 382 | 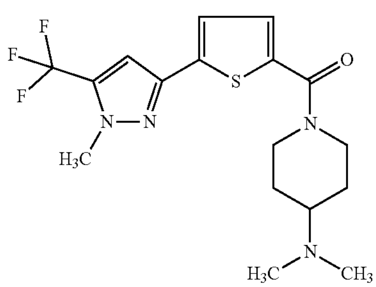 [SMILES: CN(C)C1CCN(C(=O)c2ccc(-c3cc(C(F)(F)F)n(C)n3)s2)CC1] | (4-Dimethylamino-piperidin-1-yl)-[5-(1-methyl-5-trifluoromethyl-1H-pyrazol-3-yl)-thiophen-2-yl]-methanone | 386.44 | 387.6 |
| 383 | 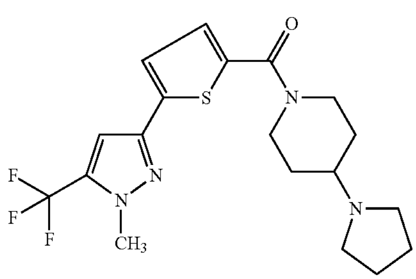 [SMILES: Cn1nc(-c2ccc(C(=O)N3CCC(N4CCCC4)CC3)s2)cc1C(F)(F)F] | [5-(1-Methyl-5-trifluoromethyl-1H-pyrazol-3-yl)-thiophen-2-yl]-(4-pyrrolidin-1-yl-piperidin-1-yl)-methanone | 412.27 | 413.7 |

-continued

| Comp. # | Structure | Compound Name | MW | LC/MS (ES+) |
|---|---|---|---|---|
| 384 | 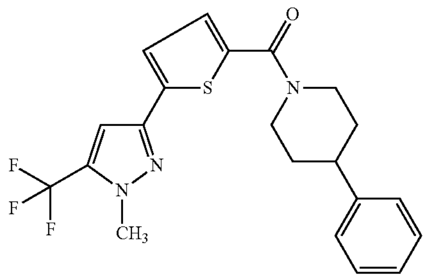 [SMILES: Cn1nc(-c2ccc(C(=O)N3CCC(c4ccccc4)CC3)s2)cc1C(F)(F)F] | [5-(1-Methyl-5-trifluoromethyl-1H-pyrazol-3-yl)-thiophen-2-yl]-(4-phenyl-piperidin-1-yl)-methanone | 419.46 | 420.6 |
| 385 | 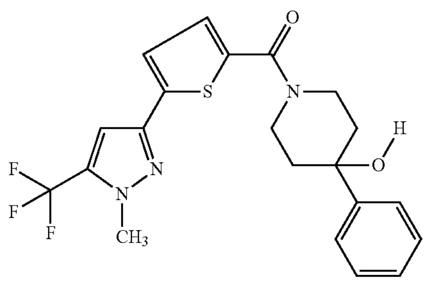 [SMILES: Cn1nc(-c2ccc(C(=O)N3CCC(O)(c4ccccc4)CC3)s2)cc1C(F)(F)F] | (4-Hydroxy-4-phenyl-piperidin-1-yl)-[5-(1-methyl-5-trifluoromethyl-1H-pyrazol-3-yl)-thiophen-2-yl]-methanone | 435.46 | 436.6 |
| 386 | 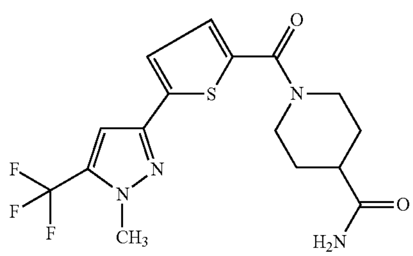 [SMILES: Cn1nc(-c2ccc(C(=O)N3CCC(C(N)=O)CC3)s2)cc1C(F)(F)F] | 1-[5-(1-Methyl-5-trifluoromethyl-1H-pyrazol-3-yl)-thiophene-2-carbonyl]-piperidine-4-carboxylic acid amide | 386.39 | 387.5 |
| 387 | 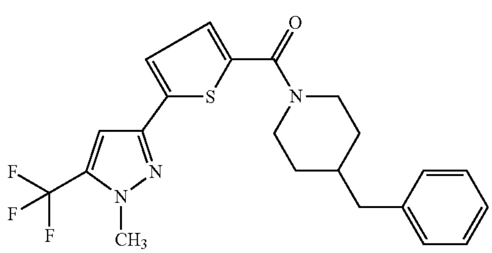 [SMILES: Cn1nc(-c2ccc(C(=O)N3CCC(Cc4ccccc4)CC3)s2)cc1C(F)(F)F] | (4-Benzyl-piperidin-1-yl)-[5-(1-methyl-5-trifluoromethyl-1H-pyrazol-3-yl)-thiophen-2-yl]-methanone | 433.49 | 434.7 |
| 388 | 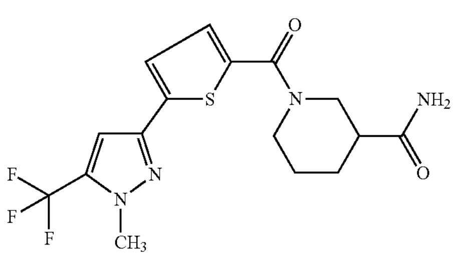 [SMILES: Cn1nc(-c2ccc(C(=O)N3CCCC(C(N)=O)C3)s2)cc1C(F)(F)F] | 1-[5-(1-Methyl-5-trifluoromethyl-1H-pyrazol-3-yl)-thiophene-2-carbonyl]-piperidine-3-carboxylic acid amide | 386.39 | 387.7 |
| 389 | 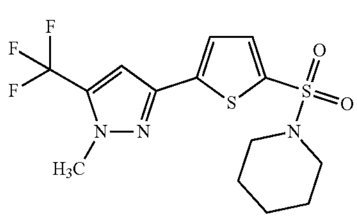 [SMILES: Cn1nc(-c2ccc(S(=O)(=O)N3CCCCC3)s2)cc1C(F)(F)F] | 1-[5-(1-Methyl-5-trifluoromethyl-1H-pyrazol-3-yl)-thiophene-2-sulfonyl]-piperidine | 379.42 | 380.5 |

| Comp. # | Structure | Compound Name | MW | LC/MS (ES+) |
|---|---|---|---|---|
| 391 | 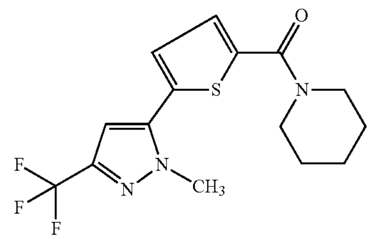 [SMILES: Cn1nc(C(F)(F)F)cc1-c1ccc(C(=O)N2CCCCC2)s1] | [5-(1-Methyl-3-trifluoromethyl-1H-pyrazol-5-yl)-thiophen-2-yl]-piperidin-1-yl-methanone | 343.37 | 344.6 |
| 392 | 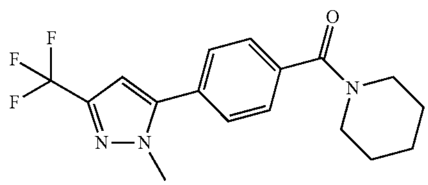 [SMILES: Cn1nc(C(F)(F)F)cc1-c1ccc(C(=O)N2CCCCC2)cc1] | [4-(1-Methyl-3-trifluoromethyl-1H-pyrazol-3-yl)-phenyl]-piperidin-1-yl-methanone | 337.34 | 338.6 |
| 393 | 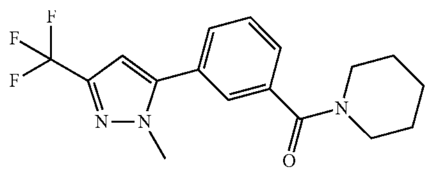 [SMILES: Cn1nc(C(F)(F)F)cc1-c1cccc(C(=O)N2CCCCC2)c1] | [3-(1-Methyl-3-trifluoromethyl-1H-pyrazol-3-yl)-phenyl]-piperidin-1-yl-methanone | 337.34 | 338.6 |
| 394 | 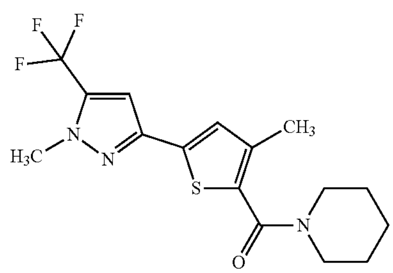 [SMILES: Cc1cc(-c2cc(C(F)(F)F)n(C)n2)sc1C(=O)N1CCCCC1] | [3-Methyl-5-(1-methyl-5-trifluoromethyl-1H-pyrazol-3-yl)-thiophen-2-yl]-piperidin-1-yl-methanone | 357.39 | 358.6 |
| 395 | 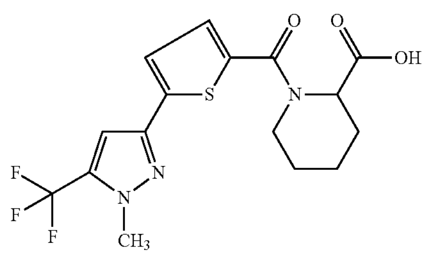 [SMILES: Cn1nc(-c2ccc(C(=O)N3CCCCC3C(=O)O)s2)cc1C(F)(F)F] | 1-[5-(1-Methyl-5-trifluoromethyl-1H-pyrazol-3-yl)-thiophene-2-carbonyl]-piperidine-2-carboxylic acid | 387.38 | 388.6 |
| 396 | 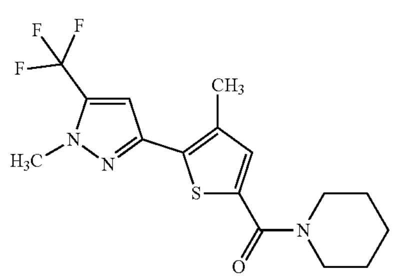 [SMILES: Cc1cc(C(=O)N2CCCCC2)sc1-c1cc(C(F)(F)F)n(C)n1] | [4-Methyl-5-(1-methyl-5-trifluoromethyl-1H-pyrazol-3-yl)-thiophen-2-yl]-piperidin-1-yl-methanone | 357.39 | 358.5 |
| 397 | 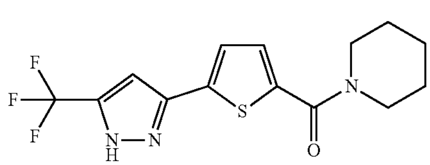 [SMILES: O=C(c1ccc(-c2cc(C(F)(F)F)[nH]n2)s1)N1CCCCC1] | Piperidin-1-yl-[5-(5-trifluoromethyl-1H-pyrazol-3-yl)-thiophen-2-yl]-methanone | 329.34 | 330.4 |

| Comp. # | Structure | Compound Name | MW | LC/MS (ES+) |
|---|---|---|---|---|
| 398 | 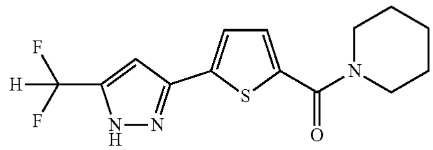 | [5-(5-Difluoromethyl-1H-pyrazol-3-yl)-thiophen-2-yl]-piperidin-1-yl-methanone | 311.36 | 312.4 |
| 399 | 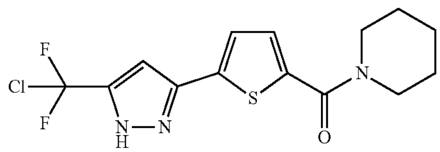 [SMILES: O=C(c1ccc(-c2cc(C(F)(F)Cl)[nH]n2)s1)N1CCCCC1] | {5-[5-(Chloro-difluoro-methyl)-1H-pyrazol-3-yl]-thiophen-2-yl}-piperidin-1-yl-methanone | 345.80 | 346.3 |
| 400 | 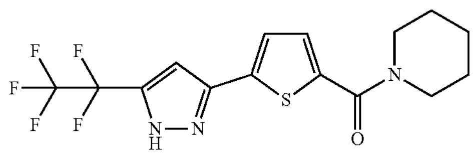 [SMILES: O=C(c1ccc(-c2cc(C(F)(F)C(F)(F)F)[nH]n2)s1)N1CCCCC1] | [5-(5-Pentafluoro-1H-pyrazol-3-yl)-thiophen-2-yl]-piperidin-1-yl-methanone | 379.35 | 380.3 |
| 401 | 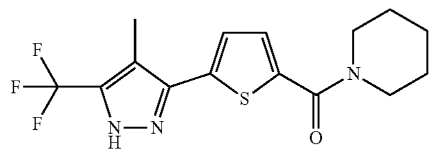 [SMILES: Cc1c(-c2ccc(C(=O)N3CCCCC3)s2)n[nH]c1C(F)(F)F] | [5-(4-Methyl-5-trifluoromethyl-1H-pyrazol-3-yl)-thiophen-2-yl]-piperidin-1-yl-methanone | 343.37 | 344.4 |
| 402 | 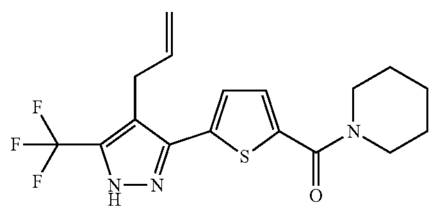 [SMILES: C=CCc1c(-c2ccc(C(=O)N3CCCCC3)s2)n[nH]c1C(F)(F)F] | [5-(4-Allyl-5-trifluoromethyl-1H-pyrazol-3-yl)-thiophen-2-yl]-piperidin-1-yl-methanone | 369.41 | 370.3 |
| 403 | 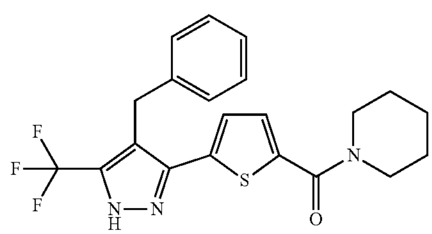 [SMILES: O=C(c1ccc(-c2n[nH]c(C(F)(F)F)c2Cc2ccccc2)s1)N1CCCCC1] | [5-(4-Benzyl-5-trifluoromethyl-1H-pyrazol-3-yl)-thiophen-2-yl]-piperidin-1-yl-methanone | 419.47 | 420.3 |
| 404 | 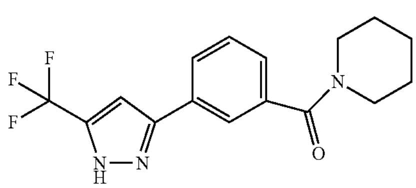 [SMILES: O=C(c1cccc(-c2cc(C(F)(F)F)[nH]n2)c1)N1CCCCC1] | Piperidin-1-yl-[3-(5-trifluoromethyl-1H-pyrazol-3-yl)-phenyl]-methanone | 323.32 | 324.4 |
| 405 | 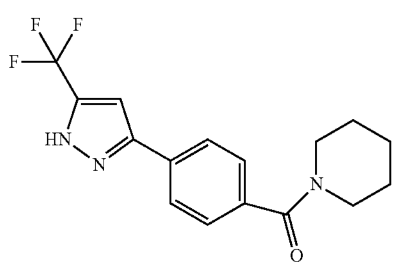 [SMILES: O=C(c1ccc(-c2cc(C(F)(F)F)[nH]n2)cc1)N1CCCCC1] | Piperidin-1-yl-[4-(5-trifluoromethyl-1H-pyrazol-3-yl)-phenyl]-methanone | 323.32 | 324.4 |

-continued

| Comp. # | Structure | Compound Name | MW | LC/MS (ES+) |
|---|---|---|---|---|
| 406 | 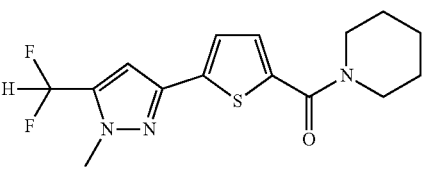 | [5-(5-Difluoromethyl-1-methyl-1H-pyrazol-3-yl)-thiophen-2-yl]-piperidin-1-yl-methanone | 325.38 | 326.4 |
| 407 | 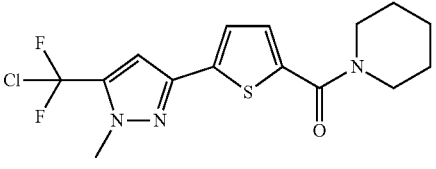 [SMILES: Cn1nc(-c2ccc(C(=O)N3CCCCC3)s2)cc1C(F)(F)Cl] | {5-[5-(Chloro-difluoro-methyl)-1-methyl-1H-pyrazol-3-yl]-thiophen-2-yl}-piperidin-1-yl-methanone | 359.82 | 360.4 |
| 408 | 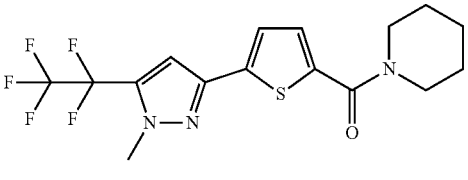 [SMILES: Cn1nc(-c2ccc(C(=O)N3CCCCC3)s2)cc1C(F)(F)C(F)(F)F] | [5-(1-Methyl-5-pentafluoroethyl-1H-pyrazol-3-yl)-thiophen-2-yl]-piperidin-1-yl-methanone | 393.78 | 394.3 |
| 409 | 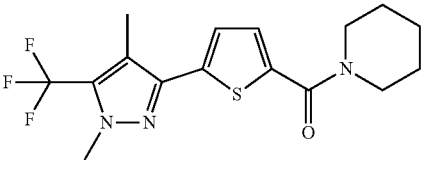 [SMILES: Cc1c(-c2ccc(C(=O)N3CCCCC3)s2)nn(C)c1C(F)(F)F] | [5-(1,4-Dimethyl-5-trifluoromethyl-1H-pyrazol-3-yl)-thiophen-2-yl]-piperidin-1-yl-methanone | 357.39 | 358.4 |
| 410 | 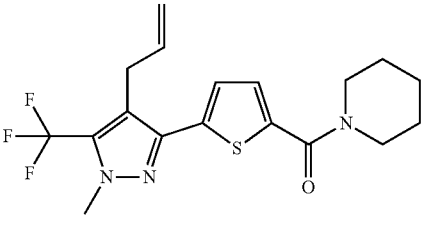 [SMILES: C=CCc1c(-c2ccc(C(=O)N3CCCCC3)s2)nn(C)c1C(F)(F)F] | [5-(4-Allyl-1-methyl-5-trifluoromethyl-1H-pyrazol-3-yl)-thiophen-2-yl]-piperidin-1-yl-methanone | 383.43 | 384.4 |
| 411 | 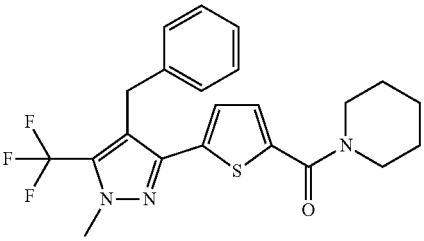 [SMILES: Cn1nc(-c2ccc(C(=O)N3CCCCC3)s2)c(Cc2ccccc2)c1C(F)(F)F] | [5-(4-Benzyl-1-methyl-5-trifluoromethyl-1H-pyrazol-3-yl)-thiophen-2-yl]-piperidin-1-yl-methanone | 433.49 | 434.4 |
| 412 | 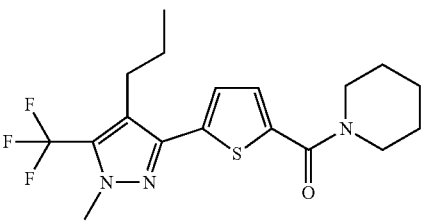 [SMILES: CCCc1c(-c2ccc(C(=O)N3CCCCC3)s2)nn(C)c1C(F)(F)F] | [5-(1-Methyl-4-propyl-5-trifluoromethyl-1H-pyrazol-3-yl)-thiophen-2-yl]-piperidin-1-yl-methanone | 385.45 | 386.4 |

-continued

| Comp. # | Structure | Compound Name | MW | LC/MS (ES+) |
|---|---|---|---|---|
| 413 | 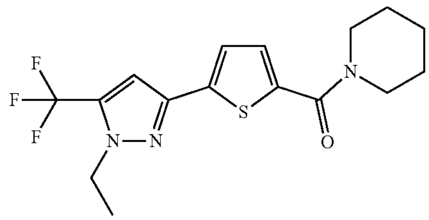 [SMILES: CCn1nc(-c2ccc(C(=O)N3CCCCC3)s2)cc1C(F)(F)F] | [5-(1-Ethyl-5-trifluoromethyl-1H-pyrazol-3-yl)-thiophen-2-yl]-piperidin-1-yl-methanone | 357.39 | 358.5 |
| 414 | 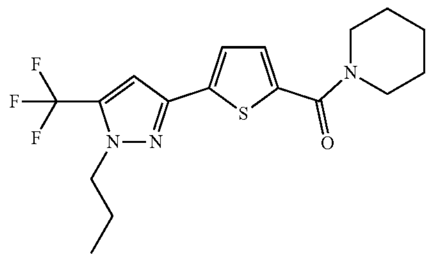 [SMILES: CCCn1nc(-c2ccc(C(=O)N3CCCCC3)s2)cc1C(F)(F)F] | Piperidin-1-yl-[5-(1-propyl-5-trifluoromethyl-1H-pyrazol-3-yl)-thiophen-2-yl]-methanone | 371.42 | 372.4 |
| 415 | 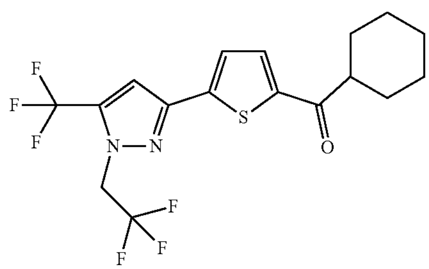 [SMILES: O=C(c1ccc(-c2cc(C(F)(F)F)n(CC(F)(F)F)n2)s1)C1CCCCC1] | Piperidin-1-yl-{5-[1-(2,2,2-trifluoro-ethyl)-5-trifluoromethyl-1H-pyrazol-3-yl]-thiophen-2-yl}-methanone | 411.37 | 412.4 |
| 416 | 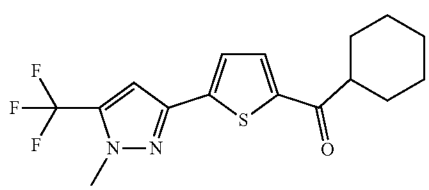 [SMILES: Cn1nc(-c2ccc(C(=O)C3CCCCC3)s2)cc1C(F)(F)F] | Cyclohexyl-[5-(1-methyl-5-trifluoromethyl-1H-pyrazol-3-yl)-thiophen-2-yl]-methanone | 342.38 | 343.5 |
| 417 | 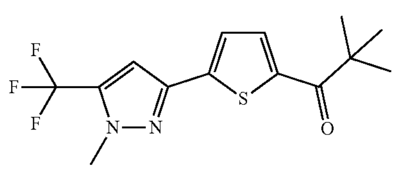 [SMILES: Cn1nc(-c2ccc(C(=O)C(C)(C)C)s2)cc1C(F)(F)F] | 2,2-Dimethyl-1-[5-(1-methyl-5-trifluoromethyl-1H-pyrazol-3-yl)-thiophen-2-yl]-propan-1-one | 316.34 | 317.5 |
| 418 | 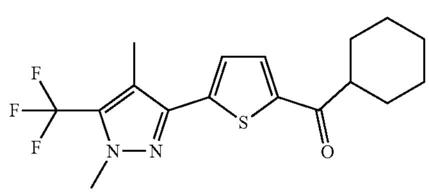 [SMILES: Cc1c(-c2ccc(C(=O)C3CCCCC3)s2)nn(C)c1C(F)(F)F] | Cyclohexyl-[5-(1,4-dimethyl-5-trifluoromethyl-1H-pyrazol-3-yl)-thiophen-2-yl]-methanone | 356.41 | 357.6 |
| 419 | 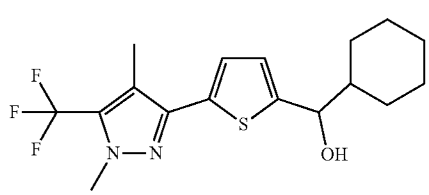 [SMILES: Cc1c(-c2ccc(C(O)C3CCCCC3)s2)nn(C)c1C(F)(F)F] | Cyclohexyl-[5-(1,4-dimethyl-5-trifluoromethyl-1H-pyrazol-3-yl)-thiophen-2-yl]-methanol | 358.43 | 359.6 |

-continued

| Comp. # | Structure | Compound Name | MW | LC/MS (ES+) |
|---|---|---|---|---|
| 420 | 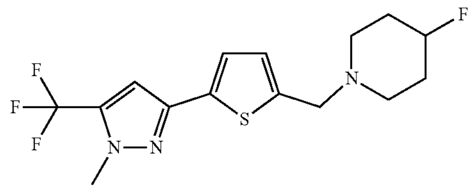 [SMILES: Cn1nc(-c2ccc(CN3CCC(F)CC3)s2)cc1C(F)(F)F] | 4-Fluoro-1-[5-(1-methyl-5-trifluoromethyl-1H-pyrazol-3-yl)-thiophen-2-ylmethyl]-piperidine | 347.38 | 348.6 |
| 421 | 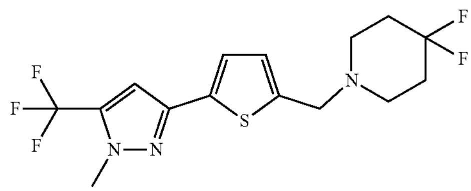 [SMILES: Cn1nc(-c2ccc(CN3CCC(F)(F)CC3)s2)cc1C(F)(F)F] | 4,4-Difluoro-1-[5-(1-methyl-5-tri-fluoromethyl-1H-pyrazol-3-yl)-thiophen-2-ylmethyl]-piperidine | 365.37 | 366.6 |
| 422 | 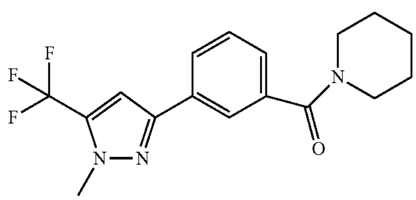 [SMILES: Cn1nc(-c2cccc(C(=O)N3CCCCC3)c2)cc1C(F)(F)F] | [3-(1-Methyl-5-trifluoromethyl-1H-pyrazol-3-yl)-phenyl]-piperidin-1-yl-methanone | 337.34 | 338.4 |
| 423 | 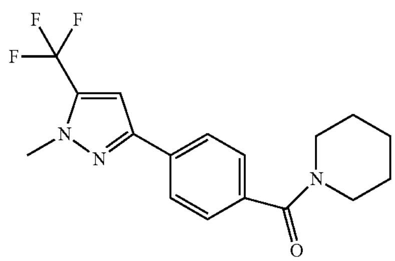 [SMILES: Cn1nc(-c2ccc(C(=O)N3CCCCC3)cc2)cc1C(F)(F)F] | [4-(1-Methyl-5-trifluoromethyl-1H-pyrazol-3-yl)-phenyl]-piperidin-1-yl-methanone | 337.34 | 338.4 |
| 424 | 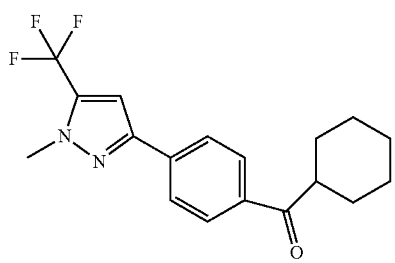 [SMILES: Cn1nc(-c2ccc(C(=O)C3CCCCC3)cc2)cc1C(F)(F)F] | Cyclohexyl-[4-(1-methyl-5-trifluoromethyl-1H-pyrazol-3-yl)-phenyl]-methanone | 336.35 | 337.6 |
| 425 | 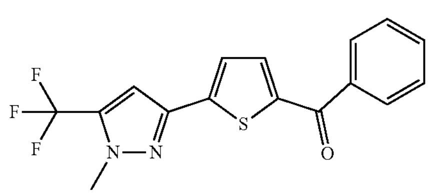 [SMILES: Cn1nc(-c2ccc(C(=O)c3ccccc3)s2)cc1C(F)(F)F] | [5-(1-Methyl-5-trifluoromethyl-1H-pyrazol-3-yl)-thiophen-2-yl]-phenyl-methanone | 336.34 | 337.6 |
| 426 | 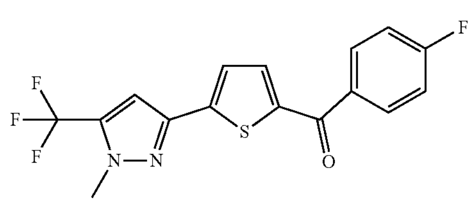 [SMILES: Cn1nc(-c2ccc(C(=O)c3ccc(F)cc3)s2)cc1C(F)(F)F] | (4-Fluoro-phenyl)-[5-(1-methyl-5-trifluoromethyl-1H-pyrazol-3-yl)-thiophen-2-yl]-methanone | 354.33 | 355.6 |

-continued

| Comp. # | Structure | Compound Name | MW | LC/MS (ES+) |
|---|---|---|---|---|
| 427 | 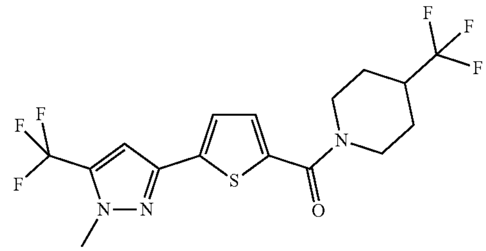 [SMILES: Cn1nc(-c2ccc(C(=O)N3CCC(C(F)(F)F)CC3)s2)cc1C(F)(F)F] | [5-(1-Methyl-5-trifluoromethyl-1H-pyrazol-3-yl)-thiophen-2-yl]-(4-trifluoromethyl-piperidin-1-yl)-methanone | 411.37 | 412.6 |
| 428 | 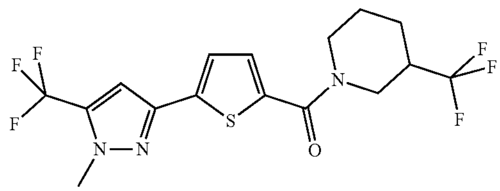 [SMILES: Cn1nc(-c2ccc(C(=O)N3CCCC(C(F)(F)F)C3)s2)cc1C(F)(F)F] | [5-(1-Methyl-5-trifluoromethyl-1H-pyrazol-3-yl)-thiophen-2-yl]-(3-trifluoromethyl-piperidin-1-yl)-methanone | 411.37 | 412.6 |
| 429 | 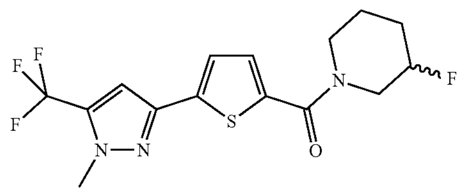 [SMILES: Cn1nc(-c2ccc(C(=O)N3CCCC(F)C3)s2)cc1C(F)(F)F] | (3-Fluoro-piperidin-1-yl)-[5-(1-methyl-5-trifluoromethyl-1H-pyrazol-3-yl)-thiophen-2-yl]-methanone | 361.36 | 362.6 |
| 430 | 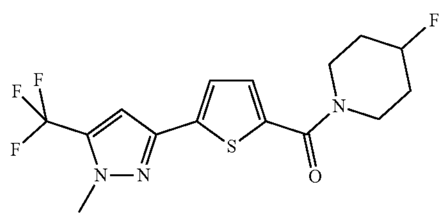 [SMILES: Cn1nc(-c2ccc(C(=O)N3CCC(F)CC3)s2)cc1C(F)(F)F] | (4-Fluoro-piperidin-1-yl)-[5-(1-methyl-5-trifluoromethyl-1H-pyrazol-3-yl)-thiophen-2-yl]-methanone | 361.36 | 362.6 |
| 431 | 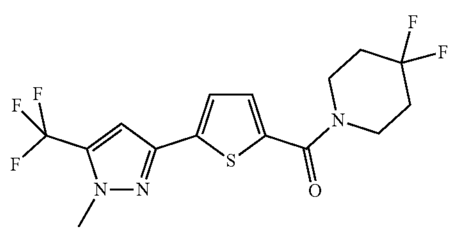 [SMILES: Cn1nc(-c2ccc(C(=O)N3CCC(F)(F)CC3)s2)cc1C(F)(F)F] | (4,4-Difluoro-piperidin-1-yl)-[5-(1-methyl-5-trifluoromethyl-1H-pyrazol-3-yl)-thiophen-2-yl]-methanone | 379.35 | 380.5 |
| 432 | 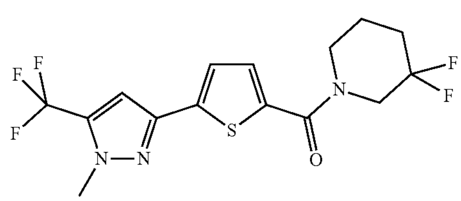 [SMILES: Cn1nc(-c2ccc(C(=O)N3CCCC(F)(F)C3)s2)cc1C(F)(F)F] | (3,3-Difluoro-piperidin-1-yl)-[5-(1-methyl-5-trifluoromethyl-1H-pyrazol-3-yl)-thiophen-2-yl]-methanone | 379.35 | 380.7 |
| 433 | 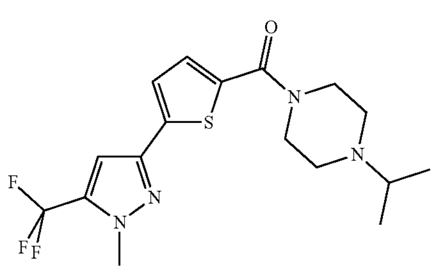 [SMILES: CC(C)N1CCN(C(=O)c2ccc(-c3cc(C(F)(F)F)n(C)n3)s2)CC1] | (4-Isopropyl-piperazin-1-yl)-[5-(1-methyl-5-trifluoromethyl-1H-pyrazol-3-yl)-thiophen-2-yl]-methanone | 386.44 | 387.6 |

| Comp. # | Structure | Compound Name | MW | LC/MS (ES+) |
|---|---|---|---|---|
| 434 | 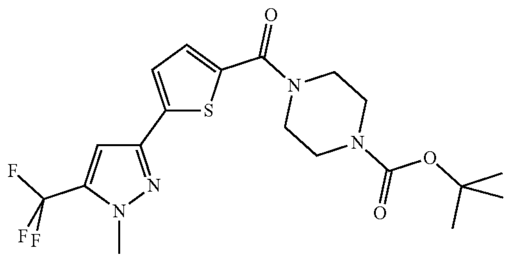 [SMILES: Cn1nc(-c2ccc(C(=O)N3CCN(C(=O)OC(C)(C)C)CC3)s2)cc1C(F)(F)F] | 4-[5-(1-Methyl-5-trifluoromethyl-1H-pyrazol-3-yl)-thiophene-2-carbonyl]-piperazine-1-carboxylic acid tert-butyl ester | 444.48 | 445.6 |
| 435 | 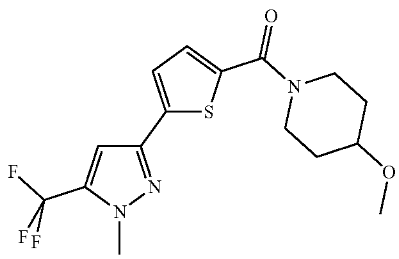 [SMILES: COC1CCN(C(=O)c2ccc(-c3cc(C(F)(F)F)n(C)n3)s2)CC1] | (4-Methoxy-piperidin-1-yl)-[5-(1-methyl-5-trifluoromethyl-1H-pyrazol-3-yl)-thiophen-2-yl]-methanone | 373.39 | 374.5 |
| 436 | 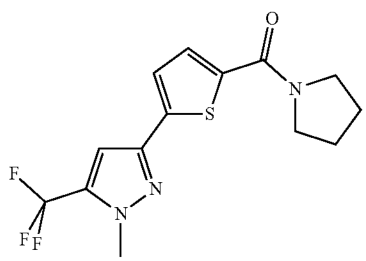 [SMILES: Cn1nc(-c2ccc(C(=O)N3CCCC3)s2)cc1C(F)(F)F] | [5-(1-Methyl-5-trifluoromethyl-1H-pyrazol-3-yl)-thiophen-2-yl]-pyrrolidin-1-yl-methanone | 329.34 | 330.5 |
| 437 | 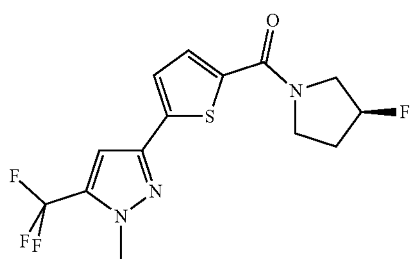 [SMILES: Cn1nc(-c2ccc(C(=O)N3CC[C@H](F)C3)s2)cc1C(F)(F)F] | ((S)-3-Fluoro-pyrrolidin-1-yl)-[5-(1-methyl-5-trifluoromethyl-1H-pyrazol-3-yl)-thiophen-2-yl]-methanone | 347.33 | 348.6 |
| 438 | 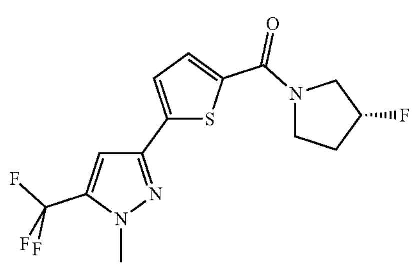 [SMILES: Cn1nc(-c2ccc(C(=O)N3CC[C@@H](F)C3)s2)cc1C(F)(F)F] | ((R)-3-Fluoro-pyrrolidin-1-yl)-[5-(1-methyl-5-trifluoromethyl-1H-pyrazol-3-yl)-thiophen-2-yl]-methanone | 347.33 | 348.6 |
| 439 | 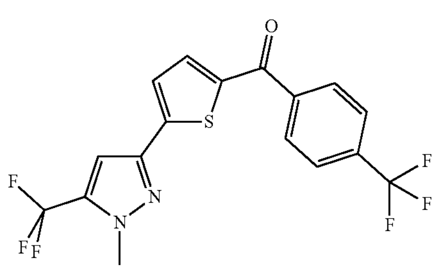 [SMILES: Cn1nc(-c2ccc(C(=O)c3ccc(C(F)(F)F)cc3)s2)cc1C(F)(F)F] | [5-(1-Methyl-5-trifluoromethyl-1H-pyrazol-3-yl)-thiophen-2-yl]-(4-trifluoromethyl-phenyl)-methanone | 404.34 | 405.5 |

-continued

| Comp. # | Structure | Compound Name | MW | LC/MS (ES+) |
|---|---|---|---|---|
| 440 | 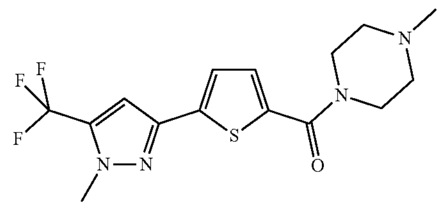 [SMILES: CN1CCN(C(=O)c2ccc(-c3cc(C(F)(F)F)n(C)n3)s2)CC1] | (4-Methyl-piperazin-1-yl)-[5-(1-methyl-5-trifluoromethyl-1H-pyrazol-3-yl)-thiophen-2-yl]-methanone | 358.38 | 359.6 |
| 441 | 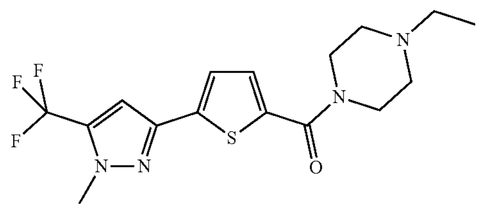 [SMILES: CCN1CCN(C(=O)c2ccc(-c3cc(C(F)(F)F)n(C)n3)s2)CC1] | (4-Ethyl-piperazin-1-yl)-[5-(1-methyl-5-trifluoromethyl-1H-pyrazol-3-yl)-thiophen-2-yl]-methanone | 372.41 | 373.6 |
| 442 | 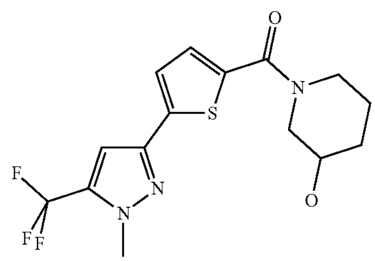 [SMILES: Cn1nc(-c2ccc(C(=O)N3CCCC(O)C3)s2)cc1C(F)(F)F] | (3-Hydroxy-piperidin-1-yl)-[5-(1-methyl-5-trifluoromethyl-1H-pyrazol-3-yl)-thiophen-2-yl]-methanone | 359.37 | 360.5 |
| 443 | 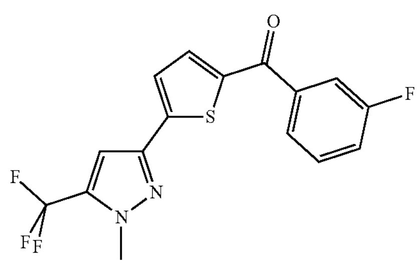 [SMILES: Cn1nc(-c2ccc(C(=O)c3cccc(F)c3)s2)cc1C(F)(F)F] | (3-Fluoro-phenyl)-[5-(1-methyl-5-trifluoromethyl-1H-pyrazol-3-yl)-thiophen-2-yl]-methanone | 354.32 | 355.5 |
| 444 | 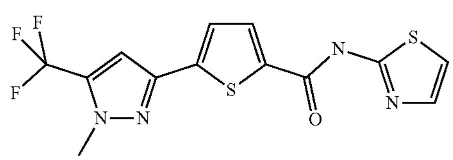 [SMILES: Cn1nc(-c2ccc(C(=O)Nc3nccs3)s2)cc1C(F)(F)F] | 5-(1-Methyl-5-trifluoromethyl-1H-pyrazol-3-yl)-thiophene-2-carboxylic acid thiazol-2-ylamide | 358.36 | 359.5 |
| 445 | 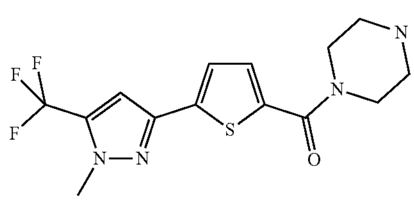 [SMILES: Cn1nc(-c2ccc(C(=O)N3CCNCC3)s2)cc1C(F)(F)F] | [5-(1-Methyl-5-trifluoromethyl-1H-pyrazol-3-yl)-thiophen-2-yl]-piperazin-1-yl-methanone | 344.36 | 345.5 |
| 446 | 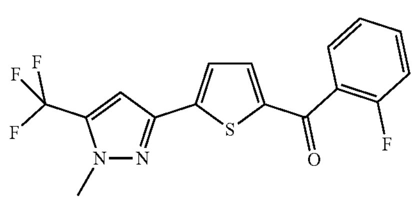 [SMILES: Cn1nc(-c2ccc(C(=O)c3ccccc3F)s2)cc1C(F)(F)F] | (2-Fluoro-phenyl)-[5-(1-methyl-5-trifluoromethyl-1H-pyrazol-3-yl)-thiophen-2-yl]-methanone | 354.32 | 355.5 |

| Comp. # | Structure | Compound Name | MW | LC/MS (ES+) |
|---|---|---|---|---|
| 447 | 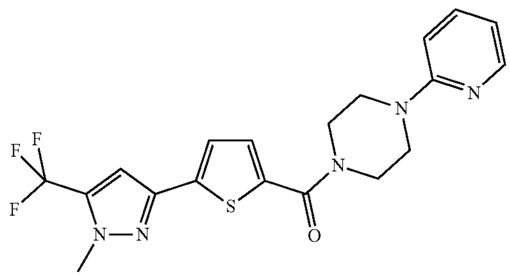 [SMILES: Cn1nc(-c2ccc(C(=O)N3CCN(c4ccccn4)CC3)s2)cc1C(F)(F)F] | [5-(1-Methyl-5-trifluoromethyl-1H-pyrazol-3-yl)-thiophen-2-yl]-(4-pyridin-2-yl-piperazin-1-yl)-methanone | 421.44 | 422.6 |
| 448 | 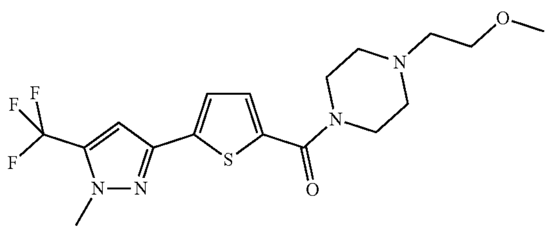 [SMILES: COCCN1CCN(C(=O)c2ccc(-c3cc(C(F)(F)F)n(C)n3)s2)CC1] | [4-(2-Methoxy-ethyl)-piperazin-1-yl]-[5-(1-methyl-5-trifluoromethyl-1H-pyrazol-3-yl)-thiophen-2-yl]-methanone | 402.44 | 403.5 |
| 449 | 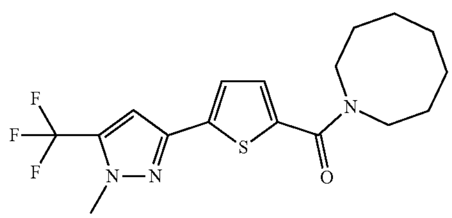 [SMILES: Cn1nc(-c2ccc(C(=O)N3CCCCCCC3)s2)cc1C(F)(F)F] | [5-(1-Methyl-5-trifluoromethyl-1H-pyrazol-3-yl)-thiophen-2-yl]-perhydro-azocin-1-yl-methanone | 371.42 | 372.5 |
| 450 | 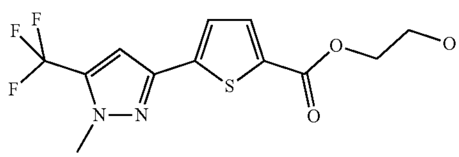 [SMILES: Cn1nc(-c2ccc(C(=O)OCCO)s2)cc1C(F)(F)F] | 5-(1-Methyl-5-trifluoromethyl-1H-pyrazol-3-yl)-thiophene-2-carboxylic acid 2-hydroxy-ethyl ester | 320.29 | 321.5 |
| 451 | 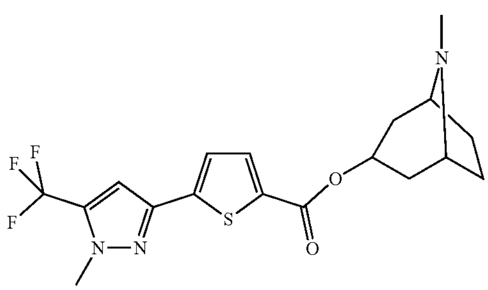 [SMILES: CN1C2CCC1CC(OC(=O)c1ccc(-c3cc(C(F)(F)F)n(C)n3)s1)C2] | 5-(1-Methyl-5-trifluoromethyl-1H-pyrazol-3-yl)-thiophene-2-carboxylic acid 8-methyl-8-aza-bicyclo[3.2.1]oct-3-yl ester | 399.43 | 400.5 |
| 452 | 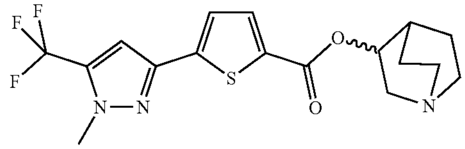 [SMILES: Cn1nc(-c2ccc(C(=O)OC3CN4CCC3CC4)s2)cc1C(F)(F)F] | 5-(1-methyl-5-trifluoromethyl-1H-pyrazol-3-yl)-thiophene-2-carboxylic acid 1-aza-bicyclo[2.2.2]oct-3-yl ester | 385.41 | 386.5 |
| 453 | 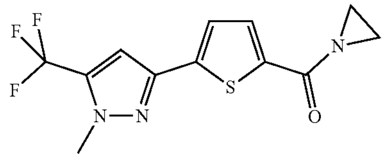 [SMILES: Cn1nc(-c2ccc(C(=O)N3CC3)s2)cc1C(F)(F)F] | Aziridin-1-yl-[5-(1-methyl-5-trifluoromethyl-1H-pyrazol-3-yl)-thiophen-2-yl]-methanone | 301.29 | 302.4 |

-continued

| Comp. # | Structure | Compound Name | MW | LC/MS (ES+) |
|---|---|---|---|---|
| 454 | 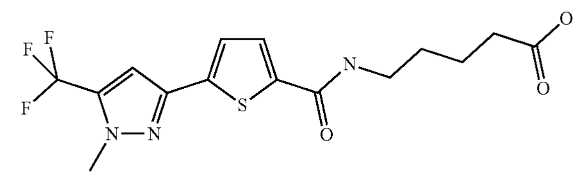 [SMILES: Cn1nc(-c2ccc(C(=O)NCCCCC(=O)O)s2)cc1C(F)(F)F] | 5-{[5-(1-Methyl-5-trifluoromethyl-1H-pyrazol-3-yl)-thiophene-2-carbonyl]-amino}-pentanoic acid | 375.37 | 376.5 |
| 455 | 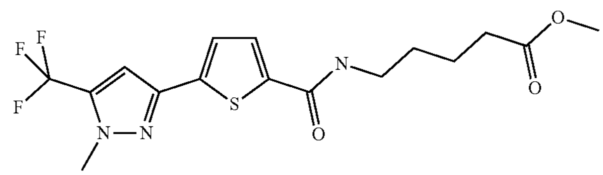 [SMILES: COC(=O)CCCCNC(=O)c1ccc(-c2cc(C(F)(F)F)n(C)n2)s1] | 5-{[5-(1-Methyl-5-trifluoromethyl-1H-pyrazol-3-yl)-thiophene-2-carbonyl]-amino}-pentanoic acid methyl ester | 389.39 | 390.5 |
| 456 | 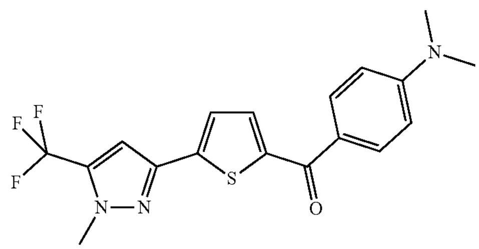 [SMILES: CN(C)c1ccc(C(=O)c2ccc(-c3cc(C(F)(F)F)n(C)n3)s2)cc1] | (4-Dimethylamino-phenyl)-[5-(1-methyl-5-trifluoromethyl-1H-pyrazol-3-yl)-thiophen-2-yl]-methanone | 379.40 | 380.5 |
| 457 | 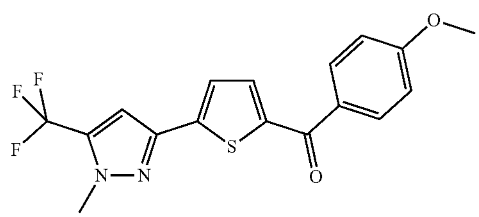 [SMILES: COc1ccc(C(=O)c2ccc(-c3cc(C(F)(F)F)n(C)n3)s2)cc1] | (4-Methoxy-phenyl)-[5-(1-(methyl-5-trifluoromethyl-1H-pyrazol-3-yl)-thiophen-2-yl]-methanone | 366.36 | 367.5 |
| 458 | 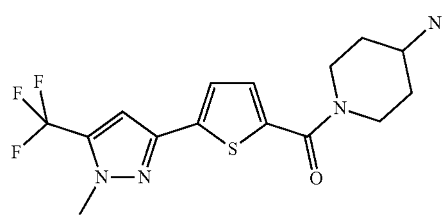 [SMILES: Cn1nc(-c2ccc(C(=O)N3CCC(N)CC3)s2)cc1C(F)(F)F] | (4-Amino-piperidin-1-yl)-[5-(1-methyl-5-trifluoromethyl-1H-pyrazol-3-yl)-thiophen-2-yl]-methanone | 358.39 | 359.5 |
| 459 | 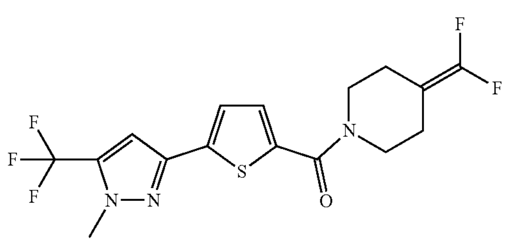 [SMILES: Cn1nc(-c2ccc(C(=O)N3CCC(=C(F)F)CC3)s2)cc1C(F)(F)F] | (4-Difluoromethylene-piperidin-1-yl)-[5-(1-methyl-5-trifluoromethyl-1H-pyrazol-3-yl)-thiophen-2-yl]-methanone | 391.36 | 392.5 |
| 460 | 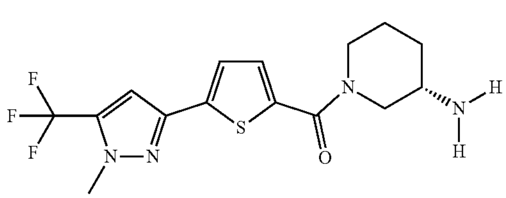 | ((S)-3-Amino-piperidin-1-yl)-[5-(1-methyl-5-trifluoromethyl-1H-pyrazol-3-yl)-thiophen-2-yl]-methanone, hydrochloride | 358.38 | 359.5 |

-continued

| Comp. # | Structure | Compound Name | MW | LC/MS (ES+) |
|---|---|---|---|---|
| 461 | Chiral | ((R)-3-Amino-piperidin-1-yl)-[5-(1-methyl-5-trifluoromethyl-1H-pyrazol-3-yl)-thiophen-2-yl]-methanone, hydrochloride | 358.38 | 359.5 |
| 462 | 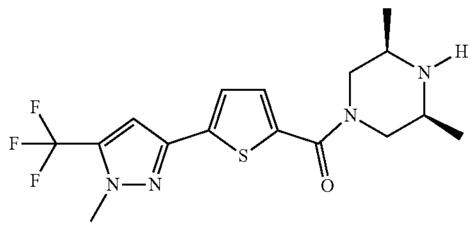 [SMILES: C[C@@H]1CN(C(=O)c2ccc(-c3cc(C(F)(F)F)n(C)n3)s2)C[C@H](C)N1] | Cis-3,5-Dimethyl-piperazin-1-yl)-[5-(1-methyl-5-trifluoromethyl-1H-pyrazol-3-yl)-thiophen-2-yl]-methanone | 372.41 | 373.6 |
| 463 | 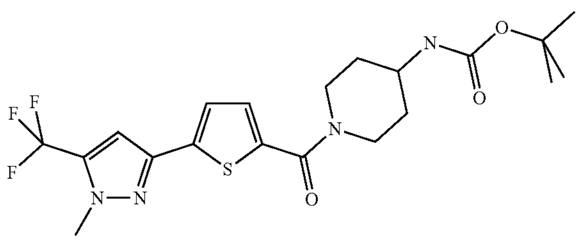 [SMILES: Cn1nc(-c2ccc(C(=O)N3CCC(NC(=O)OC(C)(C)C)CC3)s2)cc1C(F)(F)F] | {1-[5-(1-Methyl-5-trifluoromethyl-1H-pyrazol-3-yl)-thiophene-2-carbonyl]-piperidin-4-yl}-carbamic acid tert-butyl ester | 458.51 | 459.6 |
| 464 | 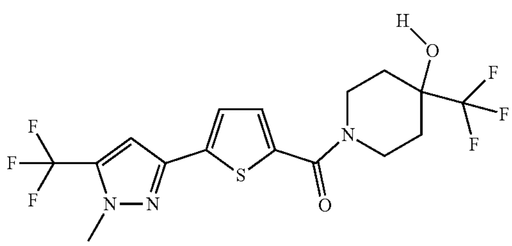 [SMILES: Cn1nc(-c2ccc(C(=O)N3CCC(O)(C(F)(F)F)CC3)s2)cc1C(F)(F)F] | (4-Hydroxy-4-trifluoromethyl-piperidin-1-yl)-[5-(1-methyl-5-trifluoromethyl-1H-pyrazol-3-yl)-thiophen-2-yl]-methanone | 427.37 | 428.4 |
| 465 | 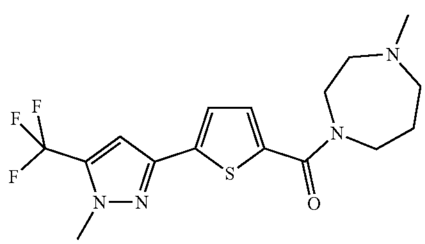 [SMILES: CN1CCCN(C(=O)c2ccc(-c3cc(C(F)(F)F)n(C)n3)s2)CC1] | (4-Methyl-[1,4]diazepan-1-yl)-[5-(1-methyl-5-trifluoromethyl-1H-pyrazol-3-yl)-thiophen-2-yl]-methanone | 372.41 | 373.5 |
| 466 | 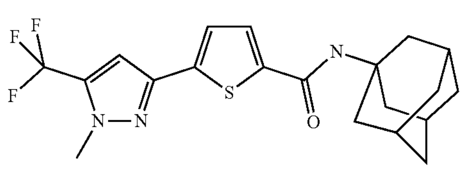 [SMILES: Cn1nc(-c2ccc(C(=O)NC34CC5CC(CC(C5)C3)C4)s2)cc1C(F)(F)F] | 5-(1-Methyl-5-trifluoromethyl-1H-pyrazol-3-yl)-thiophene-2-carboxylic acid adamantan-1-ylamide | 409.47 | 410.6 |
| 467 | 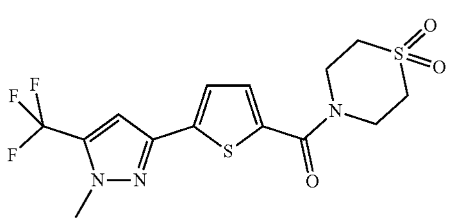 [SMILES: Cn1nc(-c2ccc(C(=O)N3CCS(=O)(=O)CC3)s2)cc1C(F)(F)F] | (1,1-Dioxo-1lambda*6*-thiomorpholin-4-yl)-[5-(1-methyl-5-trifluoromethyl-1H-pyrazol-3-yl)-thiophen-2-yl]-methanone | 393.41 | 394.4 |

| Comp. # | Structure | Compound Name | MW | LC/MS (ES+) |
|---|---|---|---|---|
| 468 | 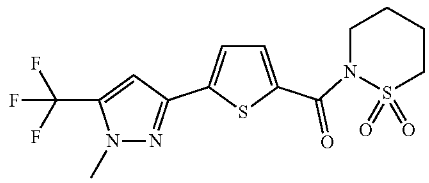 [SMILES: Cn1nc(-c2ccc(C(=O)N3CCCCS3(=O)=O)s2)cc1C(F)(F)F] | (1,1-Dioxo-1lambda*6*-[1,2]thiazinan-2-yl)-[5-(1-methyl-5-trifluoromethyl-1H-pyrazol-3-yl)-thiophen-2-yl]-methanone | 39341 | 394.4 |
| 469 | 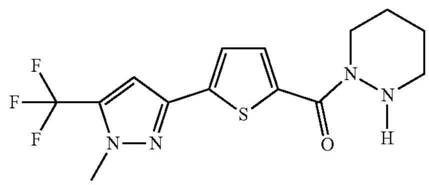 [SMILES: Cn1nc(-c2ccc(C(=O)N3CCCCN3)s2)cc1C(F)(F)F] | [5-(1-Methyl-5-trifluoromethyl-1H-pyrazol-3-yl)-thiophen-2-yl]-(tetrahydro-pyridazin-1-yl)-methanone | 344.36 | 345.4 |
| 470 | 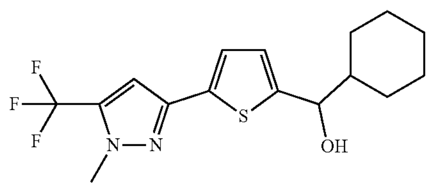 [SMILES: Cn1nc(-c2ccc(C(O)C3CCCCC3)s2)cc1C(F)(F)F] | Cyclohexyl-[5-(1-methyl-5-trifluoromethyl-1H-pyrazol-3-yl)-thiophen-2-yl]-methanol | 344.40 | 345.4 |
| 471 | 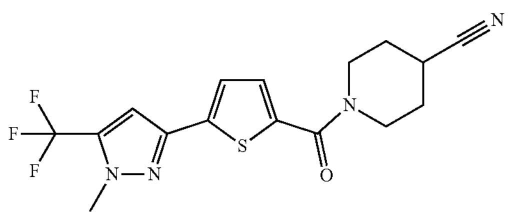 [SMILES: Cn1nc(-c2ccc(C(=O)N3CCC(C#N)CC3)s2)cc1C(F)(F)F] | 1-[5-(1-Methyl-5-trifluoromethyl-1H-pyrazol-3-yl)-thiophene-2-carbonyl]-piperidin-4-nitrile | 368.38 | 369.4 |
| 472 | 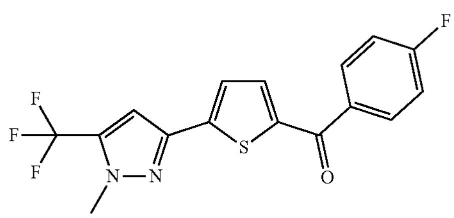 [SMILES: Cn1nc(-c2ccc(C(=O)c3ccc(F)cc3)s2)cc1C(F)(F)F] | (4-Fluoro-phenyl)-[5-(1-methyl-5-trifluoromethyl-1H-pyrazol-3-yl)-thiophen-2-yl]-methanone | 354.32 | 355.5 |
| 473 | 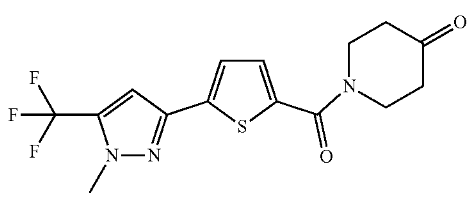 [SMILES: Cn1nc(-c2ccc(C(=O)N3CCC(=O)CC3)s2)cc1C(F)(F)F] | 1-[5-(1-Methyl-5-trifluoromethyl-1H-pyrazol-3-yl)-thiophene-2-carbonyl]-piperidin-4-one | 357.35 | 358.5 |
| 474 | 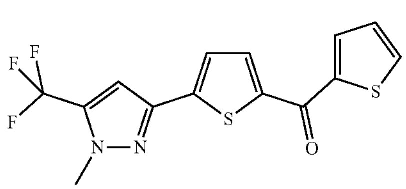 [SMILES: Cn1nc(-c2ccc(C(=O)c3cccs3)s2)cc1C(F)(F)F] | [5-(1-Methyl-5-trifluoromethyl-1H-pyrazol-3-yl)-thiophen-2-yl]-thiophene-2-yl-methanone | 342.36 | 343.4 |

| Comp. # | Structure | Compound Name | MW | LC/MS (ES+) |
|---|---|---|---|---|
| 475 | 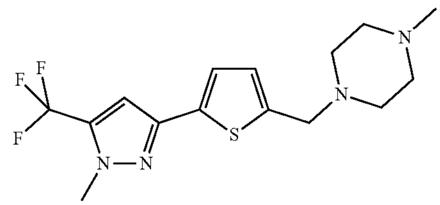 [SMILES: CN1CCN(Cc2ccc(-c3cc(C(F)(F)F)n(C)n3)s2)CC1] | 1-Methyl-4-[5-(1-methyl-5-trifluoromethyl-1H-pyrazol-3-yl)-thiophen-2-ylmethyl]-piperazine | 344.40 | 345.5 |
| 476 | 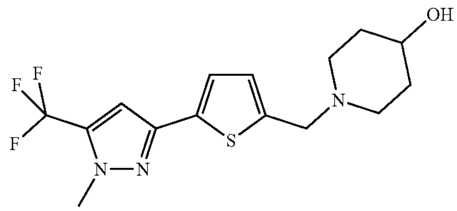 [SMILES: Cn1nc(-c2ccc(CN3CCC(O)CC3)s2)cc1C(F)(F)F] | 1-[5-(1-Methyl-5-trifluoromethyl-1H-pyrazol-3-yl)-thiophen-2-ylmethyl]-piperidin-4-ol | 345.39 | 346.4 |

Example 13

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| | mg/ml |
|---|---|
| (iv) Injection 1 (1 mg/ml) | |
| Compound X= (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | |
|---|---|
| Compound X= (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound selected from the group consisting of

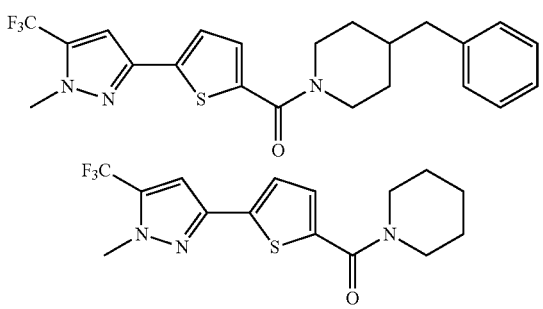

-continued

225
-continued
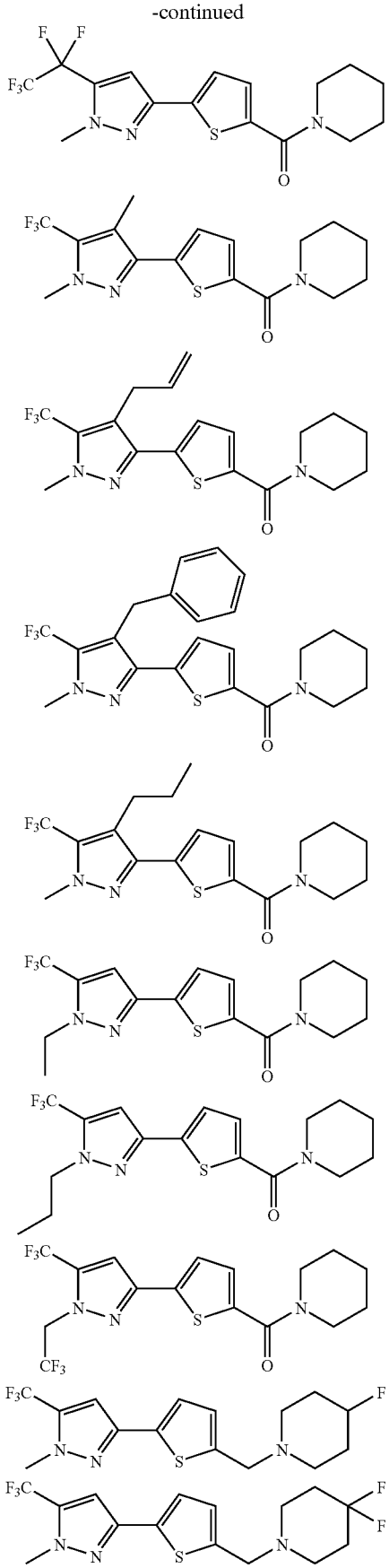
226
-continued
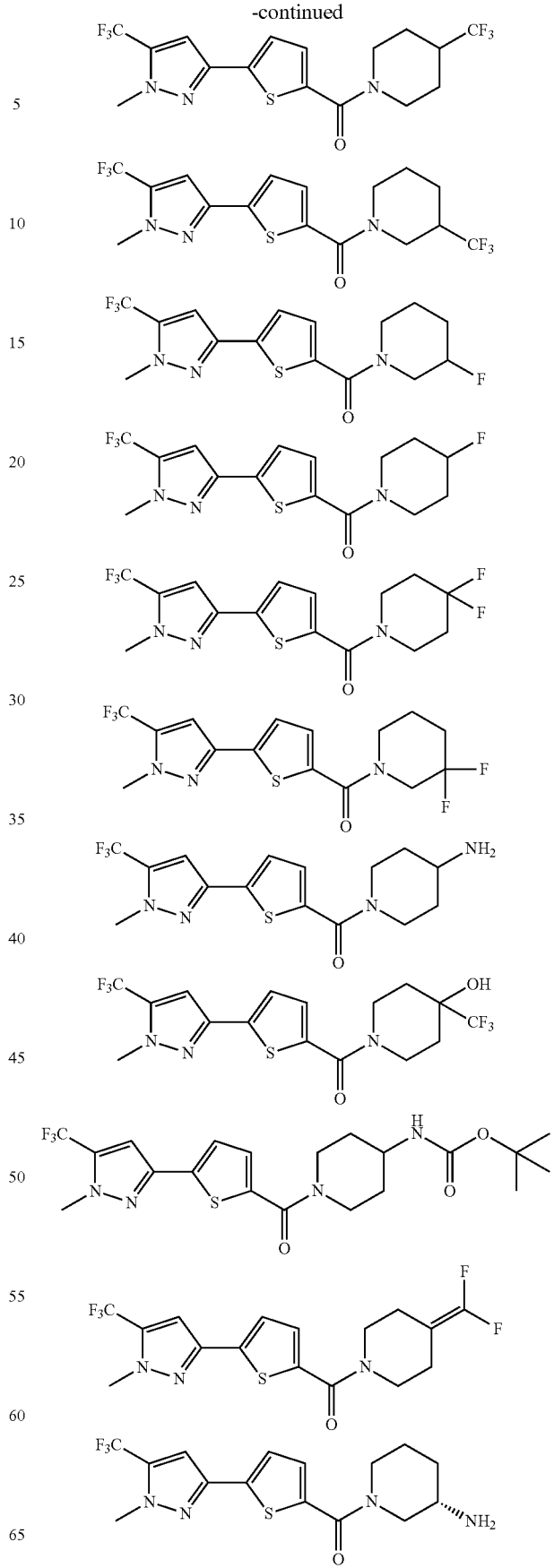

-continued

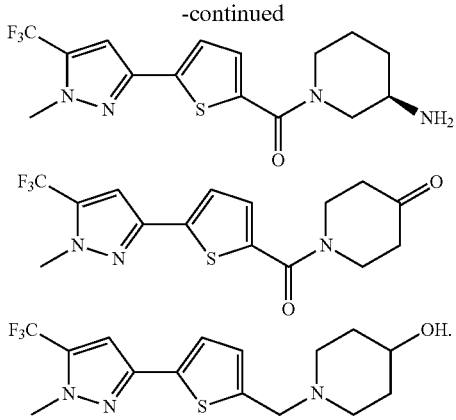

2. The compound of claim 1, wherein said compound is racemic.

3. The compound of claim 1, wherein said compound is optically pure.

4. A compound of formula I:

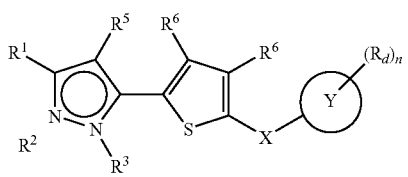

wherein:
- $R^1$ is $(C_1$-$C_6)$alkyl, $(C_1$-$C_6)$haloalkyl, or phenyl, each of which may be unsubstituted or substituted with one or more $R_e$;
- one of $R^2$ and $R^3$ is absent and the other is hydrogen, $(C_1$-$C_6)$alkyl, halo$(C_1$-$C_6)$alkyl, hydroxy$(C_1$-$C_6)$alkyl, $(C_3$-$C_8)$cycloalkyl, amino$(C_2$-$C_6)$alkyl, or aryl, each of which may be unsubstituted or substituted with one or more groups selected from alkyl, halo, haloalkyl or nitro, Het, $(C_3$-$C_8)$cycloalkyl$(C_1$-$C_6)$alkyl, aryl$(C_1$-$C_6)$alkyl, $(C_1$-$C_6)$ or Het$(C_1$-$C_6)$alkyl;
- X is —C(=O);
- Y is piperidine;
- n is an integer from 0 to 10 inclusive;
- each of the n instances of $R_d$ is independently halo, hydroxy, cyano, nitro, azido, amino, $(C_1$-$C_6)$alkylamino, amino$(C_1$-$C_6)$alkyl, amido, $(C_1$-$C_6)$alkylamido, aryl amido, carboxylic acid, $(C_1$-$C_6)$alkyl, hydroxy$(C_1$-$C_6)$alkyl, halo$(C_1$-$C_6)$alkyl, $(C_1$-$C_6)$alkoxy, halo$(C_1$-$C_6)$alkoxy, $(C_1$-$C_6)$alkanoyl, $(C_1$-$C_6)$alkoxycarbonyl, carboxy, $(C_1$-$C_6)$alkanoyloxy, halo$(C_1$-$C_6)$alkenyl, Het, aryl, Het$(C_1$-$C_6)$alkyl, or aryl$(C_1$-$C_6)$alkyl, $(C_1$-$C_6)$alkylaryl, sulfonyl, sulfonamido, urea, carbamate, unsubstituted or substituted with one or more $R_e$, or two $R_d$ come together with the atom to which they are attached to form a ketone or spirocyclic carbocyclic or heterocyclic ring, or two $R_d$ come together with the atoms to which they are attached to form a bicyclic carbocyclic or heterocyclic ring, wherein each spirocyclic or bicyclic ring is unsubstituted or substituted with one or more halo, hydroxy, cyano, nitro, azido, $(C_1$-$C_6)$alkyl, hydroxy$(C_1$-$C_6)$alkyl, halo $(C_1$-$C_6)$alkyl, $(C_1$-$C_6)$alkoxy, halo$(C_1$-$C_6)$alkoxy, $(C_1$-$C_6)$alkanoyl, $(C_1$-$C_6)$alkoxycarbonyl, carboxy, $(C_1$-$C_6)$alkanoyloxy, $NR_fR_g$, $R_fR_gNC(=O)$—, phenyl, or phenyl$(C_1$-$C_6)$alkyl, sulfonyl, sulfonamido, urea, carbamate, wherein $R_f$ and $R_g$ together with the nitrogen to which they are attached form a piperidine, pyrrolidine, morpholine, or thiomorpholine ring, unsubstituted or substituted with one or more $R_e$;
- each $R_e$ is independently selected from halo, hydroxy, cyano, nitro, azido, $(C_1$-$C_6)$alkyl, Het, aryl, $(C_1$-$C_6)$alkylHet, $(C_1$-$C_6)$alkylaryl, $(C_1$-$C_6)$alkylHet$(C_1$-$C_6)$alkyl, $(C_1$-$C_6)$alkylaryl$(C_1$-$C_6)$alkyl, $(C_1$-$C_6)$haloalkyl, $(C_1$-$C_6)$alkoxy, $(C_1$-$C_6)$haloalkoxy, $(C_1$-$C_6)$alkanoyl, $(C_1$-$C_6)$alkoxycarbonyl, carboxy, and $(C_1$-$C_6)$alkanoyloxy;
- $R^5$ is H, $(C_1$-$C_6)$alkyl, $(C_1$-$C_6)$alkenyl, $(C_1$-$C_6)$alkynyl, aryl$(C_1$-$C_6)$alkyl;
- $R^6$ is H, $(C_1$-$C_6)$alkyl, amino, amido, keto, or aryl$(C_1$-$C_6)$alkyl;

with the following proviso:
when X is CO=$R^1$ is $CF_3$, $R^3$ is $CH_3$, and Y is disubstituted at the 4-position wherein one of the substituents at the 4-position is phenyl, the other substituent at the 4-position of Y may not be (C=O)$(C_1$-$C_4)$alkyl;

or a pharmaceutically acceptable salt thereof.

* * * * *